(12) United States Patent
Hodi et al.

(10) Patent No.: US 11,584,788 B2
(45) Date of Patent: Feb. 21, 2023

(54) COMPOSITIONS AND METHODS FOR IDENTIFICATION, ASSESSMENT, PREVENTION, AND TREATMENT OF MELANOMA USING PD-L1 ISOFORMS

(71) Applicant: Dana-Farber Cancer Institute, Inc., Boston, MA (US)

(72) Inventors: F. Stephen Hodi, Framingham, MA (US); Jun Zhou, Waltham, MA (US); Gordon J. Freeman, Brookline, MA (US); Jingjing Li, Lexington, MA (US); Xinqi Wu, Chestnut Hill, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 164 days.

(21) Appl. No.: 16/365,978

(22) Filed: Mar. 27, 2019

(65) Prior Publication Data

US 2019/0375818 A1  Dec. 12, 2019

Related U.S. Application Data

(63) Continuation of application No. 15/110,808, filed as application No. PCT/US2015/011303 on Jan. 14, 2015, now abandoned.

(60) Provisional application No. 61/927,037, filed on Jan. 14, 2014.

(51) Int. Cl.

| | | |
|---|---|---|
| *C07K 16/00* | (2006.01) | |
| *C07K 14/705* | (2006.01) | |
| *C07K 16/28* | (2006.01) | |
| *C07K 16/30* | (2006.01) | |
| *G01N 33/50* | (2006.01) | |
| *G01N 33/574* | (2006.01) | |
| *A61K 9/00* | (2006.01) | |
| *A61K 38/17* | (2006.01) | |
| *A61K 39/395* | (2006.01) | |
| *A61K 45/06* | (2006.01) | |
| *C12Q 1/6886* | (2018.01) | |
| *A61K 38/00* | (2006.01) | |
| *A61K 39/00* | (2006.01) | |

(52) U.S. Cl.
CPC ...... *C07K 14/70532* (2013.01); *A61K 9/0019* (2013.01); *A61K 38/1774* (2013.01); *A61K 39/39558* (2013.01); *A61K 45/06* (2013.01); *C07K 14/70596* (2013.01); *C07K 16/2818* (2013.01); *C07K 16/2827* (2013.01); *C07K 16/3053* (2013.01); *C12Q 1/6886* (2013.01); *G01N 33/5011* (2013.01); *G01N 33/5743* (2013.01); *A61K 38/00* (2013.01); *A61K 2039/505* (2013.01); *C07K 2319/30* (2013.01); *C12Q 2600/118* (2013.01); *C12Q 2600/136* (2013.01); *C12Q 2600/158* (2013.01); *G01N 2333/70596* (2013.01); *G01N 2500/10* (2013.01); *G01N 2800/52* (2013.01)

(58) Field of Classification Search
CPC .............. A61K 39/39558; A61K 38/00; C07K 16/2818; C07K 16/2827; G01N 2333/70596; C12Q 1/6886; C12Q 2600/118; C12Q 2600/158
See application file for complete search history.

(56) References Cited

U.S. PATENT DOCUMENTS

| | | | |
|---|---|---|---|
| 6,803,192 B1 * | 10/2004 | Chen ...................... | C07K 14/47 435/320.1 |
| 2002/0095024 A1 * | 7/2002 | Mikesell .................. | A61P 9/10 530/350 |
| 2009/0176317 A1 | 7/2009 | Kwon et al. | |

FOREIGN PATENT DOCUMENTS

| | | |
|---|---|---|
| WO | WO-2001/039722 A2 | 6/2001 |
| WO | WO-200268647 A2 | 9/2002 |
| WO | WO-2010/036959 A2 | 4/2010 |
| WO | WO-2013/079174 A1 | 6/2013 |
| WO | WO-2014/197369 A1 | 12/2014 |

OTHER PUBLICATIONS

He et al, Acta Parmacologica Sinica 26:462-468, 2005 (Year: 2005).*
Grzywnowicz et al, PLoS One 7: e35178, p. 1-8, 2012 (Year: 2012).*
Extended European Search Report issued by the European Patent Office in corresponding Application No. 15737311.9, dated Sep. 26, 2017.
Hino et al., "Tumor cell expression of programmed cell death-1 ligand 1 is a prognostic factor for malignant melanoma," Cancer, 116(7): 1757-1766 (2010).
Supplementary Partial European Search Report issued by the European Patent Office in corresponding International Application No. PCT/US/2015011303, dated Jun. 14, 2017.

* cited by examiner

*Primary Examiner* — Lei Yao
(74) *Attorney, Agent, or Firm* — Foley Hoag LLP; DeAnn F. Smith; Philip S. Choi

(57) ABSTRACT

The present invention relates to compositions and methods for identifying, assessing, preventing, and treating melanoma. A variety of PD-L1 isoform biomarkers are provided, wherein alterations in the copy number of one or more of the biomarkers and/or alterations in the amount, structure, and/ or activity of one or more of the biomarkers is associated with melanoma status.

6 Claims, 14 Drawing Sheets
Specification includes a Sequence Listing.

Figure 1

Membrane form of PDL1

ATGAGGATATTTGCTGTCTTTATATTCATGACCTACTGGCATTTGCTGAACGCATTACTGTCACGGTTCCCAAGGACCTATATGTGGTAGAGTATGGTAGCAATATGACAATTGAATGCAAATTCCAGTAGAAAAACAATTAG
ACCTGGCTGCACTAATTGTCTATTGGAAATGCAGGATGCAGAGAACATTATCAATTTGTCATGATGGAGAGAGACCTGAAGGTTCAGCAAGCTACACAGACAGAGGCCCGGCTGTTGAAGGACCAGCTCTCCTGGGAAA
TGCTGCACTTCAGATCACAGATGTGAAATTGCAGGATGCAGGGGTGTACCGCTGACATGATCAGCTACACAGCGAATTACTGTGAAAGTCAATGCCCATACACAACAAATCAACCAAGAATTTGGTTGT
GGATCCAGTGCACCTCTGAACATGAACTGACATGTCAGGCTGAGGCTGAGGGTCAGGGTGAGGGCTGAGGGCTGAGGGCCAAGCATCTGACAAGCAGTGACCATCAAGTCCTGAGTGGTAAGACCAGTGACCATCTGAGTGGTAAGACCATCGAGGAGAAGCCTCCAAGAGAGGAGAAGCTTTCA
ATGTGACCAGCACACTGAGAATCAACACAACTAATGAGATTTCTACTGACACTGGCCATCTTATATGCCTGGTGTAGCACTGACATTCATCTTCCGTTAAGAAAAATGTGGCATCCAAGATACAAACTCAAGAAGCAAAGTGATACACATTTGGA
CTTGGTAATTCTGGGAGCCATCTTATATGCCTGGTGTAGCACTGACATTCATCTTCCGTTAAGAAAAATGTGGCATCCAAGATACAAACTCAAGAAGCAAAGTGATACACATTTGGA
GGAGACGTAA

Met R I F A V F I F Met T Y W H L L N A F T V T V P K D L Y V V E Y G S N Met T I E C K F P V E K Q L D L A A L I V Y W E Met E D K N
I I Q F V H G E E D L K V Q H S S Y R Q R A R L L K D Q L S L G N A A L Q I T D V K L Q D A G V Y R C Met I S Y G G A D Y K R I T V K
V N A P Y N K I N Q R I L V V D P V T S E H E L T C Q A E G Y P K A E V I W T S S D H Q V L S G K T T T T N S K R E E K L F N V T S T
L R I N T T T N E I F Y C T F R R L D P E E N H T A E L V I P E L P L A H P P N E R T H L V I L G A I L L C L G V A L T F I F R L R K
G R Met Met D V K K C G I Q D T N S K K Q S D T H L E E T

PDL1-1 splicing form

ATGAGGATATTTGCTGTCTTTATATTCATGACCTACTGGCATTTGCTGAACGCATTACTGTCACGGTTCCCAAGGACCTATATGTGGTAGAGTATGGTAGCAATATGACAATTGAATGCAAATTCCAGTAGAAAAACAATTAG
ACCTGGCTGCACTAATTGTCTATTGGAAATGCAGGATGAAGAACATTATCAATTTGTCATGATGGAGAGAGACCTGAAGGTTCAGCAAGCTACACAGACAGAGGCCCGGCTGTTGAAGGACCAGCTCTCCTGGGAAA
TGCTGCACTTCAGATCACAGATGTGAAATTGCAGGATGCAGGGGTGTACCGCTGTATGATCAGCTACGGAATTACTGTGAAAGTCAATGCCCATACACAACAAATCAACCAAGAATTTGGTTGT
GGATCCAGTGCACCTCTGAACATGAACTGACATGTCAGGCTGAGGCTGAGGGTCAGGGCTGAGGGCCATCAAGTCCTGAGTGGTAAGACCAGTGACCATCAAGTCCTGAGTGGTAAGACCATCGAGGAGAAGCCTCCAAGAGAGGAGAAGCTTTCA
ATGTGACCAGCACACTGAGAATCAACACAACTAATGAGATTTCTACTGACACTGGCCATCTTATATGCCTGGTGTAGCACTGACATTCATCTTCCGTTAAGAAAAATGTGGCATCCAAGATACAAACTCAAGAAGCAAAGTGATACACATTTGGAGGAGACTA
CTTGGTAATTCTGGGAGCCATCTTATATGCCTGGTGTAGCACTGACATTCATCTTCCGTTAAGAAAAATGTGGCATCCAAGATACAAACTCAAGAAGCAAAGTGATACACATTTGGAGGAGACTA

Met R I F A V F I F Met T Y W H L L N A F T V T V P K D L Y V V E Y G S N Met T I E C K F P V E K Q L D L A A L I V Y W E Met E D K N
I I Q F V H G E E D L K V Q H S S Y R Q R A R L L K D Q L S L G N A A L Q I T D V K L Q D A G V Y R C Met I S Y G G A D Y K R I T V K
V N A P Y N K I N Q R I L V V D P V T S E H E L T C Q A E G Y P K A E V I W T S S D H Q V L S G K T T T T N S K R E E K L F N V T S T
L R I N T T T N E I F Y C T F R R L D P E E N H T A E L V I P E L P L A H P P N E R T H L V I L G A I L L C L G V A L T F I F R L R K
D T H L E E T

PDL1-3 splicing form

ATGAGGATATTTGCTGTCTTTATATTCATGACCTACTGGCATTTGCTGAACGCATTACTGTCACGGTTCCCAAGGACCTATATGTGGTAGAGTATGGTAGCAATATGACAATTGAATGCAAATTCCAGTAGAAAAACAATTAG
ACCTGGCTGCACTAATTGTCTATTGGAAATGCAGGATGAAGAACATTATCAATTTGTCATGATGGAGAGAGACCTGAAGGTTCAGCAAGCTACACAGACAGAGGCCCGGCTGTTGAAGGACCAGCTCTCCTGGGAAA
TGCTGCACTTCAGATCACAGATGTGAAATTGCAGGATGCAGGGGTGTACCGCTGATGATCAGCTACGGAATTACTGTGAAAGTCAATGCCCATACACAACAAATCAACCAAGAATTTGGTTGT
GGATCCAGTGCACCTCTGAACATGAACTGACATGTCAGGCTGAGGCTGAGGGTCAGGGCTGAGGGCCATCAAGTCCTGAGTGGAGATTAGATCCTGAGGAGAAACCATACAGCTGAATTGGTCATCCC
AGAACTACCTCTGGCACATCCTCCAAATGAAAGGACTCACTTGGGAGAATGATGGATGTGAAAAATGTGGCATCCAAGATACAAACTCAAGAAGCAAAGTGATACACATTTGGAGGAGACTAA

Met R I F A V F I F Met T Y W H L L N A F T V T V P K D L Y V V E Y G S N Met T I E C K F P V E K Q L D L A A L I V Y W E Met E D K N
I I Q F V H G E E D L K V Q H S S Y R Q R A R L L K D Q L S L G N A A L Q I T D V K L Q D A G V Y R C Met I S Y G G A D Y K R I T V K
V N A P Y N K I N Q R I L V V D P V T S E H E L T C Q A E G Y P K A E V I W T S S D H Q V L S G D Stop I L R K T I Q L N W S S Q N Y L
W H I L Q Met K G L T W E N D G C E K Met W H P R Y K L K E A K Stop Y T F G G D

Figure 1 (cont.)

L1-9 splicing form

ATGAGGATATATTGCTGTCTTTATATTCATGACCTACTGGCATTTGCTGAACGCATTTACTGTCACGGTTCCCAAGGACCTTATATGTGGTAGAGTATGGTGACAATTGACAATTCCCAGTAGAAAAACAATTAG
ACCTGGCTGCACTTCAGATCACAGATGTGAAATTGCAGGATGGAGGATAAGAACATTATTCAATTTGTGCATGGAGGAAGACCTGAAGGTTCAGCATAGTAGCACAGACAGAGGCCCGGCTGTTGAAGGACCAGCTCTCCTGGGAAA
TGCTGCACTTCAGATCACAGATGTGAAATTGCAGGATGTGCAGGGGTGTACCGGGGTGGTGCCGACTACAGGCTATGGTGGTGCCGACAAGCGAATTACTGTGAAAGTCAATGCCCATACAACAAATCAACCAAGAATTTGGTTGT
GGATCCAGTGCACCTCGAACATGAACTGACATGTCAGGCTGAGGGCTACCCAAGGCCGAAGTCATCTGACACAGCAGTGACCATCAAGTCCTGAGTGGTAAGACACCACCACCAATTCCAAGAGAGAAGAAGCTTTCA
ATGTGACCAGACACACTGAGAATCAACACAACTAATGAGATTTTCTACTGACCTTTAGGAGATTAGATCCTGAGGAAAACCATACAGCTGAATTGGTCATCCCAGAACTACCTCTGGCACATCCTCCAAATGAAAGGACTCA
CTTGGGAGAATGATGGATGTGAAAAAATGTGGCATCCAAGATACAAACTCAAAGAAGCAAAGTGATACACATTTGGAGGAGACGTAA

Met R I F A V F I F Met T Y W H L L N A F T V T V P K D L Y V V E Y G S N Met T I E C K F P V E K Q L D L A A L I V Y W E Met E D K N
I I Q F V H G E E D L K V Q H S S Y R Q R A R L L K D Q L S L G N A A L Q I T D V K L Q D A G V Y R C Met I S Y G G A D Y K R I T V K
V N A P Y N K I N Q R I L V V D P P V T S E H E L T C Q A E G Y P K A E V I P E L P L A H P P N E R T H L G E Stop W Met Stop K N V A S K I Q T Q R S
L R I N T T T N E I F Y C T F R R L D P E E N H T A E L V I P E L P L A H P P N E R T H L G E
K V I H I W R R R

PDL1-12 splicing form

ATGAGGATATATTGCTGTCTTTATATTCATGACCTACTGGCATTTGCTGAACGCATTTACTGTCACGGTTCCCAAGGACCTTATATGTGGTAGAGTATGGTAGCAATAGACAATTGACAATTGACAATTCCCAGTAGAAAACAATTAG
ACCTGGCTGCACTTCAGATCACAGATGTGAAATTGCAGGATGGAGGATAAGAACATTATTCAATTTGTGCATGGAGGAAGACCTGAAGGTTCAGCATAGTAGCACAGACAGAGGGCCCGGCTGTTGAAGGACCAGCTCTCCTGGGAAA
TGCTGCACTTCAGATCACAGATGTGAAATTGCAGGATGTGCAGGGGTGTACCGGGGTGGTGCCGACTACAGCGAATTACTGTGAAAGTCAATGCCCATACAACAAATCAACCAAGAATTTGGTTGT
GGATCCAGTGCACCTCGAACATGAACTGACATGTCAGGCTGAGGGCTACCCAAGGCCGAAGTCATCTGACACAGCAGTGACCATCAAGTCCTGAGTGGATTAGATCCTGAGGAAACCATACAGCTGAATTGGTCATCCC
AGAACTACCTCTGGCACATCCTCCAAATGAAGAAGCTCACTGGTAATTCTGGGAGCCATCTTATTATGCCTTGGTGTAGCACTGACTGACATTCATCTTCCGTTTAAGAAAAGGGAGAATGATGATGTGAAAAATGTGGCATCCA
AGATACAAACTCAAAGAAGCAAAGTGATACAcATTTGGAGGAGACGTAA

Met R I F A V F I F Met T Y W H L L N A F T V T V P K D L Y V V E Y G S N Met T I E C K F P V E K Q L D L A A L I V Y W E Met E D K N
I I Q F V H G E E D L K V Q H S S Y R Q R A R L L K D Q L P L G N A A L Q I T D V K L Q D A G V Y R C Met I S Y G G A D Y K R I T V K
V N A P Y N K I N Q R I L V V D P P V T S E H E L T C Q A E G Y P K A E V I W T S S D H Q V L S G D Stop I L R K T I Q L N W S S Q N Y L
W H I L Q Met K G L T W Stop F W E P S Y Y A L V Stop H Stop H S S S V E K G E Stop W Met Stop K N V A S K I Q T Q R S K V I H I
W R R R

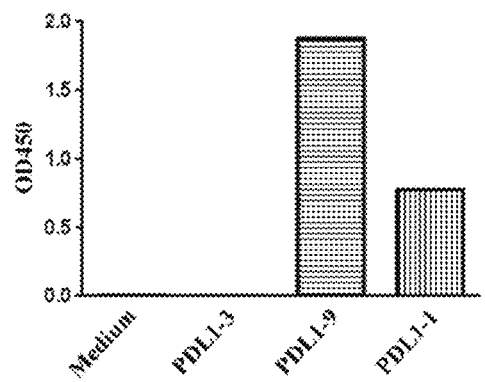
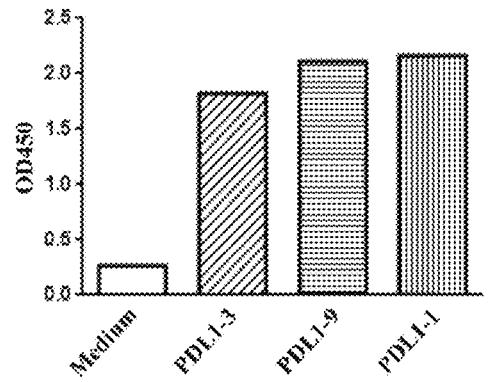
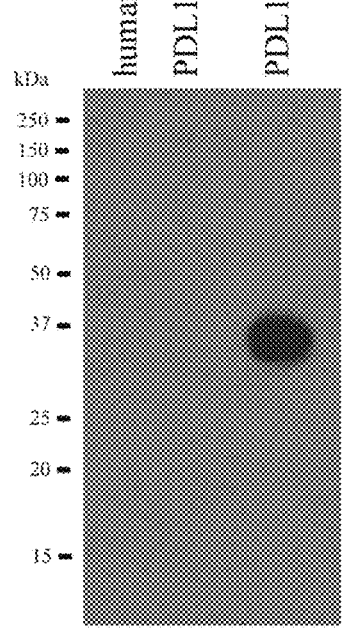
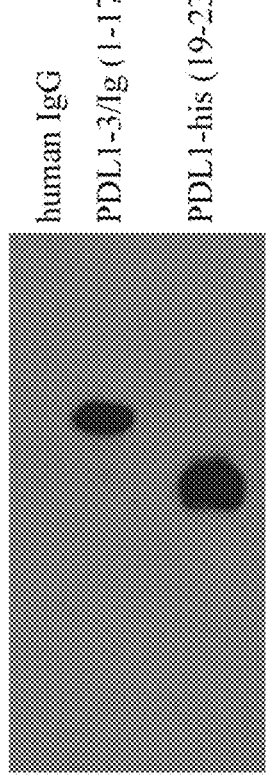
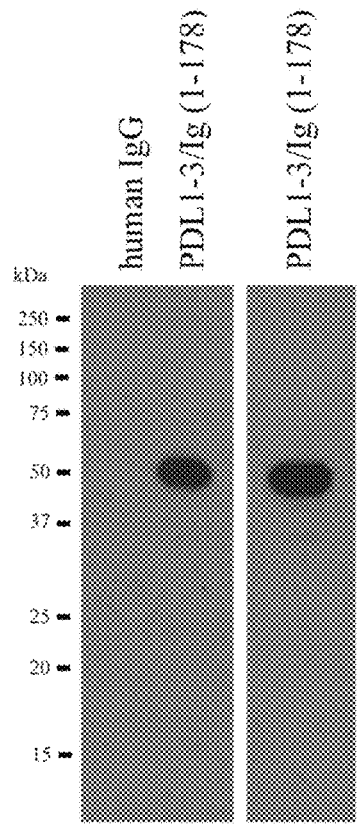

A375

K008

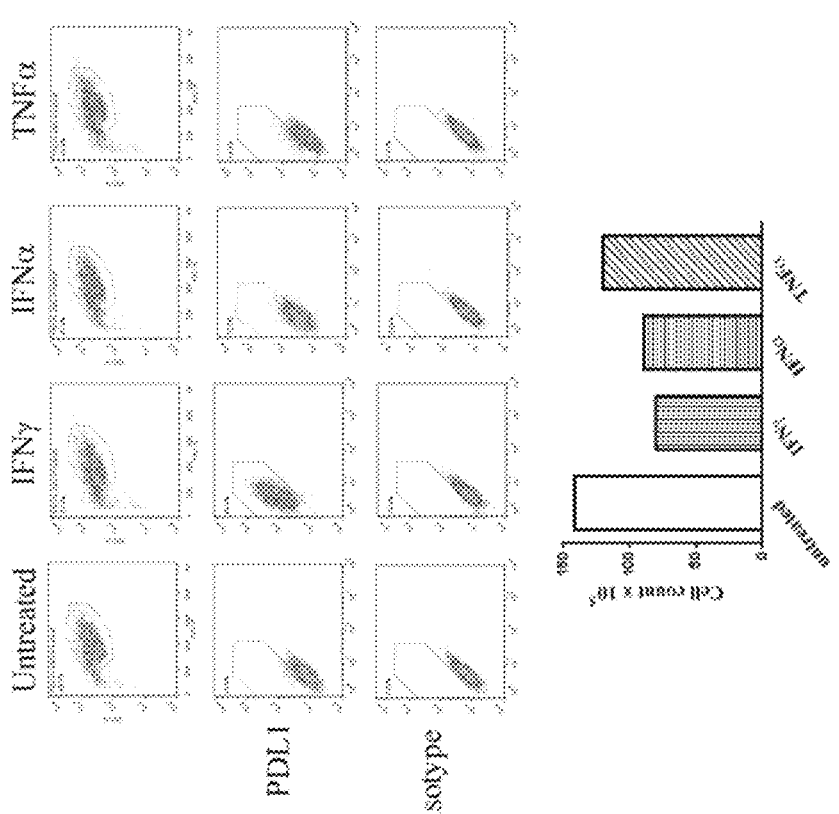
FIG. 7C
FIG. 7D
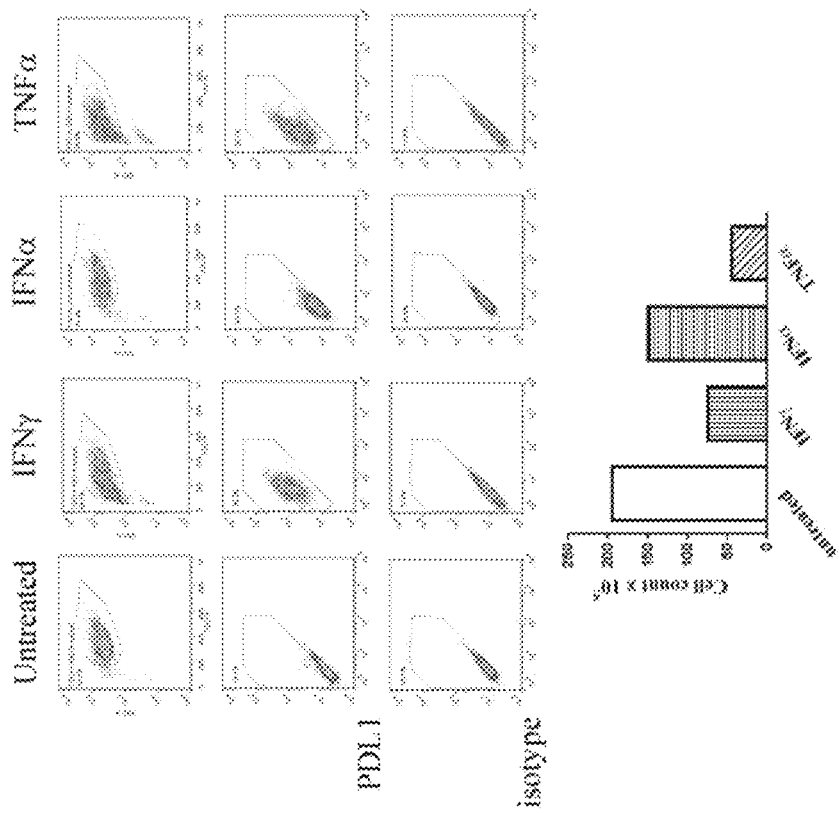

A375

A375

K028

K028

K028

K028

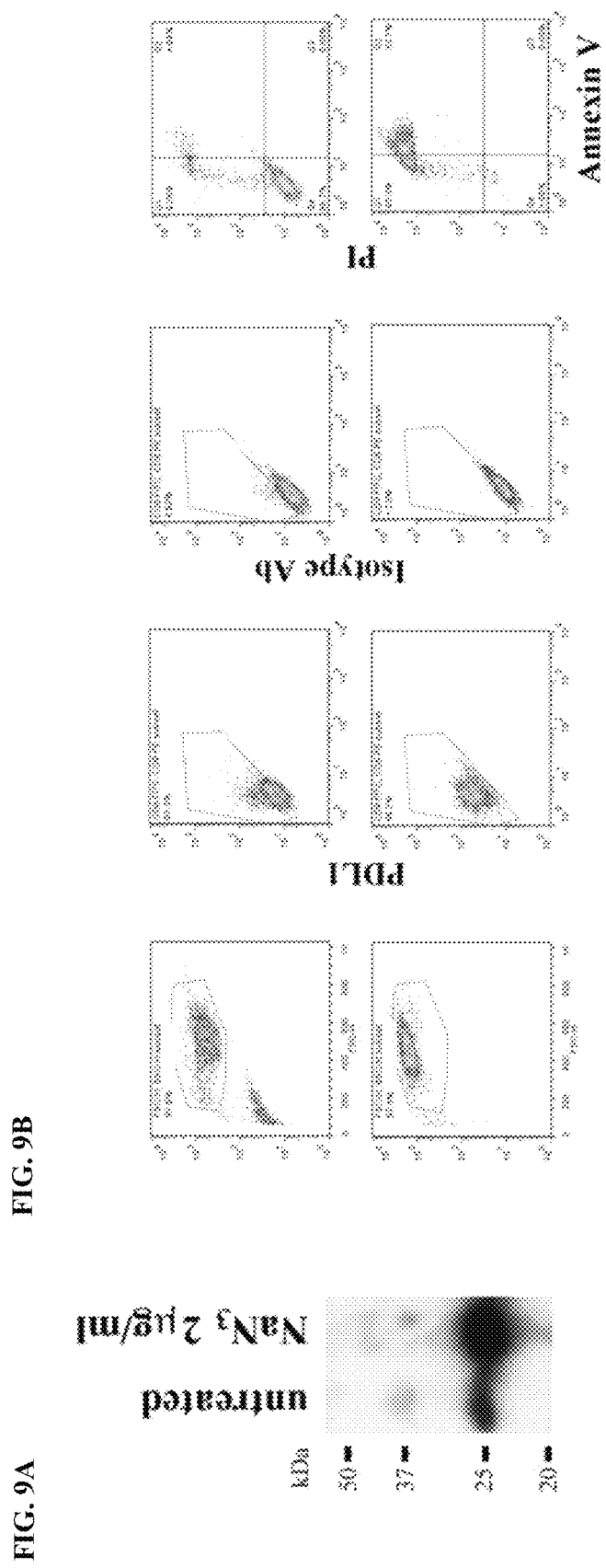

FIG. 10A
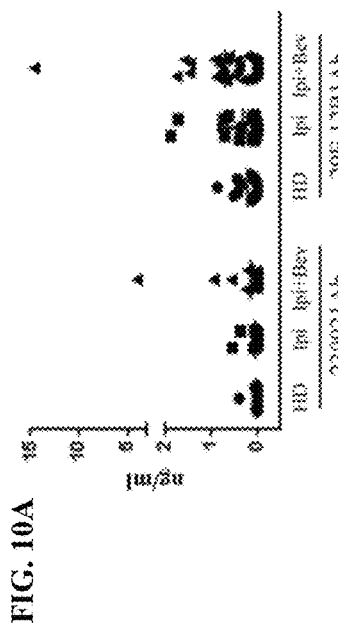
FIG. 10B
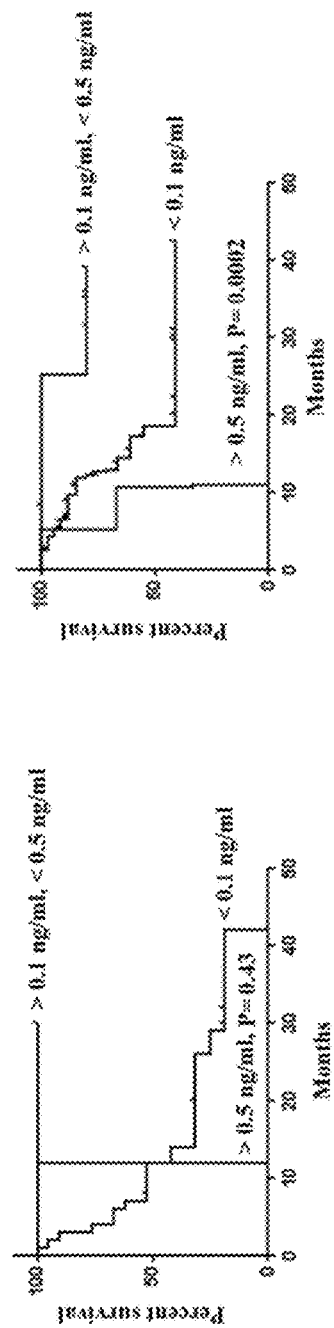
FIG. 10C
FIG. 10D
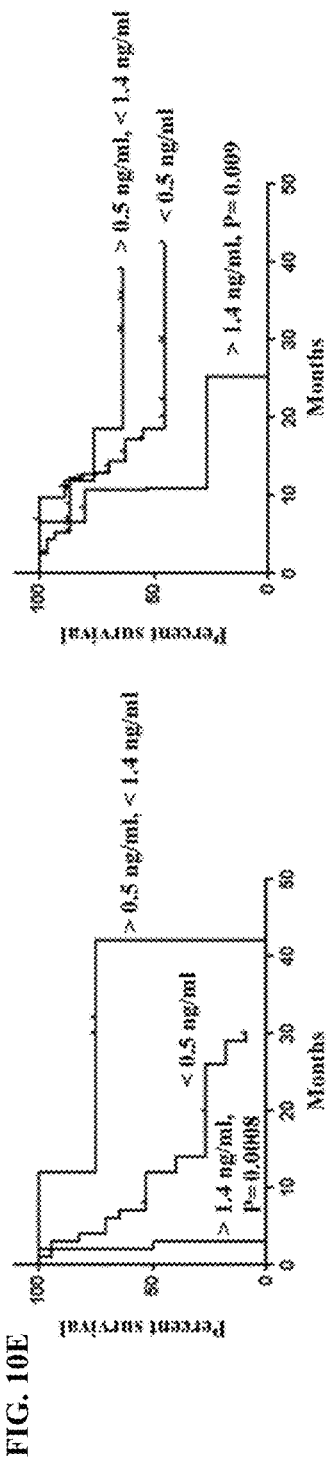
FIG. 10E
FIG. 10F

COMPOSITIONS AND METHODS FOR IDENTIFICATION, ASSESSMENT, PREVENTION, AND TREATMENT OF MELANOMA USING PD-L1 ISOFORMS

CROSS-REFERENCE TO RELATED APPLICATIONS

This application claims the benefit of U.S. Provisional Application Nos. 61/927,037, filed on 14 Jan. 2014; the entire contents of said application is incorporated herein in its entirety by this reference.

BACKGROUND OF THE INVENTION

PDL1 is a membrane bound protein. In human, it is mainly expressed on DC and monocytes (Keir et al. (2008) *Annu. Rev. Immunol.* 26:677-704). The recepter for the ligand is PD1, which is expressed on activated T cells and B cells, DC, and monocytes (Keir et al. (2008) *Annu. Rev. Immunol.* 26:677-704). During the engagement of T cells with antigen/MHC complex, interaction of PDL1 with PD1 exerts inhibitory effects on T cell activation, leading to immune suppressionb (Sharpe and Freeman (2002) *Nat. Rev. Immunol.* 2:116-126 and Keir et al. (2008) *Annu. Rev. Immunol.* 26:677-704). PDL1 expression is also present in a wide varieties of tumor cells (Thompson et al. (2004) *Proc. Natl. Acad. Sci. U.S.A.* 101:17174-17179; Ghebeh et al. (2007) *Int. J. Cancer* 121:751-758; Hamanishi et al. (2007) *Proc. Natl. Acad. Sci. U.S.A.* 104:3360-3365; and Inman et al. (2007) *Cancer* 109:1499-1505). Levels of PDL1 expression in tumor is associated with survival rate (Hino et al. (2010) *Cancer* 116:1757-1766 and Gadiot et al. (2011) *Cancer* 117:2192-2201). An increasing number of studies indicate that the disruption of the pathway increases antigen-specific T cells and decreases $T_{reg}$ suppression function (Wong et al. (2007) *Int. Immunol.* 19:1223-1234 and Wang et al. (2009) *Int. Immunol.* 21:1065-1077). An initial clinical trial with antibody PD1 blockade show promising clinical beneficial outcomes in immunotherapy on melanoma (Brahmer et al. (2010) *J. Clin. Oncol.* 28:3167-3175 and Topalian et al. (2012) *N. Engl. J. Med.* 366:2443-2454).

Recent studies indicate the existence of a soluble PDL1 (sPDL1) in human sera and culture medium of mature DC by ELISA using PDL1 specific antibodies (Chen et al. (2011) *Cytokine* 56:231-238; Frigola et al. (2011) *Clin. Cancer Res.* 17:1915-1923; and Frigola et al. (2012) *Immunol. Lett.* 142:78-82). Protein analyses show the size is around 45 kDa, confirmed by mass spectrometry. The level of PDL1 in the sera is associated with aging and aggresive renal cell carcinoma. However, the mechanism of the generation of soluble PDL1 in patient sera remains a mystery and the clinical significance of sPDL1 in cancer patients, such as melanoma patients, remains unclear. Accordingly, there is a great need to identify sPDL1 biomarkers useful for diagnostic, prognostic, and therapeutic purposes.

SUMMARY OF THE INVENTION

The present invention is based, at least in part, on the discovery of new PD-L1 isoforms, particularly those encoding soluble forms of PD-L1, that maintain the ability to transmit inhibitory signals to immune cells to thereby inhibit immune responses (e.g., T cell activation, proliferation, and cytotoxic function). Such PD-L1 isoforms and the nucleic acids that encode the PD-L1 isoforms are useful as biomarkers for the identification, assessment, prevention, and/or treatment of melanoma.

In one aspect, an isolated polypeptide selected from the group consisting of polypeptides comprising an amino acid sequence listed in Table 2, and fragments thereof, and polypeptides comprising an amino acid sequence having at least 80% identity across their full length with a nucleic acid sequence listed in Table 2, and fragments thereof, are provided. In one embodiment, the polypeptide has the ability to promote immunoinhibitory function, promote cytokine expression, inhibit T cell activation, inhibit cellular proliferation, bind to PD-1, or bind B7-1. In another embodiment, the polypeptide is expressed by melanoma cells. In still another embodiment, the polypeptide further comprises a heterologous polypeptide.

In another aspect, a pharmaceutical composition comprising a polypeptide of the present invention and a pharmaceutically acceptable agent selected from the group consisting of excipients, diluents, and carriers, is provided.

In still another aspect, an isolated nucleic acid molecule selected from the group consisting of nucleic acid molecules comprising a nucleic acid sequence listed in Table 2 and nucleic acid molecules comprising a nucleic acid sequence having at least 80% identity across their full length with a nucleic acid sequence listed in Table 2, is provided. In one embodiment, the isolated nucleic acid molecule encodes a polypeptide of the present invention.

In yet another embodiment, an isolated nucleic acid molecule comprising a nucleotide sequence which is complementary to the nucleotide sequence of a nucleic acid molecule of the present invention is provided. In one embodiment, the isolated nucleic acid molecule further comprises a nucleic acid sequence encoding a heterologous polypeptide. In another embodiment, the heterologous polypeptide is selected from the group consisting of a signal peptide, a peptide tag, a dimerization domain, an oligomerization domain, an antibody, or an antibody fragment.

In another aspect, a pharmaceutical composition comprising a nucleic acid molecule of the present invention and a pharmaceutically acceptable agent selected from the group consisting of excipients, diluents, and carriers, is provided.

In still another aspect, a vector comprising a nucleic acid molecule of the present invention is provided. In one embodiment, the vector is an expression vector.

In yet another aspect, a host cell transfected with an expression vector of the present invention.

In another aspect, a method of producing a polypeptide comprising culturing a host cell of the present invention in an appropriate culture medium to, thereby, produce the polypeptide, is provided. In one embodiment, the host cell is a bacterial cell or a eukaryotic cell. In another embodiment, the method further comprises a step of isolating the polypeptide from the medium or host cell.

In still another aspect, an antibody which selectively binds to a polypeptide of the present invention is provided. In one embodiment, the antibody is a monoclonal antibody or antigen binding portion thereof.

In yet another aspect, a non-human animal model engineered to express a polypeptide of the present invention is provided.

In another aspect, a method of prognosing melanoma progression in a subject, the method comprising: a) determining the copy number, level of expression, or level of activity of one or more biomarkers listed in Table 2 or a fragment thereof in a subject sample; b) determining the copy number, level of expression, or level of activity of the one or more biomarkers in a control sample or a predetermined reference; and c) comparing the copy number, level of expression, or level of activity of said one or more biomarkers detected in steps a) and b); wherein a significant modulation in the copy number, level of expression, or level of activity of the one or more biomarkers in the subject sample relative to the copy number, level of expression, or level of activity of the one or more biomarkers in the control sample or predetermined reference prognoses melanoma progression in the subject, is provided. In one embodiment, the subject sample and/or the control sample has not been contacted with any melanoma treatment or inhibitor of an immune checkpoint inhibitor. In another embodiment, the subject has not been administered any melanoma treatment or inhibitor of an immune checkpoint inhibitor. In still another embodiment, a significant increase in the copy number, level of expression, or level of activity of the one or more biomarkers in the subject sample relative to the copy number, level of expression, or level of activity of the one or more biomarkers in the control sample or predetermined reference indicates that subject is likely to have melanoma progression. In yet another embodiment, a significant decrease in the copy number, level of expression, or level of activity of the one or more biomarkers in the subject sample relative to the copy number, level of expression, or level of activity of the one or more biomarkers in the control sample or predetermined reference indicates that the subject is unlikely to have melanoma progression. In another embodiment, the melanoma progression is (a) shorter survival time, (b) increased metastasis, (c) increased cellular proliferation, (d) increased tumor burden, or (e) increased m-stage. In still another embodiment, the method further comprises recommending, prescribing, or administering a therapeutic agent to the subject that specifically modulates the copy number, level of expression, or level of activity of the one or more biomarkers. In yet another embodiment, the method further comprises recommending, prescribing, or administering a therapeutic agent to the subject an inhibitor of one or more immune checkpoint inhibitors.

In still another aspect, a method of prognosing subjects afflicted with melanoma according to predicted clinical outcome of treatment with one or more inhibitors of an immune checkpoint inhibitor, the method comprising: a) determining the copy number, level of expression, or level of activity of one or more biomarkers listed in Table 2 or a fragment thereof in a first subject sample at a first point in time; b) repeating step a) during at least one subsequent point in time and after administration to the subject of one or more inhibitors of an immune checkpoint inhibitor; and c) comparing the copy number, level of expression, or level of activity of said one or more biomarkers detected in steps a) and b); wherein a significant modulation in the copy number, level of expression, or level of activity of the one or more biomarkers in the first subject sample relative to at least one subsequent subject sample indicates the predicted clinical outcome of treatment with the one or more inhibitors of an immune checkpoint inhibitor, is provided. In one embodiment, the first subject sample is obtained from the subject prior to, concurrently with, or after administration of one or more inhibitors of an immune checkpoint inhibitor. In another embodiment, the subject has undergone treatment, completed treatment, and/or is in remission for the cancer between the first point in time and the subsequent point in time. In still another embodiment, the first and/or at least one subsequent sample is selected from the group consisting of ex vivo and in vivo samples. In yet another embodiment, the first and/or at least one subsequent sample is obtained from an animal model of the cancer. In another embodiment, the first and/or at least one subsequent sample is a portion of a single sample or pooled samples obtained from the subject. In still another embodiment, a significant increase in the copy number, level of expression, or level of activity of the one or more biomarkers in the subject sample relative to the copy number, level of expression, or level of activity of the one or more biomarkers in the control sample or predetermined reference indicates that subject is likely to have a beneficial outcome from treatment with the one or more inhibitors of an immune checkpoint inhibitor. In yet another embodiment, a significant decrease in the copy number, level of expression, or level of activity of the one or more biomarkers in the subject sample relative to the copy number, level of expression, or level of activity of the one or more biomarkers in the control sample or predetermined reference indicates that the subject is unlikely to have a beneficial outcome from treatment with the one or more inhibitors of an immune checkpoint inhibitor. In another embodiment, the beneficial outcome is (a) increased survival time, (b) decreased metastasis, (c) decreased cellular proliferation, (d) decreased tumor burden, or (e) increased m-stage. In still another embodiment, the method further comprises recommending, prescribing, or administering a therapeutic agent to the subject that specifically modulates the copy number, level of expression, or level of activity of the one or more biomarkers. In yet another embodiment, the method further comprises recommending, prescribing, or administering a therapeutic agent to the subject an inhibitor of one or more immune checkpoint inhibitors if the subject is likely to have a beneficial outcome from treatment with the one or more inhibitors of an immune checkpoint inhibitor.

In yet another aspect, a method of diagnosing a subject afflicted with melanoma, the method comprising: a) determining the copy number, level of expression, or level of activity of one or more biomarkers listed in Table 2 or a fragment thereof in a subject sample; b) determining the copy number, level of expression, or level of activity of the one or more biomarkers in a control sample or a predetermined reference; and c) comparing the copy number, level of expression, or level of activity of said one or more biomarkers detected in steps a) and b); wherein a significant modulation in the copy number, level of expression, or level of activity of the one or more biomarkers in the subject sample relative to the copy number, level of expression, or level of activity of the one or more biomarkers in the control sample or predetermined reference indicates melanoma, is provided. In one embodiment, the subject sample and/or the control sample has not been contacted with any melanoma treatment or inhibitor of an immune checkpoint inhibitor. In another embodiment, the subject has not been administered any melanoma treatment or inhibitor of an immune checkpoint inhibitor. In still another embodiment, a significant increase in the copy number, level of expression, or level of activity of the one or more biomarkers in the subject sample relative to the copy number, level of expression, or level of activity of the one or more biomarkers in the control sample or predetermined reference indicates that the subject likely has melanoma. In yet another embodiment, a significant decrease in the copy number, level of expression, or level of activity of the one or more biomarkers in the subject sample relative to the copy number, level of expression, or level of activity of the one or more biomarkers in the control sample or predetermined reference indicates that the subject is not likely to have melanoma. In another embodiment, the melanoma progression is (a) shorter survival time, (b) increased metastasis, (c) increased cellular proliferation, (d) increased tumor burden, or (e) increased m-stage. In still another embodiment, the method further comprises recommending, prescribing, or administering a therapeutic agent to the subject that specifically modulates the copy number, level of expression, or level of activity of the one or more biomarkers. In yet another embodiment, the method further comprises recommending, prescribing, or administering a therapeutic agent to the subject one or more Braf inhibitors, MEK inhibitors, and/or inhibitors of an immune checkpoint inhibitor.

In another aspect, a method of assessing the efficacy of an agent for treating melanoma in a subject, comprising: a) determining in a first subject sample contacted with the agent or maintained in the presence of the agent the copy number, level of expression, or level of activity of one or more biomarkers listed in Table 2; b) determining the copy number, level of expression, or level of activity of one or more biomarkers listed in Table 2 in at least one subsequent subject sample maintained in the absence of the test compound; and c) comparing the copy number, level of expression, or level of activity of one or more biomarkers listed in Table 2 from steps a) and b), wherein a significantly increased copy number, level of expression, or level of activity of the one or more biomarkers listed in Table 1 in the first subject sample relative to at least one subsequent subject sample, indicates that the agent treats the melanoma in the subject, is provided.

In still another aspect, a method of assessing the efficacy of an agent for treating melanoma in a subject, comprising: a) determining in a first subject sample the agent the copy number, level of expression, or level of activity of one or more biomarkers listed in Table 2; b) repeating step a) during at least one subsequent point in time after administration of the agent; and c) comparing the copy number, level of expression, or level of activity of the one or more biomarkers listed in Table 2 determined in steps a) and b), wherein a significantly increased copy number, level of expression, or level of activity of the at least one biomarker listed in Table 1 in the first subject sample relative to the at least one subsequent subject sample, indicates that the agent treats the cancer in the subject, is provided. In one embodiment, the subject has undergone treatment, completed treatment, and/or is in remission for the cancer in between the first point in time and the subsequent point in time. In another embodiment, the first and/or at least one subsequent sample is selected from the group consisting of ex vivo and in vivo samples. In still another embodiment, the first and/or at least one subsequent sample is obtained from an animal model of the cancer. In yet another embodiment, the first and/or at least one subsequent sample is a portion of a single sample or pooled samples obtained from the subject.

In yet another aspect, a cell-based assay for screening for cytotoxic or cytostatic agents comprising contacting a melanoma cell with a test agent, and determining the ability of the test agent to decrease the amount or activity of one or more biomarkers listed in Table 2, is provided. In one embodiment, the step of contacting occurs in vivo, ex vivo, or in vitro.

In another aspect, a cell-based assay for screening for agents that have a cytotoxic or cytostatic effect on a melanoma cell comprising, contacting the melanoma cell with a test agent, and determining the ability of the test agent to decrease the amount or activity of one or more biomarkers listed in Table 2, is provided. In one embodiment, the step of contacting occurs in vivo, ex vivo, or in vitro.

In still another aspect, a method for preventing or treating melanoma, comprising contacting a melanoma cell with an agent that inhibits the expression and/or activity of one or more polypeptides of the present invention or one or more nucleic acids of the present invention to thereby modulate the metabolic response, is provided. In one embodiment, the agent is selected from the group consisting of an antisense nucleic acid molecule, an RNA interference molecule, a blocking antibody, and a non-activating form of the biomarker polypeptide or fragment thereof. In still another embodiment, the method further comprises contacting the cell with an additional agent that prevents or treats melanoma. In yet another embodiment, the step of contacting occurs in vivo. In another embodiment, the step of contacting occurs in vitro.

In yet another aspect, a method for preventing or treating melanoma in a subject, comprising administering to the subject an agent that inhibits the expression and/or activity of one or more polypeptides of the present invention or one or more nucleic acids of the present invention in the subject, thereby preventing or treating the metabolic disorder in the subject, is provided. In one embodiment, the agent is selected from the group consisting of an antisense nucleic acid molecule, an RNA interference molecule, a blocking antibody, and a non-activating form of the biomarker polypeptide or fragment thereof. In another embodiment, the agent is administered by intravenous or subcutaneous injection. In still another embodiment, the agent is administered in a pharmaceutically acceptable formulation.

In another aspect, a method of identifying a binding partner to a polypeptide of the present invention or biologically active portion thereof comprising: a) contacting the polypeptide or biologically active portion thereof, or a cell expressing the polypeptide or biologically active portion thereof, with a test compound; and b) determining whether the polypeptide or biologically active portion thereof binds to the test compound, is provided.

In still another aspect, a cell-based assay for screening for compounds which modulate the expression and/or activity of a polypeptide of the present invention or biologically active portion thereof comprising contacting a cell expressing the polypeptide or biologically active portion thereof with a test compound and determining the ability of the test compound to modulate the expression and/or activity of the polypeptide or biologically active portion thereof, is provided.

In yet another aspect, a method for identifying a compound which modulates the expression and/or activity of a polypeptide of the present invention or biologically active portion thereof comprising: a) contacting the polypeptide or biologically active portion thereof with a test compound; and b) determining the effect of the test compound on the expression and/or activity of the polypeptide or biologically active portion thereof to thereby identify a compound which modulates the activity of the polypeptide or biologically active portion thereof, is provided.

Many embodiments are contemplated that are applicable to any method or assay of the present invention. In one embodiment, the control sample is determined from a cancerous or non-cancerous sample from either the patient or a member of the same species to which the patient belongs. In another embodiment, the control sample comprises cancer cells known to be responsive or non-responsive to the anti-immune checkpoint inhibitor therapy. In still another embodiment, the subject sample is selected from the group consisting of whole blood, serum, and plasma. In yet another embodiment, the copy number is assessed by microarray, quantitative PCR (qPCR), high-throughput sequencing, comparative genomic hybridization (CGH), or fluorescent in situ hybridization (FISH). In another embodiment, the amount of the at least one biomarker listed in Table 2 is detected using a reagent which specifically binds with the protein. In still another embodiment, the reagent is selected from the group consisting of an antibody, an antibody derivative, and an antibody fragment. In yet another embodiment, the at least one biomarker listed in Table 2 is assessed by detecting the presence in the sample of a transcribed polynucleotide or portion thereof. In another embodiment, the transcribed polynucleotide is an mRNA or a cDNA. In still another embodiment, the step of detecting further comprises amplifying the transcribed polynucleotide. In yet another embodiment, the transcribed polynucleotide is detected by identifying a nucleic acid that anneals with the biomarker nucleic acid, or a portion thereof, under stringent hybridization conditions. In another embodiment, the anti-immune checkpoint inhibitor therapy is selected from the group consisting of inhibitors of PD-L1, PD-1, CTLA-4, and combinations thereof. In still another embodiment, the anti-immune checkpoint inhibitor therapy is selected from the group consisting of anti-PD-L1 antibodies, anti-PD-1 antibodies, anti-CTLA-4 antibodies, and combinations thereof. In yet another embodiment, the responsiveness to anti-immune checkpoint inhibitor therapy is measured by at least one criteria selected from the group consisting of clinical benefit rate, survival until mortality, pathological complete response, semi-quantitative measures of pathologic response, clinical complete remission, clinical partial remission, clinical stable disease, recurrence-free survival, metastasis free survival, disease free survival, circulating tumor cell decrease, circulating marker response, and RECIST criteria. In another embodiment, the melanoma is a BRAF inhibitor-resistant melanoma or a MEK inhibitor-resistant melanoma. In still another embodiment, the subject does not have renal cell carcinoma, head and neck cancer, and/or lung cancer. In yet another embodiment, the subject is a mammal. In another embodiment, the mammal is an animal model of melanoma. In still another embodiment, the mammal is a human.

BRIEF DESCRIPTION OF FIGURES

FIG. 1 shows novel variants of human PDL1. A PDL1 library derived from M34 cells, a melanoma cell line, was generated by RT-PCR and cloned into a TA TOPO vector. Four PDL1 variants were identified by sequencing studies.

FIG. 2A shows that the full length of PDL1 consists of six exons. A membrane domain is located in exon 4. Splicing regions of PDL1-1, 3, 9, 12 are indicated with bracket symbols. FIG. 2B shows splicing variants of PDL1 in melanoma cell lines. Variants of PDL1-1, 3/12, 9 were examined by RT-PCR.

FIG. 3A-3B show the results of the A375 cell line transduced by lentiviral vectors of PDL1-1, 3, 9 variants. Soluble PDL1 variants from culture medium were examined by immunoprecipitation, SDS-PAGE and Western blot assay. Samples were normalized by cell numbers. The left and right panels shown in FIG. 3B are from the same blot. Individual culture medium was from aproximately $6\times10^6$ cells. FIG. 3C shows the effects of sPDL1 on the proliferation of human $CD4^+$ and $CD8^+$ T cells. Human $CD4^+$ and $CD8^+$ T cells were stimulated with 5 µg/ml anti CD3 antibody in the absence or presence of 10 µg/ml PDL1-3/Ig. Proliferation of the T cells were examined by $^3H$ uptake assay. Human IgG was used as a control. FIG. 3D shows the results of secretion of soluble PDL1 (sPDL1) by Braf inhibitor resistant melanoma cell line. Soluble PDL1 from culture medium of either parental or plx resistant A375 and M34 cell lines were analyzed by immunoprecipitation, SDS-PAGE and Western blot assay. Samples were normalized by cell numbers. The culture medium were from aproximately $8\times10^7$ cells of A375 and $1\times10^7$ cells of M34, respectively. FIG. 3E-FIG. 3H show the results of melanoma cell lines cultured in the absence and presence of 200 U/ml IFNγ, or 2000 U/ml IFNα, or 10 ng/ml TNFα. Soluble PDL1s in culture medium were analyzed by immunoprecipitation, SDS-PAGE and Western blot assay. Samples were normalized by cell numbers.

FIG. 4A shows a schematic diagram of primers for the detection of PDL1 variants. The primers were designed to contain two splicing ends and were specific for PDL1-1, 3/12, and 9 variants. FIG. 4B shows the generation of recombinant PDL1-3/Ig fusion protein. The recombinant PDL1-3/Ig fusion protein was analyzed by SDS-PAGE, Coomassie blue staining (left panel), and Western blot (right panel). FIG. 4C-FIG. 4D show the development of an ELISA for soluble PDL1. The detection specificity for sPDL1 were shown with either 29E.12B1 or 230021 antibody.

FIG. 5A-FIG. 5E show that PDL1 variants are differentially recognized by 29E.12B1 and 230021 antibodies. FIG. 5A shows the results of soluble PDL1 variants detected by ELISA with a 230021 antibody. FIG. 5B shows the results of soluble PDL1 variants detected by ELISA with a 29E.12B1 antibody. FIG. 5C shows that PDL1 (amino acid 19-239) represents long variants, and it was detected by SDS-PAGE and Western blotting assay with a 230021 antibody, whereas PDL1-3, the shortest variant could not be detected. FIG. 5D shows the results of the blot shown in FIG. 5C after stripping and reblotting with a 29E.1D5 antibody. FIG. 5E shows theat PDL1-3 was recognized by Western blotting assay with either a 29E.12B1 antibody (left panel) or 29E.1D5 antibody (right panel).

FIG. 6A and FIG. 6B show the results of soluble PDL1 in sera and plasma of the same patients examined by ELISA with either 230021 or 29E.12B1 antibodies. FIG. 6C shows the results of overexpression of PDL1-1 variant in A375 cells. Expression of membrane PDL1 were analyzed by flow cytometry.

FIG. 7A-FIG. 7D show the effects of cytokines on expression of membrane PDL1 and cell proliferation in melanoma cell lines. Melanoma cell lines were treated with either 2000 U/ml IFNα, or 200 U/ml IFNγ, or 10 ng/ml TNFα for 2 days. Expression of membrane PDL1 on the cells were analyzed by flow cytometry and the cell numbers were counted. Results are shown for cytokine-treated A375 cells (FIG. 7A), cytokine-treated K008 cells (FIG. 7B), cytokine-treated K028 cells (FIG. 7C), and cytokine-treated UACC257 cells (FIG. 7D).

FIG. 9A-FIG. 9B show the expression of membrane PDL1 and secretion of sPDL1 in response to sodium azide. Melanoma A375 cells were treated with sodium azide (NaN$_3$), a toxic agent, for 2 days. Expression of membrane PDL1 on the cells were analyzed by flow cytometry and secretion of sPDL1 was examined by immunoprecipitation, SDS-PAGE, and Western blotting assays.

FIG. 10A-FIG. 10F show the results of soluble PDL1 in sera of healthy donors and meanloma patients. FIG. 10A shows the levels of soluble PDL1 in sera of healthy donors and melanoma patients. FIG. 10B shows the results of soluble PDL1 variants in patient sera examined by SDS-PAGE and Western blotting assays. FIG. 10C-FIG. 10D show the associations between levels of constitutive sPDL1$^L$ in patient sera and patient survival in ipilimumab- or ipilimumab plus bevacizumab-treated groups, respectively. FIG. 10E-FIG. 10F show the associations between levels of constitutive sPDL1$^{all}$ in patient sera and patient survival in ipilimumab- or ipilimumab plus bevacizumab-treated groups, respectively.

FIG. 11A shows kinetic changes of sPDL1 and cytokines in the sera of patients, who had ≥0.5 ng/ml constitutive sPDL1$^L$ or ≥1.4 ng/ml constitutive sPDL1$^{all}$ after ipilimumab plus bevacizumab treatment. FIG. 11B shows kinetic changes of sPDL1 and cytokines in the sera of patients, who had long term increases of inducible sPDL1 after ipilimumab plus bevacizumab treatment.

DETAILED DESCRIPTION OF THE INVENTION

Figure 2A:
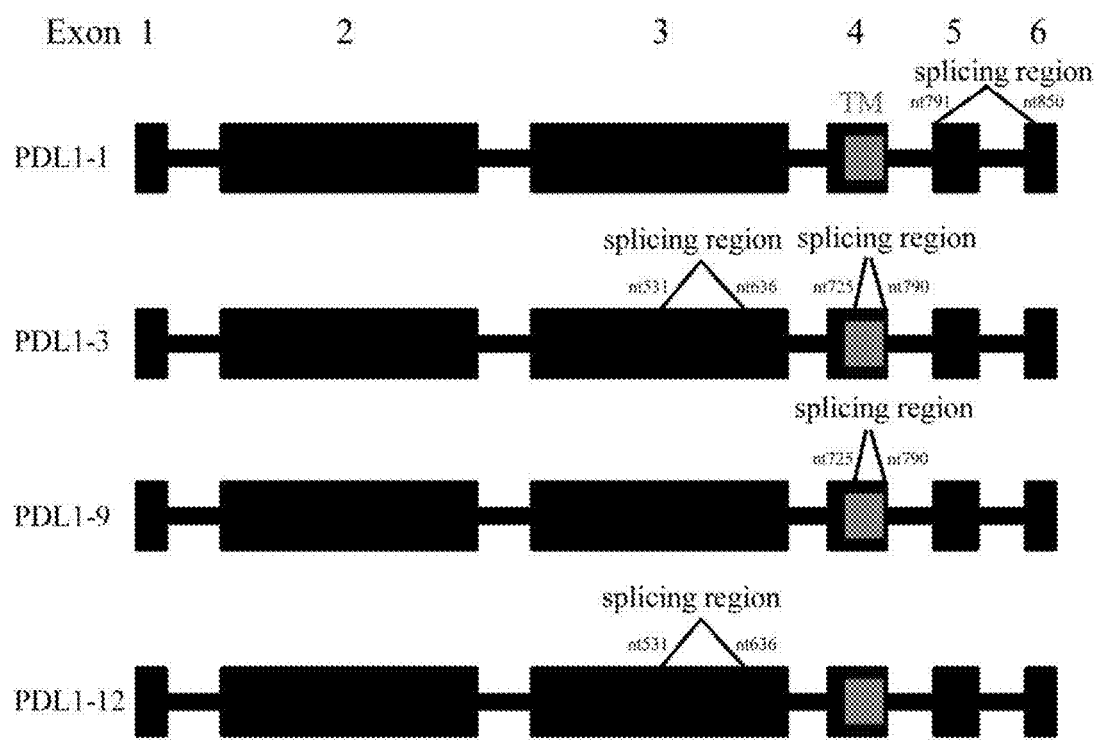
FIG. 2A-FIG. 2B show a schematic diagram of splicing variants of PDL1.

The present invention is based, at least in part, on the discovery of PD-L1 isoforms and the use thereof in distinguishing and predicting the clinical outcome of melanoma to therapeutic regimens, particularly to inhibitors of immune checkpoint inhibitors such as PD-L1, CTLA-4, and PD-1. Thus, agents such as miRNAs, miRNA analogues, small molecules, RNA interference, aptamer, peptides, peptidomimetics, antibodies that specifically bind to one or more biomarkers of the invention (e.g., biomarkers listed in Table 2) and fragments thereof can be used to identify, diagnose, prognose, assess, prevent, and treat melanoma.

I. Definitions

The articles "a" and "an" are used herein to refer to one or to more than one (i.e., to at least one) of the grammatical object of the article. By way of example, "an element" means one element or more than one element.

The term "altered amount" of a marker or "altered level" of a marker refers to increased or decreased copy number of the marker and/or increased or decreased expression level of a particular marker gene or genes in a cancer sample, as compared to the expression level or copy number of the marker in a control sample. The term "altered amount" of a marker also includes an increased or decreased protein level of a marker in a sample, e.g., a cancer sample, as compared to the protein level of the marker in a normal, control sample.

The "amount" of a marker, e.g., expression or copy number of a marker, or protein level of a marker, in a subject is "significantly" higher or lower than the normal amount of a marker, if the amount of the marker is greater or less, respectively, than the normal level by an amount greater than the standard error of the assay employed to assess amount, and preferably at least twice, and more preferably three, four, five, ten or more times that amount. Alternately, the amount of the marker in the subject can be considered "significantly" higher or lower than the normal amount if the amount is at least about two, and preferably at least about three, four, or five times, higher or lower, respectively, than the normal amount of the marker. In some embodiments, the amount of the marker in the subject can be considered "significantly" higher or lower than the normal amount if the amount is 10%, 15%, 20%, 25%, 30%, 35%, 40%, 45%, 50% or more, higher or lower, respectively, than the normal amount of the marker.

The term "altered level of expression" of a marker refers to an expression level or copy number of a marker in a test sample e.g., a sample derived from a subject suffering from cancer, that is greater or less than the standard error of the assay employed to assess expression or copy number, and is preferably at least twice, and more preferably three, four, five or ten or more times the expression level or copy number of the marker or chromosomal region in a control sample (e.g., sample from a healthy subject not having the associated disease) and preferably, the average expression level or copy number of the marker or chromosomal region in several control samples. The altered level of expression is greater or less than the standard error of the assay employed to assess expression or copy number, and is preferably at least twice, and more preferably three, four, five or ten or more times the expression level or copy number of the marker in a control sample (e.g., sample from a healthy subject not having the associated disease) and preferably, the average expression level or copy number of the marker in several control samples.

The term "altered activity" of a marker refers to an activity of a marker which is increased or decreased in a disease state, e.g., in a cancer sample, as compared to the activity of the marker in a normal, control sample. Altered activity of a marker may be the result of, for example, altered expression of the marker, altered protein level of the marker, altered structure of the marker, or, e.g., an altered interaction with other proteins involved in the same or different pathway as the marker, or altered interaction with transcriptional activators or inhibitors. For example, the term "PD-1 ligand (e.g., soluble PD-L1) activity" includes the ability of a PD-1 ligand (e.g., soluble PD-L1) polypeptide to bind its natural receptor(s) (e.g., PD-1 or B7-1), the ability to modulate immune cell costimulatory or inhibitory signals, and the ability to modulate the immune response. With respect to PD-1, the term "activity" includes the ability of a PD-1 polypeptide to modulate an inhibitory signal in an activated immune cell, e.g., by engaging a natural PD-1 ligand (e.g., soluble PD-L1) on an antigen presenting cell. PD-1 transmits an inhibitory signal to an immune cell in a manner similar to CTLA-4. Modulation of an inhibitory signal in an immune cell results in modulation of proliferation of, and/or cytokine secretion by, an immune cell. Thus, the term "PD-L1 activity" includes the ability of a PD-L1 polypeptide to bind its natural ligand(s), the ability to modulate immune cell costimulatory and/or inhibitory signals, and/or the ability to modulate the immune response.

The term "altered structure" of a marker refers to the presence of mutations or allelic variants within the marker gene or maker protein, e.g., mutations which affect expression or activity of the marker, as compared to the normal or wild-type gene or protein. For example, mutations include, but are not limited to substitutions, deletions, or addition mutations. Mutations may be present in the coding or non-coding region of the marker.

The term "altered cellular localization" of a marker refers to the mislocalization of the marker within a cell relative to the normal localization within the cell e.g., within a healthy and/or wild-type cell. An indication of normal localization of the marker can be determined through an analysis of cellular localization motifs known in the field that are harbored by marker polypeptides. For example, full-length PD-L1 is a membrane-bound protein such that altered cellular localization occurs when PD-L1 isoforms are secreted as soluble protein.

Unless otherwise specified herein, the terms "antibody" and "antibodies" broadly encompass naturally-occurring forms of antibodies (e.g., IgG, IgA, IgM, IgE) and recombinant antibodies such as single-chain antibodies, chimeric and humanized antibodies and multi-specific antibodies, as well as fragments and derivatives of all of the foregoing, which fragments and derivatives have at least an antigenic binding site. Antibody derivatives may comprise a protein or chemical moiety conjugated to an antibody.

The term "antibody" as used herein also includes an "antigen-binding portion" of an antibody (or simply "antibody portion"). The term "antigen-binding portion", as used herein, refers to one or more fragments of an antibody that retain the ability to specifically bind to an antigen. It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent polypeptides (known as single chain Fv (scFv); see e.g., Bird et al. (1988) *Science* 242:423-426; and Huston et al. (1988) *Proc. Natl. Acad. Sci. USA* 85:5879-5883; and Osbourn et al. 1998, Nature Biotechnology 16: 778). Such single chain antibodies are also intended to be encompassed within the term "antigen-binding portion" of an antibody. Any VH and VL sequences of specific scFv can be linked to human immunoglobulin constant region cDNA or genomic sequences, in order to generate expression vectors encoding complete IgG polypeptides or other isotypes. VH and VL can also be used in the generation of Fab, Fv or other fragments of immunoglobulins using either protein chemistry or recombinant DNA technology. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., et al. (1994) *Structure* 2:1121-1123).

Still further, an antibody or antigen-binding portion thereof may be part of larger immunoadhesion polypeptides, formed by covalent or noncovalent association of the antibody or antibody portion with one or more other proteins or peptides. Examples of such immunoadhesion polypeptides include use of the streptavidin core region to make a tetrameric scFv polypeptide (Kipriyanov, S. M., et al. (1995) *Human Antibodies and Hybridomas* 6:93-101) and use of a cysteine residue, a marker peptide and a C-terminal polyhistidine tag to make bivalent and biotinylated scFv polypeptides (Kipriyanov, S. M., et al. (1994) *Mol. Immunol.* 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion polypeptides can be obtained using standard recombinant DNA techniques, as described herein.

Antibodies may be polyclonal or monoclonal; xenogeneic, allogeneic, or syngeneic; or modified forms thereof (e.g., humanized, chimeric, etc.). Antibodies may also be fully human. The terms "monoclonal antibodies" and "monoclonal antibody composition", as used herein, refer to a population of antibody polypeptides that contain only one species of an antigen binding site capable of immunoreacting with a particular epitope of an antigen, whereas the term "polyclonal antibodies" and "polyclonal antibody composition" refer to a population of antibody polypeptides that contain multiple species of antigen binding sites capable of interacting with a particular antigen. A monoclonal antibody composition typically displays a single binding affinity for a particular antigen with which it immunoreacts.

The term "antisense" nucleic acid polypeptide comprises a nucleotide sequence which is complementary to a "sense" nucleic acid encoding a protein, e.g., complementary to the coding strand of a double-stranded cDNA polypeptide, complementary to an mRNA sequence or complementary to the coding strand of a gene. Accordingly, an antisense nucleic acid polypeptide can hydrogen bond to a sense nucleic acid polypeptide.

The term "body fluid" refers to fluids that are excreted or secreted from the body as well as fluids that are normally not (e.g., amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, peritoneal fluid, pus, saliva, sebum, semen, serum, sweat, synovial fluid, tears, urine, vaginal lubrication, vitreous humor, vomit). In a preferred embodiment, body fluids are restricted to blood-related fluids, including whole blood, serum, plasma, and the like.

The terms "cancer" or "tumor" or "hyperproliferative disorder" refer to the presence of cells possessing characteristics typical of cancer-causing cells, such as uncontrolled proliferation, immortality, metastatic potential, rapid growth and proliferation rate, and certain characteristic morphological features. Cancer cells are often in the form of a solid tumor, but such cells may exist alone within an animal, or may be a non-tumorigenic cancer cell, such as a leukemia cell. Cancers include, but are not limited to, B cell cancer, e.g., multiple myeloma, Waldenström's macroglobulinemia, the heavy chain diseases, such as, for example, alpha chain disease, gamma chain disease, and mu chain disease, benign monoclonal gammopathy, and immunocytic amyloidosis, melanomas, breast cancer, lung cancer, bronchus cancer, colorectal cancer, prostate cancer, pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematological tissues, and the like. Other non-limiting examples of types of cancers applicable to the methods encompassed by the present invention include human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, liver cancer, choriocarcinoma, seminoma, embryonal carcinoma, Wilms' tumor, cervical cancer, bone cancer, brain tumor, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease. In some embodiments, the cancer whose phenotype is determined by the method of the invention is an epithelial cancer such as, but not limited to, bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In other embodiments, the cancer is breast cancer, prostate cancer, lung cancer, or colon cancer. In still other embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers may be characterized in various other ways including, but not limited to, serous, endometrioid, mucinous, clear cell, brenner, or undifferentiated. In some embodiments, the present invention is used in the treatment, diagnosis, and/or prognosis of melanoma and its subtypes.

The term "classifying" includes "to associate" or "to categorize" a sample with a disease state. In certain instances, "classifying" is based on statistical evidence, empirical evidence, or both. In certain embodiments, the methods and systems of classifying use of a so-called training set of samples having known disease states. Once established, the training data set serves as a basis, model, or template against which the features of an unknown sample are compared, in order to classify the unknown disease state of the sample. In certain instances, classifying the sample is akin to diagnosing the disease state of the sample. In certain other instances, classifying the sample is akin to differentiating the disease state of the sample from another disease state.

The term "coding region" refers to regions of a nucleotide sequence comprising codons which are translated into amino acid residues, whereas the term "noncoding region" refers to regions of a nucleotide sequence that are not translated into amino acids (e.g., 5' and 3' untranslated regions).

The term "complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

The term "control" refers to any reference standard suitable to provide a comparison to the expression products in the test sample. In one embodiment, the control comprises obtaining a "control sample" from which expression product levels are detected and compared to the expression product levels from the test sample. Such a control sample may comprise any suitable sample, including but not limited to a sample from a control cancer patient (can be stored sample or previous sample measurement) with a known outcome; normal tissue or cells isolated from a subject, such as a normal patient or the cancer patient, cultured primary cells/tissues isolated from a subject such as a normal subject or the cancer patient, adjacent normal cells/tissues obtained from the same organ or body location of the cancer patient, a tissue or cell sample isolated from a normal subject, or a primary cells/tissues obtained from a depository. In another preferred embodiment, the control may comprise a reference standard expression product level from any suitable source, including but not limited to housekeeping genes, an expression product level range from normal tissue (or other previously analyzed control sample), a previously determined expression product level range within a test sample from a group of patients, or a set of patients with a certain outcome (for example, survival for one, two, three, four years, etc.) or receiving a certain treatment. It will be understood by those of skill in the art that such control samples and reference standard expression product levels can be used in combination as controls in the methods of the present invention. In one embodiment, the control may comprise normal or non-cancerous cell/tissue sample. In another preferred embodiment, the control may comprise an expression level for a set of patients, such as a set of cancer patients, or for a set of cancer patients receiving a certain treatment, or for a set of patients with one outcome versus another outcome. In the former case, the specific expression product level of each patient can be assigned to a percentile level of expression, or expressed as either higher or lower than the mean or average of the reference standard expression level. In another preferred embodiment, the control may comprise normal cells, cells from patients treated with combination chemotherapy and cells from patients having benign cancer. In another embodiment, the control may also comprise a measured value for example, average level of expression of a particular gene in a population compared to the level of expression of a housekeeping gene in the same population. Such a population may comprise normal subjects, cancer patients who have not undergone any treatment (i.e., treatment naive), cancer patients undergoing therapy, or patients having benign cancer. In another preferred embodiment, the control comprises a ratio transformation of expression product levels, including but not limited to determining a ratio of expression product levels of two genes in the test sample and comparing it to any suitable ratio of the same two genes in a reference standard; determining expression product levels of the two or more genes in the test sample and determining a difference in expression product levels in any suitable control; and determining expression product levels of the two or more genes in the test sample, normalizing their expression to expression of housekeeping genes in the test sample, and comparing to any suitable control. In particularly preferred embodiments, the control comprises a control sample which is of the same lineage and/or type as the test sample. In another embodiment, the control may comprise expression product levels grouped as percentiles within or based on a set of patient samples, such as all patients with cancer. In one embodiment a control expression product level is established wherein higher or lower levels of expression product relative to, for instance, a particular percentile, are used as the basis for predicting outcome. In another preferred embodiment, a control expression product level is established using expression product levels from cancer control patients with a known outcome, and the expression product levels from the test sample are compared to the control expression product level as the basis for predicting outcome. As demonstrated by the data below, the methods of the invention are not limited to use of a specific cut-point in comparing the level of expression product in the test sample to the control. In one embodiment, a pre-determined level of expression is used, such as greater than 0.25 ng/mL, 0.30 ng/mL, 0.35 ng/mL, 0.40 ng/mL, 0.45 ng/mL, 0.50 ng/mL, 0.55 ng/mL, 0.60 ng/mL of a serum protein or other biomarker under evaluation.

As used herein, the term "costimulate" with reference to activated immune cells includes the ability of a costimulatory molecule to provide a second, non-activating receptor mediated signal (a "costimulatory signal") that induces proliferation or effector function. For example, a costimulatory signal can result in cytokine secretion, e.g., in a T cell that has received a T cell-receptor-mediated signal. Immune cells that have received a cell-receptor mediated signal, e.g., via an activating receptor are referred to herein as "activated immune cells."

The term "diagnosing cancer" includes the use of the methods, systems, and code of the present invention to determine the presence or absence of a cancer or subtype thereof in an individual. The term also includes methods, systems, and code for assessing the level of disease activity in an individual.

As used herein, the term "diagnostic marker" includes markers described herein which are useful in the diagnosis of cancer, e.g., over- or under-activity, emergence, expression, growth, remission, recurrence or resistance of tumors before, during or after therapy. The predictive functions of the marker may be confirmed by, e.g., (1) increased or decreased copy number (e.g., by FISH, FISH plus SKY, single-molecule sequencing, e.g., as described in the art at least at J. Biotechnol., 86:289-301, or qPCR), overexpression or underexpression (e.g., by ISH, Northern Blot, or qPCR), increased or decreased protein level (e.g., by IHC), or increased or decreased activity (determined by, for example, modulation of a pathway in which the marker is involved), e.g., in more than about 5%, 6%, 7%, 8%, 9%, 10%, 11%, 12%, 13%, 14%, 15%, 20%, 25%, or more of human cancers types or cancer samples; (2) its presence or absence in a biological sample, e.g., a sample containing tissue, whole blood, serum, plasma, buccal scrape, saliva, cerebrospinal fluid, urine, stool, or bone marrow, from a subject, e.g., a human, afflicted with cancer; (3) its presence or absence in clinical subset of subjects with cancer (e.g., those responding to a particular therapy or those developing resistance). Diagnostic markers also include "surrogate markers," e.g., markers which are indirect markers of cancer progression. Such diagnostic markers may be useful to identify populations of subjects amenable to treatment with modulators of PD-1 and/or PD-L1 levels and to thereby treat such stratified patient populations.

A molecule is "fixed" or "affixed" to a substrate if it is covalently or non-covalently associated with the substrate such the substrate can be rinsed with a fluid (e.g., standard saline citrate, pH 7.4) without a substantial fraction of the molecule dissociating from the substrate.

The term "gene expression data" or "gene expression level" as used herein refers to information regarding the relative or absolute level of expression of a gene or set of genes in a cell or group of cells. The level of expression of a gene may be determined based on the level of RNA, such as mRNA, encoded by the gene. Alternatively, the level of expression may be determined based on the level of a polypeptide or fragment thereof encoded by the gene. Gene expression data may be acquired for an individual cell, or for a group of cells such as a tumor or biopsy sample. Gene expression data and gene expression levels can be stored on computer readable media, e.g., the computer readable medium used in conjunction with a microarray or chip reading device. Such gene expression data can be manipulated to generate gene expression signatures.

The term "gene expression signature" or "signature" as used herein refers to a group of coordinately expressed genes. The genes making up this signature may be expressed in a specific cell lineage, stage of differentiation, or during a particular biological response. The genes can reflect biological aspects of the tumors in which they are expressed, such as the cell of origin of the cancer, the nature of the non-malignant cells in the biopsy, and the oncogenic mechanisms responsible for the cancer.

The term "homologous" as used herein, refers to nucleotide sequence similarity between two regions of the same nucleic acid strand or between regions of two different nucleic acid strands. When a nucleotide residue position in both regions is occupied by the same nucleotide residue, then the regions are homologous at that position. A first region is homologous to a second region if at least one nucleotide residue position of each region is occupied by the same residue. Homology between two regions is expressed in terms of the proportion of nucleotide residue positions of the two regions that are occupied by the same nucleotide residue. By way of example, a region having the nucleotide sequence 5'-ATTGCC-3' and a region having the nucleotide sequence 5'-TATGGC-3' share 50% homology. Preferably, the first region comprises a first portion and the second region comprises a second portion, whereby, at least about 50%, and preferably at least about 75%, at least about 90%, or at least about 95% of the nucleotide residue positions of each of the portions are occupied by the same nucleotide residue. More preferably, all nucleotide residue positions of each of the portions are occupied by the same nucleotide residue.

The term "host cell" is intended to refer to a cell into which a nucleic acid of the invention, such as a recombinant expression vector of the invention, has been introduced. The terms "host cell" and "recombinant host cell" are used interchangeably herein. It should be understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

The term "humanized antibody," as used herein, is intended to include antibodies made by a non-human cell having variable and constant regions which have been altered to more closely resemble antibodies that would be made by a human cell, for example, by altering the non-human antibody amino acid sequence to incorporate amino acids found in human germline immunoglobulin sequences. Humanized antibodies may include amino acid residues not encoded by human germline immunoglobulin sequences (e.g., mutations introduced by random or site-specific mutagenesis in vitro or by somatic mutation in vivo), for example in the CDRs. The term "humanized antibody", as used herein, also includes antibodies in which CDR sequences derived from the germline of another mammalian species, such as a mouse, have been grafted onto human framework sequences.

The term "immune checkpoint inhibitor" means a group of molecules on the cell surface of CD4+ and/or CD8+ T cells that fine-tune immune responses by down-modulating or inhibiting an anti-tumor immune response. Immune checkpoint proteins are well known in the art and include, without limitation, CTLA-4, PD-1, VISTA, B7-H2, B7-H3, PD-L1, B7-H4, B7-H6, 2B4, ICOS, HVEM, PD-L2, CD160, gp49B, PIR-B, KIR family receptors, TIM-1, TIM-3, TIM-4, LAG-3, BTLA, SIRPalpha (CD47), CD48, 2B4 (CD244), B7.1, B7.2, ILT-2, ILT-4, TIGIT, and A2aR (see, for example, WO 2012/177624). "Anti-immune checkpoint inhibitor therapy" refers to the use of agents that inhibit immune checkpoint inhibitors. Inhibition of one or more immune checkpoint inhibitors can block or otherwise neutralize inhibitory signaling to thereby upregulate an immune response in order to more efficaciously treat cancer. Exemplary agents useful for inhibiting immune checkpoint inhibitors include antibodies, small molecules, peptides, peptidomimetics, natural ligands, and derivatives of natural ligands, that can either bind and/or inactivate or inhibit immune checkpoint proteins, or fragments thereof; as well as RNA interference, antisense, nucleic acid aptamers, etc. that can downregulate the expression and/or activity of immune checkpoint inhibitor nucleic acids, or fragments thereof. Exemplary agents for upregulating an immune response include antibodies against one or more immune checkpoint inhibitor proteins block the interaction between the proteins and its natural receptor(s); a non-activating form of one or more immune checkpoint inhibitor proteins (e.g., a dominant negative polypeptide); small molecules or peptides that block the interaction between one or more immune checkpoint inhibitor proteins and its natural receptor(s); fusion proteins (e.g. the extracellular portion of an immune checkpoint inhibition protein fused to the Fc portion of an antibody or immunoglobulin) that bind to its natural receptor(s); nucleic acid molecules that block immune checkpoint inhibitor nucleic acid transcription or translation; and the like. Such agents can directly block the interaction between the one or more immune checkpoint inhibitors and its natural receptor(s) (e.g., antibodies) to prevent inhibitory signaling and upregulate an immune response. Alternatively, agents can indirectly block the interaction between one or more immune checkpoint proteins and its natural receptor(s) to prevent inhibitory signaling and upregulate an immune response. For example, a soluble version of an immune checkpoint protein ligand such as a stabilized extracellular domain can binding to its receptor to indirectly reduce the effective concentration of the receptor to bind to an appropriate ligand. In one embodiment, anti-PD-1 antibodies, anti-PD-L1 antibodies, and anti-CTLA-4 antibodies, either alone or in combination, are used to inhibit immune checkpoint inhibitors.

As used herein, the term "immune cell" refers to cells that play a role in the immune response. Immune cells are of hematopoietic origin, and include lymphocytes, such as B cells and T cells; natural killer cells; myeloid cells, such as monocytes, macrophages, eosinophils, mast cells, basophils, and granulocytes.

As used herein, the term "immune response" includes T cell mediated and/or B cell mediated immune responses. Exemplary immune responses include T cell responses, e.g., cytokine production and cellular cytotoxicity. In addition, the term immune response includes immune responses that are indirectly effected by T cell activation, e.g., antibody production (humoral responses) and activation of cytokine responsive cells, e.g., macrophages.

The term "immunotherapeutic agent" can include any molecule, peptide, antibody or other agent which can stimulate a host immune system to generate an immune response to a tumor or cancer in the subject. Various immunotherapeutic agents are useful in the compositions and methods described herein.

As used herein, the term "inhibit" includes the decrease, limitation, or blockage, of, for example a particular action, function, or interaction. For example, cancer is "inhibited" if at least one symptom of the cancer, such as hyperproliferative growth, is alleviated, terminated, slowed, or prevented. As used herein, cancer is also "inhibited" if recurrence or metastasis of the cancer is reduced, slowed, delayed, or prevented.

As used herein, the term "inhibitory signal" refers to a signal transmitted via an inhibitory receptor (e.g., CTLA-4 or PD-1) for a polypeptide on an immune cell. Such a signal antagonizes a signal via an activating receptor (e.g., via a TCR, CD3, BCR, or Fc polypeptide) and can result in, e.g., inhibition of second messenger generation; an inhibition of proliferation; an inhibition of effector function in the immune cell, e.g., reduced phagocytosis, reduced antibody production, reduced cellular cytotoxicity, the failure of the immune cell to produce mediators, (such as cytokines (e.g., IL-2) and/or mediators of allergic responses); or the development of anergy.

As used herein, the term "interaction," when referring to an interaction between two molecules, refers to the physical contact (e.g., binding) of the molecules with one another. Generally, such an interaction results in an activity (which produces a biological effect) of one or both of said molecules. The activity may be a direct activity of one or both of the molecules. Alternatively, one or both molecules in the interaction may be prevented from binding their ligand, and thus be held inactive with respect to ligand binding activity (e.g., binding its ligand and triggering or inhibiting an immune response). To inhibit such an interaction results in the disruption of the activity of one or more molecules involved in the interaction. To enhance such an interaction is to prolong or increase the likelihood of said physical contact, and prolong or increase the likelihood of said activity.

An "isolated antibody," as used herein, is intended to refer to an antibody that is substantially free of other antibodies having different antigenic specificities. Moreover, an isolated antibody may be substantially free of other cellular material and/or chemicals.

As used herein, an "isolated protein" refers to a protein that is substantially free of other proteins, cellular material, separation medium, and culture medium when isolated from cells or produced by recombinant DNA techniques, or chemical precursors or other chemicals when chemically synthesized. An "isolated" or "purified" protein or biologically active portion thereof is substantially free of cellular material or other contaminating proteins from the cell or tissue source from which the antibody, polypeptide, peptide or fusion protein is derived, or substantially free from chemical precursors or other chemicals when chemically synthesized. The language "substantially free of cellular material" includes preparations, in which compositions of the invention are separated from cellular components of the cells from which they are isolated or recombinantly produced. In one embodiment, the language "substantially free of cellular material" includes preparations of having less than about 30%, 20%, 10%, or 5% (by dry weight) of cellular material. When an antibody, polypeptide, peptide or fusion protein or fragment thereof, e.g., a biologically active fragment thereof, is recombinantly produced, it is also preferably substantially free of culture medium, i.e., culture medium represents less than about 20%, more preferably less than about 10%, and most preferably less than about 5% of the volume of the protein preparation.

A "kit" is any manufacture (e.g., a package or container) comprising at least one reagent, e.g., a probe, for specifically detecting or modulating the expression of a marker of the invention. The kit may be promoted, distributed, or sold as a unit for performing the methods of the present invention.

A "marker" or "biomarker" includes a nucleic acid or polypeptide whose altered level of expression in a tissue or cell from its expression level in a control (e.g., normal or healthy tissue or cell) is associated with a disease state, such as a cancer or subtype thereof (e.g., melanoma). A "marker nucleic acid" is a nucleic acid (e.g., mRNA, cDNA, mature miRNA, pre-miRNA, pri-miRNA, miRNA*, anti-miRNA, or a miRNA binding site, or a variant thereof and other classes of small RNAs known to a skilled artisan) encoded by or corresponding to a marker of the invention. Such marker nucleic acids include DNA (e.g., cDNA) comprising the entire or a partial sequence of any of the nucleic acid sequences set forth in Table 2 and the Examples or the complement of such a sequence. The marker nucleic acids also include RNA comprising the entire or a partial sequence of any of the nucleic acid sequences set forth in the Sequence Listing or the complement of such a sequence, wherein all thymidine residues are replaced with uridine residues. A "marker protein" includes a protein encoded by or corresponding to a marker of the invention. A marker protein comprises the entire or a partial sequence of any of the sequences set forth in Table 2 and the Examples or the Examples. The terms "protein" and "polypeptide" are used interchangeably. In some embodiments, specific combinations of biomarkers are preferred. For example, a combination or subgroup of one or more of the biomarkers selected from the group shown in Table.

The term "melanoma" generally refers to cancers derived from melanocytes. Although melanocytes are predominantly located in skin, they are also found in other parts of the body, including the eye and bowel. Although cutaneous melanoma is most common, melanoma can originate from any melanocyte in the body. Though melanoma is less than five percent of the skin cancers, it is the seventh most common malignancy in the U.S. and is responsible for most of the skin cancer related deaths. The incidence has increased dramatically in the last several decades due to altered sun exposure habits of the population. several hereditary risk factors are also known. Other important risk factors are the number of pigment nevi, the number dysplastic nevi, and skin type. An increased risk is coupled to many nevi, both benign and dysplastic, and fair skin. Familial history of malignant melanomas is a risk factor, and approximately 8-12% of malignant melanoma cases are familial. Additional details are well known, such as described in US Pat. Publs. 2012-0269764 and 2013-0237445.

Malignant melanomas are clinically recognized based on the ABCD(E) system, where A stands for asymmetry, B for border irregularity, C for color variation, D for diameter >5 mm, and E for evolving. Further, an excision biopsy can be performed in order to corroborate a diagnosis using microscopic evaluation. Infiltrative malignant melanoma is traditionally divided into four principal histopathological subgroups: superficial spreading melanoma (SSM), nodular malignant melanoma (NMM), lentigo maligna melanoma (LMM), and acral lentiginous melanoma (ALM). Other rare types also exists, such as desmoplastic malignant melanoma. A substantial subset of malignant melanomas appear to arise from melanocytic nevi and features of dysplastic nevi are often found in the vicinity of infiltrative melanomas. Melanoma is thought to arise through stages of progression from normal melanocytes or nevus cells through a dysplastic nevus stage and further to an in situ stage before becoming invasive. Some of the subtypes evolve through different phases of tumor progression, which are called radial growth phase (RGP) and vertical growth phase (VGP).

In a preferred embodiment, a melanoma subtype is melanoma resistant to treatment with inhibitors of BRAF and/or MEK. For example, the methods described herein are useful for diagnosing and/or prognosing melanoma subtypes that are resistant to treatment with inhibitors of BRAF and/or MEK. Inhibitors of BRAF and/or MEK, especially of mutant versions implicated in cancer (e.g., BRAF$^{V600E}$) are well-known in the art.

BRAF is a member of the Raf kinase family of serine/threonine-specific protein kinases. This protein plays a role in regulating the MAP kinase/ERKs signaling pathway, which affects cell division, differentiation, and secretion. BRAF transduces cellular regulatory signals from Ras to MEK in vivo. BRAF is also referred to as v-raf murine sarcoma viral oncogene homolog B1. BRAF mutants are a mutated form of BRAF that has increased basal kinase activity relative to the basal kinase activity of wild type BRAF is also an activated form of BRAF. More than 30 mutations of the BRAF gene that are associated with human cancers have been identified. The frequency of BRAF mutations in melanomas and nevi are 80%. In 90% of the cases, a Glu for Val substitution at position 600 (referred to as V600E) in the activation segment has been found in human cancers. This mutation is observed in papillary thyroid cancer, colorectal cancer and melanoma. Other mutations which have been found are R462I, I463S, G464E, G464V, G466A, G466E, G466V, G469A, G469E, N581S, E585K, D594V, F595L, G596R, L597V, T599I, V600D, V600K, V600R, K601E or A728V. Most of these mutations are clustered to two regions: the glycine-rich P loop of the N lobe and the activation segment and flanking regions. A mutated form of BRAF that induces focus formation more efficiently than wild type BRAF is also an activated form of BRAF. As used herein, the term "inhibitor of BRAF" refers to a compound or agent, such as a small molecule, that inhibits, decreases, lowers, or reduces the activity of BRAF or a mutant version thereof. Examples of inhibitors of BRAF include, but are not limited to, vemurafenib (PLX-4032; also known as RG7204, RO5185426, and vemurafenib, C23H18ClF2N3O3S), PLX 4720 (C17H14ClF2N3O3S), sorafenib (C21H16ClF3N4O3), GSK2118436, and the like. These and other inhibitors of BRAF, as well as non-limited examples of their methods of manufacture, are described in, for example, PCT Publication Nos. WO 2007/002325, WO 2007/002433, WO 2009/047505, WO 03/086467; WO 2009/143024, WO 2010/104945, WO 2010/104973, WO 2010/111527 and WO 2009/152087; U.S. Pat. Nos. 6,187,799 and 7,329,670; and U.S. Patent Application Publication Nos. 2005/0176740 and 2009/0286783, each of which is herein incorporated by reference in its entirety).

MEK1 is a known as dual specificity mitogen-activated protein kinase kinase 1, which is an enzyme that in human is encoded by the MAP2K1 gene. Mutations of MEK1 involved in cancer are known and include, for example, mutation selected from 59delK and P387S or Q56P or C121S or P124L or F129L, and a MAP2K1 gene having a 175-177 AAG deletion or C1159T. As used herein, the term "inhibitor of MEK" refers to a compound or agent, such as a small molecule, that inhibits, decreases, lowers, or reduces the activity of MEK or a mutant version thereof. Examples of inhibitors of MEK include, but are not limited to, AZD6244 (6-(4-Bromo-2-chloro-phenylamino)-7-fluoro-3-methyl-3H-benzoimida-zole-5-carboxylic acid (2-hydroxy-ethoxy)-amide; selumetinib; Structure IV), and U0126 (1,4-diamino-2,3-dicyano-1,4-bis [2-aminophenylthio] butadiene; ARRY-142886; Structure V). Further non-limiting examples of MEK inhibitors include PD0325901, AZD2171, GDC-0973/XL-518, PD98059, PD184352, GSK1120212, RDEA436, RDEA119/BAY869766, AS703026, BIX 02188, BIX 02189, CI-1040 (PD184352), PD0325901, and PD98059. These and other inhibitors of MEK, as well as non-limiting examples of their methods of manufacture, are described in, for example, U.S. Pat. Nos. 5,525,625; 6,251,943; 7,820,664; 6,809,106; 7,759,518; 7,485,643; 7,576,072; 7,923,456; 7,732,616; 7,271,178; 7,429,667; 6,649,640; 6,495,582; 7,001,905; US Patent Publication No. US2010/0331334, US2009/0143389, US2008/0280957, US2007/0049591, US2011/0118298, International Patent Application Publication No. WO98/43960, WO99/01421, WO99/01426, WO00/41505, WO00/42002, WO00/42003, WO00/41994, WO00/42022, WO00/42029, WO00/68201, WO01/68619, WO02/06213 and WO03/077914, each of which is herein incorporated by reference in their entirety.

Malignant melanomas are staged according to the American Joint Committee on Cancer (AJCC) TNM-classification system, where Clark level is considered in T-classification. The T stage describes the local extent of the primary tumor, i.e., how far the tumor has invaded and imposed growth into surrounding tissues, whereas the N stage and M stage describe how the tumor has developed metastases, with the N stage describing spread of tumor to lymph nodes and the M stage describing growth of tumor in other distant organs. Early stages include: T0-1, N0, M0, representing localized tumors with negative lymph nodes. More advanced stages include: T2-4, N0, M0, localized tumors with more widespread growth and T1-4, N1-3, M0, tumors that have metastasized to lymph nodes and T1-4, N1-3, M1, tumors with a metastasis detected in a distant organ.

Stages I and II represent no metastatic disease and for stage I (T1a/b-2a,N0,M0) prognosis is very good. The 5-year survival for stage I disease is 90-95%, for stage II (T2b-4-b,N0,M0) the corresponding survival rate ranges from 80 to 45%. Stages III (T1a-4-b,N1a-3,M0) and IV (T(aII),N(aII),M1a-c) represent spread disease, and for these stages 5-year survival rates range from 70 to 24%, and from 19 to 7%, respectively. "Clark's level" is a measure of the layers of skin involved in a melanoma and is a melanoma prognostic factor. For example, level I involves the epidermis. Level II involves the epidermis and upper dermis. Level III involves the epidermis, upper dermis, and lower dermis. Level IV involves the epidermis, upper dermis, lower dermis, and subcutis. When the primary tumor has a thickness of >1 mm, ulceration, or Clark level IV-V, sentinel node biopsy (SNB) is typically performed. SNB is performed by identifying the first draining lymph node/s (i.e the SN) from the tumour. This is normally done by injection of radiolabelled colloid particles in the area around the tumour, followed by injection of Vital Blue dye. Rather than dissection of all regional lymph nodes, which was the earlier standard procedure, only the sentinel nodes are generally removed and carefully examined. Following complete lymph node dissection is only performed in confirmed positive cases.

In addition to staging and diagnosis, factors like T-stage, Clark level, SNB status, Breslow's depth, ulceration, and the like can be used as endpoints and/or surrogates for analyses according to the present invention. For example, patients who are diagnosed at an advanced stage with metastases generally have a poor prognosis. For patients diagnosed with a localized disease, the thickness of the tumor measured in mm (Breslow) and ulceration can be endpoints for prognosis. Breslow's depth is determined by using an ocular micrometer at a right angle to the skin. The depth from the granular layer of the epidermis to the deepest point of invasion to which tumor cells have invaded the skin is directly measured. Clark level is important for thin lesions (<1 mm). Other prognostic factors include age, anatomic site of the primary tumor and gender. The sentinel node (SN) status can also be a prognostic factor, especially since the 5-year survival of SN-negative patients has been shown to be as high as 90%. Similarly, overall survival (OS) can be used as a standard primary endpoint. OS takes in to account time to death, irrespective of cause, e.g. if the death is due to cancer or not. Loss to follow-up is censored and regional recurrence, distant metastases, second primary malignant melanomas and second other primary cancers are ignored. Other surrogate endpoints for survival can be used, as described further herein, such as disease-free survival (DFS), which includes time to any event related to the same cancer, i.e. all cancer recurrences and deaths from the same cancer are events.

In addition to endpoints, certain diagnostic and prognostic markers can be analyzed in conjunction with the methods described herein. For example, lactate dehydrogenase (LDH) can be measured as a marker for disease progression. Patients with distant metastases and elevated LDH levels belong to stage IV M1c. Another serum biomarker of interest is S100B. High S100B levels are associated with disease progression, and a decrease in the S100B level is an indicator of treatment response. Melanoma-inhibiting activity (MIA) is yet another serum biomarker that has been evaluated regarding its prognostic value. Studies have shown that elevated MIA levels are rare in stage I and II disease, whereas in stage III or IV, elevation in MIA levels can be seen in 60-100% of cases. Addition useful biomarkers include RGS1 (associated with reduced relapse-free survival (RFS)), osteopontin (associated with both reduced RFS and disease-specific survival (DSS), and predictive of SLN metastases), HER3 (associated with reduced survival), and NCOA3 (associated with poor RFS and DSS, and predictive of SLN metastases). In addition, HMB-45, Ki-67 (MIB1), MITF and MART-1/Melan-A or combinations of any described marker may be used for staining (Ivan & Prieto, 2010, Future Oncol. 6(7), 1163-1175; Linos et al., 2011, Biomarkers Med. 5(3) 333-360). In a literature review Rothberg et al. report that melanoma cell adhesion molecule (MCAM)/MUC18, matrix metalloproteinase-2, Ki-67, proliferating cell nuclear antigen (PCNA) and p16/INK4A are predictive of either all-cause mortality or melanoma specific mortality (Rothberg et al., 2009 J. Nat. Canc. Inst. 101(7) 452-474).

Currently, the typical primary treatment of malignant melanoma is radical surgery. Even though survival rates are high after excision of the primary tumour, melanomas tend to metastasize relatively early, and for patients with metastatic melanoma the prognosis is poor, with a 5-year survival rate of less than 10%. Radical removal of distant metastases with surgery can be an option and systemic chemotherapy can be applied, but response rates are normally low (in most cases less than 20%), and most treatment regiments fail to prolong overall survival. The first FDA-approved chemotherapeutic agent for treatment of metastatic melanoma was dacarbazine (DTIC), which can give response rates of approximately 20%, but where less than 5% may be complete responses. Temozolamid is an analog of DTIC that has the advantage of oral administration, and which have been shown to give a similar response as DTIC. Other chemotherapeutic agents, for example different nitrosureas, cisplatin, carboplatin, and vinca alkaloids, have been used, but without any increase in response rates. Since chemotherapy is an inefficient treatment method, immunotherapy agents have also been proposed. Most studied are interferon-alpha and interleukin-2. As single agents they have not been shown to give a better response than conventional treatment, but in combination with chemotherapeutic agents higher response rates have been reported. For patients with resected stage IIB or III melanoma, some studies have shown that adjuvant interferon alfa has led to longer disease free survival. For first- or second-line stage III and IV melanoma systemic treatments include: carboplatin, cisplatin, dacarbazine, interferon alfa, high-dose interleukin-2, paclitaxel, temozolomide, vinblastine or combinations thereof (NCCN Guidelines, ME-D, MS-9-13). Recently, the FDA approved Zelboraf™ (vemurafenib, also known as INN, PLX4032, RG7204 or R05185426) for unresectable or metastatic melanoma with the BRAF V600E mutation (Bollag et al. (2010) *Nature* 467:596-599 and Chapman et al. (2011) *New Eng. J. Med.* 364:2507-2516). Another recently approved drug for unresectable or metastatic melanoma is Yervoy®(ipilimumab) an antibody which binds to cytotoxic T-lymphocyte-associated antigen 4 (CTLA-4) (Hodi et al. (2010) *New Eng. J Med.* 363:711-723). Others recently reported that patients with KIT receptor activating mutations or over-expression responded to Gleevac® (imatinib mesylate) (Carvajal et al. (2011) *JAMA* 305:2327-2334). In addition, radiation treatment may be given as an adjuvant after removal of lymphatic metastases, but malignant melanomas are relatively radioresistant. Radiation treatment might also be used as palliative treatment. Melanoma oncologists have also noted that BRAF mutations are common in both primary and metastatic melanomas and that these mutations are reported to be present in 50-70% of all melanomas. This has led to an interest in B-raf inhibitors, such as Sorafenib, as therapeutic agents.

The term "modulate" includes up-regulation and down-regulation, e.g., enhancing or inhibiting a response.

The "normal" or "control" level of expression of a marker is the level of expression of the marker in cells of a subject, e.g., a human patient, not afflicted with a cancer. An "overexpression" or "significantly higher level of expression" of a marker refers to an expression level in a test sample that is greater than the standard error of the assay employed to assess expression, and is preferably at least twice, and more preferably 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more higher than the expression activity or level of the marker in a control sample (e.g., sample from a healthy subject not having the marker associated disease) and preferably, the average expression level of the marker in several control samples. A "significantly lower level of expression" of a marker refers to an expression level in a test sample that is at least twice, and more preferably 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more lower than the expression level of the marker in a control sample (e.g., sample from a healthy subject not having the marker associated disease) and preferably, the average expression level of the marker in several control samples.

The term "pre-malignant lesions" as described herein refers to a lesion that, while not cancerous, has potential for becoming cancerous. It also includes the term "pre-malignant disorders" or "potentially malignant disorders." In particular this refers to a benign, morphologically and/or histologically altered tissue that has a greater than normal risk of malignant transformation, and a disease or a patient's habit that does not necessarily alter the clinical appearance of local tissue but is associated with a greater than normal risk of precancerous lesion or cancer development in that tissue (leukoplakia, erythroplakia, erytroleukoplakia lichen planus (lichenoid reaction) and any lesion or an area which histological examination showed atypia of cells or dysplasia.

The term "predictive" includes the use of a biomarker nucleic acid, protein, and/or metabolite status, e.g., over- or under-activity, emergence, expression, growth, remission, recurrence or resistance of tumors before, during or after therapy, for determining an outcome, such as the likelihood of response of a cancer to anti-immune checkpoint inhibitor treatment (e.g., therapeutic antibodies against PD-1, PD-L1, and/or CTLA-4). Such predictive use of the biomarker may be confirmed by, e.g., (1) increased or decreased copy number (e.g., by FISH, FISH plus SKY, single-molecule sequencing, e.g., as described in the art at least at J. Biotechnol., 86:289-301, or qPCR), overexpression or underexpression of a biomarker nucleic acid (e.g., by ISH, Northern Blot, or qPCR), increased or decreased biomarker protein (e.g., by IHC) and/or biomarker metabolite, or increased or decreased activity (determined by, for example, modulation of the kynurenine pathway), e.g., in more than about 5%, 6%, 7%, 8%, 9%, 10%, 11%, 12%, 13%, 14%, 15%, 20%, 25%, 30%, 40%, 50%, 60%, 70%, 80%, 90%, 95%, 100%, or more of assayed human cancers types or cancer samples; (2) its absolute or relatively modulated presence or absence in a biological sample, e.g., a sample containing tissue, whole blood, serum, plasma, buccal scrape, saliva, cerebrospinal fluid, urine, stool, or bone marrow, from a subject, e.g. a human, afflicted with cancer;

(3) its absolute or relatively modulated presence or absence in clinical subset of patients with cancer (e.g., those responding to a particular anti-immune checkpoint inhibitor therapy or those developing resistance thereto).

The term "pre-determined" biomarker amount and/or activity measurement(s) may be a biomarker amount and/or activity measurement(s) used to, by way of example only, evaluate a subject that may be selected for a particular treatment, evaluate a response to a treatment such as an anti-immune checkpoint inhibitor therapy, and/or evaluate the disease state. A pre-determined biomarker amount and/or activity measurement(s) may be determined in populations of patients with or without cancer. The pre-determined biomarker amount and/or activity measurement(s) can be a single number, equally applicable to every patient, or the pre-determined biomarker amount and/or activity measurement(s) can vary according to specific subpopulations of patients. Age, weight, height, and other factors of a subject may affect the pre-determined biomarker amount and/or activity measurement(s) of the individual. Furthermore, the pre-determined biomarker amount and/or activity can be determined for each subject individually. In one embodiment, the amounts determined and/or compared in a method described herein are based on absolute measurements. In another embodiment, the amounts determined and/or compared in a method described herein are based on relative measurements, such as ratios (e.g., serum biomarker normalized to the expression of a housekeeping or otherwise generally constant biomarker). The pre-determined biomarker amount and/or activity measurement(s) can be any suitable standard. For example, the pre-determined biomarker amount and/or activity measurement(s) can be obtained from the same or a different human for whom a patient selection is being assessed. In one embodiment, the pre-determined biomarker amount and/or activity measurement(s) can be obtained from a previous assessment of the same patient. In such a manner, the progress of the selection of the patient can be monitored over time. In addition, the control can be obtained from an assessment of another human or multiple humans, e.g., selected groups of humans, if the subject is a human. In such a manner, the extent of the selection of the human for whom selection is being assessed can be compared to suitable other humans, e.g., other humans who are in a similar situation to the human of interest, such as those suffering from similar or the same condition(s) and/or of the same ethnic group.

The term "probe" refers to any molecule which is capable of selectively binding to a specifically intended target molecule, for example, a nucleotide transcript or protein encoded by or corresponding to a marker. Probes can be either synthesized by one skilled in the art, or derived from appropriate biological preparations. For purposes of detection of the target molecule, probes may be specifically designed to be labeled, as described herein. Examples of molecules that can be utilized as probes include, but are not limited to, RNA, DNA, proteins, antibodies, and organic molecules.

The term "prognosis" includes a prediction of the probable course and outcome of cancer or the likelihood of recovery from the disease. In some embodiments, the use of statistical algorithms provides a prognosis of cancer in an individual. For example, the prognosis can be surgery, development of a clinical subtype of melanoma, development of one or more clinical factors, development of intestinal cancer, or recovery from the disease. In some embodiments, the term "good prognosis" indicates that the expected or likely outcome after treatment of melanoma is good. The term "poor prognosis" indicates that the expected or likely outcome after treatment of melanoma is not good.

The term "response to cancer therapy" or "outcome of cancer therapy" relates to any response of the hyperproliferative disorder (e.g., cancer) to a cancer therapy, preferably to a change in tumor mass and/or volume after initiation of neoadjuvant or adjuvant chemotherapy. Hyperproliferative disorder response may be assessed, for example for efficacy or in a neoadjuvant or adjuvant situation, where the size of a tumor after systemic intervention can be compared to the initial size and dimensions as measured by CT, PET, mammogram, ultrasound or palpation. Response may also be assessed by caliper measurement or pathological examination of the tumor after biopsy or surgical resection for solid cancers. Responses may be recorded in a quantitative fashion like percentage change in tumor volume or in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment of hyperproliferative disorder response may be done early after the onset of neoadjuvant or adjuvant therapy, e.g., after a few hours, days, weeks or preferably after a few months. A typical endpoint for response assessment is upon termination of neoadjuvant chemotherapy or upon surgical removal of residual tumor cells and/or the tumor bed. This is typically three months after initiation of neoadjuvant therapy. In some embodiments, clinical efficacy of the therapeutic treatments described herein may be determined by measuring the clinical benefit rate (CBR). The clinical benefit rate is measured by determining the sum of the percentage of patients who are in complete remission (CR), the number of patients who are in partial remission (PR) and the number of patients having stable disease (SD) at a time point at least 6 months out from the end of therapy. The shorthand for this formula is CBR=CR+PR+SD over 6 months. In some embodiments, the CBR for a particular cancer therapeutic regimen is at least 25%, 30%, 35%, 40%, 45%, 50%, 55%, 60%, 65%, 70%, 75%, 80%, 85%, or more. Additional criteria for evaluating the response to cancer therapies are related to "survival," which includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g., time of diagnosis or start of treatment) and end point (e.g., death, recurrence or metastasis). In addition, criteria for efficacy of treatment can be expanded to include response to chemotherapy, probability of survival, probability of metastasis within a given time period, and probability of tumor recurrence. For example, in order to determine appropriate threshold values, a particular cancer therapeutic regimen can be administered to a population of subjects and the outcome can be correlated to copy number, level of expression, level of activity, etc. of one or more biomarkers listed in Table 2 and the Examples or the Examples that were determined prior to administration of any cancer therapy. The outcome measurement may be pathologic response to therapy given in the neoadjuvant setting. Alternatively, outcome measures, such as overall survival and disease-free survival can be monitored over a period of time for subjects following cancer therapy for whom the measurement values are known. In certain embodiments, the same doses of cancer therapeutic agents are administered to each subject. In related embodiments, the doses administered are standard doses known in the art for cancer therapeutic agents. The period of time for which subjects are monitored can vary. For example, subjects may be monitored for at least 2, 4, 6, 8, 10, 12, 14, 16, 18, 20, 25, 30, 35, 40, 45, 50, 55, or 60 months. Biomarker threshold values that correlate to outcome of a cancer therapy can be determined using methods such as those described in the Examples section. Outcomes can also be measured in terms of a "hazard ratio" (the ratio of death rates for one patient group to another; provides likelihood of death at a certain time point), "overall survival" (OS), and/or "progression free survival." In certain embodiments, the prognosis comprises likelihood of overall survival rate at 1 year, 2 years, 3 years, 4 years, or any other suitable time point. The significance associated with the prognosis of poor outcome in all aspects of the present invention is measured by techniques known in the art. For example, significance may be measured with calculation of odds ratio. In a further embodiment, the significance is measured by a percentage. In one embodiment, a significant risk of poor outcome is measured as odds ratio of 0.8 or less or at least about 1.2, including by not limited to: 0.1, 0.2, 0.3, 0.4, 0.5, 0.6, 0.7, 0.8, 1.2, 1.3, 1.4, 1.5, 1.6, 1.7, 1.8, 1.9, 2.0, 2.5, 3.0, 4.0, 5.0, 10.0, 15.0, 20.0, 25.0, 30.0 and 40.0. In a further embodiment, a significant increase or reduction in risk is at least about 20%, including but not limited to about 25%, 30%, 35%, 40%, 45%, 50%, 55%, 60%, 65%, 70%, 75%, 80%, 85%, 90%, 95% and 98%. In a further embodiment, a significant increase in risk is at least about 50%. Thus, the present invention further provides methods for making a treatment decision for a cancer patient, comprising carrying out the methods for prognosing a cancer patient according to the different aspects and embodiments of the present invention, and then weighing the results in light of other known clinical and pathological risk factors, in determining a course of treatment for the cancer patient. For example, a cancer patient that is shown by the methods of the invention to have an increased risk of poor outcome by combination chemotherapy treatment can be treated with more aggressive therapies, including but not limited to radiation therapy, peripheral blood stem cell transplant, bone marrow transplant, or novel or experimental therapies under clinical investigation.

The term "resistance" refers to an acquired or natural resistance of a cancer sample or a mammal to a cancer therapy (i.e., being nonresponsive to or having reduced or limited response to the therapeutic treatment), such as having a reduced response to a therapeutic treatment by 25% or more, for example, 30%, 40%, 50%, 60%, 70%, 80%, or more, to 2-fold, 3-fold, 4-fold, 5-fold, 10-fold, 15-fold, 20-fold or more. The reduction in response can be measured by comparing with the same cancer sample or mammal before the resistance is acquired, or by comparing with a different cancer sample or a mammal who is known to have no resistance to the therapeutic treatment. A typical acquired resistance to chemotherapy is called "multidrug resistance." The multidrug resistance can be mediated by P-glycoprotein or can be mediated by other mechanisms, or it can occur when a mammal is infected with a multi-drug-resistant microorganism or a combination of microorganisms. The determination of resistance to a therapeutic treatment is routine in the art and within the skill of an ordinarily skilled clinician, for example, can be measured by cell proliferative assays and cell death assays as described herein as "sensitizing." In some embodiments, the term "reverses resistance" means that the use of a second agent in combination with a primary cancer therapy (e.g., chemotherapeutic or radiation therapy) is able to produce a significant decrease in tumor volume at a level of statistical significance (e.g., $p<0.05$) when compared to tumor volume of untreated tumor in the circumstance where the primary cancer therapy (e.g., chemotherapeutic or radiation therapy) alone is unable to produce a statistically significant decrease in tumor volume compared to tumor volume of untreated tumor. This generally applies to tumor volume measurements made at a time when the untreated tumor is growing log rhythmically.

The term "sample" used for detecting or determining the presence or level of at least one biomarker is typically whole blood, plasma, serum, saliva, urine, stool (e.g., feces), tears, and any other bodily fluid (e.g., as described above under the definition of "body fluids"), or a tissue sample (e.g., biopsy) such as a small intestine, colon sample, or surgical resection tissue. In certain instances, the method of the present invention further comprises obtaining the sample from the individual prior to detecting or determining the presence or level of at least one marker in the sample.

The term "sensitize" means to alter cancer cells or tumor cells in a way that allows for more effective treatment of the associated cancer with a cancer therapy (e.g., chemotherapeutic or radiation therapy. In some embodiments, normal cells are not affected to an extent that causes the normal cells to be unduly injured by the cancer therapy (e.g., chemotherapy or radiation therapy). An increased sensitivity or a reduced sensitivity to a therapeutic treatment is measured according to a known method in the art for the particular treatment and methods described herein below, including, but not limited to, cell proliferative assays (Tanigawa N, Kern D H, Kikasa Y, Morton D L, Cancer Res 1982; 42: 2159-2164), cell death assays (Weisenthal L M, Shoemaker R H, Marsden J A, Dill P L, Baker J A, Moran E M, Cancer Res 1984; 94: 161-173; Weisenthal L M, Lippman M E, Cancer Treat Rep 1985; 69: 615-632; Weisenthal L M, In: Kaspers G J L, Pieters R, Twentyman P R, Weisenthal L M, Veerman A J P, eds. Drug Resistance in Leukemia and Lymphoma. Langhorne, P A: Harwood Academic Publishers, 1993: 415-432; Weisenthal L M, Contrib Gynecol Obstet 1994; 19: 82-90). The sensitivity or resistance may also be measured in animal by measuring the tumor size reduction over a period of time, for example, 6 month for human and 4-6 weeks for mouse. A composition or a method sensitizes response to a therapeutic treatment if the increase in treatment sensitivity or the reduction in resistance is 25% or more, for example, 30%, 40%, 50%, 60%, 70%, 80%, or more, to 2-fold, 3-fold, 4-fold, 5-fold, 10-fold, 15-fold, 20-fold or more, compared to treatment sensitivity or resistance in the absence of such composition or method. The determination of sensitivity or resistance to a therapeutic treatment is routine in the art and within the skill of an ordinarily skilled clinician. It is to be understood that any method described herein for enhancing the efficacy of a cancer therapy can be equally applied to methods for sensitizing hyperproliferative or otherwise cancerous cells (e.g., resistant cells) to the cancer therapy.

The term "synergistic effect" refers to the combined effect of two or more anticancer agents or chemotherapy drugs can be greater than the sum of the separate effects of the anticancer agents or chemotherapy drugs alone.

The term "subject" refers to any healthy animal, mammal or human, or any animal, mammal or human afflicted with a condition of interest (e.g., cancer). The term "subject" is interchangeable with "patient." In some embodiments, a subject does not have any cancer other than melanoma. In other embodiments, the subject has melanoma but does not have one or more other cancers of interest. For example, in some embodiments, a subject does not have renal cell carcinoma, head or neck cancer, and/or lung cancer.

The language "substantially free of chemical precursors or other chemicals" includes preparations of antibody, polypeptide, peptide or fusion protein in which the protein is separated from chemical precursors or other chemicals which are involved in the synthesis of the protein. In one embodiment, the language "substantially free of chemical precursors or other chemicals" includes preparations of antibody, polypeptide, peptide or fusion protein having less than about 30% (by dry weight) of chemical precursors or non-antibody, polypeptide, peptide or fusion protein chemicals, more preferably less than about 20% chemical precursors or non-antibody, polypeptide, peptide or fusion protein chemicals, still more preferably less than about 10% chemical precursors or non-antibody, polypeptide, peptide or fusion protein chemicals, and most preferably less than about 5% chemical precursors or non-antibody, polypeptide, peptide or fusion protein chemicals.

The term "substantially pure cell population" refers to a population of cells having a specified cell marker characteristic and differentiation potential that is at least about 50%, preferably at least about 75-80%, more preferably at least about 85-90%, and most preferably at least about 95% of the cells making up the total cell population. Thus, a "substantially pure cell population" refers to a population of cells that contain fewer than about 50%, preferably fewer than about 20-25%, more preferably fewer than about 10-15%, and most preferably fewer than about 5% of cells that do not display a specified marker characteristic and differentiation potential under designated assay conditions.

As used herein, the term "survival" includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g., time of diagnosis or start of treatment) and end point (e.g., death, recurrence or metastasis). In addition, criteria for efficacy of treatment can be expanded to include response to chemotherapy, probability of survival, probability of metastasis within a given time period, and probability of tumor recurrence.

A "transcribed polynucleotide" or "nucleotide transcript" is a polynucleotide (e.g., an mRNA, hnRNA, cDNA, mature miRNA, pre-miRNA, pri-miRNA, miRNA*, anti-miRNA, or a miRNA binding site, or a variant thereof or an analog of such RNA or cDNA) which is complementary to or homologous with all or a portion of a mature mRNA made by transcription of a marker of the invention and normal post-transcriptional processing (e.g., splicing), if any, of the RNA transcript, and reverse transcription of the RNA transcript.

As used herein, the term "vector" refers to a nucleic acid capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" or simply "expression vectors." In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

An "underexpression" or "significantly lower level of expression or copy number" of a marker refers to an expression level or copy number in a test sample that is greater than the standard error of the assay employed to assess expression or copy number, but is preferably at least twice, and more preferably three, four, five or ten or more times less than the expression level or copy number of the marker in a control sample (e.g., sample from a healthy subject not afflicted with cancer) and preferably, the average expression level or copy number of the marker in several control samples.

As used herein, the term "unresponsiveness" includes refractivity of immune cells to stimulation, e.g., stimulation via an activating receptor or a cytokine. Unresponsiveness can occur, e.g., because of exposure to immunosuppressants or exposure to high doses of antigen. As used herein, the term "anergy" or "tolerance" includes refractivity to activating receptor-mediated stimulation. Such refractivity is generally antigen-specific and persists after exposure to the tolerizing antigen has ceased. For example, anergy in T cells (as opposed to unresponsiveness) is characterized by lack of cytokine production, e.g., IL-2. T cell anergy occurs when T cells are exposed to antigen and receive a first signal (a T cell receptor or CD-3 mediated signal) in the absence of a second signal (a costimulatory signal). Under these conditions, reexposure of the cells to the same antigen (even if reexposure occurs in the presence of a costimulatory polypeptide) results in failure to produce cytokines and, thus, failure to proliferate. Anergic T cells can, however, proliferate if cultured with cytokines (e.g., IL-2). For example, T cell anergy can also be observed by the lack of IL-2 production by T lymphocytes as measured by ELISA or by a proliferation assay using an indicator cell line. Alternatively, a reporter gene construct can be used. For example, anergic T cells fail to initiate IL-2 gene transcription induced by a heterologous promoter under the control of the 5' IL-2 gene enhancer or by a multimer of the AP1 sequence that can be found within the enhancer (Kang et al. (1992) *Science* 257:1134).

There is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid and the amino acid sequence encoded by that nucleic acid, as defined by the genetic code.

| GENETIC CODE | |
|---|---|
| Alanine (Ala, A) | GCA, GCC, GCG, GCT |
| Arginine (Arg, R) | AGA, ACG, CGA, CGC, CGG, CGT |
| Asparagine (Asn, N) | AAC, AAT |
| Aspartic acid (Asp, D) | GAC, GAT |
| Cysteine (Cys, C) | TGC, TGT |
| Glutamic acid (Glu, E) | GAA, GAG |
| Glutamine (Gln, Q) | CAA, CAG |
| Glycine (Gly, G) | GGA, GGC, GGG, GGT |
| Histidine (His, H) | CAC, CAT |
| Isoleucine (Ile, I) | ATA, ATC, ATT |
| Leucine (Leu, L) | CTA, CTC, CTG, CTT, TTA, TTG |
| Lysine (Lys, K) | AAA, AAG |
| Methionine (Met, M) | ATG |
| Phenylalanine (Phe, F) | TTC, TTT |
| Proline (Pro, P) | CCA, CCC, CCG, CCT |
| Serine (Ser, S) | AGC, AGT, TCA, TCC, TCG, TCT |
| Threonine (Thr, T) | ACA, ACC, ACG, ACT |
| Tryptophan (Trp, W) | TGG |
| Tyrosine (Tyr, Y) | TAC, TAT |
| Valine (Val, V) | GTA, GTC, GTG, GTT |
| Termination signal (end) | TAA, TAG, TGA |

An important and well known feature of the genetic code is its redundancy, whereby, for most of the amino acids used to make proteins, more than one coding nucleotide triplet may be employed (illustrated above). Therefore, a number of different nucleotide sequences may code for a given amino acid sequence. Such nucleotide sequences are considered functionally equivalent since they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid.

In view of the foregoing, the nucleotide sequence of a DNA or RNA coding for a fusion protein or polypeptide of the invention (or any portion thereof) can be used to derive the fusion protein or polypeptide amino acid sequence, using the genetic code to translate the DNA or RNA into an amino acid sequence. Likewise, for a fusion protein or polypeptide amino acid sequence, corresponding nucleotide sequences that can encode the fusion protein or polypeptide can be deduced from the genetic code (which, because of its redundancy, will produce multiple nucleic acid sequences for any given amino acid sequence). Thus, description and/or disclosure herein of a nucleotide sequence which encodes a fusion protein or polypeptide should be considered to also include description and/or disclosure of the amino acid sequence encoded by the nucleotide sequence. Similarly, description and/or disclosure of a fusion protein or polypeptide amino acid sequence herein should be considered to also include description and/or disclosure of all possible nucleotide sequences that can encode the amino acid sequence.

Finally, nucleic acid and amino acid sequence information for the loci and biomarkers of the present invention (e.g., biomarkers listed in Table 2 and the Examples) are well known in the art and readily available on publicly available databases, such as the National Center for Biotechnology Information (NCBI). For example, exemplary nucleic acid and amino acid sequences derived from publicly available sequence databases are provided below.

The nucleic acid and amino acid sequences of a representative, known human PD-1 biomarker is available to the public at the GenBank database under NM_005018.2 and NP_005009.2 (see also Ishida et al. (1992) *EMBO J.* 11:3887; Shinohara et al. (1994) *Genomics* 23:704; and U.S. Pat. No. 5,698,520). Nucleic acid and polypeptide sequences of PD-1 orthologs in organisms other than humans are well known and include, for example, monkey PD-1 (NM_001114358.1 and NP_001107830.1), mouse PD-1 (NM_0087998.2 and NP_032824.1), rat PD-1 (NM_001106927.1 and NP_001100397.1), chicken PD-1 (XM_422723.3 and XP_422723.2), cow PD-1 (NM_001083506.1 and NP_001076975.1), and dog PD-1 (XM_543338.3 and XP_543338.3).

At least five transcript (i.e., splice) variants encoding different human PD-L1 isoforms exist and are described herein. PD-L1 proteins generally comprise a signal sequence, an IgV domain, and an IgC domain. The sequence of human PD-L1 transcript variant 1 is the canonical sequence, all positional information described with respect to the remaining isoforms are determined from this sequence, and the sequences are available to the public at the GenBank database under NM_014143.3 and NP_054862.1. In this isoform, the signal sequence is shown from about amino acid 1 to about amino acid 18, the IgV domain is shown from about amino acid 19 to about amino acid 134, the IgC domain is shown from about amino acid 135 to about amino acid 227, the transmembrane domain is shown from about amino acids 239 to about amino acid 259, and the cytoplasmic domain is shown from about amino acid 260 to about amino acid 290. The combination of IgV and IgC domains (i.e., the extracellular domain) is sufficient to confer PD-L1's immunomodulatory (e.g., immunoinhibitory) function.

The sequences of human PD-L1 transcript variant 2 can be found under NM 001267706.1 and NP 001254635.1 and the encoded protein lacks an alternate in-frame excon in the 5' coding region compared to variant 1 (i.e., missing amino acid residues 17-130) so as to result in a shorter protein.

The sequences of human PD-L1 transcript variant 3 is provided herein and encodes a naturally occurring B7-4 soluble polypeptide, i.e., having a short hydrophilic domain and no transmembrane domain. In this isoform, the signal sequence is shown from about amino acid 1 to about amino acid 18, the IgV domain is shown from about amino acid 19 to about amino acid 134, the IgC domain of SEQ ID NO:2 is shown from about amino acid 135 to about amino acid 227, and the hydrophilic tail is shown from about amino acid 228 to about amino acid 245.

In addition, another soluble PD-L1 isoform exists having the amino acid sequence shown herein. This fourth PD-L1 isoform differs from that of the first PD-L1 isoform in that there is a K to D substitution at amino acid position 178 and amino acid residues 179-290 are deleted.

Moreover, another soluble PD-L1 isoform exists having the amino acid sequence of residues 1-227 encoded by transcript variant 1 and thereby only comprising a signal sequence, the IgV domain, and the IgC domain.

Nucleic acid and polypeptide sequences of known PD-L1 orthologs in organisms other than humans are well known and include, for example, monkey PD-L1 (NM_001083889.1 and NP_001077358.1), chimpanzee PD-L1 (XM_001140705.2 and XP_001140705.1), mouse PD-L1 (NM_021893.3 and NP_068693.1), rat PD-L1 (NM_001191954.1 and NP_001178883.1), chicken PD-L1 (XM_424811.3 and XP_424811.3), cow PD-L1 (NM_001163412.1 and NP_001156884.1), and dog PD-L1 (XM_541302.3 and XP_541302.3).

In contrast to the known human PD-L1 isoforms and orthologs thereof in other species, Table 2 provides representative nucleic acid and amino acid sequences for new human PD-L1 isoforms of the present invention. Orthologs from other species can be isolated and identified using standard molecular biology techniques described herein and are intended to be included within the PD-L1 isoforms of the present invention unless otherwise stated. In some embodiments, the PD-L1 isoforms of the present invention do not contain the signal sequence as such a sequence is usually cleaved prior to secretion of the polypeptide from the cell. In other embodiments, the PD-L1 isoforms of the present invention are soluble (i.e., do not comprise a transmembrane domain and comprise some or all of the IgV domain and/or the IgC domain from the extracellular portion of the full-length, membrane-bound PD-L1). In still other embodiments, the PD-L1 isoforms of the present invention are membrane-bound, but lack some of the intracellular portion of the full-length, membrane-bound PD-L1. In yet other embodiments, the PD-L1 isoforms further comprise heterologous sequences, such as Fc domains, protein tags, conjugated therapeutics, and the like.

TABLE 1

Known PD-1 and PD-L1 Nucleic Acid and Amino Acid Sequences

```
SEQ ID NO:1 Human PD-1 cDNA Sequence
     1 atgcagatcc cacaggcgcc ctggccagtc gtctgggcgg tgctacaact gggctggcgg
    61 ccaggatggt tcttagactc cccagacagg ccctggaacc cccccacctt ctccccagcc
   121 ctgctcgtgg tgaccgaagg ggacaacgcc accttcacct gcagcttctc caacacatcg
   181 gagagcttcg tgctaaactg gtaccgcatg agccccagca accagacgga caagctggcc
   241 gccttccccg aggaccgcag ccagcccggc caggactgcc gcttccgtgt cacacaactg
   301 cccaacgggc gtgacttcca catgagcgtg gtcagggccc ggcgcaatga cagcggcacc
   361 tacctctgtg gggccatctc cctggccccc aaggcgcaga tcaaagagag cctgcgggca
   421 gagctcaggg tgacagagag aagggcagaa gtgcccacag cccaccccag ccctcaccc
   481 aggccagccg gccagttcca aaccctggtg gttggtgtcg tgggcggcct gctgggcagc
   541 ctggtgctgc tagtctgggt cctggccgtc atctgctccc gggccgcacg agggacaata
   601 ggagccaggc gcaccggcca gcccctgaag gaggaccctc agccgtgcc tgtgttctct
   661 gtggactatg gggagctgga tttccagtgg cgagagaaga ccccggagcc ccccgtgccc
   721 tgtgtccctg agcagacgga gtatgccacc attgtctttc ctagcggaat gggcacctca
   781 tcccccgccc gcaggggctc agctgacggc cctcggagtg cccagccact gagggcctgag
   841 gatggacact gctcttggcc cctctga SEQ ID NO: 2 Human PD-1 Amino Acid Sequence
     1 mqipqapwpv vwavlqlgwr pgwfldspdr pwnpptfspa llvvtegdna tftcsfsnts
    61 esfvlnwyrm spsnqtdkla afpedrsqpg qdcrfrvtql pngrdfhmsv vrarrndsgt
   121 ylcgaislap kaqikeslra elrvterrae vptahpspsp rpagqfqtlv vgvvggllgs
   181 lvllvwvlav icsraargti garrtgqplk edpsavpvfs vdygeldfqw rektpeppvp
   241 cvpeqteyat ivfpsgmgts sparrgsadg prsaqplrpe dghcswpl SEQ ID NO: 3 Mouse PD-1 cDNA Sequence
     1 atgtgggtcc ggcaggtacc ctggtcattc acttgggctg tgctgcagtt gagctggcaa
    61 tcagggtggc ttctagaggt ccccaatggg ccctggaggt ccctcacctt ctacccagcc
   121 tggctcacag tgtcagaggg agcaaatgcc accttcacct gcagcttgtc caactggtcg
   181 gaggatctta tgctgaactg gaaccgcctg agtcccagca accagactga aaaacaggcc
   241 gccttctgta atggtttgag ccaacccgtc caggatgccc gcttccagat catacagctg
   301 cccaacaggc atgacttcca catgaacatc cttgacacac ggcgcaatga cagtggcatc
   361 tacctctgtg gggccatctc cctgcacccc aaggcaaaaa tcgaggagag ccctggagca
   421 gagctcgtgg taacagagag aatcctggag acctcaacaa gatatcccag ccctcgccc
   481 aaaccagaag gccggtttca aggcatggtc attggtatca tgagtgccct agtgggtatc
   541 cctgtattgc tgctgctggc ctgggcccta gctgtcttct gctcaacaag tatgtcagag
   601 gccagaggag ctggaagcaa ggacgacact ctgaaggagg agccttcagc agcacctgtc
   661 cctagtgtgg cctatgagga gctggacttc cagggacgag agaagacacc agagctccct
   721 accgcctgtg tgcacacaga atatgccacc attgtcttca ctgaagggct gggtgcctcg
   781 gccatgggac gtaggggctc agctgatgc ctgcagggtc ctcggcctcc aagacatgag
   841 gatggacatt gttcttggcc tctttga SEQ ID NO: 4 Mouse PD-1 Amino Acid Sequence
     1 mwvrqvpwsf twavlqlswq sgwllevpng pwrsltfypa wltvsegana tftcslsnws
    61 edlmlnwnrl spsnqtekqa afcnglsgpv qdarfqiiql pnrhdfhmni ldtrrndsgi
   121 ylcgaislhp kakieespga elvvterile tstrypspsp kpegrfqgmv igimsalvgi
   181 pvllllawal avfcstsmse argagskddt lkeepsaapv psvayeeldf qgrektpelp
   241 tacvhteyat ivfteglgas amgrrgsadg lqgprpprhe dghcswpl SEQ ID NO: 5 Human PD-L1 Variant 1 cDNA Sequence
     1 atgaggatat ttgctgtctt tatattcatg acctactggc atttgctgaa cgcatttact
    61 gtcacggttc ccaaggacct atatgtggta gagtatggta gcaatatgac aattgaatgc
   121 aaattcccag tagaaaaaca attagacctg gctgcactaa ttgtctattg ggaaatggag
   181 gataagaaca ttattcaatt tgtgcatgga gaggaagacc tgaaggttca gcatagtagc
   241 tacagacaga gggcccggct gttgaaggac cagctctccc tgggaaatgc tgcacttcag
   301 atcacagatg tgaaattgca ggatgcaggg gtgtaccgct gcatgatcag ctatggtggt
   361 gccgactaca agcgaattac tgtgaaagtc aatgccccat acaacaaaat caaccaaaga
   421 attttggttg tggatccagt cacctctgaa catgaactga catgtcaggc tgagggctac
   481 cccaaggccg aagtcatctg gacaagcagt gaccatcaag tcctgagtgg taagaccacc
   541 accaccaatt ccaagagaga ggagaagctt ttcaatgtga ccagcacact gagaatcaac
   601 acaacaacta atgagatttt ctactgcact tttaggagat tagatcctga ggaaaaccat
   661 acagctgaat tggtcatccc agaactacct ctggcacatc ctccaaatga aaggactcac
   721 ttggtaattc tgggagccat cttattatgc cttggtgtag cactgacatt catcttccgt
   781 ttaagaaaag ggagaatgat ggatgtgaaa aaatgtggca tccaagatac aaactcaaag
   841 aagcaaagtg atacacattt ggaggagacg taa
```

TABLE 1-continued

Known PD-1 and PD-L1 Nucleic Acid and Amino Acid Sequences

SEQ ID NO: 6 Human PD-L1 Isoform 1 Amino Acid Sequence
```
  1 mrifavfifm tywhllnaft vtvpkdlyvv eygsnmtiec kfpvekqldl aalivyweme
 61 dkniiqfvhg eedlkvqhss yrqrarllkd qlslgnaalq itdvklqdag vyrcmisygg
121 adykritvkv napynkinqr ilvvdpvtse heltcqaegy pkaeviwtss dhqvlsgktt
181 ttnskreekl fnvtstlrin tttneifyct frrldpeenh taelvipelp lahppnerth
241 lvilgaillc lgvaltfifr lrkgrmmdvk kcgiqdtnsk kqsdthleet
```

SEQ ID NO: 7 Human PD-L1 Variant 2 cDNA Sequence
```
  1 atgaggatat tgctgtctt tatattcatg acctactggc atttgctgaa cgccccatac
 61 aacaaaatca accaaagaat tttggttgtg gatccagtca cctctgaaca tgaactgaca
121 tgtcaggctg agggctaccc caaggccgaa gtcatctgga caagcagtga ccatcaagtc
181 ctgagtggta agaccaccac caccaattcc aagagagagg agaagctttt caatgtgacc
241 agcacactga gaatcaacac aacaactaat gagatttttct actgcacttt taggagatta
301 gatcctgagg aaaaccatac agctgaattg gtcatcccag aactacctct ggcacatcct
361 ccaaatgaaa ggactcactt ggtaattctg ggagccatct tattatgcct tggtgtagca
421 ctgacattca tcttccgttt aagaaaaggg agaatgatga tgtgaaaaa atgtggcatc
481 caagatacaa actcaaagaa gcaaagtgat acacatttgg aggagacgta a
```

SEQ ID NO: 8 Human PD-L1 Isoform 2 Amino Acid Sequence
```
  1 mrifavfifm tywhllnapy nkinqrilvv dpvtsehelt cqaegypkae viwtssdhqv
 61 lsgkttttns kreeklfnvt stlrintttn eifyctfrrl dpeenhtael vipelplahp
121 pnerthlvil gaillclgva ltfifrlrkg rmmdvkkcgi qdtnskkgsd thleet
```

SEQ ID NO: 9 Human PD-L1 Isoform 3 cDNA Sequence

| | | |
|---|---|---|
| gcttcccgag gctccgcacc agccgcgctt ctgtccgcct gcagggcatt ccagaaag | | 58 |

| | | |
|---|---|---|
| atg agg ata ttt gct gtc ttt ata ttc atg acc tac tgg cat ttg ctg | | 106 |
| Met Arg Ile Phe Ala Val Phe Ile Phe Met Thr Tyr Trp His Leu Leu | | |
| 1               5                   10                  15 | | |

| | | |
|---|---|---|
| aac gca ttt act gtc acg gtt ccc aag gac cta tat gtg gta gag tat | | 154 |
| Asn Ala Phe Thr Val Thr Val Pro Lys Asp Leu Tyr Val Val Glu Tyr | | |
|         20                  25                  30 | | |

| | | |
|---|---|---|
| ggt agc aat atg aca att gaa tgc aaa ttc cca gta gaa aaa caa tta | | 202 |
| Gly Ser Asn Met Thr Ile Glu Cys Lys Phe Pro Val Glu Lys Gln Leu | | |
|     35                  40                  45 | | |

| | | |
|---|---|---|
| gac ctg gct gca cta att gtc tat tgg gaa atg gag gat aag aac att | | 250 |
| Asp Leu Ala Ala Leu Ile Val Tyr Trp Glu Met Glu Asp Lys Asn Ile | | |
| 50                  55                  60 | | |

| | | |
|---|---|---|
| att caa ttt gtg cat gga gag gaa gac ctg aag gtt cag cat agt agc | | 298 |
| Ile Gln Phe Val His Gly Glu Glu Asp Leu Lys Val Gln His Ser Ser | | |
| 65              70                  75                  80 | | |

| | | |
|---|---|---|
| tac aga cag agg gcc cgg ctg ttg aag gac cag ctc tcc ctg gga aat | | 346 |
| Tyr Arg Gln Arg Ala Arg Leu Leu Lys Asp Gln Leu Ser Leu Gly Asn | | |
|             85                  90                  95 | | |

| | | |
|---|---|---|
| gct gca ctt cag atc aca gat gtg aaa ttg cag gat gca ggg gtg tac | | 394 |
| Ala Ala Leu Gln Ile Thr Asp Val Lys Leu Gln Asp Ala Gly Val Tyr | | |
|                 100                 105                 110 | | |

| | | |
|---|---|---|
| cgc tgc atg atc agc tat ggt ggt gcc gac tac aag cga att act gtg | | 442 |
| Arg Cys Met Ile Ser Tyr Gly Gly Ala Asp Tyr Lys Arg Ile Thr Val | | |
|     115                 120                 125 | | |

| | | |
|---|---|---|
| aaa gtc aat gcc cca tac aac aaa atc aac caa aga att ttg gtt gtg | | 490 |
| Lys Val Asn Ala Pro Tyr Asn Lys Ile Asn Gln Arg Ile Leu Val Val | | |
| 130                 135                 140 | | |

| | | |
|---|---|---|
| gat cca gtc acc tct gaa cat gaa ctg aca tgt cag gct gag ggc tac | | 538 |
| Asp Pro Val Thr Ser Glu His Glu Leu Thr Cys Gln Ala Glu Gly Tyr | | |
| 145                 150                 155                 160 | | |

| | | |
|---|---|---|
| ccc aag gcc gaa gtc atc tgg aca agc agt gac cat caa gtc ctg agt | | 586 |
| Pro Lys Ala Glu Val Ile Trp Thr Ser Ser Asp His Gln Val Leu Ser | | |
|                 165                 170                 175 | | |

| | | |
|---|---|---|
| ggt aag acc acc acc acc aat tcc aag aga gag gag aag ctt ttc aat | | 634 |
| Gly Lys Thr Thr Thr Thr Asn Ser Lys Arg Glu Glu Lys Leu Phe Asn | | |
|             180                 185                 190 | | |

| | | |
|---|---|---|
| gtg acc agc aca ctg aga atc aac aca aca act aat gag att ttc tac | | 682 |
| Val Thr Ser Thr Leu Arg Ile Asn Thr Thr Thr Asn Glu Ile Phe Tyr | | |
|         195                 200                 205 | | |

TABLE 1-continued

Known PD-1 and PD-L1 Nucleic Acid and Amino Acid Sequences

```
tgc act ttt agg aga tta gat cct gag gaa aac cat aca gct gaa ttg      730
Cys Thr Phe Arg Arg Leu Asp Pro Glu Glu Asn His Thr Ala Glu Leu
    210             215                 220 gtc atc cca ggt aat att ctg aat gtg tcc att aaa ata tgt cta aca      778
Val Ile Pro Gly Asn Ile Leu Asn Val Ser Ile Lys Ile Cys Leu Thr
225             230                 235                 240 ctg tcc cct agc acc tagcatgatg tctgcctatc atagtcattc agtgattgtt     833
Leu Ser Pro Ser Thr
                245 gaataaatga atgaatgaat aacactatgt ttacaaaata tatcctaatt cctcacctcc   893 attcatccaa accatattgt tacttaataa acattcagca gatatttatg gaataaaaaa   953 aaaaaaaaaa aaaaa                                                    968
```

SEQ ID NO: 10 Human PD-L1 Isoform 3 Amino Acid Sequence

```
Met Arg Ile Phe Ala Val Phe Ile Phe Met Thr Tyr Trp His Leu Leu
 1               5                  10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
            35                  40                  45

Asp Leu Ala Ala Leu Ile Val Tyr Trp Glu Met Glu Asp Lys Asn Ile
        50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
            115                 120                 125

Lys Val Asn Ala Pro Tyr Asn Lys Ile Asn Gln Arg Ile Leu Val Val
        130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Asn Glu Ile Phe Tyr
            195                 200                 205

Cys Thr Phe Arg Arg Leu Asp Pro Glu Glu Asn His Thr Ala Glu Leu
        210                 215                 220

Val Ile Pro Gly Asn Ile Leu Asn Val Ser Ile Lys Ile Cys Leu Thr
225                 230                 235                 240

Leu Ser Pro Ser Thr
                245
```

SEQ ID NO: 11 Human PD-L1 Isoform 4 Amino Acid Sequence

```
  1 MRIFAVFIFMTYWHLLNAFTVTVPKDLYVVEYGSNMTIECKFPVEKQLDLAALIVYWEME
 61 DKNIIQFVHGEEDLKVQHSSYRQRARLLKDQLSLGNAALQITDVKLQDAGVYRCMISYGG
121 ADYKRITVKVNAPYNKINQRILVVDPVTSEHELTCQAEGYPKAEVIWTSSDHQVLSGD
```

SEQ ID NO: 12 Human PD-L1 Isoform 5 cDNA Sequence

```
ATGAGGATATTTGCTGTCTTTATATTCATGACCTACTGGCATTTGCTGAACGCATTTACTGTCACGGTTCCCAAG
GACCTATATGTGGTAGAGTATGGTAGCAATATGACAATTGAATGCAAATTCCCAGTAGAAAACAATTAGACCTGG
CTGCACTAATTGTCTATTGGGAAATGGAGGATAAGAACATTATTCAATTTGTGCATGGAGAGGAAGACCTGAAGGT
TCAGCATAGTAGCTACAGACAGAGGGCCCGGCTGTTGAAGGACCAGCTCTCCCTGGGAAATGCTGCACTTCAGATC
ACAGATGTGAAATTGCAGGATGCAGGGGTGTACCGCTGCATGATCAGCTATGGTGGTGCCGACTACAAGCGAATTA
```

TABLE 1-continued

Known PD-1 and PD-L1 Nucleic Acid and Amino Acid Sequences

CTGTGAAAGTCAATGCCCCATACAACAAAATCAACCAAAGAATTTTGGTTGTGGATCCAGTCACCTCTGAACATGA
ACTGACATGTCAGGCTGAGGGCTACCCCAAGGCCGAAGTCATCTGGACAAGCAGTGACCATCAAGTCCTGAGTGGT
AAGACCACCACCACCAATTCCAAGAGAGAGGAGAAGCTTTTCAATGTGACCAGCACACTGAGAATCAACACAACAA
CTAATGAGATTTTCTACTGCACTTTTAGGAGATTAGATCCTGAGGAAAACCATACAGCTGAATTGGTCATCCCATA
A

SEQ ID NO: 13 Human PD-L1 Isoform 5 Amino Acid Sequence
M R I F A V F I F M T Y W H L L N A F T V T V P K D L Y V V E Y G S N M T I
E C K F P V E K Q L D L A A L I V Y W E M E D K N I I Q F V H G E E D L K V
Q H S S Y R Q R A R L L K D Q L S L G N A A L Q I T D V K L Q D A G V Y R C
M I S Y G G A D Y K R I T V K V N A P Y N K I N Q R I L V V D P V T S E H E
L T C Q A E G Y P K A E V I W T S S D H Q V L S G K T T T T N S K R E E K L
F N V T S T L R I N T T T N E I F Y C T F R R L D P E E N H T A E L V I P
Stop SEQ ID NO: 14 Mouse PD-L1 cDNA Sequence
        1 atgaggatat ttgctggcat tatattcaca gcctgctgtc acttgctacg ggcgtttact
       61 atcacggctc caaaggactt gtacgtggtg gagtatggca gcaacgtcac gatggagtgc
      121 agattccctg tagaacggga gctggacctg cttgcgttag tggtgtactg ggaaaaggaa
      181 gatgagcaag tgattcagtt tgtggcagga gaggaggacc ttaagcctca gcacagcaac
      241 ttcaggggga gagcctcgct gccaaaggac cagcttttga agggaaatgc tgcccttcag
      301 atcacagacg tcaagctgca ggacgcaggc gtttactgct gcataatcag ctacggtggt
      361 gcggactaca agcgaatcac gctgaaagtc aatgcccccat accgcaaaat caaccagaga
      421 atttccgtgg atccagccac ttctgagcat gaactaatat gtcaggccga gggttatcca
      481 gaagctgagg taatctggac aaacagtgac caccaacccg tgagtgggaa gagaagtgtc
      541 accacttccc ggacagaggg gatgcttctc aatgtgacca gcagtctgag ggtcaacgcc
      601 acagcgaatg atgttttcta ctgtacgttt tggagatcac agccagggca aaaccacaca
      661 gcggagctga tcatcccaga actgcctgca cacatacctc cacagaacag gactcactgg
      721 gtgcttctgg gatccatcct gttgttcctc attgtagtgt ccacggtcct cctcttcttg
      781 agaaaacaag tgagaatgct agatgtggag aaatgtggcg ttgaagatac aagctcaaaa
      841 aaccgaaatg atacacaatt cgaggagacg taa SEQ ID NO: 15 Mouse PD-L1 Amino Acid Sequence
        1 mrifagiift acchllraft itapkdlyvv eygsnvtmec rfpvereldl lalvvyweke
       61 deqviqfvag eedlkpqhsn frgraslpkd qllkgnaalq itdvklqdag vyccisygg
      121 adykritlkv napyrkinqr isvdpatseh elicqaegyp eaeviwtnsd hqpvsgkrsv
      181 ttsrtegmll nvtsslrvna tandvfyctf wrsqpgqnht aeliipelpa thppqnrthw
      241 vllgsillfl ivvstvllfl rkqvrmldve kcgvedtssk nrndtqfeet

TABLE 2

Exemplary PD-L1 Nucleic Acid and Amino Acid
Biomarker Sequences of the Present Invention SEQ ID NO: 16
Human PD-L1-1 Isoform cDNA Sequence
ATGAGGATATTTGCTGTCTTTATATTCATGACCTACTGGCATTTGCTGAACGCATTTACTGTCACGGTTCCCAAGG

ACCTATATGTGGTAGAGTATGGTAGCAATATGACAATTGAATGCAAATTCCCAGTAGAAAAACAATTAGACCTGGC

TGCACTAATTGTCTATTGGGAAATGGAGGATAAGAACATTATTCAATTTGTGCATGGAGAGGAAGACCTGAAGGTT

CAGCATAGTAGCTACAGACAGAGGGCCCGGCTGTTGAAGGACCAGCTCTCCCTGGGAAATGCTGCACTTCAGATCA

CAGATGTGAAATTGCAGGATGCAGGGGTGTACCGCTGCATGATCAGCTATGGTGGTGCCGACTACAAGCGAATTAC

TGTGAAAGTCAATGCCCCATACAACAAAATCAACCAAAGAATTTTGGTTGTGGATCCAGTCACCTCTGAACATGAA

CTGACATGTCAGGCTGAGGGCTACCCCAAGGCCGAAGTCATCTGGACAAGCAGTGACCATCAAGTCCTGAGTGGTA

AGACCACCACCACCAATTCCAAGAGAGAGGAGAAGCTTTTCAATGTGACCAGCACACTGAGAATCAACACAACAAC

TAATGAGATTTTCTACTGCACTTTTAGGAGATTAGATCCTGAGGAAAACCATACAGCTGAATTGGTCATCCCAGAA

CTACCTCTGGCACATCCCCAAATGAAAGGACTCACTTGGTAATTCTGGGAGCCATCTTATTATGCCTTGGTGTAG

CACTGACATTCATCTTCCGTTTAAGAAAAGATACACATTTGGAGGAGACGTAA

SEQ ID NO: 17
Human PD-L1-1 Isoform Amino Acid Sequence
Met R I F A V F I F Met T Y W H L L N A F T V T V P K D L Y V V E Y G S N Met T I E C K F P V E K Q L D L A A L I V Y W E Met E D K N I I Q F V H G E E D L K V Q H S S Y R Q R A R L L K D Q L S L G N A A L Q I T D V K L Q D A G V Y R C Met I S Y TABLE 2-continued Exemplary PD-L1 Nucleic Acid and Amino Acid
Biomarker Sequences of the Present Invention G G A D Y K R I T V K V N A P Y N K I N Q R I L V V D P V T S E H E L T C Q A E G
Y P K A E V I W T S S D H Q V L S G K T T T T N S K R E E K L F N V T S T L R I N
T T T N E I F Y C T F R R L D P E E N H T A E L V I P E L P L A H P P N E R T H L
V I L G A I L L C L G V A L T F I F R L R K D T H L E E T SEQ ID NO: 18
Human PD-L1-3 Isoform cDNA Sequence
ATGAGGATATTTGCTGTCTTTATATTCATGACCTACTGGCATTTGCTGAACGCATTTACTGTCACGGTTCCCAAGGACCT
ATATGTGGTAGAGTATGGTAGCAATATGACAATTGAATGCAAATTCCCAGTAGAAAAACAATTAGACCTGGCTGCACTAA
TTGTCTATTGGGAAATGGAGGATAAGAACATTATTCAATTTGTGCATGGAGAGGAAGACCTGAAGGTTCAGCATAGTAGC
TACAGACAGAGGGCCCGGCTGTTGAAGGACCAGCTCTCCCTGGGAAATGCTGCACTTCAGATCACAGATGTGAAATTGCA
GGATGCAGGGGTGTACCGCTGCATGATCAGCTATGGTGGTGCCGACTACAAGCGAATTACTGTGAAAGTCAATGCCCCAT
ACAACAAAATCAACCAAAGAATTTTGGTTGTGGATCCAGTCACCTCTGAACATGAACTGACATGTCAGGCTGAGGGCTAC
CCCAAGGCCGAAGTCATCTGGACAAGCAGTGACCATCAAGTCCTGAGTGGAGATTAGATCCTGAGGAAAACCATACAGCT
GAATTGGTCATCCCAGAACTACCTCTGGCACATCCTCCAAATGAAAGGACTCACTTGGGAGAATGATGGATGTGAAAAAA
TGTGGCATCCAAGATACAAACTCAAAGAAGCAAAGTGATACAcATTTGGAGGAGACGTAA SEQ ID NO: 19
Human PD-L1-3 Isoform Amino Acid Sequence
Met R I F A V F I F Met T Y W H L L N A F T V T V P K D L Y V V E Y G S N
Met T I E C K F P V E K Q L D L A A L I V Y W E Met E D K N I I Q F V H G E
E D L K V Q H S S Y R Q R A R L L K D Q L S L G N A A L Q I T D V K L Q D A
G V Y R C Met I S Y G G A D Y K R I T V K V N A P Y N K I N Q R I L V V D P
V T S E H E L T C Q A E G Y P K A E V I W T S S D H Q V L S G D Stop I L R K
T I Q L N W S S Q N Y L W H I L Q Met K G L T W E N D G C E K Met W H P R Y
K L K E A K Stop Y T F G G D SEQ ID NO: 20
Human PD-L1-9 Isoform cDNA Sequence
ATGAGGATATTTGCTGTCTTTATATTCATGACCTACTGGCATTTGCTGAACGCATTTACTGTCACGGTTCCCAAGGACCT
ATATGTGGTAGAGTATGGTAGCAATATGACAATTGAATGCAAATTCCCAGTAGAAAAACAATTAGACCTGGCTGCACTAA
TTGTCTATTGGGAAATGGAGGATAAGAACATTATTCAATTTGTGCATGGAGAGGAAGACCTGAAGGTTCAGCATAGTAGC
TACAGACAGAGGGCCCGGCTGTTGAAGGACCAGCTCTCCCTGGGAAATGCTGCACTTCAGATCACAGATGTGAAATTGCA
GGATGCAGGGGTGTACCGCTGCATGATCAGCTATGGTGGTGCCGACTACAAGCGAATTACTGTGAAAGTCAATGCCCCAT
ACAACAAAATCAACCAAAGAATTTTGGTTGTGGATCCAGTCACCTCTGAACATGAACTGACATGTCAGGCTGAGGGCTAC
CCCAAGGCCGAAGTCATCTGGACAAGCAGTGACCATCAAGTCCTGAGTGGTAAGACCACCACCACCAATTCCAAGAGAGA
GGAGAAGCTTTTCAATGTGACCAGCACACTGAGAATCAACACAACAACTAATGAGATTTTCTACTGCACTTTTAGGAGAT
TAGATCCTGAGGAAAACCATACAGCTGAATTGGTCATCCCAGAA SEQ ID NO: 21
Human PD-L1-9 Isoform Amino Acid Sequence
*Met R I F A V F I F Met T Y W H L L N A F T V T V P K D L Y V V E Y G S N*
*Met T I E C K F P V E K Q L D L A A L I V Y W E Met E D K N I I Q F V H G E*
*E D L K V Q H S S Y R Q R A R L L K D Q L S L G N A A L Q I T D V K L Q D A*
*G V Y R C Met I S Y G G A D Y K R I T V K V N A P Y N K I N Q R I L V V D P*
*V T S E H E L T C Q A E G Y P K A E V I W T S S D H Q V L S G K T T T T N S*

TABLE 2-continued

Exemplary PD-L1 Nucleic Acid and Amino Acid
Biomarker Sequences of the Present Invention

*K R E E K L F N V T S T IR I N T T T N E I F Y C TF R R L D P E E N H T A*

Stop W Met Stop K N V A S K I Q T

Q R S K V I H I W R R R

SEQ ID NO: 22
Human PD-L1-12 Isoform cDNA Sequence
ATGAGGATATTTGCTGTCTTTATATTCATGACCTACTGGCATTTGCTGAACGCATTTACTGTCACGGTTCCCAAGGACCT

ATATGTGGTAGAGTATGGTAGCAATATGACAATTGAATGCAAATTCCCAGTAGAAAAACAATTAGACCTGGCTGCACTAA

TTGTCTATTGGGAAATGGAGGATAAGAACATTATTCAATTTGTGCATGGAGAGGAAGACCTGAAGGTTCAGCATAGTAGC

TACAGACAGAGGGCCCGGCTGTTGAAGGACCAGCTCTCCCTGGGAAATGCTGCACTTCAGATCACAGATGTGAAATTGCA

GGATGCAGGGGTGTACCGCTGCATGATCAGCTATGGTGGTGCCGACTACAAGCGAATTACTGTGAAAGTCAATGCCCCAT

ACAACAAATCAACCAAAGAATTTTGGTTGTGGATCCAGTCACCTCTGAACATGAACTGACATGTCAGGCTGAGGGCTAC

CCCAAGGCCGAAGTCATCTGGACAAGCAGTGACCATCAAGTCCTGAGTGGAGATTAGATCCTGAGGAAAACCATACAGCT

GAATTGGTCATCCCAGAACTACCTCTGGCACATCCTCCAAATGAAAGGACTCACTTGGTAATTCTGGGAGCCATCTTATT

ATGCCTTGGTGTAGCACTGACATTCATCTTCCGTTTAAGAAAAGGGAGAATGATGGATGTGAAAAAATGTGGCATCCAAG

ATACAAACTCAAAGAAGCAAAGTGATACAcATTTGGAGGAGACGTAA

SEQ ID NO: 23
Human PD-L1-12 Isoform Amino Acid Sequence
*Met R I F A V F I F MetT Y W H L L N A F T V T V PK D L Y V V E Y G S N*

*Met T I E C K F P V E KQ L D L A A L I V Y W E Met E D K N I I Q F V H G E*

*E D L K V Q H S S Y R QR A R L L K D Q L P L G N AA L Q I T D V K L Q D A*

*G V Y R C Met I S Y G GA D Y K R I T V K V N A P YN K I N Q R I L V V D P*

*V T S E H E L T C Q A EG Y P K A E V I W T S S D EQ V L S G D* Stop I L R K T I Q L N W S S Q N Y L W H I L Q Met K G L T W Stop F W E P S Y Y A L V Stop H Stop H S S S V Stop E K G E Stop W Met Stop K N V A S K I Q T Q R S K

V I H I W R R R

Underlined nucleic acid sequences represent alterations relative to full-length, membrane-bound PD-L1. Italicized and bold polypeptide sequences represent the amino acid sequence produced from the corresponding cDNA sequence, whereas the entire polypeptide sequence is shown to indicate translation through stop codons.

Included in Table 2 are nucleic acid molecules comprising a nucleic acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with a nucleic acid sequence of SEQ ID NO: 16, 18, 20, and/or 22 listed in Table 2. Such nucleic acid molecules can encode a polypeptide having a PD-L1 function described herein.

Included in Table 2 are polypeptide molecules comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with an amino acid sequence of SEQ ID NO: 17, 19, 21, and/or 23 listed in Table 2 (e.g., shaded amino acid sequences). Such polypeptides can have a PD-L1 function described herein.

II. PD-L1 Isoform Nucleic Acids, Polypeptides, and Antibodies, Related Agents, and Compositions Novel agents and compositions of the present invention are provided herein. Such agents and compositions can also be used for the diagnosis, prognosis, prevention, and treatment of melanoma and cancer subtypes thereof. For example, such agents and compositions can detect and/or modulate, e.g., down-regulate, expression and/or activity of gene products or fragments thereof encoded by biomarkers of the invention, including the biomarkers listed in Table 2 and the Examples. Exemplary agents include antibodies, small molecules, peptides, peptidomimetics, natural ligands, and derivatives of natural ligands, that can either bind and/or activate or inhibit protein biomarkers of the invention, including the biomarkers listed in Table 2 and the Examples, or fragments thereof; RNA interference, antisense, nucleic acid aptamers, etc. that can downregulate the expression and/or activity of the biomarkers of the invention, including the biomarkers listed in Table 2 and the Examples, or fragments thereof.

a. Isolated Nucleic Acids

In one embodiment, isolated nucleic acid molecules that specifically hybridize with or encode one or more biomarkers listed in Table 2 and the Examples, or biologically active portions thereof, are presented. The nucleic acid molecules can be all of the nucleic acid molecules shown in Table 2 or any subset thereof (e.g., the combination of PD-L1-1, PD-L1-9, and PD-L1-12 and excluding PD-L1-3). As used herein, the term "nucleic acid molecule" is intended to include DNA molecules (i.e., cDNA or genomic DNA) and RNA molecules (i.e., mRNA) and analogs of the DNA or RNA generated using nucleotide analogs. The nucleic acid molecule can be single-stranded or double-stranded, but preferably is double-stranded DNA. An "isolated" nucleic acid molecule is one which is separated from other nucleic acid molecules which are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated nucleic acid molecules corresponding to the one or more biomarkers listed in Table 2 and the Examples can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived (i.e., melanoma cell). Moreover, an "isolated" nucleic acid molecule, such as a cDNA molecule, can be substantially free of other cellular material, or culture medium when produced by recombinant techniques, or chemical precursors or other chemicals when chemically synthesized.

A nucleic acid molecule of the present invention, e.g., a nucleic acid molecule having the nucleotide sequence of one or more biomarkers listed in Table 2 and the Examples or a nucleotide sequence which is at least about 50%, preferably at least about 60%, more preferably at least about 70%, yet more preferably at least about 80%, still more preferably at least about 90%, and most preferably at least about 95% or more (e.g., about 98%) homologous to the nucleotide sequence of one or more biomarkers listed in Table 2 and the Examples or a portion thereof (i.e., 100, 200, 300, 400, 450, 500, or more nucleotides), can be isolated using standard molecular biology techniques and the sequence information provided herein. For example, a human cDNA can be isolated from a human cell line (from Stratagene, La Jolla, Calif., or Clontech, Palo Alto, Calif.) using all or portion of the nucleic acid molecule, or fragment thereof, as a hybridization probe and standard hybridization techniques (i.e., as described in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989). Moreover, a nucleic acid molecule encompassing all or a portion of the nucleotide sequence of one or more biomarkers listed in Table 2 and the Examples or a nucleotide sequence which is at least about 50%, preferably at least about 60%, more preferably at least about 70%, yet more preferably at least about 80%, still more preferably at least about 90%, and most preferably at least about 95% or more homologous to the nucleotide sequence, or fragment thereof, can be isolated by the polymerase chain reaction using oligonucleotide primers designed based upon the sequence of the one or more biomarkers listed in Table 2 and the Examples, or fragment thereof, or the homologous nucleotide sequence. For example, mRNA can be isolated from melanoma cells (i.e., by the guanidinium-thiocyanate extraction procedure of Chirgwin et al. (1979) *Biochemistry* 18: 5294-5299) and cDNA can be prepared using reverse transcriptase (i.e., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for PCR amplification can be designed according to well-known methods in the art. A nucleic acid of the invention can be amplified using cDNA or, alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to the nucleotide sequence of one or more biomarkers listed in Table 2 and the Examples can be prepared by standard synthetic techniques, i.e., using an automated DNA synthesizer.

Probes based on the nucleotide sequences of one or more biomarkers listed in Table 2 and the Examples can be used to detect transcripts or genomic sequences encoding the same or homologous proteins. In preferred embodiments, the probe further comprises a label group attached thereto, i.e., the label group can be a radioisotope, a fluorescent compound, an enzyme, or an enzyme co-factor. Such probes can be used as a part of a diagnostic test kit for identifying cells or tissue which express one or more biomarkers listed in Table 2 and the Examples, such as by measuring a level of nucleic acid in a sample of cells from a subject, i.e., detecting mRNA levels of one or more biomarkers listed in Table 2 and the Examples.

Nucleic acid molecules encoding proteins corresponding to one or more biomarkers listed in Table 2 and the Examples from different species are also contemplated. For example, rat or monkey cDNA can be identified based on the nucleotide sequence of a human and/or mouse sequence and such sequences are well known in the art. In one embodiment, the nucleic acid molecule(s) of the present invention encodes a protein or portion thereof which includes an amino acid sequence which is sufficiently homologous to an amino acid sequence of one or more biomarkers listed in Table 2 and the Examples, such that the protein or portion thereof modulates (e.g., enhance), one or more of the following biological activities: a) binding to the biomarker; b) modulating the copy number of the biomarker; c) modulating the expression level of the biomarker; and d) modulating the activity level of the biomarker. Such homologous nucleic acids and encoded polypeptides can be readily produced by the ordinarily skilled artisan based on the sequence information provided in Table 2. As described above, it is well known in the art that the IgV and IgC domains mediate PD-L1's immunoinhibitory activity by binding to PD-L1. For example, Lin et al. (2011) *Proc. Natl. Acad. Sci. USA* 105:3011-3016 disclose the structure-function relationship between human PD-L1 IgV and IgC domain residues and human PD-1 binding related to immunoinhibitory function, which is reproduced herein as Table 3.

TABLE 3

Contacts between PD-1 and PD-L1 (distances < 4.0 Å)

| PD-1 contact residue | PD-1 residue location | PD-L1 contact residue | PD-L1 residue location |
|---|---|---|---|
| M 64 | C stand | A121 | G stand |
| N 66 | C strand | A121, D122 | G strand |
| N 68 | C strand | Y123 | G strand |
| S 73 | CC loop | D26 | A strand |
| N 74 | CC' loop | R125 | G strand |
| Q 75 | CC' loop | D26, K124, R125 | A strand, G strand |
| T 76 | C' strand | Y123, K124, R125 | G strand |
| K 78 | C' strand | F19, A121, D122 | N terminus, G strand |
| V 910 | C'D loop | T20 | N terminus |

TABLE 3-continued

Contacts between PD-1 and PD-L1 (distances < 4.0 Å)

| PD-1 contact residue | PD-1 residue location | PD-L1 contact residue | PD-L1 residue location |
|---|---|---|---|
| L 122 | F strand | R125 | G strand |
| G 124 | F strand | Y123 | G strand |
| I 126 | F strand | Y123 | G strand |
| L 128 | FG (CDR3) loop | I54, M115, S117 | C strand, F strand |
| P 130 | FG (CDR3) loop | Q66 | C' strand |
| K 131 | FG (CDR3) loop | Q66 | C' strand |
| A 132 | FG (CDR3) loop | Y56, Q66 | C strand, C' strand |
| I 134 | G strand | Y56, M115 | C strand, F strand |
| E 136 | G strand | R113, Y123, R125 | F strand, G strand |

As used herein, the language "sufficiently homologous" refers to proteins or portions thereof which have amino acid sequences which include a minimum number of identical or equivalent (e.g., an amino acid residue which has a similar side chain as an amino acid residue in one or more biomarkers listed in Table 2 and the Examples, or fragment thereof) amino acid residues to an amino acid sequence of the biomarker, or fragment thereof, such that the protein or portion thereof modulates (e.g., enhance) one or more of the following biological activities: a) binding to the biomarker; b) modulating the copy number of the biomarker; c) modulating the expression level of the biomarker; and d) modulating the activity level of the biomarker.

In another embodiment, the protein is at least about 50%, preferably at least about 60%, more preferably at least about 70%, 75%, 80%, 85%, 90%, 91%, 92%, 93%, 94%, 95%, 96%, 97%, 98%, 99% or more homologous to the entire amino acid sequence of the biomarker, or a fragment thereof.

Portions of proteins encoded by nucleic acid molecules of the one or more biomarkers listed in Table 2 and the Examples are preferably biologically active portions of the protein. As used herein, the term "biologically active portion" of one or more biomarkers listed in Table 2 and the Examples is intended to include a portion, e.g., a domain/motif, that has one or more of the biological activities of the full-length protein. For example, the IgC and/or IgV domains of a biomarkers listed in Table 2 can be completely conserved while variation can occur in other portions of the biomarker. Alternatively, the IgC and/or IgV domain residues that make contact with a natural PD-L1 receptor (e.g., PD-1 or B7-1) can be completely conserved while variation can occur in other portions of the biomarker.

Standard binding assays, e.g., immunoprecipitations and yeast two-hybrid assays, as described herein, or functional assays, e.g., RNAi or overexpression experiments, can be performed to determine the ability of the protein or a biologically active fragment thereof to maintain a biological activity of the full-length protein.

The invention further encompasses nucleic acid molecules that differ from the nucleotide sequence of the one or more biomarkers listed in Table 2 and the Examples, or fragment thereof due to degeneracy of the genetic code and thus encode the same protein as that encoded by the nucleotide sequence, or fragment thereof. In another embodiment, an isolated nucleic acid molecule of the invention has a nucleotide sequence encoding a protein having an amino acid sequence of one or more biomarkers listed in Table 2 and the Examples, or fragment thereof, or a protein having an amino acid sequence which is at least about 70%, 75%, 80%, 85%, 90%, 91%, 92%, 93%, 94%, 95%, 96%, 97%, 98%, 99% or more homologous to the amino acid sequence of the one or more biomarkers listed in Table 2 and the Examples, or fragment thereof In another embodiment, a nucleic acid encoding a polypeptide consists of nucleic acid sequence encoding a portion of a full-length fragment of interest that is less than 195, 190, 185, 180, 175, 170, 165, 160, 155, 150, 145, 140, 135, 130, 125, 120, 115, 110, 105, 100, 95, 90, 85, 80, 75, or 70 amino acids in length.

It will be appreciated by those skilled in the art that DNA sequence polymorphisms that lead to changes in the amino acid sequences of the one or more biomarkers listed in Table 2 and the Examples may exist within a population (e.g., a mammalian and/or human population). Such genetic polymorphisms may exist among individuals within a population due to natural allelic variation. As used herein, the terms "gene" and "recombinant gene" refer to nucleic acid molecules comprising an open reading frame encoding one or more biomarkers listed in Table 2 and the Examples, preferably a mammalian, e.g., human, protein. Such natural allelic variations can typically result in 1-5% variance in the nucleotide sequence of the one or more biomarkers listed in Table 2 and the Examples. Any and all such nucleotide variations and resulting amino acid polymorphisms in the one or more biomarkers listed in Table 2 and the Examples that are the result of natural allelic variation and that do not alter the functional activity of the one or more biomarkers listed in Table 2 and the Examples are intended to be within the scope of the invention. Moreover, nucleic acid molecules encoding one or more biomarkers listed in Table 2 and the Examples from other species.

In addition to naturally-occurring allelic variants of the one or more biomarkers listed in Table 2 and the Examples sequence that may exist in the population, the skilled artisan will further appreciate that changes can be introduced by mutation into the nucleotide sequence, or fragment thereof, thereby leading to changes in the amino acid sequence of the encoded one or more biomarkers listed in Table 2 and the Examples, without altering the functional ability of the one or more biomarkers listed in Table 2 and the Examples. For example, nucleotide substitutions leading to amino acid substitutions at "non-essential" amino acid residues can be made in the sequence, or fragment thereof. A "non-essential" amino acid residue is a residue that can be altered from the wild-type sequence of the one or more biomarkers listed in Table 2 and the Examples without altering the activity of the one or more biomarkers listed in Table 2 and the Examples, whereas an "essential" amino acid residue is required for the activity of the one or more biomarkers listed in Table 2 and the Examples. Other amino acid residues, however, (e.g., those that are not conserved or only semi-conserved between mouse and human) may not be essential for activity and thus are likely to be amenable to alteration without altering the activity of the one or more biomarkers listed in Table 2 and the Examples.

The term "sequence identity or homology" refers to the sequence similarity between two polypeptide molecules or between two nucleic acid molecules. When a position in both of the two compared sequences is occupied by the same base or amino acid monomer subunit, e.g., if a position in each of two DNA molecules is occupied by adenine, then the molecules are homologous or sequence identical at that position. The percent of homology or sequence identity between two sequences is a function of the number of matching or homologous identical positions shared by the two sequences divided by the number of positions compared ×100. For example, if 6 of 10, of the positions in two sequences are the same then the two sequences are 60% homologous or have 60% sequence identity. By way of example, the DNA sequences ATTGCC and TATGGC share 50% homology or sequence identity. Generally, a comparison is made when two sequences are aligned to give maximum homology. Unless otherwise specified "loop out regions", e.g., those arising from, from deletions or insertions in one of the sequences are counted as mismatches.

The comparison of sequences and determination of percent homology between two sequences can be accomplished using a mathematical algorithm. Preferably, the alignment can be performed using the Clustal Method. Multiple alignment parameters include GAP Penalty=10, Gap Length Penalty=10. For DNA alignments, the pairwise alignment parameters can be Htuple=2, Gap penalty=5, Window=4, and Diagonal saved=4. For protein alignments, the pairwise alignment parameters can be Ktuple=1, Gap penalty=3, Window=5, and Diagonals Saved=5.

In a preferred embodiment, the percent identity between two amino acid sequences is determined using the Needleman and Wunsch (*J. Mol. Biol.* (48):444-453 (1970)) algorithm which has been incorporated into the GAP program in the GCG software package (available online), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available online), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (CABIOS, 4:11-17 (1989)) which has been incorporated into the ALIGN program (version 2.0) (available online), using a PAM120 weight residue table, a gap length penalty of 12 and a gap penalty of 4.

An isolated nucleic acid molecule encoding a protein homologous to one or more biomarkers listed in Table 2 and the Examples, or fragment thereof, can be created by introducing one or more nucleotide substitutions, additions or deletions into the nucleotide sequence, or fragment thereof, or a homologous nucleotide sequence such that one or more amino acid substitutions, additions or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), branched side chains (e.g., threonine, valine, isoleucine) and aromatic side chains (e.g., tyrosine, phenylalanine, tryptophan, histidine). Thus, a predicted nonessential amino acid residue in one or more biomarkers listed in Table 2 and the Examples is preferably replaced with another amino acid residue from the same side chain family. Alternatively, in another embodiment, mutations can be introduced randomly along all or part of the coding sequence of the one or more biomarkers listed in Table 2 and the Examples, such as by saturation mutagenesis, and the resultant mutants can be screened for an activity described herein to identify mutants that retain desired activity. Following mutagenesis, the encoded protein can be expressed recombinantly according to well-known methods in the art and the activity of the protein can be determined using, for example, assays described herein.

The levels of one or more biomarkers listed in Table 2 and the Examples levels may be assessed by any of a wide variety of well-known methods for detecting expression of a transcribed molecule or protein. Non-limiting examples of such methods include immunological methods for detection of proteins, protein purification methods, protein function or activity assays, nucleic acid hybridization methods, nucleic acid reverse transcription methods, and nucleic acid amplification methods.

In preferred embodiments, the levels of one or more biomarkers listed in Table 2 and the Examples levels are ascertained by measuring gene transcript (e.g., mRNA), by a measure of the quantity of translated protein, or by a measure of gene product activity. Expression levels can be monitored in a variety of ways, including by detecting mRNA levels, protein levels, or protein activity, any of which can be measured using standard techniques. Detection can involve quantification of the level of gene expression (e.g., genomic DNA, cDNA, mRNA, protein, or enzyme activity), or, alternatively, can be a qualitative assessment of the level of gene expression, in particular in comparison with a control level. The type of level being detected will be clear from the context.

In a particular embodiment, the mRNA expression level can be determined both by in situ and by in vitro formats in a biological sample using methods known in the art. The term "biological sample" is intended to include tissues, cells, biological fluids and isolates thereof, isolated from a subject, as well as tissues, cells and fluids present within a subject. Many expression detection methods use isolated RNA. For in vitro methods, any RNA isolation technique that does not select against the isolation of mRNA can be utilized for the purification of RNA from cells (see, e.g., Ausubel et al., ed., *Current Protocols in Molecular Biology*, John Wiley & Sons, New York 1987-1999). Additionally, large numbers of tissue samples can readily be processed using techniques well known to those of skill in the art, such as, for example, the single-step RNA isolation process of Chomczynski (1989, U.S. Pat. No. 4,843,155).

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 50, 100, 250 or 500 nucleotides in length and sufficient to specifically hybridize under stringent conditions to a mRNA or genomic DNA encoding one or more biomarkers listed in Table 2 and the Examples. Other suitable probes for use in the diagnostic assays of the invention are described herein. Hybridization of an mRNA with the probe indicates that one or more biomarkers listed in Table 2 and the Examples is being expressed.

In one format, the mRNA is immobilized on a solid surface and contacted with a probe, for example by running the isolated mRNA on an agarose gel and transferring the mRNA from the gel to a membrane, such as nitrocellulose. In an alternative format, the probe(s) are immobilized on a solid surface and the mRNA is contacted with the probe(s), for example, in a gene chip array, e.g., an Affymetrix™ gene chip array. A skilled artisan can readily adapt known mRNA detection methods for use in detecting the level of the One or more biomarkers listed in Table 2 and the Examples mRNA expression levels.

An alternative method for determining mRNA expression level in a sample involves the process of nucleic acid amplification, e.g., by RT-PCR (the experimental embodiment set forth in Mullis, 1987, U.S. Pat. No. 4,683,202), ligase chain reaction (Barany, 1991, *Proc. Natl. Acad. Sci. USA*, 88:189-193), self-sustained sequence replication (Guatelli et al., 1990, *Proc. Natl. Acad. Sci. USA* 87:1874-1878), transcriptional amplification system (Kwoh et al., 1989, *Proc. Natl. Acad. Sci. USA* 86:1173-1177), Q-Beta Replicase (Lizardi et al., 1988, *Bio/Technology* 6:1197), rolling circle replication (Lizardi et al., U.S. Pat. No. 5,854,033) or any other nucleic acid amplification method, followed by the detection of the amplified molecules using techniques well-known to those of skill in the art. These detection schemes are especially useful for the detection of nucleic acid molecules if such molecules are present in very low numbers. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, mRNA does not need to be isolated from the cells prior to detection. In such methods, a cell or tissue sample is prepared/processed using known histological methods. The sample is then immobilized on a support, typically a glass slide, and then contacted with a probe that can hybridize to the One or more biomarkers listed in Table 2 and the Examples mRNA.

As an alternative to making determinations based on the absolute expression level, determinations may be based on the normalized expression level of one or more biomarkers listed in Table 2 and the Examples. Expression levels are normalized by correcting the absolute expression level by comparing its expression to the expression of a non-biomarker gene, e.g., a housekeeping gene that is constitutively expressed. Suitable genes for normalization include housekeeping genes such as the actin gene, or epithelial cell-specific genes. This normalization allows the comparison of the expression level in one sample, e.g., a subject sample, to another sample, e.g., a normal sample, or between samples from different sources.

The level or activity of a protein corresponding to one or more biomarkers listed in Table 2 and the Examples can also be detected and/or quantified by detecting or quantifying the expressed polypeptide. The polypeptide can be detected and quantified by any of a number of means well known to those of skill in the art. These may include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay (MA), enzyme-linked immunosorbent assays (ELISAs), immuno-fluorescent assays, Western blotting, and the like. A skilled artisan can readily adapt known protein/antibody detection methods for use in determining whether cells express the biomarker of interest.

In some embodiments, vectors and/or host cells are further provided. Ine aspect of the present invention pertains to the use of vectors, preferably expression vectors, containing a nucleic acid encoding a biomarker listed in Table 2, or a protion or ortholog thereof. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions. In one embodiment, adenoviral vectors comprising a biomarker nucleic acid molecule are used.

The recombinant expression vectors of the present invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein.

The recombinant expression vectors of the invention can be designed for expression of the desired biomarker in prokaryotic or eukaryotic cells. For example, a biomarker can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase. Examples of suitable inducible non-fusion *E. coli* expression vectors include pTrc (Amann et al., (1988) *Gene* 69:301-315) and pET 11d (Studier et al., *Gene Expression Technology: Methods in Enzymology* 185, Academic Press, San Diego, Calif. (1990) 60-89). Examples of suitable yeast expression vectors include pYepSec1 (Baldari, et al., (1987) *EMBO 1* 6:229-234), pMFa (Kurjan and Herskowitz, (1982) *Cell* 30:933-943), pJRY88 (Schultz et al., (1987) *Gene* 54:113-123), and pYES2 (Invitrogen Corporation, San Diego, Calif.). Examples of suitable baculovirus expression vectors useful for insect cell hosts include the pAc series (Smith et al. (1983) *Mol. Cell Biol.* 3:2156-2165) and the pVL series (Lucklow and Summers (1989) *Virology* 170: 31-39). Examples of suitable mammalian expression vectors include pCDM8 (Seed, B. (1987) *Nature* 329:840) and pMT2PC (Kaufman et al. (1987) *EMBO J.* 6:187-195).

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters such as in melanoma cancer cells are well-known in the art (see, for example, Pleshkan et al. (2011) *Acta Nat.* 3:13-21).

The present invention further provides a recombinant expression vector comprising a nucleic acid molecule of the invention cloned into the expression vector in an antisense orientation. That is, the DNA molecule is operatively linked to a regulatory sequence in a manner which allows for expression (by transcription of the DNA molecule) of an RNA molecule which is antisense to a biomarker mRNA described herein. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, biomarker protein can be expressed in bacterial cells such as *E. coli*, insect cells, yeast or mammalian cells (such as Fao hepatoma cells, primary hepatocytes, Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual.* 2nd, ed., Cold Spring Harbor Laboratory, Cold Spring Harbor Laboratory Press, Cold Spring Harbor, N.Y., 1989), and other laboratory manuals.

A cell culture includes host cells, media and other byproducts. Suitable media for cell culture are well known in the art. A biomarker polypeptide or fragment thereof, may be secreted and isolated from a mixture of cells and medium containing the polypeptide. Alternatively, a biomarker polypeptide or fragment thereof, may be retained cytoplasmically and the cells harvested, lysed and the protein or protein complex isolated. A biomarker polypeptide or fragment thereof, may be isolated from cell culture medium, host cells, or both using techniques known in the art for purifying proteins, including ion-exchange chromatography, gel filtration chromatography, ultrafiltration, electrophoresis, and inmmunoaffinity purification with antibodies specific for particular epitopes of a biomarker or a fragment thereof. In other embodiments, heterologous tags can be used for purification purposes (e.g., epitope tags and FC fusion tags), according to standards methods known in the art.

Thus, a nucleotide sequence encoding all or a selected portion of a biomarker polypeptide may be used to produce a recombinant form of the protein via microbial or eukaryotic cellular processes. Ligating the sequence into a polynucleotide construct, such as an expression vector, and transforming or transfecting into hosts, either eukaryotic (yeast, avian, insect or mammalian) or prokaryotic (bacterial cells), are standard procedures. Similar procedures, or modifications thereof, may be employed to prepare recombinant biomarker polypeptides, or fragments thereof, by microbial means or tissue-culture technology in accord with the subject invention.

A host cell of the invention, such as a prokaryotic or eukaryotic host cell in culture, can be used to produce (i.e., express) biomarker protein. Accordingly, the invention further provides methods for producing biomarker protein using the host cells of the invention. In one embodiment, the method comprises culturing the host cell of invention (into which a recombinant expression vector encoding a biomarker has been introduced) in a suitable medium until biomarker protein is produced. In another embodiment, the method further comprises isolating the biomarker protein from the medium or the host cell.

The host cells of the invention can also be used to produce nonhuman transgenic animals. The nonhuman transgenic animals can be used in screening assays designed to identify agents or compounds, e.g., drugs, pharmaceuticals, etc., which are capable of ameliorating detrimental symptoms of selected disorders such as glucose homeostasis disorders, weight disorders or disorders associated with insufficient insulin activity. For example, in one embodiment, a host cell of the invention is a fertilized oocyte or an embryonic stem cell into which biomarker encoding sequences, or fragments thereof, have been introduced. Such host cells can then be used to create non-human transgenic animals in which exogenous biomarker sequences have been introduced into their genome or homologous recombinant animals in which endogenous biomarker sequences have been altered. Such animals are useful for studying the function and/or activity of biomarker, or fragments thereof, and for identifying and/or evaluating modulators of biomarker activity. As used herein, a "transgenic animal" is a nonhuman animal, preferably a mammal, more preferably a rodent such as a rat or mouse, in which one or more of the cells of the animal includes a transgene. Other examples of transgenic animals include nonhuman primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a nonhuman animal, preferably a mammal, more preferably a mouse, in which an endogenous biomarker gene has been altered by homologous recombination between the endogenous gene and an exogenous DNA molecule introduced into a cell of the animal, e.g., an embryonic cell of the animal, prior to development of the animal.

A transgenic animal of the invention can be created by introducing nucleic acids encoding a biomarker, or a fragment thereof, into the male pronuclei of a fertilized oocyte, e.g., by microinjection, retroviral infection, and allowing the oocyte to develop in a pseudopregnant female foster animal. Human biomarker cDNA sequence can be introduced as a transgene into the genome of a nonhuman animal. Alternatively, a nonhuman homologue of the human biomarker gene can be used as a transgene. Intronic sequences and polyadenylation signals can also be included in the transgene to increase the efficiency of expression of the transgene. A tissue-specific regulatory sequence(s) can be operably linked to the biomarker transgene to direct expression of biomarker protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the biomarker transgene in its genome and/or expression of biomarker mRNA in tissues or cells of the animals. A transgenic founder animal can then be used to breed additional animals carrying the transgene. Moreover, transgenic animals carrying a transgene encoding a biomarker can further be bred to other transgenic animals carrying other transgenes.

To create a homologous recombinant animal, a vector is prepared which contains at least a portion of biomarker gene into which a deletion, addition or substitution has been introduced to thereby alter, e.g., functionally disrupt, the biomarker gene. The biomarker gene can be a human gene, but more preferably, is a nonhuman homologue of a human biomarker gene. For example, a mouse biomarker gene can be used to construct a homologous recombination vector suitable for altering an endogenous biomarker gene, respectively, in the mouse genome. In a preferred embodiment, the vector is designed such that, upon homologous recombination, the endogenous biomarker gene is functionally disrupted (i.e., no longer encodes a functional protein; also referred to as a "knock out" vector). Alternatively, the vector can be designed such that, upon homologous recombination, the endogenous biomarker gene is mutated or otherwise altered but still encodes functional protein (e.g., the upstream regulatory region can be altered to thereby alter the expression of the endogenous biomarker protein). In the homologous recombination vector, the altered portion of the biomarker gene is flanked at its 5' and 3' ends by additional nucleic acid of the biomarker gene to allow for homologous recombination to occur between the exogenous biomarker gene carried by the vector and an endogenous biomarker gene in an embryonic stem cell. The additional flanking biomarker nucleic acid is of sufficient length for successful homologous recombination with the endogenous gene. Typically, several kilobases of flanking DNA (both at the 5' and 3' ends) are included in the vector (see e.g., Thomas, K. R. and Capecchi, M. R. (1987) *Cell* 51:503 for a description of homologous recombination vectors). The vector is introduced into an embryonic stem cell line (e.g., by electroporation) and cells in which the introduced biomarker gene has homologously recombined with the endogenous biomarker gene are selected (see e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinion in Biotechnology* 2:823-829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, transgenic nonhuman animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232-6236. Another example of a recombinase system is the FLP recombinase system of *Saccharomyces cerevisiae* (O'Gorman et al. (1991) *Science* 251:1351-1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the nonhuman transgenic animals described herein can also be produced according to the methods described in Wilmut, I. et al. (1997) *Nature* 385:810-813 and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring borne of this female foster animal will be a clone of the animal from which the cell, e.g., the somatic cell, is isolated.

b. Isolated Fndc5 Polypeptides

The present invention provides soluble, purified and/or isolated forms of biomarkers listed in Table 2, including fragments and orthologs thereof.

In one aspect, a biomarker polypeptide may comprise a full-length biomarker amino acid sequence shown in Table 2 or a full-length biomarker amino acid sequence with 1 to about 2, 3, 4, 5, 6, 7, 8, 9, 10, 11, 12, 13, 14, 15, 16, 17, 18, 19, or 20 conservative amino acid substitutions. Amino acid sequence of any biomarker polypeptide described herein can also be at least 50, 55, 60, 65, 70, 75, 80, 85, 90, 91, 92, 93, 94, 95, 96, 97, 98, 99, or 99.5% identical to a biomarker polypeptide sequence of interest, described herein, or a fragment or ortholog thereof. In addition, any biomarker polypeptide, or fragment thereof, described herein can have the ability of full-length, membrane-bound PD-L1 to modulate an immune responses (e.g., have an immunoinhibitory function, modulate cytokine levels, modulate T cell activation, modulate proliferation) and/or bind to PD-1. In another aspect, the present invention contemplates a composition comprising an isolated biomarker polypeptide and less than about 25%, or alternatively 15%, or alternatively 5%, contaminating biological macromolecules or polypeptides.

The present invention further provides compositions related to producing, detecting, or characterizing a biomarker polypeptide, or fragment or ortholog thereof, such as nucleic acids, vectors, host cells, and the like. Such compositions may serve as compounds that modulate a biomarker polypeptide's expression and/or activity, such as antisense nucleic acids.

In certain embodiments, a biomarker polypeptide of the invention may be a fusion protein containing a domain which increases its solubility and bioavilability and/or facilitates its purification, identification, detection, and/or structural characterization. Exemplary domains, include, for example, glutathione S-transferase (GST), protein A, protein G, calmodulin-binding peptide, thioredoxin, maltose binding protein, HA, myc, poly arginine, poly His, poly His-Asp or FLAG fusion proteins and tags. Additional exemplary domains include domains that alter protein localization in vivo, such as signal peptides, type III secretion system-targeting peptides, transcytosis domains, nuclear localization signals, etc. In various embodiments, a biomarker polypeptide of the present invention may comprise one or more heterologous fusions. Polypeptides may contain multiple copies of the same fusion domain or may contain fusions to two or more different domains. The fusions may occur at the N-terminus of the polypeptide, at the C-terminus of the polypeptide, or at both the N- and C-terminus of the polypeptide. It is also within the scope of the invention to include linker sequences between a polypeptide of the invention and the fusion domain in order to facilitate construction of the fusion protein or to optimize protein expression or structural constraints of the fusion protein. In one embodiment, the linker is a linker described herein, e.g., a linker of at least 8, 9, 10, 15, or 20 amino acids. The linker can be, e.g., an unstructured recombinant polymer (URP), e.g., a URP that is 9, 10, 11, 12, 13, 14, 15, 20 amino acids in length, i.e., the linker has limited or lacks secondary structure, e.g., Chou-Fasman algorithm. An exemplary linker comprises (e.g., consists of) the amino acid sequence GGGGAGGGG. In another embodiment, the polypeptide may be constructed so as to contain protease cleavage sites between the fusion polypeptide and polypeptide of the invention in order to remove the tag after protein expression or thereafter. Examples of suitable endoproteases, include, for example, Factor Xa and TEV proteases.

In some embodiments, biomarker polypeptides, or fragments or orthologs thereof, are fused to an antibody (e.g., IgG 1, IgG2, IgG3, IgG4) fragment (e.g., Fc polypeptides). Techniques for preparing these fusion proteins are known, and are described, for example, in WO 99/31241 and in Cosman et.al., 2001 Immunity 14:123 133. Fusion to an Fc polypeptide offers the additional advantage of facilitating purification by affinity chromatography over Protein A or Protein G columns.

In still another embodiment, a biomarker polypeptide may be labeled with a fluorescent label to facilitate their detection, purification, or structural characterization. In an exemplary embodiment, a biomarker polypeptide of the invention may be fused to a heterologous polypeptide sequence which produces a detectable fluorescent signal, including, for example, green fluorescent protein (GFP), enhanced green fluorescent protein (EGFP), Renilla Reniformis green fluorescent protein, GFPmut2, GFPuv4, enhanced yellow fluorescent protein (EYFP), enhanced cyan fluorescent protein (ECFP), enhanced blue fluorescent protein (EBFP), citrine and red fluorescent protein from discosoma (dsRED).

Another aspect of the invention pertains to the use of isolated biomarker proteins, and biologically active portions or orthologs thereof, as well as peptide fragments suitable for use as immunogens to raise anti-biomarker polypeptide antibodies. An "isolated" or "purified" protein or biologically active portion thereof is substantially free of cellular material when produced by recombinant DNA techniques, or chemical precursors or other chemicals when chemically synthesized. The language "substantially free of cellular material" includes preparations of biomarker protein in which the protein is separated from cellular components of the cells in which it is naturally or recombinantly produced. In one embodiment, the language "substantially free of cellular material" includes preparations of biomarker protein having less than about 30% (by dry weight) of non-biomarker protein (also referred to herein as a "contaminating protein"), more preferably less than about 20% of non-biomarker protein, still more preferably less than about 10% of non-biomarker protein, and most preferably less than about 5% non-biomarker protein. When the biomarker protein, or biologically active portion or ortholog thereof, is recombinantly produced, it is also preferably substantially free of culture medium, i.e., culture medium represents less than about 20%, more preferably less than about 10%, and most preferably less than about 5% of the volume of the protein preparation. The language "substantially free of chemical precursors or other chemicals" includes preparations of biomarker protein in which the protein is separated from chemical precursors or other chemicals which are involved in the synthesis of the protein. In one embodiment, the language "substantially free of chemical precursors or other chemicals" includes preparations of biomarker protein having less than about 30% (by dry weight) of chemical precursors of non-biomarker chemicals, more preferably less than about 20% chemical precursors of non-biomarker chemicals, still more preferably less than about 10% chemical precursors of non-biomarker chemicals, and most preferably less than about 5% chemical precursors of non-biomarker chemicals. In preferred embodiments, isolated proteins or biologically active portions thereof lack contaminating proteins from the same animal from which the biomarker protein is derived. Typically, such proteins are produced by recombinant expression of, for example, a human biomarker protein in a nonhuman cell.

In preferred embodiments, the protein or portion thereof comprises an amino acid sequence which is sufficiently homologous to an amino acid sequence listed in Table 2, or a fragment or ortholog thereof, such that the protein, or portion or ortholog thereof, maintains the ability to modulate an immune responses (e.g., have an immunoinhibitory function, modulate cytokine levels, modulate T cell activation, modulate proliferation) and/or bind to PD-1. The portion of the protein is preferably a biologically active portion as described herein. In another preferred embodiment, the biomarker protein has an amino acid sequence listed in Table 2, or fragment or ortholog thereof, respectively, or an amino acid sequence which is at least about 50%, 55%, 60%, 65%, 70%, 75%, 80%, 85%, 90%, 91%, 92%, 93%, 94%, 95%, 96%, 97%, 98%, 99% or more homologous to an amino acid sequence listed in Table 2, or a fragment or ortholog thereof. In yet another preferred embodiment, the Fndc5 protein has an amino acid sequence which is encoded by a nucleotide sequence which hybridizes, e.g., hybridizes under stringent conditions, to a nucleotide sequence listed in Table 2, or a fragment or ortholog thereof, or a nucleotide sequence which is at least about 50%, preferably at least about 60%, more preferably at least about 70%, yet more preferably at least about 80%, still more preferably at least about 90%, and most preferably at least about 95% or more homologous to a nucleotide sequence listed in Table 2, or a fragment or ortholog thereof. The preferred Fndc5 proteins of the present invention also preferably possess at least one of the biomarker biological activities described herein.

Biologically active portions of the biomarker protein include peptides comprising amino acid sequences derived from the amino acid sequence of a biomarker protein listed in Table 2, and maintain the ability to modulate an immune responses (e.g., have an immunoinhibitory function, modulate cytokine levels, modulate T cell activation, modulate proliferation) and/or bind to PD-1. Typically, biologically active portions (peptides, e.g., peptides which are, for example, 50, 55, 60, 65, 70, 75, 80, 85, 90, 95, 100 or more amino acids in length) comprise a domain or motif, e.g., signal peptide, extacellular domain, IgC domain, IgV domain, transmembrane domain, intracellular domain, and the like).

Biomarker proteins can be produced by recombinant DNA techniques. For example, a nucleic acid molecule encoding the protein is cloned into an expression vector (as described above), the expression vector is introduced into a host cell (as described above) and the biomarker protein is expressed in the host cell. The biomarker protein can then be isolated from the cells by an appropriate purification scheme using standard protein purification techniques. Alternative to recombinant expression, a biomarker protein, polypeptide, or peptide can be synthesized chemically using standard peptide synthesis techniques. Biomarker protein fragments or orthologs can be generated by well-known molecular biology and/or directed mutagenesis techniques. In an alternative embodiment, such biomarker proteins can be identified by screening combinatorial libraries of variants.

The invention also provides biomarker chimeric or fusion proteins. As used herein, a biomarker "chimeric protein" or "fusion protein" comprises a biomarker polypeptide described herein operatively linked to a non-biomarker polypeptide. A "biomarker polypeptide" refers to a polypeptide having an amino acid sequence corresponding to a biomarker listed in Table 2, or a fragment or ortholog thereof, whereas a "non-biomarker polypeptide" refers to a polypeptide having an amino acid sequence corresponding to a protein which is not substantially homologous to the biomarker protein, respectively, e.g., a protein which is different from the biomarker protein and which is derived from the same or a different organism. Within the fusion protein, the term "operatively linked" is intended to indicate that the biomarker polypeptide and the non-biomarker polypeptide are fused in-frame to each other. The non-biomarker polypeptide can be fused to the N-terminus or C-terminus of the biomarker polypeptide, respectively. For example, in one embodiment the fusion protein is a biomarker-GST and/or biomarker-Fc fusion protein in which the biomarker sequences, respectively, are fused to the N-terminus of the GST or Fc sequences. Such fusion proteins can facilitate the purification, expression, and/or bioavailbility of recombinant biomarker protein. In another embodiment, the fusion protein is a biomarker protein containing a heterologous signal sequence at its C-terminus. In certain host cells (e.g., mammalian host cells), expression and/or secretion of the biomarker protein can be increased through use of a heterologous signal sequence.

Preferably, a biomarker chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). A biomarker-encoding nucleic acid can be cloned into such an expression vector such that the fusion moiety is linked in-frame to the biomarker protein.

c. Antibodies

As stated above, the present invention provides compositions related to producing, detecting, characterizing, or modulating the level or activity of biomarker polypeptides, or fragments or orthologs thereof, such as nucleic acids, vectors, host cells, and the like. Such compositions may serve as compounds that modulate the expression and/or activity of one or more biomarkers listed in Table 2 and the Examples. For example, anti-PD-L1 antibodies that may bind specifically to PD-L1 or soluble PD-L1 can be used to reduce soluble PD-L1 (i.e., both forms of PD-L1 contain an extracellular domain typically targeted by antibodies) and thereby a) stop the titration of such therapeutic agents from binding to membrane-bound forms of PD-L1 and/or b) inhibit the inhibition of immunological responses promoted by the soluble forms of PD-L1. In one embodiment, the anti-PD-L1 antibodies are specific for one or more of the PD-L1 isoforms listed in Table 2 (i.e., bind to one or more of the listed PD-L1 without substantially binding to full-length, membrane-bound PD-L1 and/or other known PD-L1 isoform described herein).

An isolated polypeptide or a fragment thereof (or a nucleic acid encoding such a polypeptide) corresponding to one or more biomarkers of the invention, including the biomarkers listed in Table 2 and the Examples or fragments thereof, can be used as an immunogen to generate antibodies that bind to said immunogen, using standard techniques for polyclonal and monoclonal antibody preparation according to well-known methods in the art. An antigenic peptide comprises at least 8 amino acid residues and encompasses an epitope present in the respective full length molecule such that an antibody raised against the peptide forms a specific immune complex with the respective full length molecule. Preferably, the antigenic peptide comprises at least 10 amino acid residues. In one embodiment such epitopes can be specific for a given polypeptide molecule from one species, such as mouse or human (i.e., an antigenic peptide that spans a region of the polypeptide molecule that is not conserved across species is used as immunogen; such non conserved residues can be determined using an alignment such as that provided herein).

For example, a polypeptide immunogen typically is used to prepare antibodies by immunizing a suitable subject (e.g., rabbit, goat, mouse or other mammal) with the immunogen. An appropriate immunogenic preparation can contain, for example, a recombinantly expressed or chemically synthesized molecule or fragment thereof to which the immune response is to be generated. The preparation can further include an adjuvant, such as Freund's complete or incomplete adjuvant, or similar immunostimulatory agent. Immunization of a suitable subject with an immunogenic preparation induces a polyclonal antibody response to the antigenic peptide contained therein.

Polyclonal antibodies can be prepared as described above by immunizing a suitable subject with a polypeptide immunogen. The polypeptide antibody titer in the immunized subject can be monitored over time by standard techniques, such as with an enzyme linked immunosorbent assay (ELISA) using immobilized polypeptide. If desired, the antibody directed against the antigen can be isolated from the mammal (e.g., from the blood) and further purified by well-known techniques, such as protein A chromatography, to obtain the IgG fraction. At an appropriate time after immunization, e.g., when the antibody titers are highest, antibody-producing cells can be obtained from the subject and used to prepare monoclonal antibodies by standard techniques, such as the hybridoma technique (originally described by Kohler and Milstein (1975) *Nature* 256:495-497) (see also Brown et al. (1981) *J. Immunol.* 127:539-46; Brown et al. (1980) *J. Biol. Chem.* 255:4980-83; Yeh et al. (1976) *Proc. Natl. Acad. Sci.* 76:2927-31; Yeh et al. (1982) *Int. J. Cancer* 29:269-75), the more recent human B cell hybridoma technique (Kozbor et al. (1983) *Immunol. Today* 4:72), the EBV-hybridoma technique (Cole et al. (1985) *Monoclonal Antibodies and Cancer Therapy*, Alan R. Liss, Inc., pp. 77-96) or trioma techniques. The technology for producing monoclonal antibody hybridomas is well known (see generally Kenneth, R. H. in *Monoclonal Antibodies: A New Dimension In Biological Analyses*, Plenum Publishing Corp., New York, N.Y. (1980); Lerner, E. A. (1981) *Yale J. Biol. Med.* 54:387-402; Gefter, M. L. et al. (1977) *Somatic Cell Genet.* 3:231-36). Briefly, an immortal cell line (typically a myeloma) is fused to lymphocytes (typically splenocytes) from a mammal immunized with an immunogen as described above, and the culture supernatants of the resulting hybridoma cells are screened to identify a hybridoma producing a monoclonal antibody that binds to the polypeptide antigen, preferably specifically.

Any of the many well-known protocols used for fusing lymphocytes and immortalized cell lines can be applied for the purpose of generating a monoclonal antibody against one or more biomarkers of the invention, including the biomarkers listed in Table 2 and the Examples, or a fragment thereof (see, e.g., Galfre, G. et al. (1977) *Nature* 266:55052; Gefter et al. (1977) supra; Lerner (1981) supra; Kenneth (1980) supra). Moreover, the ordinary skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from the American Type Culture Collection (ATCC), Rockville, Md. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind a given polypeptide, e.g., using a standard ELISA assay.

As an alternative to preparing monoclonal antibody-secreting hybridomas, a monoclonal specific for one of the above described polypeptides can be identified and isolated by screening a recombinant combinatorial immunoglobulin library (e.g., an antibody phage display library) with the appropriate polypeptide to thereby isolate immunoglobulin library members that bind the polypeptide. Kits for generating and screening phage display libraries are commercially available (e.g., the Pharmacia *Recombinant Phage Antibody System*, Catalog No. 27-9400-01; and the Stratagene *SurfZAP™ Phage Display Kit*, Catalog No. 240612). Additionally, examples of methods and reagents particularly amenable for use in generating and screening an antibody display library can be found in, for example, Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Biotechnology* (NY) 9:1369-1372; Hay et al. (1992) *Hum. Antibod. Hybridomas* 3:81-85; Huse et al. (1989) *Science* 246:1275-1281; Griffiths et al. (1993) *EMBO J.* 12:725-734; Hawkins et al. (1992) *J. Mol. Biol.* 226:889-896; Clarkson et al. (1991) *Nature* 352:624-628; Gram et al. (1992) *Proc. Natl. Acad. Sci. USA* 89:3576-3580; Garrard et al. (1991) *Biotechnology* (NY) 9:1373-1377; Hoogenboom et al. (1991) *Nucleic Acids Res.* 19:4133-4137; Barbas et al. (1991) *Proc. Natl. Acad. Sci. USA* 88:7978-7982; and McCafferty et al. (1990) *Nature* 348:552-554.

Additionally, recombinant polypeptide antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Patent Publication PCT/US86/02269; Akira et al. European Patent Application 184,187; Taniguchi, M. European Patent Application 171,496; Morrison et al. European Patent Application 173,494; Neuberger et al. PCT Application WO 86/01533; Cabilly et al. U.S. Pat. No. 4,816,567; Cabilly et al. European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci.* 84:214-218; Nishimura et al. (1987) *Cancer Res.* 47:999-1005; Wood et al. (1985) *Nature* 314:446-449; Shaw et al. (1988) *J. Natl. Cancer Inst.* 80:1553-1559); Morrison, S. L. (1985) *Science* 229:1202-1207; Oi et al. (1986) *Biotechniques* 4:214; Winter U.S. Pat. No. 5,225,539; Jones et al. (1986) *Nature* 321:552-525; Verhoeyan et al. (1988) *Science* 239:1534; and Beidler et al. (1988) *J. Immunol.* 141:4053-4060.

In addition, humanized antibodies can be made according to standard protocols such as those disclosed in U.S. Patent 5,565,332. In another embodiment, antibody chains or specific binding pair members can be produced by recombination between vectors comprising nucleic acid molecules encoding a fusion of a polypeptide chain of a specific binding pair member and a component of a replicable generic display package and vectors containing nucleic acid molecules encoding a second polypeptide chain of a single binding pair member using techniques known in the art, e.g., as described in U.S. Pat. Nos. 5,565,332, 5,871,907, or 5,733,743. The use of intracellular antibodies to inhibit protein function in a cell is also known in the art (see e.g., Carlson, J. R. (1988) *Mol. Cell. Biol.* 8:2638-2646; Biocca, S. et al. (1990) *EMBO J.* 9:101-108; Werge, T. M. et al. (1990) *FEBS Lett.* 274:193-198; Carlson, J. R. (1993) *Proc. Natl. Acad. Sci. USA* 90:7427-7428; Marasco, W. A. et al. (1993) *Proc. Natl. Acad. Sci. USA* 90:7889-7893; Biocca, S. et al. (1994) *Biotechnology* (NY) 12:396-399; Chen, S-Y. et al. (1994) *Hum. Gene Ther.* 5:595-601; Duan, L et al. (1994) *Proc. Natl. Acad. Sci. USA* 91:5075-5079; Chen, S-Y. et al. (1994) *Proc. Natl. Acad. Sci. USA* 91:5932-5936; Beerli, R. R. et al. (1994) *J. Biol. Chem.* 269:23931-23936; Beerli, R. R. et al. (1994) *Biochem. Biophys. Res. Commun.* 204:666-672; Mhashilkar, A. M. et al. (1995) *EMBO J.* 14:1542-1551; Richardson, J. H. et al. (1995) *Proc. Natl. Acad. Sci. USA* 92:3137-3141; PCT Publication No. WO 94/02610 by Marasco et al.; and PCT Publication No. WO 95/03832 by Duan et al.).

Additionally, fully human antibodies could be made against biomarkers of the invention, including the biomarkers listed in Table 2 and the Examples, or fragments thereof. Fully human antibodies can be made in mice that are transgenic for human immunoglobulin genes, e.g., according to Hogan, et al., "Manipulating the Mouse Embryo: A Laboratory Manuel," Cold Spring Harbor Laboratory. Briefly, transgenic mice are immunized with purified immunogen. Spleen cells are harvested and fused to myeloma cells to produce hybridomas. Hybridomas are selected based on their ability to produce antibodies which bind to the immunogen. Fully human antibodies would reduce the immunogenicity of such antibodies in a human.

In one embodiment, an antibody for use in the instant invention is a bispecific antibody. A bispecific antibody has binding sites for two different antigens within a single antibody polypeptide. Antigen binding may be simultaneous or sequential. Triomas and hybrid hybridomas are two examples of cell lines that can secrete bispecific antibodies. Examples of bispecific antibodies produced by a hybrid hybridoma or a trioma are disclosed in U.S. Pat. No. 4,474,893. Bispecific antibodies have been constructed by chemical means (Staerz et al. (1985) *Nature* 314:628, and Perez et al. (1985) *Nature* 316:354) and hybridoma technology (Staerz and Bevan (1986) *Proc. Natl. Acad. Sci. USA,* 83:1453, and Staerz and Bevan (1986) *Immunol. Today* 7:241). Bispecific antibodies are also described in U.S. Pat. No. 5,959,084. Fragments of bispecific antibodies are described in U.S. Pat. No. 5,798,229.

Bispecific agents can also be generated by making heterohybridomas by fusing hybridomas or other cells making different antibodies, followed by identification of clones producing and co-assembling both antibodies. They can also be generated by chemical or genetic conjugation of complete immunoglobulin chains or portions thereof such as Fab and Fv sequences. The antibody component can bind to a polypeptide or a fragment thereof of one or more biomarkers of the invention, including one or more biomarkers listed in Table 2 and the Examples, or a fragment thereof. In one embodiment, the bispecific antibody could specifically bind to both a polypeptide or a fragment thereof and its natural binding partner(s) or a fragment(s) thereof.

d. Other Useful Agents

In another aspect of this invention, peptides or peptide mimetics can be used to antagonize or promote the activity of one or more biomarkers of the invention, including one or more biomarkers listed in Table 2 and the Examples, or a fragment(s) thereof In one embodiment, variants of one or more biomarkers listed in Table 2 and the Examples which function as a modulating agent for the respective full length protein, can be identified by screening combinatorial libraries of mutants, e.g., truncation mutants, for antagonist activity. In one embodiment, a variegated library of variants is generated by combinatorial mutagenesis at the nucleic acid level and is encoded by a variegated gene library. A variegated library of variants can be produced, for instance, by enzymatically ligating a mixture of synthetic oligonucleotides into gene sequences such that a degenerate set of potential polypeptide sequences is expressible as individual polypeptides containing the set of polypeptide sequences therein. There are a variety of methods which can be used to produce libraries of polypeptide variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential polypeptide sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of a polypeptide coding sequence can be used to generate a variegated population of polypeptide fragments for screening and subsequent selection of variants of a given polypeptide. In one embodiment, a library of coding sequence fragments can be generated by treating a double stranded PCR fragment of a polypeptide coding sequence with a nuclease under conditions wherein nicking occurs only about once per polypeptide, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the polypeptide.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of polypeptides. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of interest (Arkin and Youvan (1992) *Proc. Natl. Acad. Sci. USA* 89:7811-7815; Delagrave et al. (1993) *Protein Eng.* 6(3): 327-331). In one embodiment, cell based assays can be exploited to analyze a variegated polypeptide library. For example, a library of expression vectors can be transfected into a cell line which ordinarily synthesizes one or more biomarkers of the invention, including one or more biomarkers listed in Table 2 and the Examples, or a fragment thereof. The transfected cells are then cultured such that the full length polypeptide and a particular mutant polypeptide are produced and the effect of expression of the mutant on the full length polypeptide activity in cell supernatants can be detected, e.g., by any of a number of functional assays. Plasmid DNA can then be recovered from the cells which score for inhibition, or alternatively, potentiation of full length polypeptide activity, and the individual clones further characterized.

Systematic substitution of one or more amino acids of a polypeptide amino acid sequence with a D-amino acid of the same type (e.g., D-lysine in place of L-lysine) can be used to generate more stable peptides. In addition, constrained peptides comprising a polypeptide amino acid sequence of interest or a substantially identical sequence variation can be generated by methods known in the art (Rizo and Gierasch (1992) *Annu. Rev. Biochem.* 61:387, incorporated herein by reference); for example, by adding internal cysteine residues capable of forming intramolecular disulfide bridges which cyclize the peptide.

The amino acid sequences disclosed herein will enable those of skill in the art to produce polypeptides corresponding peptide sequences and sequence variants thereof. Such polypeptides can be produced in prokaryotic or eukaryotic host cells by expression of polynucleotides encoding the peptide sequence, frequently as part of a larger polypeptide. Alternatively, such peptides can be synthesized by chemical methods. Methods for expression of heterologous proteins in recombinant hosts, chemical synthesis of polypeptides, and in vitro translation are well known in the art and are described further in Maniatis et al. *Molecular Cloning: A Laboratory Manual* (1989), 2nd Ed., Cold Spring Harbor, N.Y.; Berger and Kimmel, Methods in Enzymology, Volume 152, Guide to Molecular Cloning Techniques (1987), Academic Press, Inc., San Diego, Calif.; Merrifield, J. (1969) *J. Am. Chem. Soc.* 91:501; Chaiken I. M. (1981) *CRC Crit. Rev. Biochem.* 11: 255; Kaiser et al. (1989) *Science* 243:187; Merrifield, B. (1986) *Science* 232:342; Kent, S. B. H. (1988) *Annu. Rev. Biochem.* 57:957; and Offord, R. E. (1980) *Semisynthetic Proteins*, Wiley Publishing, which are incorporated herein by reference).

Peptides can be produced, typically by direct chemical synthesis. Peptides can be produced as modified peptides, with nonpeptide moieties attached by covalent linkage to the N-terminus and/or C-terminus. In certain preferred embodiments, either the carboxy-terminus or the amino-terminus, or both, are chemically modified. The most common modifications of the terminal amino and carboxyl groups are acetylation and amidation, respectively. Amino-terminal modifications such as acylation (e.g., acetylation) or alkylation (e.g., methylation) and carboxy-terminal-modifications such as amidation, as well as other terminal modifications, including cyclization, can be incorporated into various embodiments of the invention. Certain amino-terminal and/or carboxy-terminal modifications and/or peptide extensions to the core sequence can provide advantageous physical, chemical, biochemical, and pharmacological properties, such as: enhanced stability, increased potency and/or efficacy, resistance to serum proteases, desirable pharmacokinetic properties, and others. Peptides disclosed herein can be used therapeutically to treat disease, e.g., by altering costimulation in a patient.

Peptidomimetics (Fauchere, J. (1986) *Adv. Drug Res.* 15:29; Veber and Freidinger (1985) TINS p.392; and Evans et al. (1987) *J. Med. Chem.* 30:1229, which are incorporated herein by reference) are usually developed with the aid of computerized molecular modeling. Peptide mimetics that are structurally similar to therapeutically useful peptides can be used to produce an equivalent therapeutic or prophylactic effect. Generally, peptidomimetics are structurally similar to a paradigm polypeptide (i.e., a polypeptide that has a biological or pharmacological activity), but have one or more peptide linkages optionally replaced by a linkage selected from the group consisting of: —CH2NH—, —CH2S—, —CH2-CH2-, —CH=CH— (cis and trans), —COCH2-, —CH(OH)CH2-, and —CH2SO—, by methods known in the art and further described in the following references: Spatola, A. F. in "*Chemistry and Biochemistry of Amino Acids, Peptides, and Proteins*" Weinstein, B., ed., Marcel Dekker, New York, p. 267 (1983); Spatola, A. F., Vega Data (March 1983), Vol. 1, Issue 3, "Peptide Backbone Modifications" (general review); Morley, J. S. (1980) *Trends Pharm. Sci.* pp. 463-468 (general review); Hudson, D. et al. (1979) *Int. J. Pept. Prot. Res.* 14:177-185 (—CH2NH—, CH2CH2-); Spatola, A. F. et al. (1986) *Life Sci.* 38:1243-1249 (—CH2-S); Hann, M. M. (1982) *J. Chem. Soc. Perkin Trans. I.* 307-314 (—CH—CH—, cis and trans); Almquist, R. G. et al. (190) *J. Med. Chem.* 23:1392-1398 (—COCH2-); Jennings-White, C. et al. (1982) *Tetrahedron Lett.* 23:2533 (—COCH2-); Szelke, M. et al. European Appln. EP 45665 (1982) CA: 97:39405 (1982)(—CH(OH) CH2-); Holladay, M. W. et al. (1983) *Tetrahedron Lett.* (1983) 24:4401-4404 (—C(OH)CH2-); and Hruby, V. J. (1982) *Life Sci.* (1982) 31:189-199 (—CH2-S—); each of which is incorporated herein by reference. A particularly preferred non-peptide linkage is —CH2NH—. Such peptide mimetics may have significant advantages over polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others. Labeling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with the macropolypeptides(s) to which the peptidomimetic binds to produce the therapeutic effect. Derivitization (e.g., labeling) of peptidomimetics should not substantially interfere with the desired biological or pharmacological activity of the peptidomimetic.

Also encompassed by the present invention are small molecules which can modulate (either enhance or inhibit) interactions, e.g., between biomarkers listed in Table 2 and the Examples and their natural binding partners, or inhibit activity. The small molecules of the present invention can be obtained using any of the numerous approaches in combinatorial library methods known in the art, including: spatially addressable parallel solid phase or solution phase libraries; synthetic library methods requiring deconvolution; the 'one-bead one-compound' library method; and synthetic library methods using affinity chromatography selection. (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. USA* 90:6909; Erb et al. (1994) *Proc. Natl. Acad. Sci. USA* 91:11422; Zuckermann et al. (1994) *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds can be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner USP '409), plasmids (Cull et al. (1992) *Proc. Natl. Acad. Sci. USA* 89:1865-1869) or on phage (Scott and Smith (1990) *Science* 249:386-390); (Devlin (1990) *Science* 249:404-406); (Cwirla et al. (1990) *Proc. Natl. Acad. Sci. USA* 87:6378-6382); (Felici (1991) *J. Mol. Biol.* 222:301-310); (Ladner supra.). Compounds can be screened in cell based or non-cell based assays. Compounds can be screened in pools (e.g., multiple compounds in each testing sample) or as individual compounds.

The invention also relates to chimeric or fusion proteins of the biomarkers of the invention, including the biomarkers listed in Table 2 and the Examples, or fragments thereof. As used herein, a "chimeric protein" or "fusion protein" comprises one or more biomarkers of the invention, including one or more biomarkers listed in Table 2 and the Examples, or a fragment thereof, operatively linked to another polypeptide having an amino acid sequence corresponding to a protein which is not substantially homologous to the respective biomarker. In a preferred embodiment, the fusion protein comprises at least one biologically active portion of one or more biomarkers of the invention, including one or more biomarkers listed in Table 2 and the Examples, or fragments thereof. Within the fusion protein, the term "operatively linked" is intended to indicate that the biomarker sequences and the non-biomarker sequences are fused in-frame to each other in such a way as to preserve functions exhibited when expressed independently of the fusion. The "another" sequences can be fused to the N-terminus or C-terminus of the biomarker sequences, respectively.

Such a fusion protein can be produced by recombinant expression of a nucleotide sequence encoding the first peptide and a nucleotide sequence encoding the second peptide. The second peptide may optionally correspond to a moiety that alters the solubility, affinity, stability or valency of the first peptide, for example, an immunoglobulin constant region. In another preferred embodiment, the first peptide consists of a portion of a biologically active molecule (e.g., the extracellular portion of the polypeptide or the ligand binding portion). The second peptide can include an immunoglobulin constant region, for example, a human C$\gamma$1 domain or C$\gamma$4 domain (e.g., the hinge, CH2 and CH3 regions of human IgC$\gamma$1, or human IgC$\gamma$ 4, see e.g., Capon et al. U.S. Pat. Nos. 5,116,964; 5,580,756; 5,844,095 and the like, incorporated herein by reference). Such constant regions may retain regions which mediate effector function (e.g., Fc receptor binding) or may be altered to reduce effector function. A resulting fusion protein may have altered solubility, binding affinity, stability and/or valency (i.e., the number of binding sites available per polypeptide) as compared to the independently expressed first peptide, and may increase the efficiency of protein purification. Fusion proteins and peptides produced by recombinant techniques can be secreted and isolated from a mixture of cells and medium containing the protein or peptide. Alternatively, the protein or peptide can be retained cytoplasmically and the cells harvested, lysed and the protein isolated. A cell culture typically includes host cells, media and other byproducts. Suitable media for cell culture are well known in the art. Protein and peptides can be isolated from cell culture media, host cells, or both using techniques known in the art for purifying proteins and peptides. Techniques for transfecting host cells and purifying proteins and peptides are known in the art.

Preferably, a fusion protein of the invention is produced by standard recombinant DNA techniques. For example, DNA fragments coding for the different polypeptide sequences are ligated together in-frame in accordance with conventional techniques, for example employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992).

In another embodiment, the fusion protein contains a heterologous signal sequence at its N-terminus. In certain host cells (e.g., mammalian host cells), expression and/or secretion of a polypeptide can be increased through use of a heterologous signal sequence.

The fusion proteins of the invention can be used as immunogens to produce antibodies in a subject. Such antibodies may be used to purify the respective natural polypeptides from which the fusion proteins were generated, or in screening assays to identify polypeptides which inhibit the interactions between one or more biomarkers polypeptide or a fragment thereof and its natural binding partner(s) or a fragment(s) thereof.

Also provided herein are compositions comprising one or more nucleic acids comprising or capable of expressing at least 1, 2, 3, 4, 5, 10, 20 or more small nucleic acids or antisense oligonucleotides or derivatives thereof, wherein said small nucleic acids or antisense oligonucleotides or derivatives thereof in a cell specifically hybridize (e.g., bind) under cellular conditions, with cellular nucleic acids (e.g., small non-coding RNAS such as miRNAs, pre-miRNAs, pri-miRNAs, miRNA*, anti-miRNA, a miRNA binding site, a variant and/or functional variant thereof, cellular mRNAs or a fragments thereof). In one embodiment, expression of the small nucleic acids or antisense oligonucleotides or derivatives thereof in a cell can enhance or upregulate one or more biological activities associated with the corresponding wild-type, naturally occurring, or synthetic small nucleic acids. In another embodiment, expression of the small nucleic acids or antisense oligonucleotides or derivatives thereof in a cell can inhibit expression or biological activity of cellular nucleic acids and/or proteins, e.g., by inhibiting transcription, translation and/or small nucleic acid processing of, for example, one or more biomarkers of the invention, including one or more biomarkers listed in Table 2 and the Examples, or fragment(s) thereof In one embodiment, the small nucleic acids or antisense oligonucleotides or derivatives thereof are small RNAs (e.g., microRNAs) or complements of small RNAs. In another embodiment, the small nucleic acids or antisense oligonucleotides or derivatives thereof can be single or double stranded and are at least six nucleotides in length and are less than about 1000, 900, 800, 700, 600, 500, 400, 300, 200, 100, 50, 40, 30, 25, 24, 23, 22, 21,20, 19, 18, 17, 16, 15, or 10 nucleotides in length. In another embodiment, a composition may comprise a library of nucleic acids comprising or capable of expressing small nucleic acids or antisense oligonucleotides or derivatives thereof, or pools of said small nucleic acids or antisense oligonucleotides or derivatives thereof. A pool of nucleic acids may comprise about 2-5, 5-10, 10-20, 10-30 or more nucleic acids comprising or capable of expressing small nucleic acids or antisense oligonucleotides or derivatives thereof.

In one embodiment, binding may be by conventional base pair complementarity, or, for example, in the case of binding to DNA duplexes, through specific interactions in the major groove of the double helix. In general, "antisense" refers to the range of techniques generally employed in the art, and includes any process that relies on specific binding to oligonucleotide sequences.

It is well known in the art that modifications can be made to the sequence of a miRNA or a pre-miRNA without disrupting miRNA activity. As used herein, the term "functional variant" of a miRNA sequence refers to an oligonucleotide sequence that varies from the natural miRNA sequence, but retains one or more functional characteristics of the miRNA (e.g., cancer cell proliferation inhibition, induction of cancer cell apoptosis, enhancement of cancer cell susceptibility to chemotherapeutic agents, specific miRNA target inhibition). In some embodiments, a functional variant of a miRNA sequence retains all of the functional characteristics of the miRNA. In certain embodiments, a functional variant of a miRNA has a nucleobase sequence that is a least about 60%, 65%, 70%, 75%, 80%, 85%, 90%, 91%, 92%, 93%, 94%, 95%, 96%, 97%, 98% or 99% identical to the miRNA or precursor thereof over a region of about 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleobases, or that the functional variant hybridizes to the complement of the miRNA or precursor thereof under stringent hybridization conditions. Accordingly, in certain embodiments the nucleobase sequence of a functional variant is capable of hybridizing to one or more target sequences of the miRNA.

miRNAs and their corresponding stem-loop sequences described herein may be found in miRBase, an online searchable database of miRNA sequences and annotation, found on the world wide web at microrna.sanger.ac.uk. Entries in the miRBase Sequence database represent a predicted hairpin portion of a miRNA transcript (the stem-loop), with information on the location and sequence of the mature miRNA sequence. The miRNA stem-loop sequences in the database are not strictly precursor miRNAs (pre-miRNAs), and may in some instances include the pre-miRNA and some flanking sequence from the presumed primary transcript. The miRNA nucleobase sequences described herein encompass any version of the miRNA, including the sequences described in Release 10.0 of the miRBase sequence database and sequences described in any earlier Release of the miRBase sequence database. A sequence database release may result in the re-naming of certain miRNAs. A sequence database release may result in a variation of a mature miRNA sequence.

In some embodiments, miRNA sequences of the invention may be associated with a second RNA sequence that may be located on the same RNA molecule or on a separate RNA molecule as the miRNA sequence. In such cases, the miRNA sequence may be referred to as the active strand, while the second RNA sequence, which is at least partially complementary to the miRNA sequence, may be referred to as the complementary strand. The active and complementary strands are hybridized to create a double-stranded RNA that is similar to a naturally occurring miRNA precursor. The activity of a miRNA may be optimized by maximizing uptake of the active strand and minimizing uptake of the complementary strand by the miRNA protein complex that regulates gene translation. This can be done through modification and/or design of the complementary strand.

In some embodiments, the complementary strand is modified so that a chemical group other than a phosphate or hydroxyl at its 5' terminus. The presence of the 5' modification apparently eliminates uptake of the complementary strand and subsequently favors uptake of the active strand by the miRNA protein complex. The 5' modification can be any of a variety of molecules known in the art, including $NH_2$, $NHCOCH_3$, and biotin. In another embodiment, the uptake of the complementary strand by the miRNA pathway is reduced by incorporating nucleotides with sugar modifications in the first 2-6 nucleotides of the complementary strand. It should be noted that such sugar modifications can be combined with the 5' terminal modifications described above to further enhance miRNA activities.

In some embodiments, the complementary strand is designed so that nucleotides in the 3' end of the complementary strand are not complementary to the active strand. This results in double-strand hybrid RNAs that are stable at the 3' end of the active strand but relatively unstable at the 5' end of the active strand. This difference in stability enhances the uptake of the active strand by the miRNA pathway, while reducing uptake of the complementary strand, thereby enhancing miRNA activity.

Small nucleic acid and/or antisense constructs of the methods and compositions presented herein can be delivered, for example, as an expression plasmid which, when transcribed in the cell, produces RNA which is complementary to at least a unique portion of cellular nucleic acids (e.g., small RNAs, mRNA, and/or genomic DNA). Alternatively, the small nucleic acid molecules can produce RNA which encodes mRNA, miRNA, pre-miRNA, pri-miRNA, miRNA*, anti-miRNA, or a miRNA binding site, or a variant thereof. For example, selection of plasmids suitable for expressing the miRNAs, methods for inserting nucleic acid sequences into the plasmid, and methods of delivering the recombinant plasmid to the cells of interest are within the skill in the art. See, for example, Zeng et al. (2002), Molecular Cell 9:1327-1333; Tuschl (2002), Nat. Biotechnol, 20:446-448; Brummelkamp et al. (2002), Science 296: 550-553; Miyagishi et al. (2002), Nat. Biotechnol. 20:497-500; Paddison et al. (2002), Genes Dev. 16:948-958; Lee et al. (2002), Nat. Biotechnol. 20:500-505; and Paul et al. (2002), Nat. Biotechnol. 20:505-508, the entire disclosures of which are herein incorporated by reference.

Alternatively, small nucleic acids and/or antisense constructs are oligonucleotide probes that are generated ex vivo and which, when introduced into the cell, results in hybridization with cellular nucleic acids. Such oligonucleotide probes are preferably modified oligonucleotides that are resistant to endogenous nucleases, e.g., exonucleases and/or endonucleases, and are therefore stable in vivo. Exemplary nucleic acid molecules for use as small nucleic acids and/or antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by Van der Krol et al. (1988) BioTechniques 6:958-976; and Stein et al. (1988) Cancer Res 48:2659-2668.

Antisense approaches may involve the design of oligonucleotides (either DNA or RNA) that are complementary to cellular nucleic acids (e.g., complementary to biomarkers listed in Table 2 and the Examples). Absolute complementarity is not required. In the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with a nucleic acid (e.g., RNA) it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the mRNA, e.g., the 5' untranslated sequence up to and including the AUG initiation codon, should work most efficiently at inhibiting translation. However, sequences complementary to the 3' untranslated sequences of mRNAs have recently been shown to be effective at inhibiting translation of mRNAs as well (Wagner, R. (1994) Nature 372:333). Therefore, oligonucleotides complementary to either the 5' or 3' untranslated, non-coding regions of genes could be used in an antisense approach to inhibit translation of endogenous mRNAs. Oligonucleotides complementary to the 5' untranslated region of the mRNA may include the complement of the AUG start codon. Antisense oligonucleotides complementary to mRNA coding regions are less efficient inhibitors of translation but could also be used in accordance with the methods and compositions presented herein. Whether designed to hybridize to the 5', 3' or coding region of cellular mRNAs, small nucleic acids and/or antisense nucleic acids should be at least six nucleotides in length, and can be less than about 1000, 900, 800, 700, 600, 500, 400, 300, 200, 100, 50, 40, 30, 25, 24, 23, 22, 21,20, 19, 18, 17, 16, 15, or 10 nucleotides in length.

Regardless of the choice of target sequence, it is preferred that in vitro studies are first performed to quantitate the ability of the antisense oligonucleotide to inhibit gene expression. In one embodiment these studies utilize controls that distinguish between antisense gene inhibition and non-specific biological effects of oligonucleotides. In another embodiment these studies compare levels of the target nucleic acid or protein with that of an internal control nucleic acid or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

Small nucleic acids and/or antisense oligonucleotides can be DNA or RNA or chimeric mixtures or derivatives or modified versions thereof, single-stranded or double-stranded. Small nucleic acids and/or antisense oligonucleotides can be modified at the base moiety, sugar moiety, or phosphate backbone, for example, to improve stability of the molecule, hybridization, etc., and may include other appended groups such as peptides (e.g., for targeting host cell receptors), or agents facilitating transport across the cell membrane (see, e.g., Letsinger et al. (1989) Proc. Natl. Acad. Sci. U.S.A. 86:6553-6556; Lemaitre et al. (1987) Proc. Natl. Acad. Sci. 84:648-652; PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al. (1988) BioTechniques 6:958-976) or intercalating agents. (See, e.g., Zon (1988), Pharm. Res. 5:539-549). To this end, small nucleic acids and/or antisense oligonucleotides may be conjugated to another molecule, e.g., a peptide, hybridization triggered cross-linking agent, transport agent, hybridization-triggered cleavage agent, etc.

Small nucleic acids and/or antisense oligonucleotides may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxytiethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Small nucleic acids and/or antisense oligonucleotides may also comprise at least one modified sugar moiety selected from the group including but not limited to arabinose, 2-fluoroarabinose, xylulose, and hexose.

In certain embodiments, a compound comprises an oligonucleotide (e.g., a miRNA or miRNA encoding oligonucleotide) conjugated to one or more moieties which enhance the activity, cellular distribution or cellular uptake of the resulting oligonucleotide. In certain such embodiments, the moiety is a cholesterol moiety (e.g., antagomirs) or a lipid moiety or liposome conjugate. Additional moieties for conjugation include carbohydrates, phospholipids, biotin, phenazine, folate, phenanthridine, anthraquinone, acridine, fluoresceins, rhodamines, coumarins, and dyes. In certain embodiments, a conjugate group is attached directly to the oligonucleotide. In certain embodiments, a conjugate group is attached to the oligonucleotide by a linking moiety selected from amino, hydroxyl, carboxylic acid, thiol, unsaturations (e.g., double or triple bonds), 8-amino-3,6-dioxaoctanoic acid (ADO), succinimidyl 4-(N-maleimidomethyl) cyclohexane-1-carboxylate (SMCC), 6-aminohexanoic acid (AHEX or AHA), substituted C1-C10 alkyl, substituted or unsubstituted C2-C10 alkenyl, and substituted or unsubstituted C2-C10 alkynyl. In certain such embodiments, a substituent group is selected from hydroxyl, amino, alkoxy, carboxy, benzyl, phenyl, nitro, thiol, thioalkoxy, halogen, alkyl, aryl, alkenyl and alkynyl.

In certain such embodiments, the compound comprises the oligonucleotide having one or more stabilizing groups that are attached to one or both termini of the oligonucleotide to enhance properties such as, for example, nuclease stability. Included in stabilizing groups are cap structures. These terminal modifications protect the oligonucleotide from exonuclease degradation, and can help in delivery and/or localization within a cell. The cap can be present at the 5'-terminus (5'-cap), or at the 3'-terminus (3'-cap), or can be present on both termini. Cap structures include, for example, inverted deoxy abasic caps.

Suitable cap structures include a 4',5'-methylene nucleotide, a 1-(beta-D-erythrofuranosyl) nucleotide, a 4'-thio nucleotide, a carbocyclic nucleotide, a 1,5-anhydrohexitol nucleotide, an L-nucleotide, an alpha-nucleotide, a modified base nucleotide, a phosphorodithioate linkage, a threopentofuranosyl nucleotide, an acyclic 3',4'-seco nucleotide, an acyclic 3,4-dihydroxybutyl nucleotide, an acyclic 3,5-dihydroxypentyl nucleotide, a 3'-3'-inverted nucleotide moiety, a 3'-3'-inverted abasic moiety, a 3'-2'-inverted nucleotide moiety, a 3'-2'-inverted abasic moiety, a 1,4-butanediol phosphate, a 3'-phosphoramidate, a hexylphosphate, an aminohexyl phosphate, a 3'-phosphate, a 3'-phosphorothioate, a phosphorodithioate, a bridging methylphosphonate moiety, and a non-bridging methylphosphonate moiety 5'-aminoalkyl phosphate, a 1,3-diamino-2-propyl phosphate, 3-aminopropyl phosphate, a 6-aminohexyl phosphate, a 1,2-aminododecyl phosphate, a hydroxypropyl phosphate, a 5'-5'-inverted nucleotide moiety, a 5'-5'-inverted abasic moiety, a 5'-phosphoramidate, a 5'-phosphorothioate, a 5'-amino, a bridging and/or non-bridging 5'-phosphoramidate, a phosphorothioate, and a 5'-mercapto moiety.

Small nucleic acids and/or antisense oligonucleotides can also contain a neutral peptide-like backbone. Such molecules are termed peptide nucleic acid (PNA)-oligomers and are described, e.g., in Perry-O'Keefe et al. (1996) Proc. Natl. Acad. Sci. U.S.A. 93:14670 and in Eglom et al. (1993) Nature 365:566. One advantage of PNA oligomers is their capability to bind to complementary DNA essentially independently from the ionic strength of the medium due to the neutral backbone of the DNA. In yet another embodiment, small nucleic acids and/or antisense oligonucleotides comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In a further embodiment, small nucleic acids and/or antisense oligonucleotides are α-anomeric oligonucleotides. An α-anomeric oligonucleotide forms specific double-stranded hybrids with complementary RNA in which, contrary to the usual b-units, the strands run parallel to each other (Gautier et al. (1987) Nucl. Acids Res. 15:6625-6641). The oligonucleotide is a 2'-0-methylribonucleotide (Inoue et al. (1987) Nucl. Acids Res. 15:6131-6148), or a chimeric RNA-DNA analogue (Inoue et al. (1987) FEBS Lett. 215: 327-330).

Small nucleic acids and/or antisense oligonucleotides of the methods and compositions presented herein may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. (1988) Nucl. Acids Res. 16:3209, methylphosphonate oligonucleotides can be prepared by use of controlled pore glass polymer supports (Sarin et al. (1988) Proc. Natl. Acad. Sci. U.S.A. 85:7448-7451), etc. For example, an isolated miRNA can be chemically synthesized or recombinantly produced using methods known in the art. In some instances, miRNA are chemically synthesized using appropriately protected ribonucleoside phosphoramidites and a conventional DNA/RNA synthesizer. Commercial suppliers of synthetic RNA molecules or synthesis reagents include, e.g., Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA), Cruachem (Glasgow, UK), and Exiqon (Vedbaek, Denmark).

Small nucleic acids and/or antisense oligonucleotides can be delivered to cells in vivo. A number of methods have been developed for delivering small nucleic acids and/or antisense oligonucleotides DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systematically.

In one embodiment, small nucleic acids and/or antisense oligonucleotides may comprise or be generated from double stranded small interfering RNAs (siRNAs), in which sequences fully complementary to cellular nucleic acids (e.g., mRNAs) sequences mediate degradation or in which sequences incompletely complementary to cellular nucleic acids (e.g., mRNAs) mediate translational repression when expressed within cells. In another embodiment, double stranded siRNAs can be processed into single stranded antisense RNAs that bind single stranded cellular RNAs (e.g., microRNAs) and inhibit their expression. RNA interference (RNAi) is the process of sequence-specific, post-transcriptional gene silencing in animals and plants, initiated by double-stranded RNA (dsRNA) that is homologous in sequence to the silenced gene. in vivo, long dsRNA is cleaved by ribonuclease III to generate 21- and 22-nucleotide siRNAs. It has been shown that 21-nucleotide siRNA duplexes specifically suppress expression of endogenous and heterologous genes in different mammalian cell lines, including human embryonic kidney (293) and HeLa cells (Elbashir et al. (2001) *Nature* 411:494-498). Accordingly, translation of a gene in a cell can be inhibited by contacting the cell with short double stranded RNAs having a length of about 15 to 30 nucleotides or of about 18 to 21 nucleotides or of about 19 to 21 nucleotides. Alternatively, a vector encoding for such siRNAs or short hairpin RNAs (shRNAs) that are metabolized into siRNAs can be introduced into a target cell (see, e.g., McManus et al. (2002) RNA 8:842; Xia et al. (2002) Nature Biotechnology 20:1006; and Brummelkamp et al. (2002) Science 296:550). Vectors that can be used are commercially available, e.g., from OligoEngine under the name pSuper RNAi System™.

Ribozyme molecules designed to catalytically cleave cellular mRNA transcripts can also be used to prevent translation of cellular mRNAs and expression of cellular polypeptides, or both (See, e.g., PCT International Publication WO90/11364, published Oct. 4, 1990; Sarver et al. (1990) Science 247:1222-1225 and U.S. Pat. No. 5,093,246). While ribozymes that cleave mRNA at site specific recognition sequences can be used to destroy cellular mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach (1988) Nature 334:585-591. The ribozyme may be engineered so that the cleavage recognition site is located near the 5' end of cellular mRNAs; i.e., to increase efficiency and minimize the intracellular accumulation of non-functional mRNA transcripts.

The ribozymes of the methods and compositions presented herein also include RNA endoribonucleases (hereinafter "Cech-type ribozymes") such as the one which occurs naturally in *Tetrahymena thermophila* (known as the IVS, or L-19 IVS RNA) and which has been extensively described by Thomas Cech and collaborators (Zaug, et al. (1984) Science 224:574-578; Zaug, et al. (1986) Science 231:470-475; Zaug, et al. (1986) Nature 324:429-433; published International patent application No. WO88/04300 by University Patents Inc.; Been, et al. (1986) Cell 47:207-216). The Cech-type ribozymes have an eight base pair active site which hybridizes to a target RNA sequence whereafter cleavage of the target RNA takes place. The methods and compositions presented herein encompasses those Cech-type ribozymes which target eight base-pair active site sequences that are present in cellular genes.

As in the antisense approach, the ribozymes can be composed of modified oligonucleotides (e.g., for improved stability, targeting, etc.). A preferred method of delivery involves using a DNA construct "encoding" the ribozyme under the control of a strong constitutive pol III or pol II promoter, so that transfected cells will produce sufficient quantities of the ribozyme to destroy endogenous cellular messages and inhibit translation. Because ribozymes unlike antisense molecules, are catalytic, a lower intracellular concentration is required for efficiency.

Nucleic acid molecules to be used in triple helix formation for the inhibition of transcription of cellular genes are preferably single stranded and composed of deoxyribonucleotides. The base composition of these oligonucleotides should promote triple helix formation via Hoogsteen base pairing rules, which generally require sizable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in CGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizable stretch of either purines or pyrimidines to be present on one strand of a duplex.

Small nucleic acids (e.g., miRNAs, pre-miRNAs, pri-miRNAs, miRNA*, anti-miRNA, or a miRNA binding site, or a variant thereof), antisense oligonucleotides, ribozymes, and triple helix molecules of the methods and compositions presented herein may be prepared by any method known in the art for the synthesis of DNA and RNA molecules. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Moreover, various well-known modifications to nucleic acid molecules may be introduced as a means of increasing intracellular stability and half-life. Possible modifications include but are not limited to the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone. One of skill in the art will readily understand that polypeptides, small nucleic acids, and antisense oligonucleotides can be further linked to another peptide or polypeptide (e.g., a heterologous peptide), e.g., that serves as a means of protein detection. Non-limiting examples of label peptide or polypeptide moieties useful for detection in the invention include, without limitation, suitable enzymes such as horseradish peroxidase, alkaline phosphatase, beta-galactosidase, or acetylcholinesterase; epitope tags, such as FLAG, MYC, HA, or HIS tags; fluorophores such as green fluorescent protein; dyes; radioisotopes; digoxygenin; biotin; antibodies; polymers; as well as others known in the art, for example, in Principles of Fluorescence Spectroscopy, Joseph R. Lakowicz (Editor), Plenum Pub Corp, 2nd edition (July 1999).

In addition to the agents described herein, additional agents are particularly useful for upregulating or downregulating immune responses according to the present invention. For example, modulation of the interaction between PD-1 and PD-1 ligand (e.g., membrane-bound PD-L1 and/or soluble PD-L1), or between PD-1 ligand (e.g., soluble PD-L1) (e.g., membrane-bound PD-L1 and/or soluble PD-L1) and a B7 polypeptide, results in modulation of the immune response. In general, in embodiments where PD-L1 binds to a costimulatory receptor such as B7-1, upregulation of PD-L1 activity results in upregulation of immune responses, whereas downregulation of PD-L1 activity results in downregulation of immune responses. In embodiments where PD-L1 binds to inhibitory receptors such as PD-1, upregulation of PD-L1 activity results in downregulation of immune responses, whereas downregulation of PD-L1 activity results in upregulation of immune responses. It is also believed that soluble forms of PD-L1, whether naturally occurring or cleavage products of membrane-bound PD-L1, can still interact with PD-L1 receptors, such as B7-1 or PD-L1, to modulate immune responses as the membrane-bound version.

Non-limiting examples of how such agents can modify immune responses include the observation that the interaction between a B7 polypeptide and a PD-1 ligand (e.g., soluble PD-L1) polypeptide prevents PD-1 ligand (e.g., soluble PD-L1) from binding to PD-1 and, thus, inhibits delivery of an inhibitory immune signal. Thus, in one embodiment, agents which block the interaction between PD-1 and PD-1 ligand (e.g., soluble PD-L1) can prevent inhibitory signaling. In one embodiment, agents that block the binding of a B7 polypeptide to a PD-1 ligand (e.g., soluble PD-L1) polypeptide allow PD-1 ligand (e.g., soluble PD-L1) to bind PD-1 and provide an inhibitory signal to an immune cell. PD-1 ligand (e.g., soluble PD-L1), by binding to a B7 polypeptide, also reduces the B7 polypeptide binding to the inhibitory receptor CTLA4. In one embodiment, agents that block the binding of a B7 polypeptide to a PD-1 ligand (e.g., soluble PD-L1) polypeptide allow the B7 polypeptide to bind CTLA4 and provide an inhibitory signal to an immune cell. In another embodiment, PD-L1, by binding to a B7 polypeptide, also reduces the B7 polypeptide binding to the costimulatory receptor CD28. Thus, in one embodiment, agents that block the binding of a B7 polypeptide to a PD-1 ligand (e.g., soluble PD-L1) polypeptide allow the B7 polypeptide to bind CD28, and provide a costimulatory signal to an immune cell.

For example, in one embodiment, agents that increase the interaction between a PD-1 ligand (e.g., soluble PD-L1) and a B7 polypeptide can enhance an immune response while agents that decrease the interaction between a PD-1 ligand (e.g., soluble PD-L1) and a B7 polypeptide can reduce an immune response by enhancing the interaction between the PD-1 ligand (e.g., soluble PD-L1) and PD-1 and/or the interaction between the B7 polypeptide and CTLA4. In one embodiment, agents that modulate the interaction between a PD-1 ligand (e.g., soluble PD-L1) and a B7 polypeptide do not produce inhibition of the interaction between a PD-1 ligand (e.g., soluble PD-L1) and PD-1 and/or between the B7 polypeptide and CTLA4. In another embodiment, agents that increase a PD-1 ligand (e.g., soluble PD-L1) interaction with a B7 polypeptide, also decrease the interaction between the PD-1 ligand (e.g., soluble PD-L1) and PD-1, and/or between the B7 polypeptide and CTLA4. In yet another embodiment, agents that decrease the interaction of a PD-1 ligand (e.g., soluble PD-L1) and a B7 polypeptide, enhance or increase the interaction between the PD-1 ligand (e.g., soluble PD-L1) and PD-1, and/or between the B7 polypeptide and CTLA4.

Exemplary agents for modulating (e.g., reducing) an immune response include antibodies against PD-1, a PD-1 ligand (e.g., soluble PD-L1), or a B7 polypeptide which inhibit the interaction of the PD-1 ligand (e.g., soluble PD-L1) with PD-1 or B7 polypeptide; bispecific antibodies that enhance PD-1 signaling, such as bispecific antibodies against PD-1 and PD-L1; agents that reduce the expression of inhibitory receptor-ligand interactions, such as antisense nucleic acid molecules, triplex oligonucleotides, or ribozymes targeting PD-1 and/or PD-L1; small molecules or peptides which inhibit the interaction of the PD-1 ligand (e.g., soluble PD-L1) with the B7 polypeptide; and fusion proteins (e.g., the extracellular portion of the PD-1 ligand (e.g., soluble PD-L1) or B7 polypeptide, fused to the Fc portion of an antibody) which bind to the B7 polypeptide or PD-1 ligand (e.g., soluble PD-L1), respectively, and prevent the interaction between the PD-1 ligand (e.g., soluble PD-L1) and B7 polypeptide.

In another embodiment, agents that increase the interaction between a PD-1 ligand (e.g., soluble PD-L1) and a B7 polypeptide, decrease an immune response by decreasing the ability of the B7 polypeptide to bind to CD28. In yet another embodiment, agents that decrease the interaction between a PD-1 ligand (e.g., soluble PD-L1) and a B7 polypeptide can increase the immune response by increasing the interaction between the B7 polypeptide and CD28.

Agents that modulate the interaction between a PD-1 ligand (e.g., soluble PD-L1) and a PD-1 polypeptide can also be used to up or down regulate the immune response. For example, agents that increase the interaction between the PD-1 ligand (e.g., soluble PD-L1) and PD-1 polypeptide can decrease an immune response while agents that decrease the interaction between the PD-1 ligand (e.g., soluble PD-L1) and PD-1 polypeptide can increase an immune response. Preferably, agents that modulate the interaction between the PD-1 ligand (e.g., soluble PD-L1) and PD-1, do not modulate (have no direct affect on) the interaction between the PD-1 ligand (e.g., soluble PD-L1) and a B7 polypeptide. In another embodiment, agents that increase the interaction between the PD-1 ligand (e.g., soluble PD-L1) and PD-1, decrease the interaction between the PD-1 ligand (e.g., soluble PD-L1) and the B7 polypeptide. In yet another embodiment, agents that decrease the interaction between the PD-L1 ligand and PD-1 increase the interaction between the PD-1 ligand (e.g., soluble PD-L1) and the B7 polypeptide. Exemplary agents for modulating (e.g., enhancing) an immune response include antibodies against PD-1 or a PD-1 ligand (e.g., soluble PD-L1) which block the interaction between PD-1 and the PD-1 ligand (e.g., soluble PD-L1); bispecific antibodies that enhance B7 signaling, such as bispecific antibodies against PD-L1 and B7-1; multivalent antibodies against such a target that ligate many such molecules together in order to increase local concentrations and stimulate interactions; agents that reduce the expression of costimulatory receptor-ligand interactions, such as antisense nucleic acid molecules, triplex oligonucleotides, or ribozymes targeting B7-1; small molecules or peptides which block the interaction between PD-1 and the PD-1 ligand (e.g., soluble PD-L1); and fusion proteins (e.g., the extracellular portion of a PD-1 ligand (e.g., soluble PD-L1) or PD-1 polypeptide fused to the Fc portion of an antibody) which bind to PD-1 or a PD-1 ligand (e.g., soluble PD-L1) and prevent the interaction between the PD-1 ligand (e.g., soluble PD-L1) and PD-1.

In some embodiments, agents useful for upregulating or downregulating PD-1 and/or PD-L1 in particular are useful. Combinations of any such agents are contemplated.

Exemplary agents for use in downmodulating PD-L1 (i.e., PD-L1 antagonists) include (for example): antisense molecules, antibodies that recognize PD-L1, compounds that block interaction of PD-L1 and one of its naturally occurring receptors on a immune cell (e.g., soluble, monovalent PD-L1 molecules, and soluble forms of B7-4 ligands or compounds identified in the subject screening assays). In some embodiments, combinations of antibodies that target either the membrane-bound PD-L1 form or the soluble PD-L1 form are useful for functionally inactivating both forms of PD-L1. Exemplary agents for use in downmodulating PD-1 (i.e., PD-1 antagonists) include (for example): antisense molecules, antibodies that bind to PD-1, but do not transduce an inhibitory signal to the immune cell ("non-activating antibodies"), and soluble forms of PD-1.

Exemplary agents for use in upmodulating PD-L1 (i.e., PD-L1 agonists) include (for example): nucleic acid molecules encoding PD-L1 polypeptides, multivalent forms of PD-L1, compounds that increase the expression of PD-L1, and cells that express PD-L1, and the like. Exemplary agents for use in upmodulating PD-1 (i.e., PD-1 agonists) include (for example): antibodies that transmit an inhibitory signal via PD-1, compounds that enhance the expression of PD-1, nucleic acid molecules encoding PD-1, and forms of B7-4 that transduce a signal via PD-1.

The mechanisms and agents described above for the modulation of immunoregulatory ligands (e.g., PD-L1) with their natural immunoregulatory receptors (e.g., PD-1) apply to the other immune checkpoint inhibitors described herein, such as CTLA-4, LAG3, and the like.

The modulatory agents described herein (e.g., antibodies, small molecules, peptides, fusion proteins, or small nucleic acids) can be incorporated into pharmaceutical compositions and administered to a subject in vivo. The compositions may contain a single such molecule or agent or any combination of agents described herein. Based on the genetic pathway analyses described herein, it is believed that such combinations of agents is especially effective in diagnosing, prognosing, preventing, and treating melanoma. Thus, "single active agents" described herein can be combined with other pharmacologically active compounds ("second active agents") known in the art according to the methods and compositions provided herein. It is believed that certain combinations work synergistically in the treatment of particular types of melanoma. Second active agents can be large molecules (e.g., proteins) or small molecules (e.g., synthetic inorganic, organometallic, or organic molecules).

Examples of large molecule active agents include, but are not limited to, hematopoietic growth factors, cytokines, and monoclonal and polyclonal antibodies. Typical large molecule active agents are biological molecules, such as naturally occurring or artificially made proteins. Proteins that are particularly useful in this invention include proteins that stimulate the survival and/or proliferation of hematopoietic precursor cells and immunologically active poietic cells in vitro or in vivo. Others stimulate the division and differentiation of committed erythroid progenitors in cells in vitro or in vivo. Particular proteins include, but are not limited to: interleukins, such as IL-2 (including recombinant IL-II ("rIL2") and canarypox IL-2), IL-10, IL-12, and IL-18; interferons, such as interferon alfa-2a, interferon alfa-2b, interferon alpha-n1, interferon alpha-n3, interferon beta-Ia, and interferon gamma-Ib; GM-CF and GM-CSF; and EPO.

Particular proteins that can be used in the methods and compositions provided herein include, but are not limited to: filgrastim, which is sold in the United States under the trade name Neupogen® (Amgen, Thousand Oaks, Calif.); sargramostim, which is sold in the United States under the trade name Leukine® (Immunex, Seattle, Wash.); and recombinant EPO, which is sold in the United States under the trade name Epogen® (Amgen, Thousand Oaks, Calif.). Recombinant and mutated forms of GM-CSF can be prepared as described in U.S. Pat. Nos. 5,391,485; 5,393,870; and 5,229,496; all of which are incorporated herein by reference. Recombinant and mutated forms of G-CSF can be prepared as described in U.S. Pat. Nos. 4,810,643; 4,999,291; 5,528,823; and 5,580,755; all of which are incorporated herein by reference.

When antibodies are used, the therapy is called immunotherapy. Antibodies that can be used in combination with the methods described herein include monoclonal and polyclonal antibodies. Examples of antibodies include, but are not limited to, ipilimumab (Yervoy®), trastuzumab (Herceptin®), rituximab (Rituxan®), bevacizumab (Avastin®), pertuzumab (Omnitarg®), tositumomab (Bexxar®), edrecolomab (Panorex®), and G250. Compounds of the invention can also be combined with, or used in combination with, anti-TNF-α antibodies. Large molecule active agents may be administered in the form of anti-cancer vaccines. For example, vaccines that secrete, or cause the secretion of, cytokines such as IL-2, G-CSF, and GM-CSF can be used in the methods, pharmaceutical compositions, and kits provided herein. See, e.g., Emens, L. A., et al., Curr. Opinion Mol. Ther. 3(1):77-84 (2001).

Second active agents that are small molecules can also be used to in combination as provided herein. Examples of small molecule second active agents include, but are not limited to, anti-cancer agents, antibiotics, immunosuppressive agents, and steroids.

In some embodiments, well known "combination chemotherapy" regimens can be used. In one embodiment, the combination chemotherapy comprises a combination of two or more of cyclophosphamide, hydroxydaunorubicin (also known as doxorubicin or adriamycin), oncovorin (vincristine), and prednisone. In another preferred embodiment, the combination chemotherapy comprises a combination of cyclophsophamide, oncovorin, prednisone, and one or more chemotherapeutics selected from the group consisting of anthracycline, hydroxydaunorubicin, epirubicin, and motixantrone.

Examples of other anti-cancer agents include, but are not limited to: acivicin; aclarubicin; acodazole hydrochloride; acronine; adozelesin; aldesleukin; altretamine; ambomycin; ametantrone acetate; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib (COX-2 inhibitor); chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium;

porfiromycin; prednimustine; procarbazine hydrochloride; puromycin; puromycin hydrochloride; pyrazofurin; riboprine; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; beta-clamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cyclosporin A; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib (e.g., Gleevec®), imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; Erbitux, human chorionic gonadotrophin; monophosphoryl lipid A+myobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen (Genasense®); O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RH retinamide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine;

triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer.

Specific second active agents include, but are not limited to, chlorambucil, fludarabine, dexamethasone (Decadron®), hydrocortisone, methylprednisolone, cilostamide, doxorubicin (Doxil®), forskolin, rituximab, cyclosporin A, cisplatin, vincristine, PDE7 inhibitors such as BRL-50481 and IR-202, dual PDE4/7 inhibitors such as IR-284, cilostazol, meribendan, milrinone, vesnarionone, enoximone and pimobendan, Syk inhibitors such as fostamatinib disodium (R406/R788), R343, R-112 and Excellair® (ZaBeCor Pharmaceuticals, Bala Cynwyd, Pa.).

IV. Methods of Selecting Agents and Compositions

Another aspect of the invention relates to methods of selecting agents (e.g., antibodies, fusion proteins, peptides, small molecules, or small nucleic acids) which bind to, upregulate, downregulate, or modulate one or more biomarkers of the invention listed in Table 2 and the Examples and/or a cancer (e.g., melanoma). Such methods can use screening assays, including cell based and non-cell based assays.

In one embodiment, the invention relates to assays for screening candidate or test compounds which bind to or modulate the expression or activity level of, one or more biomarkers of the invention, including one or more biomarkers listed in Table 2 and the Examples, or a fragment or ortholog thereof. Such compounds include, without limitation, antibodies, proteins, fusion proteins, nucleic acid molecules, and small molecules.

In one embodiment, an assay is a cell-based assay, comprising contacting a cell expressing one or more biomarkers of the invention, including one or more biomarkers listed in Table 2 and the Examples, or a fragment thereof, with a test compound and determining the ability of the test compound to modulate (e.g., stimulate or inhibit) the level of interaction between the biomarker and its natural binding partners as measured by direct binding or by measuring a parameter of cancer.

For example, in a direct binding assay, the biomarker polypeptide, a binding partner polypeptide of the biomarker, or a fragment(s) thereof, can be coupled with a radioisotope or enzymatic label such that binding of the biomarker polypeptide or a fragment thereof to its natural binding partner(s) or a fragment(s) thereof can be determined by detecting the labeled molecule in a complex. For example, the biomarker polypeptide, a binding partner polypeptide of the biomarker, or a fragment(s) thereof, can be labeled with $^{125}$I, $^{35}$S, $^{14}$C, or $^{3}$H, either directly or indirectly, and the radioisotope detected by direct counting of radioemmission or by scintillation counting. Alternatively, the polypeptides of interest a can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound to modulate the interactions between one or more biomarkers of the invention, including one or more biomarkers listed in Table 2 and the Examples, or a fragment thereof, and its natural binding partner(s) or a fragment(s) thereof, without the labeling of any of the interactants (e.g., using a microphysiometer as described in McConnell, H. M. et al. (1992) *Science* 257:1906-1912). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between compound and receptor.

In a preferred embodiment, determining the ability of the blocking agents (e.g., antibodies, fusion proteins, peptides, nucleic acid molecules, or small molecules) to antagonize the interaction between a given set of polypeptides can be accomplished by determining the activity of one or more members of the set of interacting molecules. For example, the activity of one or more biomarkers of the invention, including one or more biomarkers listed in Table 2 and the Examples, or a fragment thereof, can be determined by detecting induction of cytokine or chemokine response, detecting catalytic/enzymatic activity of an appropriate substrate, detecting the induction of a reporter gene (comprising a target-responsive regulatory element operatively linked to a nucleic acid encoding a detectable marker, e.g., chloramphenicol acetyl transferase), or detecting a cellular response regulated by the biomarker or a fragment thereof (e.g., modulations of biological pathways identified herein, such as modulated proliferation, apoptosis, cell cycle, and/or ligand-receptor binding activity). Determining the ability of the blocking agent to bind to or interact with said polypeptide can be accomplished by measuring the ability of an agent to modulate immune responses, for example, by detecting changes in type and amount of cytokine secretion, changes in apoptosis or proliferation, changes in gene expression or activity associated with cellular identity, or by interfering with the ability of said polypeptide to bind to antibodies that recognize a portion thereof.

In yet another embodiment, an assay of the present invention is a cell-free assay in which one or more biomarkers of the invention, including one or more biomarkers listed in Table 2 and the Examples or a fragment thereof, e.g., a biologically active fragment thereof, is contacted with a test compound, and the ability of the test compound to bind to the polypeptide, or biologically active portion thereof, is determined. Binding of the test compound to the biomarker or a fragment thereof, can be determined either directly or indirectly as described above. Determining the ability of the biomarker or a fragment thereof to bind to its natural binding partner(s) or a fragment(s) thereof can also be accomplished using a technology such as real-time Biomolecular Interaction Analysis (BIA) (Sjolander, S. and Urbaniczky, C. (1991) *Anal. Chem.* 63:2338-2345 and Szabo et al. (1995) *Curr. Opin. Struct. Biol.* 5:699-705). As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological polypeptides. One or more biomarkers polypeptide or a fragment thereof can be immobilized on a BIAcore chip and multiple agents, e.g., blocking antibodies, fusion proteins, peptides, or small molecules, can be tested for binding to the immobilized biomarker polypeptide or fragment thereof. An example of using the BIA technology is described by Fitz et al. (1997) *Oncogene* 15:613.

The cell-free assays of the present invention are amenable to use of both soluble and/or membrane-bound forms of proteins. In the case of cell-free assays in which a membrane-bound form protein is used it may be desirable to utilize a solubilizing agent such that the membrane-bound form of the protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3-cholamidopropyl) dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

In one or more embodiments of the above described assay methods, it may be desirable to immobilize either the biomarker polypeptide, the natural binding partner(s) polypeptide of the biomarker, or fragments thereof, to facilitate separation of complexed from uncomplexed forms of one or both of the proteins, as well as to accommodate automation of the assay. Binding of a test compound in the assay can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase-base fusion proteins, can be adsorbed onto glutathione Sepharose® beads (Sigma Chemical, St. Louis, Mo.) or glutathione derivatized microtiter plates, which are then combined with the test compound, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of binding or activity determined using standard techniques.

In an alternative embodiment, determining the ability of the test compound to modulate the activity of one or more biomarkers of the invention, including one or more biomarkers listed in Table 2 and the Examples, or a fragment thereof, or of natural binding partner(s) thereof can be accomplished by determining the ability of the test compound to modulate the expression or activity of a gene, e.g., nucleic acid, or gene product, e.g., polypeptide, that functions downstream of the interaction. For example, inflammation (e.g., cytokine and chemokine) responses can be determined, the activity of the interactor polypeptide on an appropriate target can be determined, or the binding of the interactor to an appropriate target can be determined as previously described.

In another embodiment, modulators of one or more biomarkers of the invention, including one or more biomarkers listed in Table 2 and the Examples, or a fragment thereof, are identified in a method wherein a cell is contacted with a candidate compound and the expression or activity level of the biomarker is determined. The level of expression of biomarker mRNA or polypeptide or fragments thereof in the presence of the candidate compound is compared to the level of expression of biomarker mRNA or polypeptide or fragments thereof in the absence of the candidate compound. The candidate compound can then be identified as a modulator of biomarker expression based on this comparison. For example, when expression of biomarker mRNA or polypeptide or fragments thereof is greater (statistically significantly greater) in the presence of the candidate compound than in its absence, the candidate compound is identified as a stimulator of biomarker expression. Alternatively, when expression of biomarker mRNA or polypeptide or fragments thereof is reduced (statistically significantly less) in the presence of the candidate compound than in its absence, the candidate compound is identified as an inhibitor of biomarker expression. The expression level of biomarker mRNA or polypeptide or fragments thereof in the cells can be determined by methods described herein for detecting biomarker mRNA or polypeptide or fragments thereof.

In yet another aspect of the invention, a biomarker of the invention, including one or more biomarkers listed in Table 2 and the Examples, or a fragment thereof, can be used as "bait proteins" in a two-hybrid assay or three-hybrid assay (see, e.g., U.S. Pat. No. 5,283,317; Zervos et al. (1993) Cell 72:223-232; Madura et al. (1993) J. Biol. Chem. 268:12046-12054; Bartel et al. (1993) Biotechniques 14:920-924; Iwabuchi et al. (1993) Oncogene 8:1693-1696; and Brent WO94/10300), to identify other polypeptides which bind to or interact with the biomarker or fragments thereof and are involved in activity of the biomarkers. Such biomarker-binding proteins are also likely to be involved in the propagation of signals by the biomarker polypeptides or biomarker natural binding partner(s) as, for example, downstream elements of one or more biomarkers-mediated signaling pathway.

The two-hybrid system is based on the modular nature of most transcription factors, which consist of separable DNA-binding and activation domains. Briefly, the assay utilizes two different DNA constructs. In one construct, the gene that codes for one or more biomarkers polypeptide is fused to a gene encoding the DNA binding domain of a known transcription factor (e.g., GAL-4). In the other construct, a DNA sequence, from a library of DNA sequences, that encodes an unidentified polypeptide ("prey" or "sample") is fused to a gene that codes for the activation domain of the known transcription factor. If the "bait" and the "prey" polypeptides are able to interact, in vivo, forming one or more biomarkers-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the polypeptide which interacts with one or more biomarkers polypeptide of the invention, including one or more biomarkers listed in Table 2 and the Examples or a fragment thereof.

In another aspect, the invention pertains to a combination of two or more of the assays described herein. For example, a modulating agent can be identified using a cell-based or a cell-free assay, and the ability of the agent to modulate the activity of one or more biomarkers polypeptide or a fragment thereof can be confirmed in vivo, e.g., in an animal such as an animal model for cellular transformation and/or tumorigenesis.

This invention further pertains to novel agents identified by the above-described screening assays. Accordingly, it is within the scope of this invention to further use an agent identified as described herein in an appropriate animal model. For example, an agent identified as described herein can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

V. Uses and Methods of the Invention

The biomarkers of the invention described herein, including the biomarkers listed in Table 2 and the Examples or fragments thereof, can be used in one or more of the following methods: a) screening assays; b) predictive medicine (e.g., diagnostic assays, prognostic assays, and monitoring of clinical trials); and c) methods of treatment (e.g., therapeutic and prophylactic, e.g., by up- or down-modulating the copy number, level of expression, and/or level of activity of the one or more biomarkers).

The biomarkers described herein or agents that modulate the expression and/or activity of such biomarkers can be used, for example, to (a) express one or more biomarkers of the invention, including one or more biomarkers listed in Table 2 and the Examples or a fragment thereof (e.g., via a recombinant expression vector in a host cell in gene therapy applications or synthetic nucleic acid molecule), (b) detect biomarker mRNA or a fragment thereof (e.g., in a biological sample) or a genetic alteration in one or more biomarkers gene, and/or (c) modulate biomarker activity, as described further below. The biomarkers or modulatory agents thereof can be used to treat conditions or disorders characterized by insufficient or excessive production of one or more biomarkers polypeptide or fragment thereof or production of biomarker polypeptide inhibitors. In addition, the biomarker polypeptides or fragments thereof can be used to screen for naturally occurring biomarker binding partner(s), to screen for drugs or compounds which modulate biomarker activity, as well as to treat conditions or disorders characterized by insufficient or excessive production of biomarker polypeptide or a fragment thereof or production of biomarker polypeptide forms which have decreased, aberrant or unwanted activity compared to biomarker wild-type polypeptides or fragments thereof (e.g., melanoma).

A. Screening Assays

In one aspect, the present invention relates to a method for preventing in a subject, a disease or condition associated with an unwanted, more than desirable, or less than desirable, expression and/or activity of one or more biomarkers described herein. Subjects at risk for a disease that would benefit from treatment with the claimed agents or methods can be identified, for example, by any one or combination of diagnostic or prognostic assays known in the art and described herein (see, for example, agents and assays described in III. Methods of Selecting Agents and Compositions).

B. Predictive Medicine

The present invention also pertains to the field of predictive medicine in which diagnostic assays, prognostic assays, and monitoring of clinical trials are used for prognostic (predictive) purposes to thereby treat an individual prophylactically. Accordingly, one aspect of the present invention relates to diagnostic assays for determining the expression and/or activity level of biomarkers of the invention, including biomarkers listed in Table 2 and the Examples or fragments thereof, in the context of a biological sample (e.g., blood, serum, cells, or tissue) to thereby determine whether an individual is afflicted with a disease or disorder, or is at risk of developing a disorder, associated with aberrant or unwanted biomarker expression or activity. The present invention also provides for prognostic (or predictive) assays for determining whether an individual is at risk of developing a disorder associated with biomarker polypeptide, nucleic acid expression or activity. For example, mutations in one or more biomarkers gene can be assayed in a biological sample.

Such assays can be used for prognostic or predictive purpose to thereby prophylactically treat an individual prior to the onset of a disorder characterized by or associated with biomarker polypeptide, nucleic acid expression or activity.

Another aspect of the invention pertains to monitoring the influence of agents (e.g., drugs, compounds, and small nucleic acid-based molecules) on the expression or activity of biomarkers of the invention, including biomarkers listed in Table 2 and the Examples, or fragments thereof, in clinical trials. These and other agents are described in further detail in the following sections.

1. Diagnostic Assays

The present invention provides, in part, methods, systems, and code for accurately classifying whether a biological sample is associated with a melanoma or a clinical subtype thereof. In some embodiments, the present invention is useful for classifying a sample (e.g., from a subject) as a cancer sample using a statistical algorithm and/or empirical data (e.g., the presence or level of one or biomarkers described herein).

An exemplary method for detecting the level of expression or activity of one or more biomarkers of the invention, including one or more biomarkers listed in Table 2 and the Examples or fragments thereof, and thus useful for classifying whether a sample is associated with melanoma or a clinical subtype thereof, involves obtaining a biological sample from a test subject and contacting the biological sample with a compound or an agent capable of detecting the biomarker (e.g., polypeptide or nucleic acid that encodes the biomarker or fragments thereof) such that the level of expression or activity of the biomarker is detected in the biological sample. In some embodiments, the presence or level of at least one, two, three, four, five, six, seven, eight, nine, ten, fifty, hundred, or more biomarkers of the invention are determined in the individual's sample. In certain instances, the statistical algorithm is a single learning statistical classifier system. Exemplary statistical analyses are presented in the Examples and can be used in certain embodiments. In other embodiments, a single learning statistical classifier system can be used to classify a sample as a cancer sample, a cancer subtype sample, or a non-cancer sample based upon a prediction or probability value and the presence or level of one or more biomarkers described herein. The use of a single learning statistical classifier system typically classifies the sample as a cancer sample with a sensitivity, specificity, positive predictive value, negative predictive value, and/or overall accuracy of at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

Other suitable statistical algorithms are well known to those of skill in the art. For example, learning statistical classifier systems include a machine learning algorithmic technique capable of adapting to complex data sets (e.g., panel of markers of interest) and making decisions based upon such data sets. In some embodiments, a single learning statistical classifier system such as a classification tree (e.g., random forest) is used. In other embodiments, a combination of 2, 3, 4, 5, 6, 7, 8, 9, 10, or more learning statistical classifier systems are used, preferably in tandem. Examples of learning statistical classifier systems include, but are not limited to, those using inductive learning (e.g., decision/classification trees such as random forests, classification and regression trees (C&RT), boosted trees, etc.), Probably Approximately Correct (PAC) learning, connectionist learning (e.g., neural networks (NN), artificial neural networks (ANN), neuro fuzzy networks (NFN), network structures, perceptrons such as multi-layer perceptrons, multi-layer feed-forward networks, applications of neural networks, Bayesian learning in belief networks, etc.), reinforcement learning (e.g., passive learning in a known environment such as naive learning, adaptive dynamic learning, and temporal difference learning, passive learning in an unknown environment, active learning in an unknown environment, learning action-value functions, applications of reinforcement learning, etc.), and genetic algorithms and evolutionary programming. Other learning statistical classifier systems include support vector machines (e.g., Kernel methods), multivariate adaptive regression splines (MARS), Levenberg-Marquardt algorithms, Gauss-Newton algorithms, mixtures of Gaussians, gradient descent algorithms, and learning vector quantization (LVQ). In certain embodiments, the method of the present invention further comprises sending the cancer classification results to a clinician, e.g., an oncologist or hematologist.

In another embodiment, the method of the present invention further provides a diagnosis in the form of a probability that the individual has melanoma or a clinical subtype thereof. For example, the individual can have about a 0%, 5%, 10%, 15%, 20%, 25%, 30%, 35%, 40%, 45%, 50%, 55%, 60%, 65%, 70%, 75%, 80%, 85%, 90%, 95%, or greater probability of having cancer or a clinical subtype thereof. In yet another embodiment, the method of the present invention further provides a prognosis of cancer in the individual. For example, the prognosis can be surgery, development of melanoma or a clinical subtype thereof, development of one or more symptoms, development of malignant cancer, or recovery from the disease. In some instances, the method of classifying a sample as a cancer sample is further based on the symptoms (e.g., clinical factors) of the individual from which the sample is obtained. The symptoms or group of symptoms can be, for example, those associated with the IPI. In some embodiments, the diagnosis of an individual as having melanoma or a clinical subtype thereof is followed by administering to the individual a therapeutically effective amount of a drug useful for treating one or more symptoms associated with melanoma or a clinical subtype thereof.

In some embodiments, an agent for detecting biomarker mRNA, genomic DNA, or fragments thereof is a labeled nucleic acid probe capable of hybridizing to biomarker mRNA, genomic DNA, or fragments thereof. The nucleic acid probe can be, for example, full-length biomarker nucleic acid, or a portion thereof, such as an oligonucleotide of at least 15, 30, 50, 100, 250 or 500 nucleotides in length and sufficient to specifically hybridize under stringent conditions well known to a skilled artisan to biomarker mRNA or genomic DNA. Other suitable probes for use in the diagnostic assays of the invention are described herein. In some embodiments, the nucleic acid probe is designed to detect transcript variants (i.e., different splice forms) of a gene.

A preferred agent for detecting one or more biomarkers listed in Table 2 and the Examples or a fragment thereof is an antibody capable of binding to the biomarker, preferably an antibody with a detectable label. Antibodies can be polyclonal, or more preferably, monoclonal. An intact antibody, or a fragment thereof (e.g., Fab or F(ab')2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells, and biological fluids isolated from a subject, as well as tissues, cells, and fluids present within a subject. That is, the detection method of the invention can be used to detect biomarker mRNA, polypeptide, genomic DNA, or fragments thereof, in a biological sample in vitro as well as in vivo. For example, in vitro techniques for detection of biomarker mRNA or a fragment thereof include Northern hybridizations and in situ hybridizations. In vitro techniques for detection of biomarker polypeptide include enzyme linked immunosorbent assays (ELISAs), Western blots, immunoprecipitations and immunofluorescence. In vitro techniques for detection of biomarker genomic DNA or a fragment thereof include Southern hybridizations. Furthermore, in vivo techniques for detection of one or more biomarkers polypeptide or a fragment thereof include introducing into a subject a labeled anti-biomarker antibody. For example, the antibody can be labeled with a radioactive marker whose presence and location in a subject can be detected by standard imaging techniques.

In one embodiment, the biological sample contains polypeptide molecules from the test subject. Alternatively, the biological sample can contain mRNA molecules from the test subject or genomic DNA molecules from the test subject. A preferred biological sample is a hematological tissue (e.g., a sample comprising blood, plasma, B cell, bone marrow, etc.) sample isolated by conventional means from a subject.

In another embodiment, the methods further involve obtaining a control biological sample from a control subject, contacting the control sample with a compound or agent capable of detecting polypeptide, mRNA, cDNA, small RNAs, mature miRNA, pre-miRNA, pri-miRNA, miRNA*, anti-miRNA, or a miRNA binding site, or a variant thereof, genomic DNA, or fragments thereof of one or more biomarkers listed in Table 2 and the Examples such that the presence of biomarker polypeptide, mRNA, genomic DNA, or fragments thereof, is detected in the biological sample, and comparing the presence of biomarker polypeptide, mRNA, cDNA, small RNAs, mature miRNA, pre-miRNA, pri-miRNA, miRNA*, anti-miRNA, or a miRNA binding site, or a variant thereof, genomic DNA, or fragments thereof in the control sample with the presence of biomarker polypeptide, mRNA, cDNA, small RNAs, mature miRNA, pre-miRNA, pri-miRNA, miRNA*, anti-miRNA, or a miRNA binding site, or a variant thereof, genomic DNA, or fragments thereof in the test sample.

The invention also encompasses kits for detecting the presence of a polypeptide, mRNA, cDNA, small RNAs, mature miRNA, pre-miRNA, pri-miRNA, miRNA*, anti-miRNA, or a miRNA binding site, or a variant thereof, genomic DNA, or fragments thereof, of one or more biomarkers listed in Table 2 and the Examples in a biological sample. For example, the kit can comprise a labeled compound or agent capable of detecting one or more biomarkers polypeptide, mRNA, cDNA, small RNAs, mature miRNA, pre-miRNA, pri-miRNA, miRNA*, anti-miRNA, or a miRNA binding site, or a variant thereof, genomic DNA, or fragments thereof, in a biological sample; means for determining the amount of the biomarker polypeptide, mRNA, cDNA, small RNAs, mature miRNA, pre-miRNA, pri-miRNA, miRNA*, anti-miRNA, or a miRNA binding site, or a variant thereof, genomic DNA, or fragments thereof,f in the sample; and means for comparing the amount of the biomarker polypeptide, mRNA, cDNA, small RNAs, mature miRNA, pre-miRNA, pri-miRNA, miRNA*, anti-miRNA, or a miRNA binding site, or a variant thereof, genomic DNA, or fragments thereof, in the sample with a standard. The compound or agent can be packaged in a suitable container. The kit can further comprise instructions for using the kit to detect the biomarker polypeptide, mRNA, cDNA, small RNAs, mature miRNA, pre-miRNA, pri-miRNA, miRNA*, anti-miRNA, or a miRNA binding site, or a variant thereof, genomic DNA, or fragments thereof.

In some embodiments, therapies tailored to treat stratified patient populations based on the described diagnostic assays are further administered, such as melanoma standards of treatment, immune therapy, and combinations thereof described herein.

2. Prognostic Assays

The diagnostic methods described herein can furthermore be utilized to identify subjects having or at risk of developing a disease or disorder associated with aberrant expression or activity of one or more biomarkers of the invention, including one or more biomarkers listed in Table 2 and the Examples, or a fragment thereof. As used herein, the term "aberrant" includes biomarker expression or activity levels which deviates from the normal expression or activity in a control.

The assays described herein, such as the preceding diagnostic assays or the following assays, can be utilized to identify a subject having or at risk of developing a disorder associated with a misregulation of biomarker activity or expression, such as in a melanoma. Alternatively, the prognostic assays can be used to identify a subject having or at risk for developing a disorder associated with a misregulation of biomarker activity or expression. Thus, the present invention provides a method for identifying and/or classifying a disease associated with aberrant expression or activity of one or more biomarkers of the invention, including one or more biomarkers listed in Table 2 and the Examples, or a fragment thereof. Furthermore, the prognostic assays described herein can be used to determine whether a subject can be administered an agent (e.g., an agonist, antagonist, peptidomimetic, polypeptide, peptide, nucleic acid, small molecule, or other drug candidate) to treat a disease or disorder associated with aberrant biomarker expression or activity. For example, such methods can be used to determine whether a subject can be effectively treated with an agent for a melanoma. Thus, the present invention provides methods for determining whether a subject can be effectively treated with an agent for a disease associated with aberrant biomarker expression or activity in which a test sample is obtained and biomarker polypeptide or nucleic acid expression or activity is detected (e.g., wherein a significant increase or decrease in biomarker polypeptide or nucleic acid expression or activity relative to a control is diagnostic for a subject that can be administered the agent to treat a disorder associated with aberrant biomarker expression or activity). In some embodiments, significant increase or decrease in biomarker expression or activity comprises at least 2 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more higher or lower, respectively, than the expression activity or level of the marker in a control sample.

The methods of the invention can also be used to detect genetic alterations in one or more biomarkers of the invention, including one or more biomarkers listed in Table 2 and the Examples or a fragment thereof, thereby determining if a subject with the altered biomarker is at risk for melanoma characterized by aberrant biomarker activity or expression levels. In preferred embodiments, the methods include detecting, in a sample of cells from the subject, the presence or absence of a genetic alteration characterized by at least one alteration affecting the integrity of a gene encoding one or more biomarkers polypeptide, or the mis-expression of the biomarker (e.g., mutations and/or splice variants). For example, such genetic alterations can be detected by ascertaining the existence of at least one of 1) a deletion of one or more nucleotides from one or more biomarkers gene, 2) an addition of one or more nucleotides to one or more biomarkers gene, 3) a substitution of one or more nucleotides of one or more biomarkers gene, 4) a chromosomal rearrangement of one or more biomarkers gene, 5) an alteration in the level of a messenger RNA transcript of one or more biomarkers gene, 6) aberrant modification of one or more biomarkers gene, such as of the methylation pattern of the genomic DNA, 7) the presence of a non-wild type splicing pattern of a messenger RNA transcript of one or more biomarkers gene, 8) a non-wild type level of one or more biomarkers polypeptide, 9) allelic loss of one or more biomarkers gene, and 10) inappropriate post-translational modification of one or more biomarkers polypeptide. As described herein, there are a large number of assays known in the art which can be used for detecting alterations in one or more biomarkers gene. A preferred biological sample is a tissue or serum sample isolated by conventional means from a subject.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077-1080; and Nakazawa et al. (1994) Proc. Natl. Acad. Sci. USA 91:360-364), the latter of which can be particularly useful for detecting point mutations in one or more biomarkers gene (see Abravaya et al. (1995) Nucleic Acids Res. 23:675-682). This method can include the steps of collecting a sample of cells from a subject, isolating nucleic acid (e.g., genomic DNA, mRNA, cDNA, small RNA, mature miRNA, pre-miRNA, pri-miRNA, miRNA*, anti-miRNA, or a miRNA binding site, or a variant thereof) from the cells of the sample, contacting the nucleic acid sample with one or more primers which specifically hybridize to one or more biomarkers gene of the invention, including the biomarker genes listed in Table 2 and the Examples, or fragments thereof, under conditions such that hybridization and amplification of the biomarker gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self-sustained sequence replication (Guatelli, J. C. et al. (1990) Proc. Natl. Acad. Sci. USA 87:1874-1878), transcriptional amplification system (Kwoh, D. Y. et al. (1989) Proc. Natl. Acad. Sci. USA 86:1173-1177), Q-Beta Replicase (Lizardi, P. M. et al. (1988) Bio-Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in one or more biomarkers gene of the invention, including one or more biomarkers listed in Table 2 and the Examples, or a fragment thereof, from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in one or more biomarkers gene of the invention, including a gene listed in Table 2 and the Examples, or a fragment thereof, can be identified by hybridizing a sample and control nucleic acids, e.g., DNA, RNA, mRNA, small RNA, cDNA, mature miRNA, pre-miRNA, pri-miRNA, miRNA*, anti-miRNA, or a miRNA binding site, or a variant thereof, to high density arrays containing hundreds or thousands of oligonucleotide probes (Cronin, M. T. et al. (1996) Hum. Mutat. 7:244-255; Kozal, M. J. et al. (1996) Nat. Med. 2:753-759). For example, genetic mutations in one or more biomarkers can be identified in two dimensional arrays containing light-generated DNA probes as described in Cronin et al. (1996) supra. Briefly, a first hybridization array of probes can be used to scan through long stretches of DNA in a sample and control to identify base changes between the sequences by making linear arrays of sequential, overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence one or more biomarkers gene of the invention, including a gene listed in Table 2 and the Examples, or a fragment thereof, and detect mutations by comparing the sequence of the sample biomarker gene with the corresponding wild-type (control) sequence. Examples of sequencing reactions include those based on techniques developed by Maxam and Gilbert (1977) Proc. Natl. Acad. Sci. USA 74:560 or Sanger (1977) Proc. Natl. Acad Sci. USA 74:5463. It is also contemplated that any of a variety of automated sequencing procedures can be utilized when performing the diagnostic assays (Naeve, C. W. (1995) Biotechniques 19:448-53), including sequencing by mass spectrometry (see, e.g., PCT International Publication No. WO 94/16101; Cohen et al. (1996) Adv. Chromatogr. 36:127-162; and Griffin et al. (1993) Appl. Biochem. Biotechnol. 38:147-159).

Other methods for detecting mutations in one or more biomarkers gene of the invention, including a gene listed in Table 2 and the Examples, or fragments thereof, include methods in which protection from cleavage agents is used to detect mismatched bases in RNA/RNA or RNA/DNA heteroduplexes (Myers et al. (1985) Science 230:1242). In general, the art technique of "mismatch cleavage" starts by providing heteroduplexes formed by hybridizing (labeled) RNA or DNA containing the wild-type sequence with potentially mutant RNA or DNA obtained from a tissue sample. The double-stranded duplexes are treated with an agent which cleaves single-stranded regions of the duplex such as which will exist due to base pair mismatches between the control and sample strands. For instance, RNA/DNA duplexes can be treated with RNase and DNA/DNA hybrids treated with SI nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) Proc. Natl. Acad. Sci. USA 85:4397 and Saleeba et al. (1992) Methods Enzymol. 217:286-295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in biomarker genes of the invention, including genes listed in Table 2 and the Examples, or fragments thereof, obtained from samples of cells. For example, the mutY enzyme of E. coli cleaves A at G/A mismatches and the thymidine DNA glycosylase from HeLa cells cleaves T at G/T mismatches (Hsu et al. (1994) Carcinogenesis 15:1657-1662). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in biomarker genes of the invention, including genes listed in Table 2 and the Examples, or fragments thereof. For example, single strand conformation polymorphism (SSCP) may be used to detect differences in electrophoretic mobility between mutant and wild type nucleic acids (Orita et al. (1989) Proc Natl. Acad. Sci USA 86:2766; see also Cotton (1993) Mutat. Res. 285:125-144 and Hayashi (1992) Genet. Anal. Tech. Appl. 9:73-79). Single-stranded DNA fragments of sample and control nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) Trends Genet. 7:5).

In yet another embodiment the movement of mutant or wild-type fragments in polyacrylamide gels containing a gradient of denaturant is assayed using denaturing gradient gel electrophoresis (DGGE) (Myers et al. (1985) Nature 313:495). When DGGE is used as the method of analysis, DNA will be modified to ensure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) Biophys. Chem. 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) Nature 324:163; Saiki et al. (1989) Proc. Natl. Acad. Sci. USA 86:6230). Such allele specific oligonucleotides are hybridized to PCR amplified target DNA or a number of different mutations when the oligonucleotides are attached to the hybridizing membrane and hybridized with labeled target DNA. In some embodiments, the hybridization reactions can occur using biochips, microarrays, etc., or other array technology that are well known in the art.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) Nucleic Acids Res. 17:2437-2448) or at the extreme 3' end of one primer where, under appropriate conditions, mismatch can prevent, or reduce polymerase extension (Prossner (1993) Tibtech 11:238). In addition it may be desirable to introduce a novel restriction site in the region of the mutation to create cleavage-based detection (Gasparini et al. (1992) Mol. Cell Probes 6:1). It is anticipated that in certain embodiments amplification may also be performed using Taq ligase for amplification (Barany (1991) Proc. Natl. Acad. Sci USA 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving one or more biomarkers of the invention, including one or more biomarkers listed in Table 2 and the Examples, or fragments thereof.

3. Monitoring of Effects During Clinical Trials

Monitoring the influence of agents (e.g., drugs) on the expression or activity of one or more biomarkers of the invention, including one or more biomarkers listed in Table 2 and the Examples, or a fragment thereof (e.g., the modulation of a cancer state) can be applied not only in basic drug screening, but also in clinical trials. For example, the effectiveness of an agent determined by a screening assay as described herein to increase expression and/or activity of one or more biomarkers of the invention, including one or more biomarkers listed in Table 2 and the Examples or a fragment thereof, can be monitored in clinical trials of subjects exhibiting decreased expression and/or activity of one or more biomarkers of the invention, including one or more biomarkers of the invention, including one or more biomarkers listed in Table 2 and the Examples, or a fragment thereof, relative to a control reference. Alternatively, the effectiveness of an agent determined by a screening assay to decrease expression and/or activity of one or more biomarkers of the invention, including one or more biomarkers listed in Table 2 and the Examples, or a fragment thereof, can be monitored in clinical trials of subjects exhibiting decreased expression and/or activity of the biomarker of the invention, including one or more biomarkers listed in Table 2 and the Examples or a fragment thereof relative to a control reference. In such clinical trials, the expression and/or activity of the biomarker can be used as a "read out" or marker of the phenotype of a particular cell.

In some embodiments, the present invention provides a method for monitoring the effectiveness of treatment of a subject with an agent (e.g., an agonist, antagonist, peptidomimetic, polypeptide, peptide, nucleic acid, small molecule, or other drug candidate identified by the screening assays described herein) including the steps of (i) obtaining a pre-administration sample from a subject prior to administration of the agent; (ii) detecting the level of expression and/or activity of one or more biomarkers of the invention, including one or more biomarkers listed in Table 2 and the Examples or fragments thereof in the preadministration sample; (iii) obtaining one or more post-administration samples from the subject; (iv) detecting the level of expression or activity of the biomarker in the post-administration samples; (v) comparing the level of expression or activity of the biomarker or fragments thereof in the pre-administration sample with the that of the biomarker in the post administration sample or samples; and (vi) altering the administration of the agent to the subject accordingly. For example, increased administration of the agent may be desirable to increase the expression or activity of one or more biomarkers to higher levels than detected (e.g., to increase the effectiveness of the agent.) Alternatively, decreased administration of the agent may be desirable to decrease expression or activity of the biomarker to lower levels than detected (e.g., to decrease the effectiveness of the agent). According to such an embodiment, biomarker expression or activity may be used as an indicator of the effectiveness of an agent, even in the absence of an observable phenotypic response.

D. Methods of Treatment

The present invention provides for both prophylactic and therapeutic methods of treating a subject at risk of (or susceptible to) a disorder characterized by insufficient or excessive production of biomarkers of the invention, including biomarkers listed in Table 2 and the Examples or fragments thereof, which have aberrant expression or activity compared to a control. Moreover, agents of the invention described herein can be used to detect and isolate the biomarkers or fragments thereof, regulate the bioavailability of the biomarkers or fragments thereof, and modulate biomarker expression levels or activity.

1. Prophylactic Methods

In one aspect, the invention provides a method for preventing in a subject, a disease or condition associated with an aberrant expression or activity of one or more biomarkers of the invention, including one or more biomarkers listed in Table 2 and the Examples or a fragment thereof, by administering to the subject an agent which modulates biomarker expression or at least one activity of the biomarker. Subjects at risk for a disease or disorder which is caused or contributed to by aberrant biomarker expression or activity can be identified by, for example, any or a combination of diagnostic or prognostic assays as described herein. Administration of a prophylactic agent can occur prior to the manifestation of symptoms characteristic of the biomarker expression or activity aberrancy, such that a disease or disorder is prevented or, alternatively, delayed in its progression.

2. Therapeutic Methods

Another aspect of the invention pertains to methods of modulating the expression or activity or interaction with natural binding partner(s) of one or more biomarkers of the invention, including one or more biomarkers listed in Table 2 and the Examples or fragments thereof, for therapeutic purposes. The biomarkers of the invention have been demonstrated to correlate with melanoma. Accordingly, the activity and/or expression of the biomarker, as well as the interaction between one or more biomarkers or a fragment thereof and its natural binding partner(s) or a fragment(s) thereof can be modulated in order to modulate the immune response.

Modulatory methods of the invention involve contacting a cell with one or more biomarkers of the invention, including one or more biomarkers of the invention, including one or more biomarkers listed in Table 2 and the Examples or a fragment thereof or agent that modulates one or more of the activities of biomarker activity associated with the cell. In some embodiments, the biomarkers are or encode secreted molecules such that contacting a cell with one or more biomarkers of the invention or agent that modulates one or more of the activities of biomarker activity is unnecessary and contact with a bodily fluid (e.g., blood, serum, lung pleural fluid, etc.) is sufficient. An agent that modulates biomarker activity can be an agent as described herein, such as a nucleic acid or a polypeptide, a naturally-occurring binding partner of the biomarker, an antibody against the biomarker, a combination of antibodies against the biomarker and antibodies against other immune related targets, one or more biomarkers agonist or antagonist, a peptidomimetic of one or more biomarkers agonist or antagonist, one or more biomarkers peptidomimetic, other small molecule, or small RNA directed against or a mimic of one or more biomarkers nucleic acid gene expression product.

An agent that modulates the expression of one or more biomarkers of the invention, including one or more biomarkers of the invention, including one or more biomarkers listed in Table 2 and the Examples or a fragment thereof is, e.g., an antisense nucleic acid molecule, RNAi molecule, shRNA, mature miRNA, pre-miRNA, pri-miRNA, miRNA*, anti-miRNA, or a miRNA binding site, or a variant thereof, or other small RNA molecule, triplex oligonucleotide, ribozyme, or recombinant vector for expression of one or more biomarkers polypeptide. For example, an oligonucleotide complementary to the area around one or more biomarkers polypeptide translation initiation site can be synthesized. One or more antisense oligonucleotides can be added to cell media, typically at 200 µg/ml, or administered to a patient to prevent the synthesis of one or more biomarkers polypeptide. The antisense oligonucleotide is taken up by cells and hybridizes to one or more biomarkers mRNA to prevent translation. Alternatively, an oligonucleotide which binds double-stranded DNA to form a triplex construct to prevent DNA unwinding and transcription can be used. As a result of either, synthesis of biomarker polypeptide is blocked. When biomarker expression is modulated, preferably, such modulation occurs by a means other than by knocking out the biomarker gene.

Agents which modulate expression, by virtue of the fact that they control the amount of biomarker in a cell, also modulate the total amount of biomarker activity in a cell.

In one embodiment, the agent stimulates one or more activities of one or more biomarkers of the invention, including one or more biomarkers listed in Table 2 and the Examples or a fragment thereof. Examples of such stimulatory agents include active biomarker polypeptide or a fragment thereof and a nucleic acid molecule encoding the biomarker or a fragment thereof that has been introduced into the cell (e.g., cDNA, mRNA, shRNAs, siRNAs, small RNAs, mature miRNA, pre-miRNA, pri-miRNA, miRNA*, anti-miRNA, or a miRNA binding site, or a variant thereof, or other functionally equivalent molecule known to a skilled artisan). In another embodiment, the agent inhibits one or more biomarker activities. In one embodiment, the agent inhibits or enhances the interaction of the biomarker with its natural binding partner(s). Examples of such inhibitory agents include antisense nucleic acid molecules, anti-biomarker antibodies, biomarker inhibitors, and compounds identified in the screening assays described herein.

These modulatory methods can be performed in vitro (e.g., by contacting the cell with the agent) or, alternatively, by contacting an agent with cells in vivo (e.g., by administering the agent to a subject). As such, the present invention provides methods of treating an individual afflicted with a condition or disorder that would benefit from up- or down-modulation of one or more biomarkers of the invention listed in Table 2 and the Examples or a fragment thereof, e.g., a disorder characterized by unwanted, insufficient, or aberrant expression or activity of the biomarker or fragments thereof. In one embodiment, the method involves administering an agent (e.g., an agent identified by a screening assay described herein), or combination of agents that modulates (e.g., upregulates or downregulates) biomarker expression or activity. In another embodiment, the method involves administering one or more biomarkers polypeptide or nucleic acid molecule as therapy to compensate for reduced, aberrant, or unwanted biomarker expression or activity.

Stimulation of biomarker activity is desirable in situations in which the biomarker is abnormally downregulated and/or in which increased biomarker activity is likely to have a beneficial effect. Likewise, inhibition of biomarker activity is desirable in situations in which biomarker is abnormally upregulated and/or in which decreased biomarker activity is likely to have a beneficial effect.

In addition, these modulatory agents can also be administered in combination therapy with, e.g., chemotherapeutic agents, hormones, antiangiogens, radiolabelled, compounds, or with surgery, cryotherapy, and/or radiotherapy. The preceding treatment methods can be administered in conjunction with other forms of conventional therapy (e.g., standard-of-care treatments for cancer well known to the skilled artisan), either consecutively with, pre- or post-conventional therapy. For example, these modulatory agents can be administered with a therapeutically effective dose of chemotherapeutic agent. In another embodiment, these modulatory agents are administered in conjunction with chemotherapy to enhance the activity and efficacy of the chemotherapeutic agent. The Physicians' Desk Reference (PDR) discloses dosages of chemotherapeutic agents that have been used in the treatment of various cancers. The dosing regimen and dosages of these aforementioned chemotherapeutic drugs that are therapeutically effective will depend on the particular melanoma, being treated, the extent of the disease and other factors familiar to the physician of skill in the art and can be determined by the physician.

IV. Pharmaceutical Compositions

In another aspect, the present invention provides pharmaceutically acceptable compositions which comprise a therapeutically-effective amount of an agent that modulates (e.g., increases or decreases) PD-L1 levels, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "therapeutically-effective amount" as used herein means that amount of an agent that modulates (e.g., inhibits) PD-L1 levels, or expression and/or activity of the receptor/ligand complex, or composition comprising an agent that modulates (e.g., inhibits) PD-L1 levels, or expression and/or activity of the receptor/ligand complex, which is effective for producing some desired therapeutic effect, e.g., cancer treatment, at a reasonable benefit/risk ratio.

The phrase "pharmaceutically acceptable" is employed herein to refer to those agents, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the subject. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Formulations useful in the methods of the present invention include those suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient, which can be combined with a carrier material to produce a single dosage form will generally be that amount of the compound which produces a therapeutic effect. Generally, out of one hundred percent, this amount will range from about 1% to about 99% of active ingredient, preferably from about 5% to about 70%, most preferably from about 10% to about 30%.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a respiration uncoupling agent as an active ingredient. A compound may also be administered as a bolus, electuary or paste.

In solid dosage forms for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered peptide or peptidomimetic moistened with an inert liquid diluent.

Tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions, which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions, which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active agent may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more respiration uncoupling agents with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Formulations which are suitable for vaginal administration also include pessaries, tampons, creams, gels, pastes, foams or spray formulations containing such carriers as are known in the art to be appropriate.

Dosage forms for the topical or transdermal administration of an agent that modulates (e.g., increases or decreases) PD-L1 levels include powders, sprays, ointments, pastes, creams, lotions, gels, solutions, patches and inhalants. The active component may be mixed under sterile conditions with a pharmaceutically-acceptable carrier, and with any preservatives, buffers, or propellants which may be required.

The ointments, pastes, creams and gels may contain, in addition to a respiration uncoupling agent, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an agent that modulates (e.g., increases or decreases) PD-L1 levels, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The agent that modulates (e.g., increases or decreases) PD-L1 levels, can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a respiration uncoupling agent to the body. Such dosage forms can be made by dissolving or dispersing the agent in the proper medium. Absorption enhancers can also be used to increase the flux of the peptidomimetic across the skin. The rate of such flux can be controlled by either providing a rate controlling membrane or dispersing the peptidomimetic in a polymer matrix or gel.

Ophthalmic formulations, eye ointments, powders, solutions and the like, are also contemplated as being within the scope of this invention.

Pharmaceutical compositions of this invention suitable for parenteral administration comprise one or more respiration uncoupling agents in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of an agent that modulates (e.g., increases or decreases) PD-L1 levels, in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly (anhydrides). Depot injectable formulations are also prepared by entrapping the drug in liposomes or microemulsions, which are compatible with body tissue.

When the respiration uncoupling agents of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

Actual dosage levels of the active ingredients in the pharmaceutical compositions of this invention may be determined by the methods of the present invention so as to obtain an amount of the active ingredient, which is effective to achieve the desired therapeutic response for a particular subject, composition, and mode of administration, without being toxic to the subject.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) Proc. Natl. Acad. Sci. USA 91:3054 3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

V. Administration of Agents

The cancer diagnostic, prognostic, prevention, and/or treatment modulating agents of the invention are administered to subjects in a biologically compatible form suitable for pharmaceutical administration in vivo, to either enhance or suppress immune cell mediated immune responses. By "biologically compatible form suitable for administration in vivo" is meant a form of the protein to be administered in which any toxic effects are outweighed by the therapeutic effects of the protein. The term "subject" is intended to include living organisms in which an immune response can be elicited, e.g., mammals. Examples of subjects include humans, dogs, cats, mice, rats, and transgenic species thereof. Administration of an agent as described herein can be in any pharmacological form including a therapeutically active amount of an agent alone or in combination with a pharmaceutically acceptable carrier.

Administration of a therapeutically active amount of the therapeutic composition of the present invention is defined as an amount effective, at dosages and for periods of time necessary, to achieve the desired result. For example, a therapeutically active amount of a blocking antibody may vary according to factors such as the disease state, age, sex, and weight of the individual, and the ability of peptide to elicit a desired response in the individual. Dosage regimens can be adjusted to provide the optimum therapeutic response. For example, several divided doses can be administered daily or the dose can be proportionally reduced as indicated by the exigencies of the therapeutic situation.

The agents of the invention described herein can be administered in a convenient manner such as by injection (subcutaneous, intravenous, etc.), oral administration, inhalation, transdermal application, or rectal administration. Depending on the route of administration, the active compound can be coated in a material to protect the compound from the action of enzymes, acids and other natural conditions which may inactivate the compound. For example, for administration of agents, by other than parenteral administration, it may be desirable to coat the agent with, or co-administer the agent with, a material to prevent its inactivation.

An agent can be administered to an individual in an appropriate carrier, diluent or adjuvant, co-administered with enzyme inhibitors or in an appropriate carrier such as liposomes. Pharmaceutically acceptable diluents include saline and aqueous buffer solutions. Adjuvant is used in its broadest sense and includes any immune stimulating compound such as interferon. Adjuvants contemplated herein include resorcinols, non-ionic surfactants such as polyoxyethylene oleyl ether and n-hexadecyl polyethylene ether. Enzyme inhibitors include pancreatic trypsin inhibitor, diisopropylfluorophosphate (DEEP) and trasylol. Liposomes include water-in-oil-in-water emulsions as well as conventional liposomes (Sterna et al. (1984) *J. Neuroimmunol.* 7:27).

The agent may also be administered parenterally or intraperitoneally. Dispersions can also be prepared in glycerol, liquid polyethylene glycols, and mixtures thereof, and in oils. Under ordinary conditions of storage and use, these preparations may contain a preservative to prevent the growth of microorganisms.

Pharmaceutical compositions of agents suitable for injectable use include sterile aqueous solutions (where water soluble) or dispersions and sterile powders for the extemporaneous preparation of sterile injectable solutions or dispersion. In all cases the composition will preferably be sterile and must be fluid to the extent that easy syringeability exists. It will preferably be stable under the conditions of manufacture and storage and preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it is preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating an agent of the invention (e.g., an antibody, peptide, fusion protein or small molecule) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the agent plus any additional desired ingredient from a previously sterile-filtered solution thereof.

When the agent is suitably protected, as described above, the protein can be orally administered, for example, with an inert diluent or an assimilable edible carrier. As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions.

It is especially advantageous to formulate parenteral compositions in dosage unit form for ease of administration and uniformity of dosage. "Dosage unit form", as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by, and directly dependent on, (a) the unique characteristics of the active compound and the particular therapeutic effect to be achieved, and (b) the limitations inherent in the art of compounding such an active compound for the treatment of sensitivity in individuals.

In one embodiment, an agent of the invention is an antibody. As defined herein, a therapeutically effective amount of antibody (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an antibody can include a single treatment or, preferably, can include a series of treatments. In a preferred example, a subject is treated with antibody in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody used for treatment may increase or decrease over the course of a particular treatment. Changes in dosage may result from the results of diagnostic assays. In addition, an antibody of the invention can also be administered in combination therapy with, e.g., chemotherapeutic agents, hormones, antiangiogens, radiolabelled, compounds, or with surgery, cryotherapy, and/or radiotherapy. An antibody of the invention can also be administered in conjunction with other forms of conventional therapy, either consecutively with, pre- or post-conventional therapy. For example, the antibody can be administered with a therapeutically effective dose of chemotherapeutic agent. In another embodiment, the antibody can be administered in conjunction with chemotherapy to enhance the activity and efficacy of the chemotherapeutic agent. The Physicians' Desk Reference (PDR) discloses dosages of chemotherapeutic agents that have been used in the treatment of various cancers. The dosing regimen and dosages of these aforementioned chemotherapeutic drugs that are therapeutically effective will depend on the particular immune disorder, e.g., Hodgkin lymphoma, being treated, the extent of the disease and other factors familiar to the physician of skill in the art and can be determined by the physician.

In addition, the agents of the invention described herein can be administered using nanoparticle-based composition and delivery methods well known to the skilled artisan. For example, nanoparticle-based delivery for improved nucleic acid (e.g., small RNAs) therapeutics are well known in the art (*Expert Opinion on Biological Therapy* 7:1811-1822).

EXEMPLIFICATION

This invention is further illustrated by the following examples, which should not be construed as limiting.

EXAMPLE 1

Figure 4A:
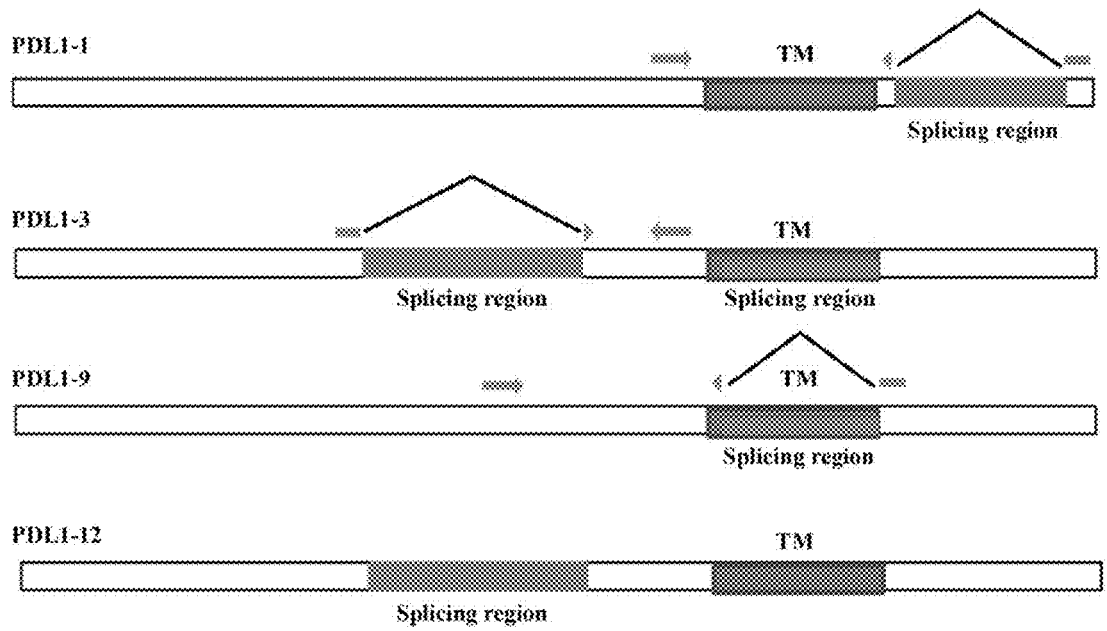
FIG. 4A-FIG. 4D show details of soluble PDL1 analyses.
Figure 4B:
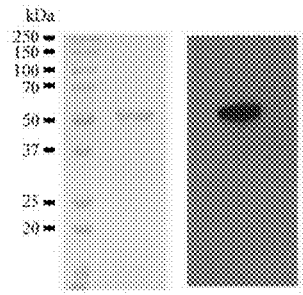
Figure 4C:
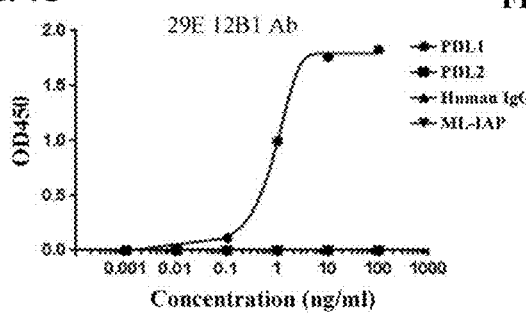
Figure 4D:
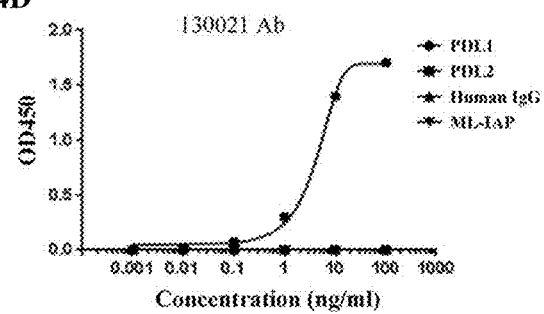

Materials and Methods for Examples 2-5 a. Cells and Cell Culture
A375, K008, K028, K029, K033, UACC257, and M34 melanoma cell lines were cultured in DMEM medium with 10% fetal bovine serum. 293T cells were cultured in complete DMEM.

b. RT-PCR and Human PDL1 Variant Cloning
Total RNA of melanoma cells lines were generated with Rneasy Mini kit (Qiagen, Valencia, Calif.). One µg of RNA of each melanoma cell line was reverse-transcripted to cDNA with SuperScript reverse transcriptase (Life technologies, Grand Island, N.Y.). PDL1 library were cloned by PCR with a XbaI restriction site tagged forward primer: GCGTCGTCTAGAGCCACCATGAGGATAT-TTGCTGTCT (SEQ ID NO:24) and a SalI tagged reverse primer: SalI GCGCCAGTCGACTTACGTCTCCTC-CAAATGTGT (SEQ ID NO:25). The PCR products were cloned into a TA TOPO vector (Life Technologies) for sequencing analysis. The variants of PDL1 were further inserted into a lentiviral transfer vector pELNS. To detect mRNA splicing variants of PDL1-1, PDL1-3, and PDL1-9 in melanoma cell lines, primers were designed to contain both ends of splice donor and acceptor, and were specific for PDL1-1, 3/12, and 9 variants (FIGS. 4C-4D). The specific primers of PDL1-1, PDL1-3, and PDL1-9 were CCAAAT-GAAAGGACTCACTTG (SEQ ID NO:26)/CGTCTCCTC-CAAATGTGTATCTT (SEQ ID NO:27), AAGTCCT-GAGTGGAGATTAGATC(SEQ ID NO:28)/ CATTCTCCCAAGTGAGTCC (SEQ ID NO:29), and ACCAGCACACTGAGAATCAAC (SEQ ID NO:30)/CA-CATCCATCATTCTCCCAAG (SEQ ID NO:31), respectively. The sizes of PCR products were 103, 104, and 161 bps, respectively. The sequences of PCR products were confirmed by sequencing PCR conducted by Etonbioscience Inc.

c. Transfection, Lentiviral Production, and Lentiviral Transduction
The pELNS expressing PDL1 variants were co-transfected into 293T cells with three packaging plasmids expressing gag/pol, VSV-g, and REV using TransfectIT-293 Madison, Wis.). Lentiviral supernatants were collected and filtered. PDL1-1, PDL1-3, and PDL1-9 were transduced into $1\times10^5$ A375 cells with the supernatant in the presence of 8 µg/ml polybrene (EMD Millipore, Billerica, Mass.).

d. Immunoprecipitation, SDS-PAGE and Western blotting
$5\times10^5$ cells of A375 and M34 melanoma cell lines were cultured complete DMEM medium in tissue culture dishes for 2 days. After PBS washes, the cells were further cultured in Opti-reduced serum medium (Life technologies, Grand Island, N.Y.) in the absence or presence of 200 U/ml IFN-γ (Biolegend, San Diego, Calif.), or 2000 U/ml IFN-α (EMD Millipore, Billerica, Mass.), or TNF-α (R&D systems, Minneapolis, Minn.) for additional two days. The culture medium were collected, filtered and concentrated with a Centricon® spin column (EMD Millipore, Billerica, Mass.). One ml concentrated supernatant was rotated with 1.0 µg mouse anti PDL1 (clone 29E.2A3, Biolegend) and 20 µl protein G plus agarose (Santa Cruz biotechnology, Santa Cruz, Calif.) at 4° C. overnight. After being washed, the agarose beads were resuspended in Laemmli's reducing buffer (Boston Bioproducts, Worcester, Mass.), and further heated. Immunoprecipitated proteins were subjected to 12% SDS-polyacrylamide gel electrophoresis (PAGE), and transferred onto PVDF membranes. The membranes were immunoblotted overnight at 4° C. with a biotinylated goat anti-human PDL1 antibody at 0.1 µg/ml (R&D systems), and further incubated with HRP conjugated streptavidin at 2.5 µg/ml (Jackson ImmunoResearch, West Grove, Pa.) at room temperature for 2 hours. The protein bands were detected with chemiluminescent solution (PerkinElmer, Waltham, Mass.).

e. PDL1-3/Ig fusion protein

PDL1-3 was fused to CH2 and CH3 domains of human IgG1 in pELNS vector. PDL1-3/Ig was transduced into A375 cells by lentiviral supernatant in the presence of 8 µg/ml polybrene (EMD). PDL1-3/Ig expressing A375 cells were cultured in Opti-reduced serum medium. The culture medium were collected and concentrated with a centricon spin column (EMD). PDL1-3/Ig was purified with protein G agarose (Life Technologies).

f. Proliferation Assay $1 \times 10^5$ cells/well human CD4$^+$ or CD8$^+$ T cells were stimulated with 5 µg/ml coated anti-CD3 antibody (BD Biosciences, San Jose, Calif.) in the absence or presence of 10 µg/ml coated either PDL1-3 fusion protein or human IgG for 3 days, and further pulsed with [$^3$H]thymidine (0.25 µCi H$^3$/well) for 6 hours. The incorporated radioactivity was measured in a liquid scintillation counter (Wallac 1450 Microbeta Trilux, Perkin Elmer, Waltham, Mass.).

g. Soluble PDL1 ELISA

To determine soluble PDL1 in patient sera responses, ELISA was established. 0.1 µg/well of mouse anti-PDL1 Ab (clone: 29E.12B1 or 130021, R&D systems) were coated on Nunc-Immuno-plates overnight at 4° C. Plates were then washed with PBS and blocked with protein-free blocking buffer (Pierce, Rockford, Ill.) for 4 hours. Patient sera were diluted with PBS in a 1:1 ratio. 100 µl A per well of diluted patient sera were added and incubated overnight at 4° C. Plates were washed with PBS/Tween-20, and incubated with 100 µl per well of 0.5 µg/µl biotinylated mouse anti-PDL1 Ab (clone: 29E.2A3, Biolegend) in protein-free blocking buffer at room temperature for 2 hours. Plates were washed and incubated with 1 mg/ml streptavidin-HRP (Jackson ImmunoResearch) diluted in 1:40,000 in protein-free blocking buffer for 2 hours. Plates were washed and treated with tyramine (Perkin Elmer) for 30 min. Plates were then washed and incubated with 1 mg/ml streptavidin-HRP (Jackson ImmunoResearch) diluted in 1:400,000 in protein-free blocking buffer for 2 hours for further development with NBT (Pierce). Plates were read at an optical density (O.D.) of 450 nm. All samples were performed in duplicate.

To assess the specificity of the assay, a series of concentrations from 100 ng/ml to 0.001 ng/ml of human IgG1 (Southern Biotect, Birmingham, Ala.), and recombinant proteins of ML-IAP, XIAP, and PDL1 (R&D systems), PDL2 (Novoprotein, Summit, N.J.) in diluted normal healthy donor sera (1:1 ratio with PBS) were detected. Results in FIG. 4A indicated that all mouse anti-PDL1 monoclonal antibodies were specific for PDL1. The detection sensitivity ranged from 0.1 to 100 ng/ml of PDL1 in the sera. The standard curve also performed during each assay.

h. Luminex Bead ELISA for Cytokines

To determine IFNα and γ, and TNFα in patient sera, luminex bead ELISA were conducted. Briefly, a luminex beads kit for detection of IFNα and γ, and TNFα was purchased from EMD Millipore. Patient sera were diluted with assay buffer in 1:1 ratio. 25 µl/well antibody coupled beads and 50 µl/well diluted patient sera were added into a 96 well plate and incubated overnight at 4° C. Plates were washed with washing buffer, and incubated with 25 µl per well of cytokine detection antibody at room temperature for one hour. Plates were further incubated with 25 µl per well streptavidin-PE for 30 min. Plates were washed and read by Luminex 200. All samples were performed in duplicate. The standard curve also performed during each assay.

i. ELISA for Soluble PD-L

To determine soluble PDL1 variants in patient sera, ELISA was established. Both 0.1 µg/well of mouse anti-PDL1 Ab (230021, R&D systems) and 0.2 µg/well mouse anti-PDL1 Ab (29E.12B1) were coated on Nunc-Immmuno-plates overnight at 4° C. Plates were then washed with PBS and blocked with protein-free blocking buffer (Pierce, Rockford, Ill.) for 4 hours. Patient sera or plasma were diluted with PBS in 1:1 volume ratio. One hundred µl per well of diluted patient sera were added and incubated overnight at 4° C. Plates were washed with PBS+Tween-20, and incubated with 100 µl per well of 0.5 µg/µl biotinylated mouse anti-PDL1 Ab (29E.2A3, Biolegend) in protein-free blocking buffer at room temperature for 2 hours. Plates were washed and incubated with 1 mg/ml streptavidin-HRP (Jackson ImmunoResearch) diluted in 1:40000 in protein-free blocking buffer for 2 hours. Plates were washed and treated with tyramine (Perkin Elmer) for 30 min. Plates were then washed and incubated with 1 mg/ml streptavidin-HRP (Jackson ImmunoResearch) diluted in 1:400,000 in protein-free blocking buffer for 2 hours for further development with NBT (Pierce). Plates were read at an optical density (O.D.) of 450 nm. All samples were performed in duplicate.

To assess the specificity of the assay, a series of concentrations from 100 ng/ml to 0.001 ng/ml of human IgG1 (Southern Biotect, Birmingham, Ala.), and recombinant proteins of ML-IAP (R&D systems), and PDL1 (R&D systems), PDL2 (Novoprotein, Summit, N.J.) were detected. The two mouse anti-PDL1 monoclonal antibodies were determined to be specific for PDL1 (FIG. 4C-FIG. 4D). The detection sensitivity ranged from 0.1 to 100 ng/ml of PDL1 in the sera. The standard curve was also performed during each assay.

The specificity of antibodies to the soluble PDL1 variants was also analyzed. The supernatants of either PDL1-3, or PDL1-9, or PDL1-1 expressing A375 cells were examined by ELISA as described above. As shown in FIG. 5A-FIG. 5B, the clone 230021 Ab was able to detect soluble PDL1-9 and PDL1-1 variants, which are two longer forms. By contrast, clone 29E.12B1 Ab recognized all three soluble PDL1 variants. The epitopes for the antibodies, amino acid regions of soluble PDL1 variants, and amino acid regions of recombinant PDL1-3/Ig and PDL1-his are shown in Table 5A, Table 5B, and Table 5C, respectively. To further clarify the different recognitions of these two antibodies, recombinant PDL1-3/Ig and PDL1-his were detected with the antibodies by SDS-PAGE and Western blotting. As shown in FIG. 5C-FIG. 5E, the 230021 Ab only recognized PDL1-his, which represents long forms, whereas the 29E.12B1 Ab was able to detect PDL1-3/Ig, which is the shortest form. Taken together, the data demonstrate that both antibodies have different recognition patterns.

Figure 6A:
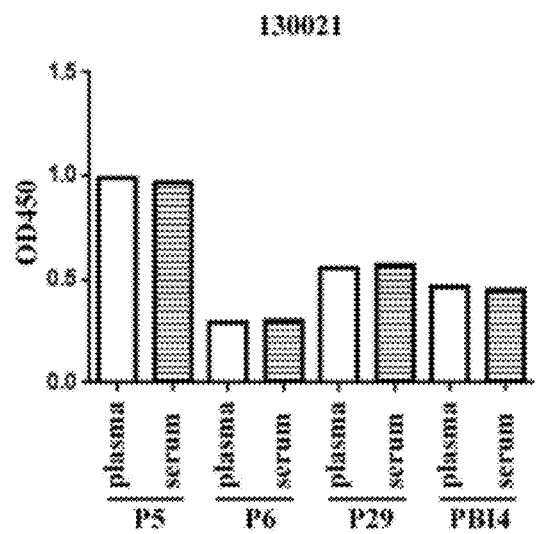
FIG. 6A-FIG. 6C the results of soluble PDL1 detected in various sample types.
Figure 6B:
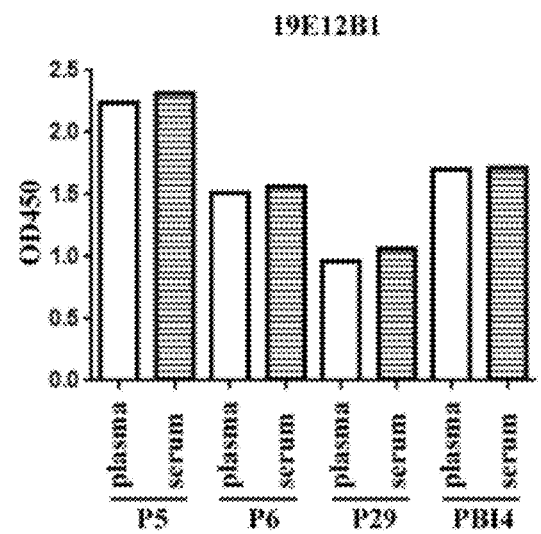

Since sPDL1 in sera and plasma of patients were detected, the impacts of sera and plasma on sPDL1 concentrations were investigated. sPDL1 in sera and plasma from the same patients were examined by two different ELISA (FIG. 6A-FIG. 6B). The data show that there are no differences in sPDL1 concentrations from either sera or plasma of the same patient.

Figure 6C:
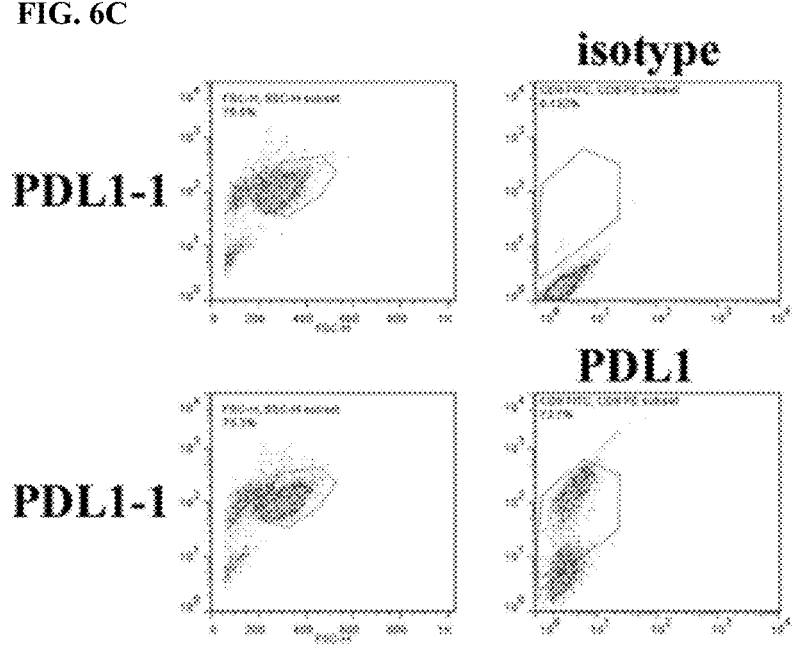

Thus, FIG. 4C, FIG. 4D, and FIG. 5, and Tables 5A-5C demonstrate that at least two antibodies were found to have different binding capacities for soluble PDL1s (e.g., R&D antibody (clone #130021) binds sPDL1-1 and sPDL1-9, which are two long variants, whereas another mouse antibody (clone #29E12B1), binds all sPDL1 variants). In addition, FIG. 6A-FIG. 6C demonstrate the impact of sera and plasma preparations on detection of sPDL1.

EXAMPLE 2

Novel Splicing Variants of PDL1 in Melanoma

A human PDL1 library from M34, a melanoma cell line, was generated by RT-PCR. Besides full length of PDL1, four splicing variants were found by sequencing the PDL1 library (FIG. 1). As shown in FIG. 1 and FIG. 2A, the PDL1-1 variant has a 60 bp deletion from nucleotide (nt)-791 to 850 in the region of intracellular domain of original PDL1. It corresponds to 20 amino acids. The splicing activity occurs from the beginning of exon 5 to the middle of exon 6. The PDL1-3 variant has two deletions in extracellular domain. One is a 106 bp deletion from nt-531 to 636 within exon 3 region; another is a 66 bp deletion from nt-725 to 790 (i.e., from the middle to end of exon 4). The first deletion results in amino acid reading frame change leading to a stop codon at 4 nt after nt-530. PDL1-9 has the same deletion region as PDL1-3 in exon 4. It also results in amino acid reading frame change leading to a stop codon at 4 nt after nt-725. PDL1-12 has the same deletion region in exon 3 and amino acid sequence as PDL1-3 does. The data indicate that there are splicing activities on PDL1 in M34.

Figure 2B:
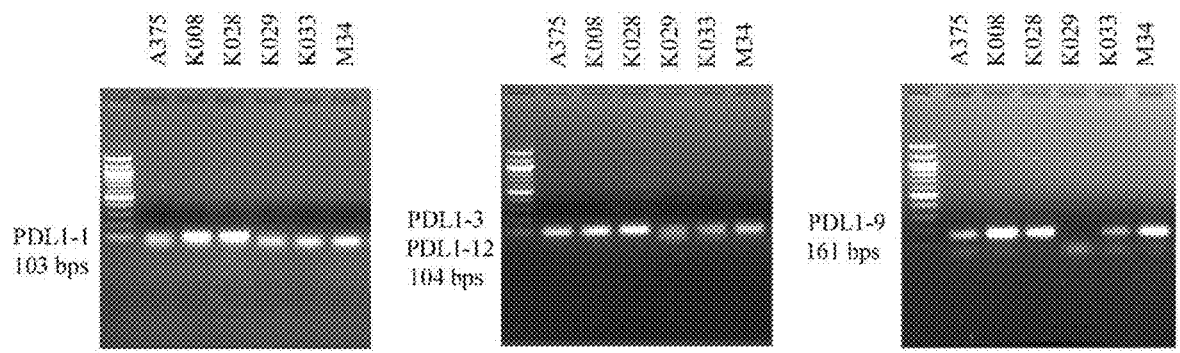

To assess existence of the PDL1 splicing activities, five additional melanoma cell lines were examined with specific primers by RT-PCR. RT-PCR data indicated that almost all variants exist in all five melanoma cell lines, except the absence of PDL1-9 in K029 (FIG. 2B). These results indicate that PDL1 splicing activities are common in melanoma. Furthermore, it is known the transmembrane domain of PDL1 spans from nt-715 to 780. PDL1-3, 9, 12 do not have this domain, indicating that that these variants could be secreted.

EXAMPLE 3

Secretion of PDL1 Variants

Figure 3A:
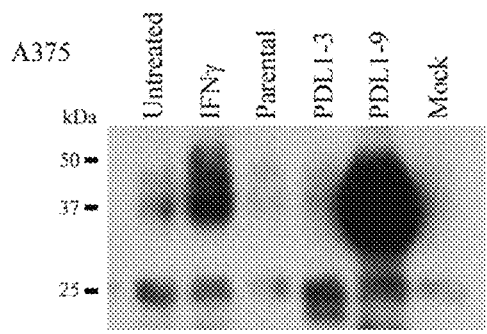
FIG. 3A-FIG. 3H show secretion of soluble PDL1 from melanoma cell lines.
Figure 3B:
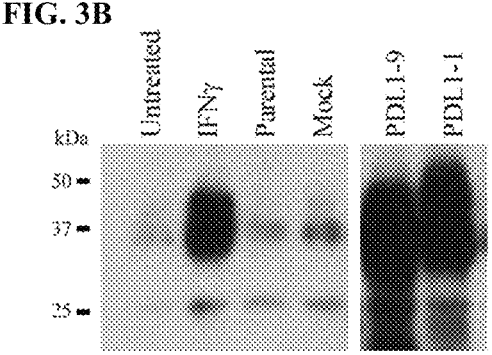
Figure 3C:
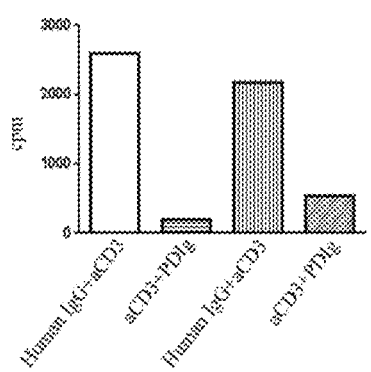
Figure 3D:
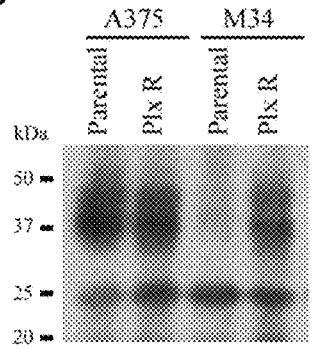

To assess whether melanoma cells are able to generate soluble PDL1, culture supernatant of A375 and M34 examined. As depicted in FIG. 3A and FIG. 3D, there were three PDL1 bands corresponding to 24, 38, and 45 kDa, respectively, in culture medium. These results indicate that melanoma cells produce soluble PDL1 variants.

To further investigate whether the spliced variants of PDL1 are associated with the detected PDL1 variants in the culture medium, PDL1-3 and 9 variants, which did not have trans-membrane domain were over-expressed in A375 by lentiviral transduction. Analysis of culture medium from the A375 cells showed increased soluble PDL1 in comparison with the medium of parental cells (FIG. 3A-FIG. 3B). The bands of PDL1-3 and 9 corresponded to 24 and 38 kDa of soluble PDL1 from parental cells. To further clarify the origin of soluble 45 kDa PDL1, A375 cells were transduced with PDL1-1 lentiviral vector. Surprisingly, over-expression of PDL1-1 increases not only the membrane form on the cell surface (FIG. 4), but also the soluble 38 and 45 kDa bands in the culture medium (FIG. 3B). These data indicate that melanoma cells produce soluble PDL1s and that the spliced variants contribute to the secretion of the soluble PDL1s.

Figure 3E:
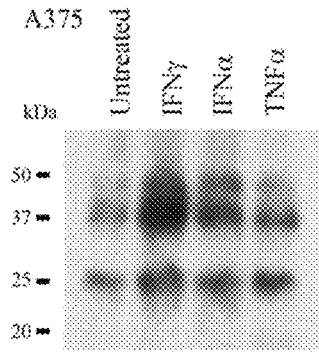
Figure 3F:
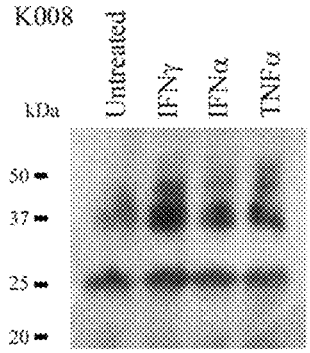
Figure 3G:
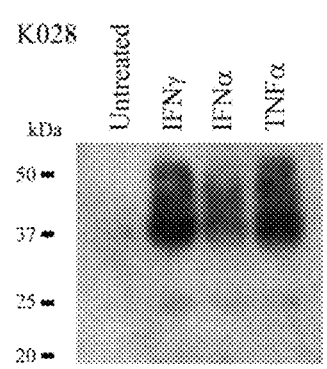
Figure 3H:
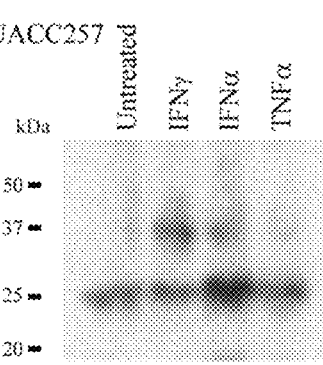
Figure 7A:
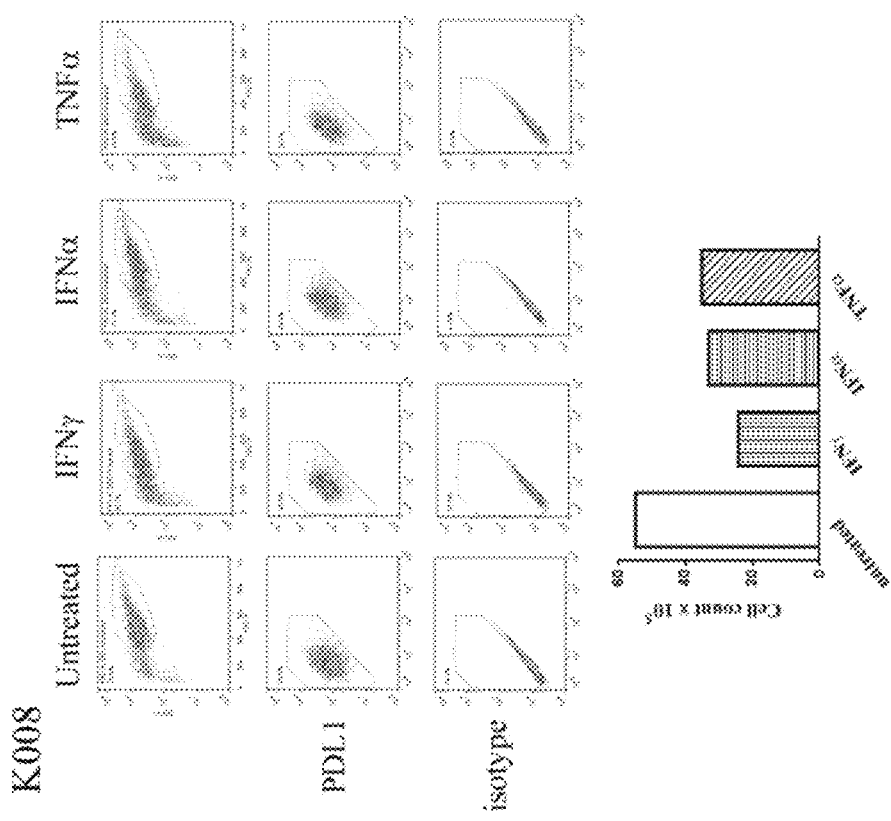
Figure 7B:
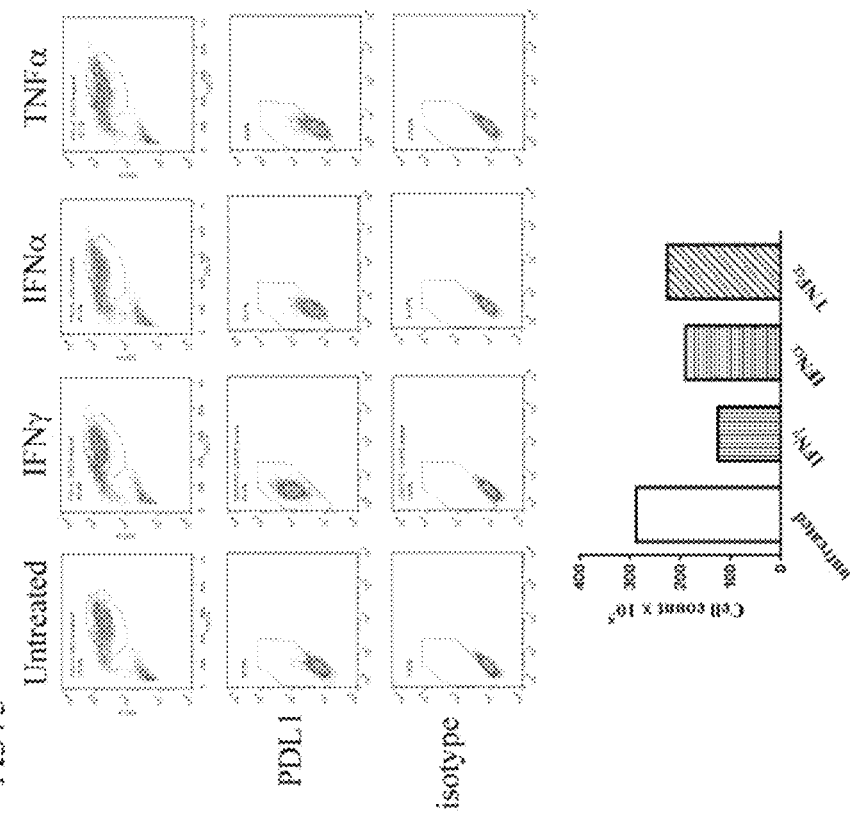
Figure 8A:
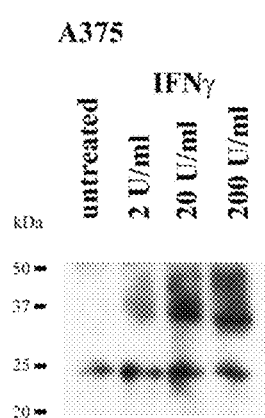
FIG. 8A-FIG. 8F show the correlation between sPDL1 secretions and membrane PDL1 expression in response to cytokine stimulations in melanoma cell lines. Results are shown for IFNγ-treated A375 cells (FIG. 8A-FIG. 8B), IFNγ-treated K028 cells (FIG. 8C-FIG. 8D), and TNFα-treated K028 cells (FIG. 8E-FIG. 8F).
Figure 8B:
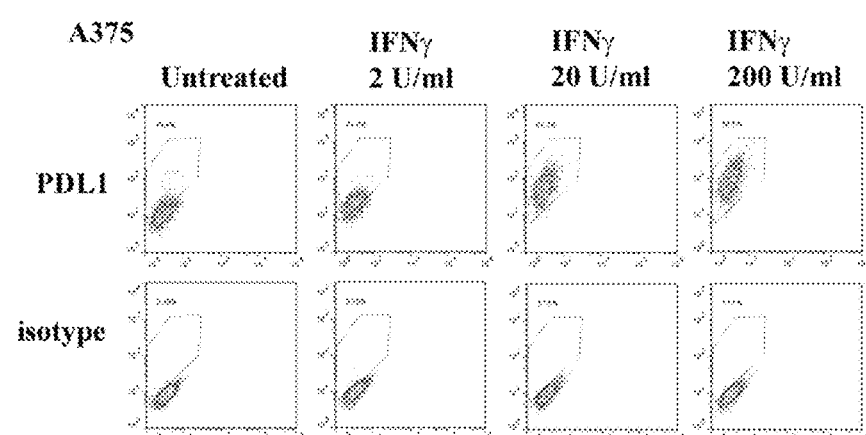
Figure 8C:
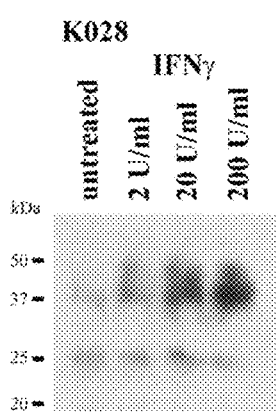
Figure 8D:
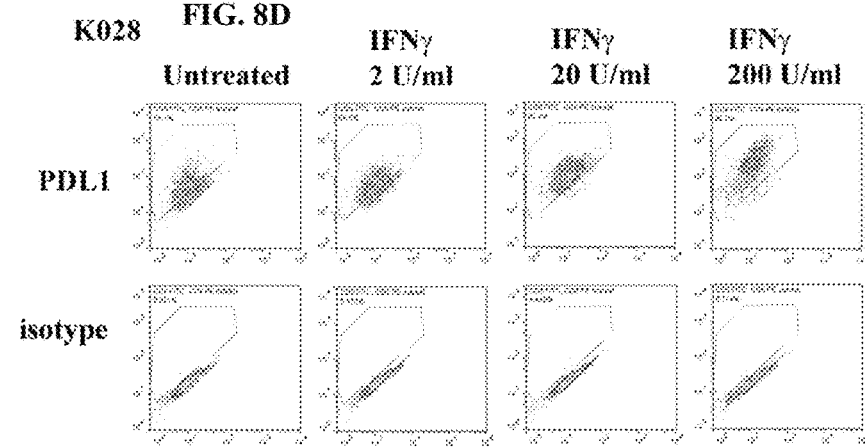
Figure 8E:
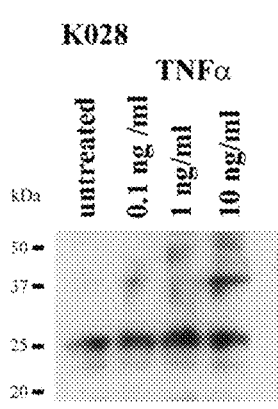
Figure 8F:
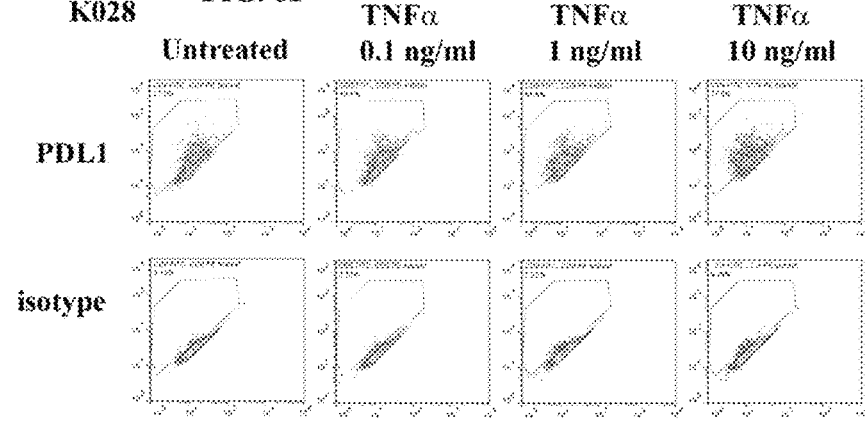

IFN-$\gamma$ is an inducer of membrane form of PDL1. To assess effects of IFN-$\gamma$ on the soluble PDL1 variants, A375 cells were cultured in the absence or presence of 200 U/ml IFN-$\gamma$ for 2 days. As showed in FIG. 3A-FIG. 3B, IFN-$\gamma$ dramatically increases 38 and 45 kDa bands of soluble PDL1. In order to examine the effects of IFN-$\alpha$ and TNF-$\alpha$ on soluble PDL1 variants, A375 cells were cultured in the absence or presence of 2000 U/ml IFN-$\alpha$ and 10 ng/ml TNF-$\alpha$ for 2 days. As depicted in FIG. 3E, IFN-$\alpha$ also resulted in remarkable increase of 38 and 45 kDa bands in the culture medium whereas TNF-$\alpha$ resulted in a slightly increased amount of the 38 kDa band. FIG. 3E-FIG. 3F and FIG. 8A-FIG. 8F further demonstrate that soluble PDL1s are differentially secreted in response to cytokines in a variety of cell lines. These results indicate that IFN-$\gamma$ and $\alpha$ and TNF-$\alpha$ are able to induce both membrane and soluble forms of PDL1. The 38 and 45 kDa PDL1s are most likely cytokine-induced soluble forms. Interestingly, secretions of soluble PDL1 were parallel to expression of membrane PDL1 in response to cytokines and the expressions of membrane PDL1 were correlated with the secretions of soluble PDL1 (FIG. 3, FIG. 7, and FIG. 8).

To assess biological activities of the soluble spliced variants, PDL1-3/Ig fusion protein was generated. The production of the fusion protein was confirmed by Coomassie blue staining and Western blotting (FIG. 4B). PDL1-3 is the shortest form among spliced PDL1 variants. Human $CD4^+$ or $CD8^+$ T cells were stimulated with anti-CD3 antibody in the absence or presence of either PDL1-3/Ig or human IgG1 for 3 days. PDL1-3/Ig markedly reduced the H3 uptakes of both $CD4^+$ and $CD8^+$ T cells (FIG. 3C). Whereas, control human IgG1 failed to show any inhibitory effects. This indicates that soluble spliced PDL1 variants inhibit T cell activation and proliferation.

In addition, the expression of membrane PDL1 and the secretion of soluble PDL1 were observed in response to sodium azide ($NaN_3$), which is a toxic agent (FIG. 9A-FIG. 9B). These data indicate that both membrane and soluble PDL1 represent injury- or death-response genes.

EXAMPLE 4

Soluble PDL1s in Braf Inhibitor Resistant Cell Lines

Previous studies showed increased expression of the membrane PDL1 form on Braf inhibitor resistant melanoma cell lines. To further examine the soluble PDL1 form on Braf inhibitor resistant cell lines, culture media from p1x4032-resistant A375 and M34 cells were analyzed. FIG. 3D shows that more soluble PDL1s were generated from the resistant cell lines (e.g., more 24 kDa PDL1 from the A375 cells and more 38 and 45 kDa PDL1 from the M34 cells). These results indicate that p1x4032 resistant cells secreted more soluble PDL1s.

EXAMPLE 5

Soluble PDL1 in Melanoma Patients

To detect soluble PDL1 in sera of melanoma patients, ELISA was established as described above. In particular, two mouse antibody clones were found to have different binding abilities to soluble PDL1 variants (FIG. 5). The term "sPDL1$^L$" refers to the two longer forms of soluble PDL1 detected by an antibody clone 230021, whereas the term "sPDL1$^{all}$" refers to the set of three forms of soluble PDL1 recognized by another antibody clone 29E.12B1. To further investigate soluble PDL1 variants, plasma from twenty five normal healthy donors, twenty three ipilimumab-treated, and forty six ipilimumab-plus-bevacizumab-treated stage IV melanoma patients were analyzed by ELISA. As shown in FIG. 10A, there were sPDL1 in the sera from healthy donor. Higher levels of soluble PDL1 existed in the melanoma patients in comparison with normal healthy donors. Soluble PDL1 in pre-treatment patient sera is referred to as "constitutive sPDL1." Because of 0.1 ng/ml cutoff, the distributions of soluble PDL1 values between healthy donors and melanoma patients were not statistically significant.

Western blot analyses further indicated the existences of the sPDL1 variants in melanoma patient plasma. For instance, P173 had high levels (1.87 ng/ml) of sPDL1$^{all}$ and low level of (<0.01 ng/ml) sPDL1$^L$ in sera by ELISA (Table 5). This indicates that the majority of sPDL1 might be PDL1-3 variant, the shortest form. As shown in the left panel of FIG. 10B, the data confirm that the sPDL1 variant in the patient plasma is a PDL1-3 or PDL1-12 variant. There were both sPDL1$^{all}$ (14.63 ng/ml) and sPDL1$^L$ (0.94 ng/ml) in P21 plasma (Table 4A-4B). The right panel of FIG. 10B confirms variants of sPDL1-3/12 and sPDL1-9 in the patient plasma.

Based on the sensitivities of the ELISA assays, levels of sPDL1 in healthy donor plasma, and the associations between levels of sPDL1 in patient plasma and clinical responses, the patients were divided into three groups for sPDL1$^L$ and sPDL1$^{all}$, respectively, e.g. for sPDL1$^L$, there were groups of <0.1 ng/ml, ≥0.1 ng/ml and <0.5 ng/ml, ≥0.5 ng/ml, whereas for sPDL1$^{all}$, there were groups of <0.5 ng/ml, ≥0.5 ng/ml and <1.4 ng/ml, and ≥1.4 ng/ml. As shown in FIG. 10C-FIG. 10D, Tables 4A-4B, and Tables 6D-6E, the patients with ≥0.5 ng/ml sPDL1$^L$ or ≥1.4 ng/ml sPDL1$^{all}$ showed the worst survival rate in both ipilimumab and ipilimumab plus bevacizumab trials, whereas patients with ≥0.1 ng/ml and <0.5 ng/ml sPDL1$^L$ or ≥0.5 ng/ml and <1.4 ng/ml sPDL1$^{all}$ showed the best clinical responses and survival rate.

Figure 11A:
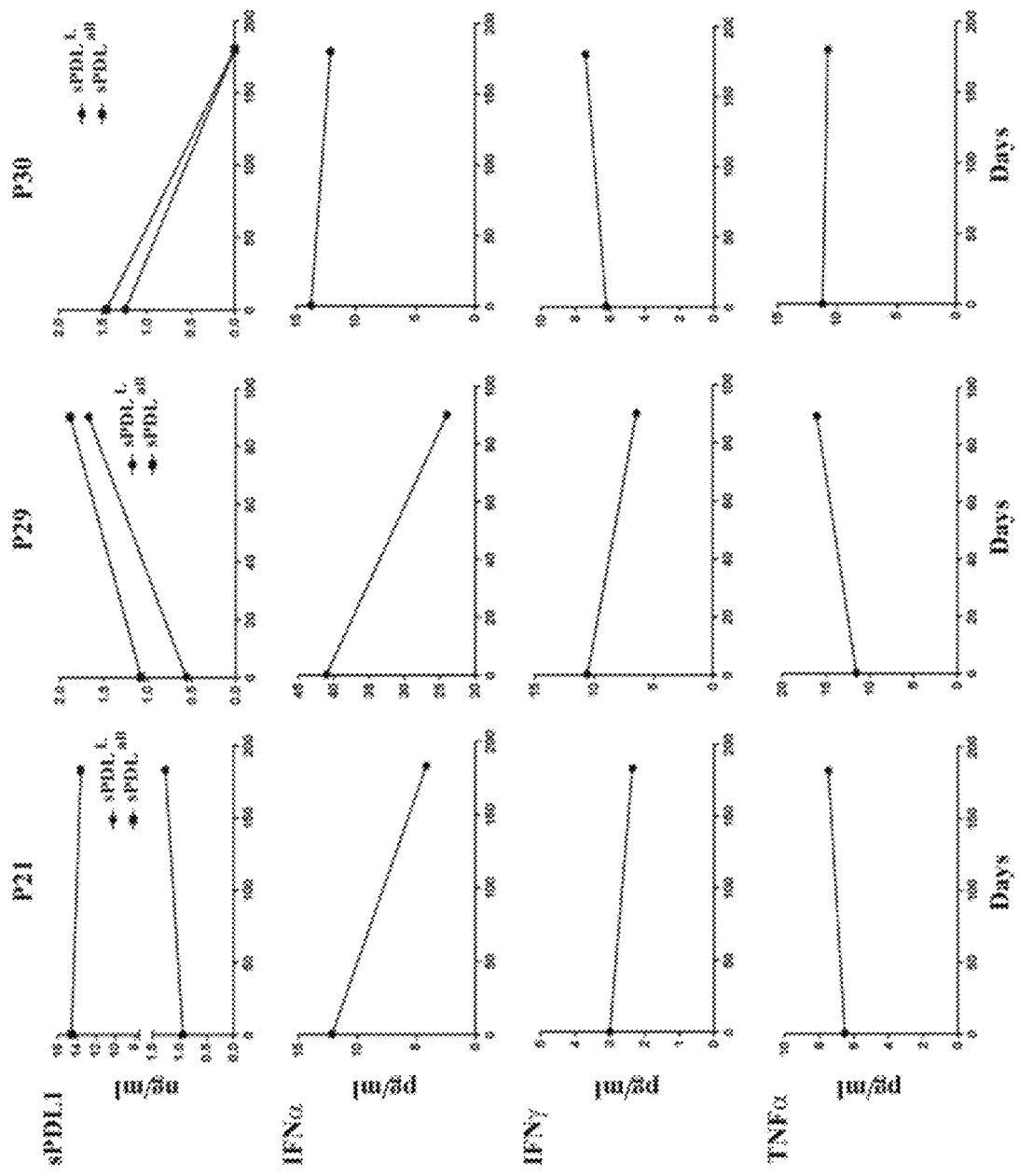
FIG. 11A-FIG. 11B show the relationship between sPDL1 and cytokines in patient sera.

Kinetic changes of sPDL1 and cytokines in these patient sera were further examined. Among four patients with ≥0.5 ng/ml sPDL1$^L$ in pre-treated patient sera, P21 and P29 showed increases in sPDL1$^L$, and decreases of sPDL1$^L$ in P30 were observed after the treatment, and the levels of sPDL1$^L$ remained in P183 after the treatment (FIG. 10C, Table 4A, and Table 5D). None of the patients showed any increases of the productions of IFNα, IFNγ, and TNFα after treatment (FIG. 11A). Among eight patients with ≥1.4 ng/ml sPDL1$^{all}$ in pre-treated patient sera, five patients showed slightly increased levels of sPDL1$^{all}$, and three patients (P30, P166, and P173) showed decreases in sPDL1$^{all}$ after the treatment (Table 4B and 5E). No increases in the cytokine levels were observed in the patients (FIG. 11A). These data indicate that high levels of constitutive sPDL1 (baseline) lead to the suppression of immune responses by the treatment of either ipilimumab or ipilimumab plus bevacizumab.

Figure 11B:
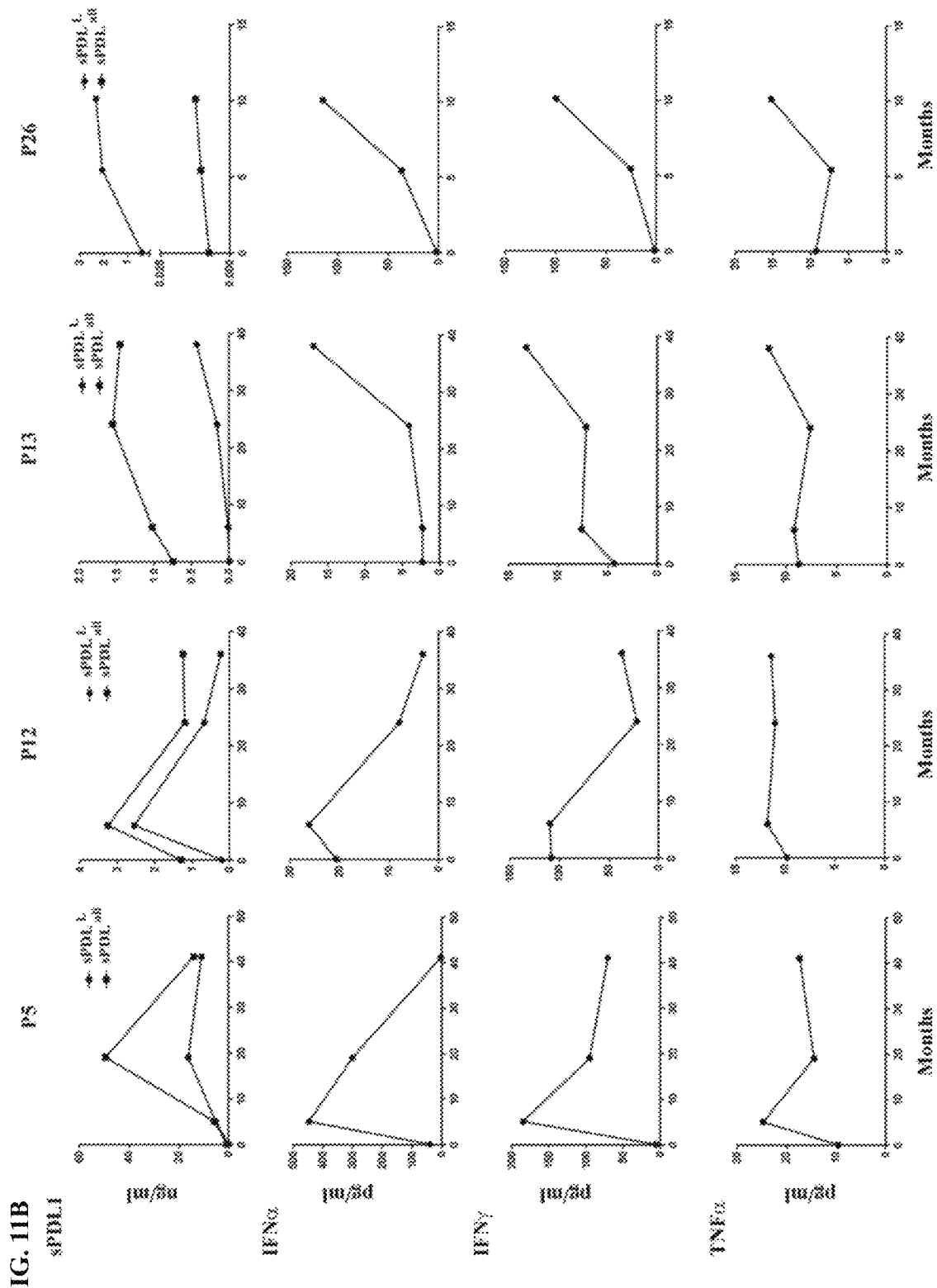

Furthermore, sixteen patients showed ≥1.5 fold increases in either sPDL1$^L$ or sPDL$^{all}$ after the treatment in both ipilimumab and ipilimumab plus bevacizumab trials (FIG. 10C-FIG. 10D and FIG. 11B and Table 4A-4B and 5E). Among them, twelve patients showed the increases over five months. Surprisingly, the long term elevations of soluble PDL1 levels were associated with beneficial clinical responses and longer survival length. Kinetic changes of cytokines from patients with PR were also examined as shown in FIG. 11B. Certain levels of cytokines were observed in the pre-treated sera, and there are correlations between levels of inducible sPDL1 and productions of cytokines in the post-treated sera except PBI4. Notably, levels of sPDL1$^{all}$ in this patient are greater than 1.4 ng/ml. This further supports the notion that high levels of sPDL1 lead to the suppression of immune responses. The increased soluble PDL1 in post-treatment patient sera is referred to as "inducible sPDL1." Taken together, different secretions of sPDL1 variants occurred in melanoma patients. Higher than 0.5 ng/ml of sPDL1$^L$ and 1.4 ng/ml of PDL1$^{all}$ in melanoma patient sera showed the lowest survival rate and the worst clinical outcomes. Secretions of sPDL1 variants are increased differentially post the ipilimumab and ipilimumab plus bevacizumab treatment. The long term increases post-treatment are significantly associated with longer survival length and clinical beneficial outcomes.

Taken together, these results indicate that splicing events occur in all tested melanoma cell lines and 4 splicing variants of PDL1 were found. These splicing variants are responsible for the secretion of soluble PDL1s. At least two variants can be increased by IFNα and γ, and TNFα. Levels of sPDL1 in melanoma patient sera are elevated in comparison with normal healthy donors. Patients with higher constitutive sPDL1 showed progressive disease and lower survival rate. Notably, patients with higher inducible sPDL1 are associated with beneficial outcome and longer term survival rate.

Alternative splicing of membrane proteins results in in-frame stop codon in extracellular domain and leads to secretion of the splice variants (Venables (2004) *Cancer. Res.* 64:7647-7654). Splicing long interspersed nuclear element-1 at exon 25 generates a stop codon in extracellular domain and leads to secretion of attractin (Tang et al. (2000) *Proc. Natl. Acad. Sci. U.S.A.* 97(11):6025-6030). Similarly, incorporation of a novel sequence into extracellular domain introduces a stop codon and results in secretion of soluble neural cell adhesion molecule (Gower et al. (1988) *Cell* 55:955-964). Two spliced variants of CXCL16 lacking transmembrane domain are associated with the secretion of soluble CXCL16 (van der Voort et al. (2010) *J. Leukoc. Biol.* 87:1029-1039). The present studies indicate that at least two splicing variants lacking transmembrane domain result in the secretions of the truncated PDL1s by the fact that the truncated PDL1s are increased in the cell culture medium by overexpression of the PDL1 variants. One variant that splices out its intracellular domain also leads to its secretion. It indicates that the intracellular domain of membrane PDL1 is able to stabilize PDL1 on the cell surface. Notably, overexpressed variants of PDL1 correspond to wild type versions of soluble PDL1. These results indicate that a majority of soluble PDL1s originate from three splicing variants in melanoma cells.

Pre-mRNA alternative splicing activities occur in varieties of cancers. These events are associated with transcriptional factors, cell signaling, and membrane proteins (Venables (2004) *Cancer. Res.* 64:7647-7654). Functional changes of these spliced proteins are involved in the development, aberrant proliferation and metastasis of cancers (Venables (2004) *Cancer. Res.* 64:7647-7654). A splice form of androgen receptor lacking exon 3 is found in all eight breast tumors (Zhu et al. (1997) *Int. J. Cancer* 72:574-580). A splice variant of neurofibromatosis type 1 protein partially loses function of its tumor suppressor on ras signaling (Scheurlen and Senf (1995) *Int. J. Cancer* 64:234-238). A splicing variant of insulin receptor kinase involving exon 11 has higher affinity for insulin like growth factor and is associated with tumor proliferation (Frasca et al. (1999) *Mol. Cell Biol.* 19:3278-3288; Vella et al. (2002) *J. Clin. Endocrinol. Metab.* 87:245-254). In melanoma, aberrant splice in Bin1, a tumor suppressor, results in loss of its function (Ge et al. (1999) *Proc. Natl. Acad. Sci. U.S.A.* 96:9689-9694). Splice variants of CDKN2A co-segregate with familial melanoma (Loo et al. (2003) *Oncogene* 22:6387-6394). Furthermore, SF3B1 encodes a component of spliceosome, and mutations of SF3B1 are associated with alternative splicing and poorer prognosis (Furney et al. (2013) *Cancer Discov.* 3:1122-1129). The data described herein indicate that the alternative splicing activities of PDL1 can be detected in all six melanoma cell lines. Furthermore, higher levels of constitutive sPDL1 in melanoma patient sera are associated with progressive diseases. These indicate that splicing activities are common events in melanoma and other cancers. Levels of constitutive sPDL1 in the patient sera may reflect the extent of overall splicing activities in tumor cells or tumor malignancy. This notion is further supported by the finding that splicing activities of PDL1 were increased in Braf inhibitor resistant melanoma cell lines, and the fact that acquired resistance to Braf inhibitor is associated with not only mutation but also induced splicing variants of Braf V600E (Poulikakos et al. (2011) *Nature* 480:387-390).

Membrane PDL1 expression has been found in a variety of cancers. It is well known that interactions of PDL1 and PD1 results in immune suppression. Higher expression of membrane PDL1 is associated with poorer prognosis and lower survival rate in patients with different types of tumors (Hino et al. (2010) *Cancer* 116:1757-1766; Gadiot et al. (2011) *Cancer* 117:2192-2201; and Chen et al. (2013) *Clin. Cancer Res.* 19:3462-3473). A recent study showed that sPDL1 in patient sera with renal tumors is associated with T cell apoptosis and tumor malignancy (Frigola et al. (2011) *Clin. Cancer Res.* 17:1915-1923). However, these studies show that sPDL1 is found in the sera from normal healthy donors. The significance of sPDL1 in healthy donor sera is unclear. It is shown that higher levels of sPDL1 were found in aging healthy donor sera (Chen et al. (2011) *Cytokine* 56:231-238). It might reflect lower or aberrant immune statues of healthy donors. The results described herein show that increased levels of constitutive sPDL1 occur in melanoma patient sera, in comparison with healthy donors. Although sPDL1 can be secreted from mature DC, the data described herein indicate that the increasing presence of constitutive sPDL1 originate from tumor cells. Furthermore, the data indicate that only melanoma patients with higher level of constitutive sPDL1 in pre-treatment sera than normal healthy sera correlate with progressive disease and shorter survival length in spite of efforts of immunotherapies. These suggest that higher sPDL1 levels reflect the extent of aberrant splicing activities in tumor cells.

Inflammation is a critical factor of tumor progression (Coussens and Werb (2002) *Nature* 420:860-867 and Dranoff (2004) *Nat. Rev. Cancer* 4:11-22). In the tumor site, inflammatory cells indispensably participate in neoplastic process. Pro-inflammatory cytokines are secreted, and they have important impacts on tumor proliferation, survival, and migration. The data described herein show that cytokines, such as IFNα, IFNγ, and TNFα, increase splicing activities of PDL1 leading to secretion of sPDL1. Therefore, it is possible that constitutive sPDL1 results from inflammatory reactions in tumor site.

Cytokine secretions are triggered during immune activation and reflect patient immune responses, particularly during immunotherapies. Inhibitory effects of IFNα, γ, and TNFα on cancers have been well documented (Chada et al. (2003) *Curr. Opin. Mol. Ther.* 5:463-474 and Dranoff (2004) *Nat. Rev. Cancer* 4:11-22). It is a paradoxical scenario that IFNγ is able to increase the expression of membrane PDL1 on varieties of cancer cells (Dong et al. (2002) *Nat. Med.* 8:793-800; Lee et al. (2006) *FEBS Lett.* 580:755-762; Liu et al. (2007) *Blood* 110:296-304; and Abiko and Mandai et al. (2013) *Clin. Cancer Res.* 19:1363-1374). The data described herein further show that IFNα and γ, and TNFα induces not only membrane PDL1 expression but also soluble PDL1 secretion in melanoma cancer cells.

Furthermore, expression of membrane PDL1 runs in parallel with the secretion of inducible PDL1 in response to the cytokines. The data described herein further indicate that patients with some levels of constitutive sPDL1 show best clinical responses and survival during ipilimumab plus bevacizumab therapy. Therefore, it cannot be ruled out that constitutive sPDL1 is due to local immune responses at tumor site in some cancer patients. The data described herein are also consistent with the fact that some had favorable clinical responses and others did not in all patients with membrane PDL1 positive tumors (Topalian et al. (2012) *N. Engl. J. Med.* 366:2443-2454), and that those membrane PDL1 positive tumors might reflect local immune responses (Spranger et al. (2013) *Sci. Transl. Med.* 5:200ra116).

Furthermore, the data described herein indicate that levels of the cytokines are associated with the extent of inducible sPDL1 secretion in the sera of melanoma patients during the immunotherapies. These may suggest that cytokine-induced tumor cell stresses result in the protective responses of PDL1 expression. It is surprisingly contrary to the belief that elevated inducible sPDL1 correlated with patient immune responses, clinical beneficial outcomes and longer survival length. More surprisingly, in patient 12, inducible sPDL1 was dramatically increased without obvious enhancements of the cytokines. The result indicates that levels of inducible sPDL1 reflect local immune response to tumors, and more precisely represent a symbol for a cascade of immune responses against tumors. Upregulated PDL1 in the melanoma tumor microenvironment is driven by $CD8^+$ T cells, and $PD1^+TIL$ from melanoma patients showed higher IFNγ production in response to tumor, and PDL1 induced immune suppression can be attenuated by CD28 signal in dose dependent manner (Freeman et al. (2000) *J. Exp. Med.* 192:1027-1034; Latchman et al. (2001) *Nat. Immunol.* 2:261-268; Inozume et al. (2010) *J. Immunother.* 33:956-964; and Spranger et al. (2013) *Sci. Transl. Med.* 5:200ra116). Therefore, it can be interpreted that levels of inducible sPDL1 reflects extent of immune responses, which overcome the negative barriers of PDL1 and other factors, such as $T_{reg}$ and IDO. All these factors play crucial roles in tumor immune escape (Spranger et al. (2013) *Sci. Transl. Med.* 5:200ra116). It cannot be waived that the sPDL are from mature DCs. Nevertheless, it still indicates the presence of tumor related mature DC or immune responses. In addition, anti-PDL1 IgG was detected in melanoma patient sera. It is possible that PDL1 is shielded by the IgG in the immune responses. Taken together, the data described herein indicate that inducible sPDL1 reflects tumor cell stress induced by anti-tumor immune responses and efficacy of immunotherapies. Detection of kinetic changes inducible sPDL1 provides a useful approach to precisely monitor dose versus responses during immunotherapy. It is shown that tumor antigen specific CD8+ TIL express with higher levels of PD1 are functionally impaired (Ahmadzadeh et al. (2009) *Blood* 114:1537-1544). This finding, in connection with the data described herein, provide further rationale for combination immunotherapy with PD1 blockade.

Anti-VEGF antibody has been shown to have anti-angiogenic effects in cancer therapies (Ellis and Hicklin (2008) *Nat. Rev. Cancer* 8:579-591). Also, VEGF has inhibitory effects on DC maturation (Gabrilovich et al. (1996) *Nat. Med.* 2:1096-1103). Synergistic effects of ipilimumab plus bevacizumab should be considered by the fact that the combination therapy proved better survival rate of melanoma patients in comparison with ipilimumab treatment. Three patients without detectable sPDL1 and cytokines showed clinical favorable responses and long term survival. These results indicate the existence of different anti-tumor mechanism. Given the fact that constitutive sPDL1 correlated with poorer immune responses, progressive disease, and shorter survival length, whereas, inducible sPDL1 were associated with favorable immune responses, beneficial clinical outcome, and longer survival length, sPDL1 is a useful biomarker for prediction of progressive cancer diseases and efficacy of immunotherapy agents.

TABLE 4

A
Associations between levels of sPDL1$^L$ and survival of patients

| Patients | sPDL1$^L$ ng/ml | | Clinical responses | Survival (months) |
|---|---|---|---|---|
| | Pre-treatment | post-treatmnet | | |
| P21 | 0.94 | 1.27 | PD | 10.8 |
| P29 | 0.57 | 1.68 | SD | 5.1 |
| P30 | 3.99 | — | PD | 10.5 |
| P5 | 0.21 | 16.33 | PR | 39.1* |
| P6 | 0.25 | 1.35 | PR | 36.0* |
| P8 | 0.21 | 0.49 | PR | 35.3* |
| P12 | 0.22 | 1.35 | CR | 31.5 |
| P13 | — | 0.44 | PR | 31.1* |
| PB14 | 0.19 | 0.37 | PR | 25.1 |

B
Associations between levels of sPDL1$^{all}$ and survival of patients

| Patients | sPDL1$^{all}$ ng/ml | | Clinical responses | Survival (months) |
|---|---|---|---|---|
| | Pre-treatment | post-treatmnet | | |
| P21 | 14.63 | 13.64 | PD | 10.8 |
| P29 | 1.41 | 2.06 | SD | 5.1 |
| P30 | 1.46 | — | PD | 10.5 |
| PB14 | 1.45 | 2.01 | PR | 25.11 |
| PMGH2 | 1.57 | 1.84 | PD | 6.4 |
| PMGH6 | 1.74 | 2.16 | PD | 18.7 |
| P5 | 0.81 | 49.56 | PR | 39.1* |
| P6 | 0.92 | 1.71 | PR | 36.0* |
| P8 | 1.04 | 1.60 | PR | 35.3 |
| P12 | 1.31 | 3.26 | PR | 31.5* |
| P13 | 0.75 | 1.56 | PR | 31.3* |
| P26 | 0.42 | 2.34 | SD | 20.0* |
| P27 | — | 0.27 | PR | 12.5* |
| P37 | — | 0.13 | SD | 10.8* |
| PD19 | — | 0.12 | SD | 7.1* |
| PB110 | — | 0.18 | SD | 17.3* |

TABLE 4-continued

| P3 | 0.13 | 0.50# | PD | 4.2 |
|---|---|---|---|---|
| P10 | — | 0.14# | PD | 5.2 |
| PB17 | 0.19 | 0.41# | PD | 2.4 |

*indicates patient are still alive.
— indicates less than 0.1 ng/ml.
+ indicates the highest concentrations of post-treatment.
indicates only post-treatment samples 3 months, and there are no any post-treatment samples available after 3 months.

TABLE 5

A
Anti-PDL1 antibody epitope regions

| Antibody clones | epitope regions |
|---|---|
| 29E12B1 | 1-122 |
| 130021 | 19-239 |

B
Amino acid regions of sPDL1 variants

| sPDL1 variants | Amino acid regions |
|---|---|
| PDL1-3 | 1-178 |
| PDL1-9 | 1-243 |
| PDL1-1 | 1-294 |

C
Amino acid regions of recombinant PDL1 proteins

| recombinant proteins | Amino acid regions |
|---|---|
| PDL1-3/Ig | 1-178 |
| PDL1-his | 19-239 |

D
Association between levels of sPDL1$^L$ and patient survival

| Patients | sPDL1$^L$ ng/ml | | Clinical responses | Survival (months) |
|---|---|---|---|---|
| | Pre-treatment | Post-treatment+ | | |
| P183 | 0.542 | 0.579 | SD | 12 |

+indicates the highest concentration of post-treatment samples.

E
Association between levels of sPDL1$^{all}$ and patient survival

| Patients | sPDL1$^{all}$ ng/ml | | Clinical responses | Survival (months) |
|---|---|---|---|---|
| | Pre-treatment | Post-treatment+ | | |
| P166 | 1.71 | 0.94 | Unevaluble | 2 |
| P173 | 1.87 | 0.91 | PD | 3 |
| P168 | 0.12 | 0.77# | PD | 7 |
| P187 | — | 0.12 | PR | 29 | indicates the first post-treatment samples within 3 months after pre-treatment sample, and there are no any post-treatment samples available after the first post-treatment sample.
+indicates the highest concentration of post-treatment samples.

INCORPORATION BY REFERENCE

The contents of all references, patent applications, patents, and published patent applications, as well as the Figures and the Sequence Listing, cited throughout this application are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A fusion protein comprising i) a PD-L1-1 polypeptide comprising the amino acid sequence shown in SEQ ID NO: 17 and ii) a heterologous moiety selected from the group consisting of a signal peptide, a peptide tag, a dimerization domain, an oligomerization domain, an antibody, and an antibody fragment, wherein the PD-L1-1 polypeptide has the ability to promote immunoinhibitory function, promote cytokine expression, inhibit T cell activation, inhibit cellular proliferation, bind to PD-1, or bind to B7-1.

2. The fusion protein of claim 1, wherein the PD-L1-1 polypeptide is expressed by melanoma cells.

3. A pharmaceutical composition comprising the fusion protein of claim 1 and a pharmaceutically acceptable agent selected from the group consisting of excipients, diluents, and carriers.

4. A pharmaceutical composition comprising the fusion protein of claim 2 and a pharmaceutically acceptable agent selected from the group consisting of excipients, diluents, and carriers.

5. A fusion protein comprising i) a PD-L1-1 polypeptide comprising the amino acid sequence shown in SEQ ID NO: 17 and ii) a heterologous moiety selected from the group consisting of a signal peptide, a peptide tag, a dimerization domain, an oligomerization domain, an antibody, and an antibody fragment, wherein the PD-L1-1 polypeptide is expressed by melanoma cells.

6. A pharmaceutical composition comprising the fusion protein of claim 5 and a pharmaceutically acceptable agent selected from the group consisting of excipients, diluents, and carriers.

* * * * *

SEQUENCE LISTING

<160> NUMBER OF SEQ ID NOS: 42

<210> SEQ ID NO 1
<211> LENGTH: 867
<212> TYPE: DNA
<213> ORGANISM: Homo sapiens

<400> SEQUENCE: 1

```
atgcagatcc cacaggcgcc ctggccagtc gtctgggcgg tgctacaact gggctggcgg      60
ccaggatggt tcttagactc cccagacagg ccctggaacc cccccacctt ctccccagcc     120
ctgctcgtgg tgaccgaagg ggacaacgcc accttcacct gcagcttctc caacacatcg     180
gagagcttcg tgctaaactg gtaccgcatg agccccagca accagacgga caagctggcc     240
gccttccccg aggaccgcag ccagcccggc caggactgcc gcttccgtgt cacacaactg     300
cccaacgggc gtgacttcca catgagcgtg tcagggccc  ggcgcaatga cagcggcacc     360
tacctctgtg gggccatctc cctggccccc aaggcgcaga tcaaagagag cctgcgggca     420
gagctcaggg tgacagagag aagggcagaa gtgcccacag cccaccccag cccctcaccc     480
aggccagccg gccagttcca aaccctggtg gttggtgtcg tgggcggcct gctgggcagc     540
ctggtgctgc tagtctgggt cctggccgtc atctgctccc gggccgcacg agggacaata     600
ggagccaggc gcaccggcca gcccctgaag gaggaccct  cagccgtgcc tgtgttctct     660
gtggactatg gggagctgga tttccagtgg cgagagaaga cccggagcc ccccgtgccc     720
tgtgtccctg agcagacgga gtatgccacc attgtctttc ctagcggaat gggcacctca     780
tcccccgccc caggggctc agctgacggc cctcggagtg cccagccact gaggcctgag     840
gatggacact gctcttggcc cctctga                                          867
```

<210> SEQ ID NO 2
<211> LENGTH: 288
<212> TYPE: PRT
<213> ORGANISM: Homo sapiens

<400> SEQUENCE: 2

```
Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
```

165                 170                 175
Leu Leu Gly Ser Leu Val Leu Val Trp Val Leu Ala Val Ile Cys
            180                 185                 190

Ser Arg Ala Ala Arg Gly Thr Ile Gly Ala Arg Arg Thr Gly Gln Pro
            195                 200                 205

Leu Lys Glu Asp Pro Ser Ala Val Pro Val Phe Ser Val Asp Tyr Gly
            210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
            245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
            275                 280                 285

<210> SEQ ID NO 3
<211> LENGTH: 867
<212> TYPE: DNA
<213> ORGANISM: Mus musculus

<400> SEQUENCE: 3
atgtgggtcc ggcaggtacc ctggtcattc acttgggctg tgctgcagtt gagctggcaa        60
tcagggtggc ttctagaggt ccccaatggg ccctggaggt ccctcacctt ctacccagcc       120
tggctcacag tgtcagaggg agcaaatgcc accttcacct gcagcttgtc caactggtcg       180
gaggatctta tgctgaactg gaaccgcctg agtcccagca accagactga aaacaggcc        240
gccttctgta tggtttgag ccaacccgtc caggatgccc gcttccagat catacagctg       300
cccaacaggc atgacttcca catgaacatc cttgacacac ggcgcaatga cagtggcatc       360
tacctctgtg gggccatctc cctgcacccc aaggcaaaaa tcgaggagag ccctggagca       420
gagctcgtgg taacagagag aatcctggag acctcaacaa gatatcccag cccctcgccc       480
aaaccagaag gccggtttca aggcatggtc attggtatca tgagtgccct agtgggtatc       540
cctgtattgc tgctgctggc ctgggcccta gctgtcttct gctcaacaag tatgtcagag       600
gccagaggag ctggaagcaa ggacgacact ctgaaggagg agccttcagc agcacctgtc       660
cctagtgtgg cctatgagga gctggacttc agggacgag agaagacacc agagctccct       720
accgcctgtg tgcacacaga atatgccacc attgtcttca ctgaagggct gggtgcctcg       780
gccatgggac gtaggggctc agctgatggc ctgcagggtc ctcggcctcc aagacatgag       840
gatggacatt gttcttggcc tctttga                                           867

<210> SEQ ID NO 4
<211> LENGTH: 288
<212> TYPE: PRT
<213> ORGANISM: Mus musculus

<400> SEQUENCE: 4

Met Trp Val Arg Gln Val Pro Trp Ser Phe Thr Trp Ala Val Leu Gln
1               5                   10                  15

Leu Ser Trp Gln Ser Gly Trp Leu Leu Glu Val Pro Asn Gly Pro Trp
            20                  25                  30

Arg Ser Leu Thr Phe Tyr Pro Ala Trp Leu Thr Val Ser Glu Gly Ala
        35                  40                  45

Asn Ala Thr Phe Thr Cys Ser Leu Ser Asn Trp Ser Glu Asp Leu Met

```
                50                  55                  60
Leu Asn Trp Asn Arg Leu Ser Pro Ser Asn Gln Thr Glu Lys Gln Ala
 65                  70                  75                  80

Ala Phe Cys Asn Gly Leu Ser Gln Pro Val Gln Asp Ala Arg Phe Gln
                 85                  90                  95

Ile Ile Gln Leu Pro Asn Arg His Asp Phe His Met Asn Ile Leu Asp
                100                 105                 110

Thr Arg Arg Asn Asp Ser Gly Ile Tyr Leu Cys Gly Ala Ile Ser Leu
                115                 120                 125

His Pro Lys Ala Lys Ile Glu Glu Ser Pro Gly Ala Glu Leu Val Val
                130                 135                 140

Thr Glu Arg Ile Leu Glu Thr Ser Thr Arg Tyr Pro Ser Pro Ser Pro
145                 150                 155                 160

Lys Pro Glu Gly Arg Phe Gln Gly Met Val Ile Gly Ile Met Ser Ala
                165                 170                 175

Leu Val Gly Ile Pro Val Leu Leu Leu Leu Ala Trp Ala Leu Ala Val
                180                 185                 190

Phe Cys Ser Thr Ser Met Ser Glu Ala Arg Gly Ala Gly Ser Lys Asp
                195                 200                 205

Asp Thr Leu Lys Glu Glu Pro Ser Ala Ala Pro Val Pro Ser Val Ala
                210                 215                 220

Tyr Glu Glu Leu Asp Phe Gln Gly Arg Glu Lys Thr Pro Glu Leu Pro
225                 230                 235                 240

Thr Ala Cys Val His Thr Glu Tyr Ala Thr Ile Val Phe Thr Glu Gly
                245                 250                 255

Leu Gly Ala Ser Ala Met Gly Arg Arg Gly Ser Ala Asp Gly Leu Gln
                260                 265                 270

Gly Pro Arg Pro Pro Arg His Glu Asp Gly His Cys Ser Trp Pro Leu
                275                 280                 285

<210> SEQ ID NO 5
<211> LENGTH: 873
<212> TYPE: DNA
<213> ORGANISM: Homo sapiens

<400> SEQUENCE: 5
atgaggatat  ttgctgtctt  tatattcatg  acctactggc  atttgctgaa  cgcatttact    60
gtcacggttc  ccaaggacct  atatgtggta  gagtatggta  gcaatatgac  aattgaatgc   120
aaattcccag  tagaaaaaca  attagacctg  gctgcactaa  ttgtctattg  ggaaatggag   180
gataagaaca  ttattcaatt  tgtgcatgga  gaggaagacc  tgaaggttca  gcatagtagc   240
tacagacaga  gggcccggct  gttgaaggac  cagctctccc  tgggaaatgc  tgcacttcag   300
atcacagatg  tgaaattgca  ggatgcaggg  gtgtaccgct  gcatgatcag  ctatggtggt   360
gccgactaca  agcgaattac  tgtgaaagtc  aatgccccat  acaacaaaat  caaccaaaga   420
attttggttg  tggatccagt  cacctctgaa  catgaactga  catgtcaggc  tgagggctac   480
cccaaggccg  aagtcatctg  acaagcagt   gaccatcaag  tcctgagtgg  taagaccacc   540
accaccaatt  ccaagagaga  ggagaagctt  tcaatgtga  ccagcacact  gagaatcaac   600
acaacaacta  tgagattttt  ctactgcact  tttaggagat  tagatcctga  ggaaaaccat   660
acagctgaat  tggtcatccc  agaactacct  ctggcacatc  ctccaaatga  aaggactcac   720
ttggtaattc  tgggagccat  cttattatgc  cttggtgtag  cactgacatt  catcttccgt   780
ttaagaaaag  ggagaatgat  ggatgtgaaa  aaatgtggca  tccaagatac  aaactcaaag   840
```
aagcaaagtg atacacattt ggaggagacg taa                                        873

<210> SEQ ID NO 6
<211> LENGTH: 290
<212> TYPE: PRT
<213> ORGANISM: Homo sapiens

<400> SEQUENCE: 6

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
    290

<210> SEQ ID NO 7
<211> LENGTH: 531
<212> TYPE: DNA
<213> ORGANISM: Homo sapiens

<400> SEQUENCE: 7
atgaggatat ttgctgtctt tatattcatg acctactggc atttgctgaa cgccccatac      60
aacaaaatca accaaagaat tttggttgtg gatccagtca cctctgaaca tgaactgaca     120

```
tgtcaggctg agggctaccc caaggccgaa gtcatctgga caagcagtga ccatcaagtc    180
ctgagtggta agaccaccac caccaattcc aagagagagg agaagctttt caatgtgacc    240
agcacactga gaatcaacac aacaactaat gagattttct actgcacttt taggagatta    300
gatcctgagg aaaaccatac agctgaattg gtcatcccag aactacctct ggcacatcct    360
ccaaatgaaa ggactcactt ggtaattctg ggagccatct tattatgcct tggtgtagca    420
ctgacattca tcttccgttt aagaaaaggg agaatgatgg atgtgaaaaa atgtggcatc    480
caagatacaa actcaaagaa gcaaagtgat acacatttgg aggagacgta a             531

<210> SEQ ID NO 8
<211> LENGTH: 176
<212> TYPE: PRT
<213> ORGANISM: Homo sapiens

<400> SEQUENCE: 8

Met Arg Ile Phe Ala Val Phe Ile Phe Met Thr Tyr Trp His Leu Leu
1               5                   10                  15

Asn Ala Pro Tyr Asn Lys Ile Asn Gln Arg Ile Leu Val Val Asp Pro
            20                  25                  30

Val Thr Ser Glu His Glu Leu Thr Cys Gln Ala Glu Gly Tyr Pro Lys
        35                  40                  45

Ala Glu Val Ile Trp Thr Ser Ser Asp His Gln Val Leu Ser Gly Lys
    50                  55                  60

Thr Thr Thr Thr Asn Ser Lys Arg Glu Glu Lys Leu Phe Asn Val Thr
65                  70                  75                  80

Ser Thr Leu Arg Ile Asn Thr Thr Thr Asn Glu Ile Phe Tyr Cys Thr
                85                  90                  95

Phe Arg Arg Leu Asp Pro Glu Glu Asn His Thr Ala Glu Leu Val Ile
            100                 105                 110

Pro Glu Leu Pro Leu Ala His Pro Pro Asn Glu Arg Thr His Leu Val
        115                 120                 125

Ile Leu Gly Ala Ile Leu Leu Cys Leu Gly Val Ala Leu Thr Phe Ile
    130                 135                 140

Phe Arg Leu Arg Lys Gly Arg Met Met Asp Val Lys Lys Cys Gly Ile
145                 150                 155                 160

Gln Asp Thr Asn Ser Lys Lys Gln Ser Asp Thr His Leu Glu Glu Thr
                165                 170                 175

<210> SEQ ID NO 9
<211> LENGTH: 968
<212> TYPE: DNA
<213> ORGANISM: Homo sapiens
<220> FEATURE:
<221> NAME/KEY: CDS
<222> LOCATION: (59)..(793)

<400> SEQUENCE: 9
gcttcccgag gctccgcacc agccgcgctt ctgtccgcct gcagggcatt ccagaaag      58 atg agg ata ttt gct gtc ttt ata ttc atg acc tac tgg cat ttg ctg     106
Met Arg Ile Phe Ala Val Phe Ile Phe Met Thr Tyr Trp His Leu Leu
1               5                   10                  15 aac gca ttt act gtc acg gtt ccc aag gac cta tat gtg gta gag tat     154
Asn Ala Phe Thr Val Thr Val Pro Lys Asp Leu Tyr Val Val Glu Tyr
            20                  25                  30 ggt agc aat atg aca att gaa tgc aaa ttc cca gta gaa aaa caa tta     202
Gly Ser Asn Met Thr Ile Glu Cys Lys Phe Pro Val Glu Lys Gln Leu
```

```
gac ctg gct gca cta att gtc tat tgg gaa atg gag gat aag aac att     250
Asp Leu Ala Ala Leu Ile Val Tyr Trp Glu Met Glu Asp Lys Asn Ile
 50                  55                  60 att caa ttt gtg cat gga gag gaa gac ctg aag gtt cag cat agt agc     298
Ile Gln Phe Val His Gly Glu Glu Asp Leu Lys Val Gln His Ser Ser
 65                  70                  75                  80 tac aga cag agg gcc cgg ctg ttg aag gac cag ctc tcc ctg gga aat     346
Tyr Arg Gln Arg Ala Arg Leu Leu Lys Asp Gln Leu Ser Leu Gly Asn
                 85                  90                  95 gct gca ctt cag atc aca gat gtg aaa ttg cag gat gca ggg gtg tac     394
Ala Ala Leu Gln Ile Thr Asp Val Lys Leu Gln Asp Ala Gly Val Tyr
            100                 105                 110 cgc tgc atg atc agc tat ggt ggt gcc gac tac aag cga att act gtg     442
Arg Cys Met Ile Ser Tyr Gly Gly Ala Asp Tyr Lys Arg Ile Thr Val
        115                 120                 125 aaa gtc aat gcc cca tac aac aaa atc aac caa aga att ttg gtt gtg     490
Lys Val Asn Ala Pro Tyr Asn Lys Ile Asn Gln Arg Ile Leu Val Val
130                 135                 140 gat cca gtc acc tct gaa cat gaa ctg aca tgt cag gct gag ggc tac     538
Asp Pro Val Thr Ser Glu His Glu Leu Thr Cys Gln Ala Glu Gly Tyr
145                 150                 155                 160 ccc aag gcc gaa gtc atc tgg aca agc agt gac cat caa gtc ctg agt     586
Pro Lys Ala Glu Val Ile Trp Thr Ser Ser Asp His Gln Val Leu Ser
                165                 170                 175 ggt aag acc acc acc acc aat tcc aag aga gag gag aag ctt ttc aat     634
Gly Lys Thr Thr Thr Thr Asn Ser Lys Arg Glu Glu Lys Leu Phe Asn
            180                 185                 190 gtg acc agc aca ctg aga atc aac aca aca act aat gag att ttc tac     682
Val Thr Ser Thr Leu Arg Ile Asn Thr Thr Thr Asn Glu Ile Phe Tyr
        195                 200                 205 tgc act ttt agg aga tta gat cct gag gaa aac cat aca gct gaa ttg     730
Cys Thr Phe Arg Arg Leu Asp Pro Glu Glu Asn His Thr Ala Glu Leu
    210                 215                 220 gtc atc cca ggt aat att ctg aat gtg tcc att aaa ata tgt cta aca     778
Val Ile Pro Gly Asn Ile Leu Asn Val Ser Ile Lys Ile Cys Leu Thr
225                 230                 235                 240 ctg tcc cct agc acc tagcatgatg tctgcctatc atagtcattc agtgattgtt    833
Leu Ser Pro Ser Thr
                245 gaataaatga atgaatgaat aacactatgt ttacaaaata tatcctaatt cctcacctcc    893 attcatccaa accatattgt tacttaataa acattcagca gatatttatg gaataaaaaa    953 aaaaaaaaaa aaaaa                                                     968

<210> SEQ ID NO 10
<211> LENGTH: 245
<212> TYPE: PRT
<213> ORGANISM: Homo sapiens

<400> SEQUENCE: 10

Met Arg Ile Phe Ala Val Phe Ile Phe Met Thr Tyr Trp His Leu Leu
 1               5                  10                  15

Asn Ala Phe Thr Val Thr Val Pro Lys Asp Leu Tyr Val Val Glu Tyr
                 20                  25                  30

Gly Ser Asn Met Thr Ile Glu Cys Lys Phe Pro Val Glu Lys Gln Leu
            35                  40                  45

Asp Leu Ala Ala Leu Ile Val Tyr Trp Glu Met Glu Asp Lys Asn Ile
 50                  55                  60
```

-continued

```
Ile Gln Phe Val His Gly Glu Glu Asp Leu Lys Val Gln His Ser Ser
 65                  70                  75                  80

Tyr Arg Gln Arg Ala Arg Leu Leu Lys Asp Gln Leu Ser Leu Gly Asn
                 85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Gly Asn Ile Leu Asn Val Ser Ile Lys Ile Cys Leu Thr
225                 230                 235                 240

Leu Ser Pro Ser Thr
                245

<210> SEQ ID NO 11
<211> LENGTH: 178
<212> TYPE: PRT
<213> ORGANISM: Homo sapiens

<400> SEQUENCE: 11

Met Arg Ile Phe Ala Val Phe Ile Phe Met Thr Tyr Trp His Leu Leu
  1               5                  10                  15

Asn Ala Phe Thr Val Thr Val Pro Lys Asp Leu Tyr Val Val Glu Tyr
                 20                  25                  30

Gly Ser Asn Met Thr Ile Glu Cys Lys Phe Pro Val Glu Lys Gln Leu
            35                  40                  45

Asp Leu Ala Ala Leu Ile Val Tyr Trp Glu Met Glu Asp Lys Asn Ile
 50                  55                  60

Ile Gln Phe Val His Gly Glu Glu Asp Leu Lys Val Gln His Ser Ser
 65                  70                  75                  80

Tyr Arg Gln Arg Ala Arg Leu Leu Lys Asp Gln Leu Ser Leu Gly Asn
                 85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Asp
```

<210> SEQ ID NO 12
<211> LENGTH: 685
<212> TYPE: DNA
<213> ORGANISM: Homo sapiens

<400> SEQUENCE: 12

```
atgaggatat ttgctgtctt tatattcaat gacctactgg catttgctga acgcatttac      60
tgtcacggtt cccaaggacc tatatgtggt agagtatggt agcaatatga caattgaatg     120
caaattccca gtagaaaaac aattagacct ggctgcacta attgtctatt gggaaatgga     180
ggataagaac attattcaat ttgtgcatgg agaggaagac ctgaaggttc agcatagtag     240
ctacagacag agggcccggc tgttgaagga ccagctctcc ctgggaaatg ctgcacttca     300
gatcacagat gtgaaattgc aggatgcagg ggtgtaccgc tgcatgatca gctatggtgg     360
tgccgactac aagcgaatta ctgtgaaagt caatgcccca tacaacaaaa tcaaccaaag     420
aattttggtt gtggatccag tcacctctga acatgaactg acatgtcagg ctgagggcta     480
ccccaaggcc gaagtcatct ggacaagcag tgaccatcaa gtcctgagtg gtaagaccac     540
caccaccaat tccaagagag aggagaagct tttcaatgtg accagcacac tgagaatcaa     600
cacaacaact aatgagattt tctactgcac ttttaggaga ttagatcctg aggaaaacca     660
tacagctgaa ttggtcatcc cataa                                            685
```

<210> SEQ ID NO 13
<211> LENGTH: 227
<212> TYPE: PRT
<213> ORGANISM: Homo sapiens

<400> SEQUENCE: 13

```
Met Arg Ile Phe Ala Val Phe Ile Phe Met Thr Tyr Trp His Leu Leu
  1               5                  10                  15

Asn Ala Phe Thr Val Thr Val Pro Lys Asp Leu Tyr Val Val Glu Tyr
             20                  25                  30

Gly Ser Asn Met Thr Ile Glu Cys Lys Phe Pro Val Glu Lys Gln Leu
         35                  40                  45

Asp Leu Ala Ala Leu Ile Val Tyr Trp Glu Met Glu Asp Lys Asn Ile
     50                  55                  60

Ile Gln Phe Val His Gly Glu Glu Asp Leu Lys Val Gln His Ser Ser
 65                  70                  75                  80

Tyr Arg Gln Arg Ala Arg Leu Leu Lys Asp Gln Leu Ser Leu Gly Asn
                 85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205
```

Cys Thr Phe Arg Arg Leu Asp Pro Glu Glu Asn His Thr Ala Glu Leu
            210                 215                 220

Val Ile Pro
225

<210> SEQ ID NO 14
<211> LENGTH: 873
<212> TYPE: DNA
<213> ORGANISM: Mus musculus

<400> SEQUENCE: 14
atgaggatat tgctggcat tatattcaca gcctgctgtc acttgctacg ggcgtttact      60
atcacggctc caaaggactt gtacgtggtg gagtatggca gcaacgtcac gatggagtgc    120
agattccctg tagaacggga gctggacctg cttgcgttag tggtgtactg ggaaaaggaa    180
gatgagcaag tgattcagtt tgtggcagga gaggaggacc ttaagcctca gcacagcaac    240 ttcagggga gagcctcgct gccaaaggac cagcttttga agggaaatgc tgcccttcag    300
atcacagacg tcaagctgca ggacgcaggc gtttactgct gcataatcag ctacggtggt    360
gcggactaca gcgaatcac gctgaaagtc aatgccccat accgcaaaat caaccagaga    420
atttccgtgg atccagccac ttctgagcat gaactaatat gtcaggccga gggttatcca    480
gaagctgagg taatctggac aaacagtgac caccaacccg tgagtgggaa gagaagtgtc    540
accacttccc ggacagaggg gatgcttctc aatgtgacca gcagtctgag ggtcaacgcc    600
acagcgaatg atgttttcta ctgtacgttt tggagatcac agccagggca aaaccacaca    660
gcggagctga tcatcccaga actgcctgca acacatcctc cacagaacag gactcactgg    720
gtgcttctgg gatccatcct gttgttcctc attgtagtgt ccacggtcct cctcttcttg    780
agaaaacaag tgagaatgct agatgtggag aaatgtggcg ttgaagatac aagctcaaaa    840
aaccgaaatg atacacaatt cgaggagacg taa                                 873

<210> SEQ ID NO 15
<211> LENGTH: 290
<212> TYPE: PRT
<213> ORGANISM: Mus musculus

<400> SEQUENCE: 15

Met Arg Ile Phe Ala Gly Ile Ile Phe Thr Ala Cys Cys His Leu Leu
1               5                   10                  15

Arg Ala Phe Thr Ile Thr Ala Pro Lys Asp Leu Tyr Val Val Glu Tyr
            20                  25                  30

Gly Ser Asn Val Thr Met Glu Cys Arg Phe Pro Val Glu Arg Glu Leu
        35                  40                  45

Asp Leu Leu Ala Leu Val Val Tyr Trp Glu Lys Glu Asp Glu Gln Val
    50                  55                  60

Ile Gln Phe Val Ala Gly Glu Glu Asp Leu Lys Pro Gln His Ser Asn
65                  70                  75                  80

Phe Arg Gly Arg Ala Ser Leu Pro Lys Asp Gln Leu Leu Lys Gly Asn
                85                  90                  95

Ala Ala Leu Gln Ile Thr Asp Val Lys Leu Gln Asp Ala Gly Val Tyr
            100                 105                 110

Cys Cys Ile Ile Ser Tyr Gly Gly Ala Asp Tyr Lys Arg Ile Thr Leu
        115                 120                 125

Lys Val Asn Ala Pro Tyr Arg Lys Ile Asn Gln Arg Ile Ser Val Asp
    130                 135                 140

```
Pro Ala Thr Ser Glu His Glu Leu Ile Cys Gln Ala Glu Gly Tyr Pro
145                 150                 155                 160

Glu Ala Glu Val Ile Trp Thr Asn Ser Asp His Gln Pro Val Ser Gly
                165                 170                 175

Lys Arg Ser Val Thr Thr Ser Arg Thr Glu Gly Met Leu Leu Asn Val
            180                 185                 190

Thr Ser Ser Leu Arg Val Asn Ala Thr Ala Asn Asp Val Phe Tyr Cys
        195                 200                 205

Thr Phe Trp Arg Ser Gln Pro Gly Gln Asn His Thr Ala Glu Leu Ile
    210                 215                 220

Ile Pro Glu Leu Pro Ala Thr His Pro Pro Gln Asn Arg Thr His Trp
225                 230                 235                 240

Val Leu Leu Gly Ser Ile Leu Leu Phe Leu Ile Val Val Ser Thr Val
                245                 250                 255

Leu Leu Phe Leu Arg Lys Gln Val Arg Met Leu Asp Val Glu Lys Cys
            260                 265                 270

Gly Val Glu Asp Thr Ser Ser Lys Asn Arg Asn Asp Thr Gln Phe Glu
        275                 280                 285

Glu Thr
    290

<210> SEQ ID NO 16
<211> LENGTH: 813
<212> TYPE: DNA
<213> ORGANISM: Homo sapiens

<400> SEQUENCE: 16
atgaggatat ttgctgtctt tatattcatg acctactggc atttgctgaa cgcatttact     60
gtcacggttc ccaaggacct atatgtggta gagtatggta gcaatatgac aattgaatgc    120
aaattcccag tagaaaaaca attagacctg gctgcactaa ttgtctattg ggaaatggag    180
gataagaaca ttattcaatt tgtgcatgga gaggaagacc tgaaggttca gcatagtagc    240
tacagacaga gggcccggct gttgaaggac cagctctccc tgggaaatgc tgcacttcag    300
atcacagatg tgaaattgca ggatgcaggg gtgtaccgct gcatgatcag ctatggtggt    360
gccgactaca agcgaattac tgtgaaagtc aatgccccat acaacaaaat caaccaaaga    420 atttggttg tggatccagt cacctctgaa catgaactga catgtcaggc tgagggctac    480
cccaaggccg aagtcatctg acaagcagt gaccatcaag tcctgagtgg taagaccacc    540
accaccaatt ccaagagaga ggagaagctt ttcaatgtga ccagcacact gagaatcaac    600
acaacaacta tgagattttt ctactgcact tttaggagat tagatcctga ggaaaaccat    660
acagctgaat tggtcatccc agaactacct ctggcacatc ccccaaatga aaggactcac    720
ttggtaattc tgggagccat cttattatgc cttggtgtag cactgacatt catcttccgt    780
ttaagaaaag atacacattt ggaggagacg taa                                 813

<210> SEQ ID NO 17
<211> LENGTH: 270
<212> TYPE: PRT
<213> ORGANISM: Homo sapiens

<400> SEQUENCE: 17

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
```

```
            20                  25                  30
Gly Ser Asn Met Thr Ile Glu Cys Lys Phe Pro Val Glu Lys Gln Leu
         35                  40                  45
Asp Leu Ala Ala Leu Ile Val Tyr Trp Glu Met Glu Asp Lys Asn Ile
 50                  55                  60
Ile Gln Phe Val His Gly Glu Glu Asp Leu Lys Val Gln His Ser Ser
 65                  70                  75                  80
Tyr Arg Gln Arg Ala Arg Leu Leu Lys Asp Gln Leu Ser Leu Gly Asn
                 85                  90                  95
Ala Ala Leu Gln Ile Thr Asp Val Lys Leu Gln Asp Ala Gly Val Tyr
                100                 105                 110
Arg Cys Met Ile Ser Tyr Gly Gly Ala Asp Tyr Lys Arg Ile Thr Val
                115                 120                 125
Lys Val Asn Ala Pro Tyr Asn Lys Ile Asn Gln Arg Ile Leu Val Val
            130                 135                 140
Asp Pro Val Thr Ser Glu His Glu Leu Thr Cys Gln Ala Glu Gly Tyr
145                 150                 155                 160
Pro Lys Ala Glu Val Ile Trp Thr Ser Ser Asp His Gln Val Leu Ser
                165                 170                 175
Gly Lys Thr Thr Thr Thr Asn Ser Lys Arg Glu Lys Leu Phe Asn
                180                 185                 190
Val Thr Ser Thr Leu Arg Ile Asn Thr Thr Thr Asn Glu Ile Phe Tyr
            195                 200                 205
Cys Thr Phe Arg Arg Leu Asp Pro Glu Glu Asn His Thr Ala Glu Leu
        210                 215                 220
Val Ile Pro Glu Leu Pro Leu Ala His Pro Pro Asn Glu Arg Thr His
225                 230                 235                 240
Leu Val Ile Leu Gly Ala Ile Leu Leu Cys Leu Gly Val Ala Leu Thr
                245                 250                 255
Phe Ile Phe Arg Leu Arg Lys Asp Thr His Leu Glu Glu Thr
            260                 265                 270

<210> SEQ ID NO 18
<211> LENGTH: 700
<212> TYPE: DNA
<213> ORGANISM: Homo sapiens

<400> SEQUENCE: 18
atgaggatat ttgctgtctt tatattcatg acctactggc atttgctgaa cgcatttact      60
gtcacggttc ccaaggacct atatgtggta gagtatggta gcaatatgac aattgaatgc     120
aaattcccag tagaaaaaca attagacctg ctgcactaa ttgtctattg ggaaatggag      180
gataagaaca ttattcaatt tgtgcatgga gaggaagacc tgaaggttca gcatagtagc     240
tacagacaga gggcccggct gttgaaggac cagctctccc tgggaaatgc tgcacttcag     300
atcacagatg tgaaattgca ggatgcaggg gtgtaccgct gcatgatcag ctatggtggt     360
gccgactaca agcgaattac tgtgaaagtc aatgccccat acaacaaaat caaccaaaga     420
attttggttg tggatccagt cacctctgaa catgaactga catgtcaggc tgagggctac     480
cccaaggccg aagtcatctg gacaagcagt gaccatcaag tcctgagtgg aagattagatc    540
ctgaggaaaa ccatacagct gaattggtca tcccagaact acctctggca catcctccaa     600
atgaaaggac tcacttggga gaatgatgga tgtgaaaaaa tgtggcatcc aagatacaaa     660
ctcaaagaag caagtgtgata cacatttgga ggagacgtaa                          700
```

<210> SEQ ID NO 19
<211> LENGTH: 230
<212> TYPE: PRT
<213> ORGANISM: Homo sapiens

<400> SEQUENCE: 19

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Asp Ile Leu Arg Lys Thr Ile Gln Leu Asn Trp Ser Gln Asn
            180                 185                 190

Tyr Leu Trp His Ile Leu Gln Met Lys Gly Leu Thr Trp Glu Asn Asp
        195                 200                 205

Gly Cys Glu Lys Met Trp His Pro Arg Tyr Leu Lys Glu Ala Lys
    210                 215                 220

Tyr Thr Phe Gly Gly Asp
225                 230

<210> SEQ ID NO 20
<211> LENGTH: 806
<212> TYPE: DNA
<213> ORGANISM: Homo sapiens

<400> SEQUENCE: 20
atgaggatat tgctgtctt tatattcatg acctactggc atttgctgaa cgcatttact      60
gtcacggttc ccaaggacct atatgtggta gagtatggta gcaatatgac aattgaatgc    120
aaattcccag tagaaaaaca attagacctg gctgcactaa ttgtctattg ggaaatggag    180
gataagaaca ttattcaatt tgtgcatgga gaggaagacc tgaaggttca gcatagtagc    240
tacagacaga gggcccggct gttgaaggac cagctctccc tgggaaatgc tgcacttcag    300
atcacagatg tgaaattgca ggatgcaggg gtgtaccgct gcatgatcag ctatggtggt    360
gccgactaca gcgaattac tgtgaaagtc aatgcccat acaacaaaat caaccaaaga    420
attttggttg tggatccagt cacctctgaa catgaactga catgtcaggc tgagggctac    480
cccaaggccg aagtcatctg gacaagcagt gaccatcaag tcctgagtgg taagaccacc    540

```
accaccaatt ccaagagaga ggagaagctt tcaatgtga ccagcacact gagaatcaac      600
acaacaacta atgagatttt ctactgcact tttaggagat tagatcctga ggaaaaccat      660
acagctgaat tggtcatccc agaactacct ctggcacatc ctccaaatga aaggactcac      720
ttgggagaat gatggatgtg aaaaaatgtg gcatccaaga tacaaactca agaagcaaa       780 gtgatacaca tttggaggag acgtaa                                            806
```

<210> SEQ ID NO 21
<211> LENGTH: 224
<212> TYPE: PRT
<213> ORGANISM: Homo sapiens

<400> SEQUENCE: 21

```
Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Asp Ile Leu Arg Lys Thr Ile Gln Leu Asn Trp Ser Ser Gln Asn
            180                 185                 190

Tyr Leu Trp His Ile Leu Gln Met Lys Gly Leu Thr Trp Glu Asn Asp
        195                 200                 205

Gly Cys Glu Lys Met Trp His Pro Arg Tyr Lys Leu Lys Glu Ala Lys
    210                 215                 220
```

<210> SEQ ID NO 22
<211> LENGTH: 767
<212> TYPE: DNA
<213> ORGANISM: Homo sapiens

<400> SEQUENCE: 22

```
atgaggatat ttgctgtctt tatattcatg acctactggc atttgctgaa cgcatttact       60
gtcacggttc ccaaggacct atatgtggta gagtatggta gcaatatgac aattgaatgc      120
aaattcccag tagaaaaaca attagacctg gctgcactaa ttgtctattg ggaaatggag      180
gataagaaca ttattcaatt tgtgcatgga gaggaagacc tgaaggttca gcatagtagc      240
tacagacaga gggcccggct gttgaaggac cagctctccc tgggaaatgc tgcacttcag      300
atcacagatg tgaaattgca ggatgcaggg gtgtaccgct gcatgatcag ctatggtggt      360
```

```
gccgactaca agcgaattac tgtgaaagtc aatgccccat acaacaaaat caaccaaaga     420
attttggttg tggatccagt cacctctgaa catgaactga catgtcaggc tgagggctac     480
cccaaggccg aagtcatctg acaagcagt gaccatcaag tcctgagtgg agattagatc      540
ctgaggaaaa ccatacagct gaattggtca tcccagaact acctctggca catcctccaa     600
atgaaaggac tcacttggta attctggag ccatcttatt atgccttggt gtagcactga      660
cattcatctt ccgtttaaga aagggagaa tgatggatgt gaaaaaatgt ggcatccaag      720
atacaaactc aaagaagcaa agtgatacac atttggagga gacgtaa                   767
```

```
<210> SEQ ID NO 23
<211> LENGTH: 266
<212> TYPE: PRT
<213> ORGANISM: Homo sapiens

<400> SEQUENCE: 23

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Gly Glu Trp Met Lys Asn Val Ala Ser Lys Ile Gln Thr Gln Arg
                245                 250                 255

Ser Lys Val Ile His Ile Trp Arg Arg Arg
            260                 265

<210> SEQ ID NO 24
<211> LENGTH: 243
<212> TYPE: PRT
<213> ORGANISM: Homo sapiens
```

<400> SEQUENCE: 24

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
                20                  25                  30

Gly Ser Asn Met Thr Ile Glu Cys Lys Phe Pro Val Glu Lys Gln Leu
            35                  40                  45

Asp Leu Ala Ala Leu Ile Val Tyr Trp Glu Met Glu Asp Lys Asn Ile
        50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Gly Glu

<210> SEQ ID NO 25
<211> LENGTH: 245
<212> TYPE: PRT
<213> ORGANISM: Homo sapiens

<400> SEQUENCE: 25

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
                20                  25                  30

Gly Ser Asn Met Thr Ile Glu Cys Lys Phe Pro Val Glu Lys Gln Leu
            35                  40                  45

Asp Leu Ala Ala Leu Ile Val Tyr Trp Glu Met Glu Asp Lys Asn Ile
        50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

```
Arg Cys Met Ile Ser Tyr Gly Gly Ala Asp Tyr Lys Arg Ile Thr Val
            115                 120                 125

Lys Val Asn Ala Pro Tyr Asn Lys Ile Asn Gln Arg Ile Leu Val Val
        130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Gly Glu Trp Met
                245
```

<210> SEQ ID NO 26
<211> LENGTH: 873
<212> TYPE: DNA
<213> ORGANISM: Homo sapiens

<400> SEQUENCE: 26

```
atgaggatat tgctgtctt tatattcatg acctactggc atttgctgaa cgcatttact      60
gtcacggttc ccaaggacct atatgtggta gagtatggta gcaatatgac aattgaatgc    120
aaattcccag tagaaaaaca attagacctg gctgcactaa ttgtctattg ggaaatggag    180
gataagaaca ttattcaatt tgtgcatgga gaggaagacc tgaaggttca gcatagtagc    240
tacagacaga gggcccggct gttgaaggac cagctctccc tgggaaatgc tgcacttcag    300
atcacagatg tgaaattgca ggatgcaggg gtgtaccgct gcatgatcag ctatggtggt    360
gccgactaca gcgaattact gtgaaagtc aatgccccat acaacaaaat caaccaaaga    420
attttggttg tggatccagt cacctctgaa catgaactga catgtcaggc tgagggctac    480
cccaaggccg aagtcatctg gacaagcagt gaccatcaag tcctgagtgg taagaccacc    540
accaccaatt ccaagagaga ggagaagctt ttcaatgtga ccagcacact gagaatcaac    600
acaacaacta atgagatttt ctactgcact tttaggagat tagatcctga ggaaaaccat    660
acagctgaat tggtcatccc agaactacct ctggcacatc ctccaaatga aaggactcac    720
ttggtaattc tgggagccat cttattatgc cttggtgtag cactgacatt catcttccgt    780
ttaagaaaag ggagaatgat ggatgtgaaa aaatgtggca tccaagatac aaactcaaag    840
aagcaaagtg atacacattt ggaggagacg taa                                 873
```

<210> SEQ ID NO 27
<211> LENGTH: 248
<212> TYPE: PRT
<213> ORGANISM: Homo sapiens

<400> SEQUENCE: 27

```
Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30
```

Gly Ser Asn Met Thr Ile Glu Cys Lys Phe Pro Val Glu Lys Gln Leu
            35                  40                  45

Asp Leu Ala Ala Leu Ile Val Tyr Trp Glu Met Glu Asp Lys Asn Ile
 50                  55                  60

Ile Gln Phe Val His Gly Glu Glu Asp Leu Lys Val Gln His Ser Ser
 65                  70                  75                  80

Tyr Arg Gln Arg Ala Arg Leu Leu Lys Asp Gln Leu Pro Leu Gly Asn
                 85                  90                  95

Ala Ala Leu Gln Ile Thr Asp Val Lys Leu Gln Asp Ala Gly Val Tyr
                100                 105                 110

Arg Cys Met Ile Ser Tyr Gly Gly Ala Asp Tyr Lys Arg Ile Thr Val
            115                 120                 125

Lys Val Asn Ala Pro Tyr Asn Lys Ile Asn Gln Arg Ile Leu Val Val
130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Asp Ile Leu Arg Lys Thr Ile Gln Leu Asn Trp Ser Ser Gln Asn
            180                 185                 190

Tyr Leu Trp His Ile Leu Gln Met Lys Gly Leu Thr Trp Phe Trp Glu
            195                 200                 205

Pro Ser Tyr Tyr Ala Leu Val His His Ser Ser Ser Val Glu Lys Gly
            210                 215                 220

Glu Trp Met Lys Asn Val Ala Ser Lys Ile Gln Thr Gln Arg Ser Lys
225                 230                 235                 240

Val Ile His Ile Trp Arg Arg Arg
                245

<210> SEQ ID NO 28
<211> LENGTH: 178
<212> TYPE: PRT
<213> ORGANISM: Homo sapiens

<400> SEQUENCE: 28

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
                20                  25                  30

Gly Ser Asn Met Thr Ile Glu Cys Lys Phe Pro Val Glu Lys Gln Leu
            35                  40                  45

Asp Leu Ala Ala Leu Ile Val Tyr Trp Glu Met Glu Asp Lys Asn Ile
 50                  55                  60

Ile Gln Phe Val His Gly Glu Glu Asp Leu Lys Val Gln His Ser Ser
 65                  70                  75                  80

Tyr Arg Gln Arg Ala Arg Leu Leu Lys Asp Gln Leu Pro Leu Gly Asn
                 85                  90                  95

Ala Ala Leu Gln Ile Thr Asp Val Lys Leu Gln Asp Ala Gly Val Tyr
                100                 105                 110

Arg Cys Met Ile Ser Tyr Gly Gly Ala Asp Tyr Lys Arg Ile Thr Val
            115                 120                 125

Lys Val Asn Ala Pro Tyr Asn Lys Ile Asn Gln Arg Ile Leu Val Val
130                 135                 140

Asp Pro Val Thr Ser Glu His Glu Leu Thr Cys Gln Ala Glu Gly Tyr
145                 150                 155                 160

```
Pro Lys Ala Glu Val Ile Trp Thr Ser Ser Asp His Gln Val Leu Ser
            165                 170                 175

Gly Asp

<210> SEQ ID NO 29
<211> LENGTH: 205
<212> TYPE: PRT
<213> ORGANISM: Homo sapiens

<400> SEQUENCE: 29

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
                20                  25                  30

Gly Ser Asn Met Thr Ile Glu Cys Lys Phe Pro Val Glu Lys Gln Leu
            35                  40                  45

Asp Leu Ala Ala Leu Ile Val Tyr Trp Glu Met Glu Asp Lys Asn Ile
        50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Pro Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Asp Ile Leu Arg Lys Thr Ile Gln Leu Asn Trp Ser Ser Gln Asn
            180                 185                 190

Tyr Leu Trp His Ile Leu Gln Met Lys Gly Leu Thr Trp
        195                 200                 205

<210> SEQ ID NO 30
<211> LENGTH: 215
<212> TYPE: PRT
<213> ORGANISM: Homo sapiens

<400> SEQUENCE: 30

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
                20                  25                  30

Gly Ser Asn Met Thr Ile Glu Cys Lys Phe Pro Val Glu Lys Gln Leu
            35                  40                  45

Asp Leu Ala Ala Leu Ile Val Tyr Trp Glu Met Glu Asp Lys Asn Ile
        50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Pro Leu Gly Asn
                85                  90                  95
```

```
Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
            115                 120                 125

Lys Val Asn Ala Pro Tyr Asn Lys Ile Asn Gln Arg Ile Leu Val Val
            130                 135             140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Asp Ile Leu Arg Lys Thr Ile Gln Leu Asn Trp Ser Ser Gln Asn
            180                 185                 190

Tyr Leu Trp His Ile Leu Gln Met Lys Gly Leu Thr Trp Phe Trp Glu
            195                 200                 205

Pro Ser Tyr Tyr Ala Leu Val
            210             215

<210> SEQ ID NO 31
<211> LENGTH: 216
<212> TYPE: PRT
<213> ORGANISM: Homo sapiens

<400> SEQUENCE: 31

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
            35                  40                  45

Asp Leu Ala Ala Leu Ile Val Tyr Trp Glu Met Glu Asp Lys Asn Ile
        50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Pro Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
            115                 120                 125

Lys Val Asn Ala Pro Tyr Asn Lys Ile Asn Gln Arg Ile Leu Val Val
            130                 135             140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Asp Ile Leu Arg Lys Thr Ile Gln Leu Asn Trp Ser Ser Gln Asn
            180                 185                 190

Tyr Leu Trp His Ile Leu Gln Met Lys Gly Leu Thr Trp Phe Trp Glu
            195                 200                 205

Pro Ser Tyr Tyr Ala Leu Val His
            210             215

<210> SEQ ID NO 32
<211> LENGTH: 221
<212> TYPE: PRT
<213> ORGANISM: Homo sapiens
```

<400> SEQUENCE: 32

```
Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Pro Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Asp Ile Leu Arg Lys Thr Ile Gln Leu Asn Trp Ser Ser Gln Asn
            180                 185                 190

Tyr Leu Trp His Ile Leu Gln Met Lys Gly Leu Thr Trp Phe Trp Glu
        195                 200                 205

Pro Ser Tyr Tyr Ala Leu Val His Ser Ser Val
    210                 215                 220
```

<210> SEQ ID NO 33
<211> LENGTH: 225
<212> TYPE: PRT
<213> ORGANISM: Homo sapiens

<400> SEQUENCE: 33

```
Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Pro Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
130                 135                 140
```

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
            165                 170                 175

Gly Asp Ile Leu Arg Lys Thr Ile Gln Leu Asn Trp Ser Ser Gln Asn
        180                 185                 190

Tyr Leu Trp His Ile Leu Gln Met Lys Gly Leu Thr Trp Phe Trp Glu
    195                 200                 205

Pro Ser Tyr Tyr Ala Leu Val His Ser Ser Ser Val Glu Lys Gly
        210                 215                 220

Glu
225

<210> SEQ ID NO 34
<211> LENGTH: 227
<212> TYPE: PRT
<213> ORGANISM: Homo sapiens

<400> SEQUENCE: 34

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Pro Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
            165                 170                 175

Gly Asp Ile Leu Arg Lys Thr Ile Gln Leu Asn Trp Ser Ser Gln Asn
        180                 185                 190

Tyr Leu Trp His Ile Leu Gln Met Lys Gly Leu Thr Trp Phe Trp Glu
    195                 200                 205

Pro Ser Tyr Tyr Ala Leu Val His Ser Ser Ser Val Glu Lys Gly
        210                 215                 220

Glu Trp Met
225

<210> SEQ ID NO 35
<211> LENGTH: 37
<212> TYPE: DNA
<213> ORGANISM: Artificial Sequence
<220> FEATURE:
<223> OTHER INFORMATION: /note="Description of Artificial Sequence:

Synthetic primer"

<400> SEQUENCE: 35
gcgtcgtcta gagccaccat gaggatattt gctgtct          37

<210> SEQ ID NO 36
<211> LENGTH: 33
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 36
gcgccagtcg acttacgtct cctccaaatg tgt          33

<210> SEQ ID NO 37
<211> LENGTH: 21
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 37
ccaaatgaaa ggactcactt g          21

<210> SEQ ID NO 38
<211> LENGTH: 23
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 38
cgtctcctcc aaatgtgtat ctt          23

<210> SEQ ID NO 39
<211> LENGTH: 23
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 39
aagtcctgag tggagattag atc          23

<210> SEQ ID NO 40
<211> LENGTH: 19
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 40
cattctccca agtgagtcc          19

<210> SEQ ID NO 41
<211> LENGTH: 21
<212> TYPE: DNA
<213> ORGANISM: Artificial Sequence
<220> FEATURE:
<223> OTHER INFORMATION: /note="Description of Artificial Sequence:
      Synthetic primer"

```
<400> SEQUENCE: 41
accagcacac tgagaatcaa c                                               21

<210> SEQ ID NO 42
<211> LENGTH: 21
<212> TYPE: DNA
<213> ORGANISM: Artificial Sequence
<220> FEATURE:
<223> OTHER INFORMATION: /note="Description of Artificial Sequence:
      Synthetic primer"

<400> SEQUENCE: 42
cacatccatc attctcccaa g                                               21
```